United States Patent
Fan et al.

(10) Patent No.: US 8,637,516 B2
(45) Date of Patent: Jan. 28, 2014

(54) COMPOUNDS AND COMPOSITIONS AS TRK INHIBITORS

(75) Inventors: Yi Fan, Poway, CA (US); Jon Loren, San Diego, CA (US); Valentina Molteni, San Diego, CA (US); Pamela A. Albaugh, Redlands, CA (US); Gregory Chopiuk, Vancouver (CA); Jeffrey M. Smith, San Diego, CA (US); Brenton T. Flatt, Poway, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 13/227,957

(22) Filed: Sep. 8, 2011

(65) Prior Publication Data

US 2012/0065184 A1    Mar. 15, 2012

Related U.S. Application Data

(60) Provisional application No. 61/381,373, filed on Sep. 9, 2010.

(51) Int. Cl.
 *A01N 43/58*  (2006.01)
 *A61K 31/50*  (2006.01)
 *C07D 487/00* (2006.01)

(52) U.S. Cl.
 USPC ........................................... 514/250

(58) Field of Classification Search
 USPC .......................... 544/236; 514/250
 See application file for complete search history.

(56) References Cited

U.S. PATENT DOCUMENTS

| | | | |
|---|---|---|---|
| 7,306,631 | B2 | 12/2007 | Glenn et al. |
| 7,723,336 | B2 | 5/2010 | Vaccaro et al. |
| 2007/0049591 | A1 | 3/2007 | Pinkerton et al. |
| 2007/0078136 | A1 | 4/2007 | Vaccaro et al. |
| 2007/0093490 | A1 | 4/2007 | Prien et al. |
| 2008/0045536 | A1 | 2/2008 | Vaccaro et al. |
| 2008/0153813 | A1 | 6/2008 | Chen et al. |

FOREIGN PATENT DOCUMENTS

| | | |
|---|---|---|
| WO | WO0100213 | 1/2001 |
| WO | WO2005097052 | 10/2005 |
| WO | WO2007013673 | 2/2007 |
| WO | WO2007025090 | 3/2007 |
| WO | WO2007038314 | 4/2007 |
| WO | WO2007147647 | 12/2007 |
| WO | WO2008079880 | 7/2008 |
| WO | WO2008138889 | 11/2008 |
| WO | WO2009017954 | 1/2009 |
| WO | WO2009016286 | 2/2009 |
| WO | WO2009060197 | 5/2009 |
| WO | WO2009106577 | 9/2009 |
| WO | WO2009140128 | 11/2009 |
| WO | WO2010033941 | 3/2010 |
| WO | WO2010048314 | 4/2010 |
| WO | WO2010051549 | 5/2010 |
| WO | WO2010117787 | 10/2010 |
| WO | WO2011006074 | 6/2011 |

OTHER PUBLICATIONS

Pinedo et al (2001) McMahon et al (2001).*
Pogacic Vanda et al., "Structural Analysis Identifies Imidazo[1,2-b]Pyridazines as PIM Kinase Inhibitors with In vitro Antileukemic Activity", Cancer Res 2007; pp. 6916-6924, 67: (14).

* cited by examiner

*Primary Examiner* — Paul V. Ward
(74) *Attorney, Agent, or Firm* — Ann R. Pokalsky, Esq.; Dilworth & Barrese, LLP

(57) ABSTRACT

The invention provides compounds, pharmaceutical compositions comprising such compounds and methods of using such compounds to treat or prevent diseases or disorders associated with abnormal or deregulated TRK kinase activity.

29 Claims, No Drawings

COMPOUNDS AND COMPOSITIONS AS TRK INHIBITORS

CROSS-REFERENCE TO RELATED APPLICATIONS

This application claims the benefit of U.S. Provisional Patent Application No. 61/381,373, filed Sep. 9, 2010. The disclosure of the priority application is incorporated herein by reference in its entirety and for all purposes.

FIELD OF THE INVENTION

The invention relates to protein kinase inhibitors, and methods of using such compounds.

BACKGROUND OF THE INVENTION

Protein kinases (PK) are a large set of structurally related phosphoryl transferases having highly conserved structures and catalytic functions. Protein kinases are enzymatic components of the signal transduction pathways which catalyze the transfer of the terminal phosphate from ATP to the hydroxy group of tyrosine, serine and/or threonine residues of proteins, and are therefore categorized into families by the substrates they phosphorylate: Protein Tyrosine Kinases (PTK), and Protein Serine/Threonine Kinases.

Protein kinases play a critical role in the control of cell growth and differentiation and are responsible for the control of a wide variety of cellular signal transduction processes, wherein protein kinases are key mediators of cellular signals leading to the production of growth factors and cytokines. The overexpression or inappropriate expression of normal or mutant protein kinases plays a significant role in the development of many diseases and disorders including, central nervous system disorders such as Alzheimer's, inflammatory disorders such as arthritis, bone diseases such as osteoporosis, metabolic disorders such as diabetes, blood vessel proliferative disorders such as angiogenesis, autoimmune diseases such as rheumatoid arthritis, ocular diseases, cardiovascular disease, atherosclerosis, cancer, thrombosis, psoriasis, restenosis, schizophrenia, pain sensation, transplant rejection and infectious diseases such as viral, and fungal infections.

Examples of protein-tyrosine kinases include, but are not limited to, Irk, IGFR-1, Syk, Zap-70, Bmx, Btk, CHK (Csk homologous kinase), CSK (C-terminal Src Kinase), Itk-1, Src (c-Src, Lyn, Fyn, Lck, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (α and β), Tie-1, Tie-2 (also Tek-1 or Tek), VEGFR1 (also FLT-1), VEGFR2 (also KDR), FLT-3, FLT-4, c-KIT, JAK1, JAK2, JAK3, TYK2, LOK, RET, TRKA, TRKB, TRKC, PYK2, ALK (Anaplastic Lymphoma Kinase), EPHA (1-8), EPHB (1-6), RON, Ros, Fes, Fer or EPHB4 (also EPHB4-1).

Examples of protein-serine/threonine kinases include, but are not limited to, Ark, ATM (1-3), CamK (1-IV), CamKK, Chk1 and 2 (Checkpoint kinases), CKI, CK2, Erk, IKK-I (also IKK-ALPHA or CHUK), IKK-2 (also IKK-BETA), Ilk, Jnk (1-3), LimK (1 and 2), MLK3Raf (A, B and C), CDK (1-10), PKC (including all PKC subtypes), Plk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 or Tp1-2 (also COT).

SUMMARY OF THE INVENTION

Provide herein are compounds and pharmaceutical compositions thereof, which are useful as inhibitors of Tropomyosin-Related Kinases (TRKA, TRKB and/or TRKC).

In one aspect, the present invention provides compounds having Formula (I), and the pharmaceutically acceptable salts, pharmaceutically acceptable solvates (e.g. hydrates), the N-oxide derivatives, prodrug derivatives, protected derivatives, individual stereoisomers and mixture of stereoisomers thereof:

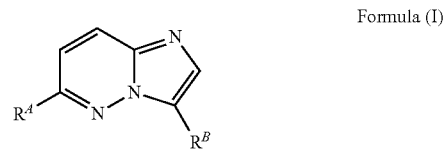

Formula (I)

wherein:
$R^A$ is

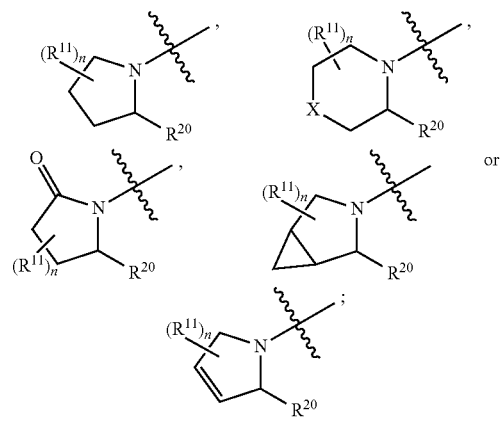

$X$ is $C(R^3)_2$, O or $NR^3$;
$R^B$ is halo, —CN, —C(O)NH$_2$, -L$^1$R$^2$, -L$^2$R$^7$, —C(O)NHOR$^3$, —C(O)NR$^3$OR$^8$, —C(O)NHNH$_2$, —C(O)NR$^3$C(O)OR$^3$, —C(O)NR$^3$C(O)NH$_2$, —NR$^3$C(O)NR$^3$R$^5$,

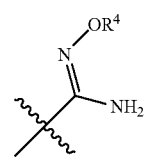

or —SO$_2$NR$^3$R$^3$;
$L^1$ is —C(O)NR$^3$—, —C(O)NR$^3$(CR$^4$R$^4$)$_q$—, —C(O)—, —C(O)NR$^3$O(CR$^4$R$^4$)$_q$—, —C(O)O—, —C(O)—C$_1$-C$_8$alkylene or —C(O)—C$_2$-C$_8$alkenylene;
$L^2$ is —NR$^3$C(O)(CR$^4$R$^4$)$_q$—;
each $L^3$ is independently selected from a C$_1$-C$_8$alkylene and a C$_1$-C$_8$alkylene substituted with 1 to 3 substituents independently selected from C$_1$-C$_6$alkyl;
$R^2$ is selected from $R^9$, —N(R$^3$)$_2$, C$_1$-C$_6$alkyl, phenyl, C$_{10}$aryl, C$_{10}$aryl, C$_3$-C$_8$cycloalkyl, 4-6 membered heterocycloalkyl containing 1 to 2 heteroatoms selected from N, O and S, 5, 6, 9 or 10 membered heteroaryl containing 1 to 3 N heteroatoms and $C_1$-$C_8$alkyl substituted with 1 to 6 groups independently selected from halo, $C_1$-$C_4$alkyl, and —$R^6$, or $R^2$ is selected from the phenyl, $C_{10}$aryl, $C_{14}$aryl, $C_3$-$C_8$cycloalkyl, a 4-6 membered heterocycloalkyl containing 1 to 2 heteroatoms selected from N, O and S, and a 5, 6, 9 or 10 membered heteroaryl containing 1 to 3 N heteroatoms, each of which is substituted with 1 to 3 substituents independently selected from halo, $C_1$-$C_6$alkyl, $C_1$-$C_6$alkyl substituted with 1 to 4 hydroxyl groups, 4-6 membered heterocycloalkyl containing 1 to 2 heteroatoms selected from N, O and S, —CN, —$R^8$, —$OR^4$, —$C(O)R^4$, —$C(O)OR^4$, —$C(O)L^3R^6$, —$S(O)_2R^4$, and —$S(O)_2NR^4R^4$;

each $R^3$ is independently selected from H, $C_1$-$C_6$alkyl;

each $R^4$ is independently selected from H, $C_1$-$C_6$alkyl, and $C_1$-$C_6$alkyl substituted with 1 to 4 hydroxyl groups;

$R^5$ is $C_1$-$C_4$haloalkyl or —$OR^3$;

$R^6$ is selected from —$OC(O)R^4$, —$NHC(O)OR^4$, —$NR^3R^3$, —$C(O)N(R^3R^3)$, —$S(O)_2R^4$, —$S(O)_2NR^4R^4$, —$C(O)OR^4$ and —$OR^4$;

$R^7$ is halo, —$OC(O)R^{12}$, —$OR^{12}$, —CN, —$NHC(O)OR^{12}$, —$NHC(O)R^{12}$ or —$NR^3R^3$;

$R^8$ is a 4-6 membered heterocycloalkyl containing 1 to 2 heteroatoms selected from N, O and S or 4-6 membered heterocycloalkyl containing 1 to 2 heteroatoms selected from N, O and S substituted with 1 to 4 substituents independently selected from halo, —$OR^4$, $C_1$-$C_6$alkyl and $C_1$-$C_6$haloalkyl;

$R^9$ is cyclohexyl having a $C_1$-$C_6$alkyl bridge,

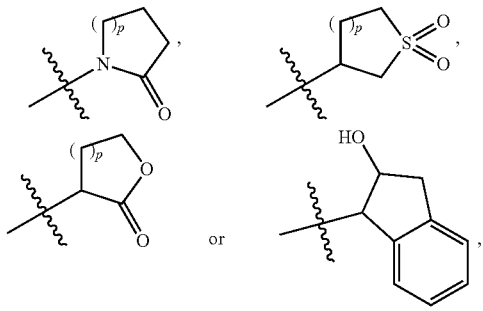

wherein each is optionally substituted with 1-3 substituents independently selected from halo, —CN, $C_1$-$C_6$alkyl, —$R^8$, and —$OR^3$;

each $R^{10}$ is independently selected from halo, $C_1$-$C_6$alkyl, $C_1$-$C_6$haloalkyl, —C=$NOR^3$, —CN, —$(CR^4R^4)_qCN$, —$NR^3R^3$, —$C(O)OR^4$, —$C(O)NR^3R^3$, —$(CR^4R^4)_qR^6$, —$NR^3C(O)NR^3R^3$, —$NR^3S(O)_2R^4$, —$NR^3S(O)_2NR^4R^4$, —$S(O)_2NR^4R^4$, —$S(O)_2R^4$, —$OR^4$, 4-6 membered heterocycloalkyl containing 1 to 2 heteroatoms selected from N, O and S and a 5 membered heteroaryl containing 1 to 4 N heteroatoms;

each $R^{11}$ is independently selected from halo, —$OR^3$, deuterium, $C_1$-$C_6$alkyl, hydroxyl substituted $C_1$-$C_6$alkyl, $C_1$-$C_6$halolkyl;

$R^{12}$ is H, $C_1$-$C_6$alkyl, phenyl or phenyl substituted with 1 to 3 groups independently selected from halo, $C_1$-$C_4$alkyl, and —$R^6$;

$R^{20}$ is selected from

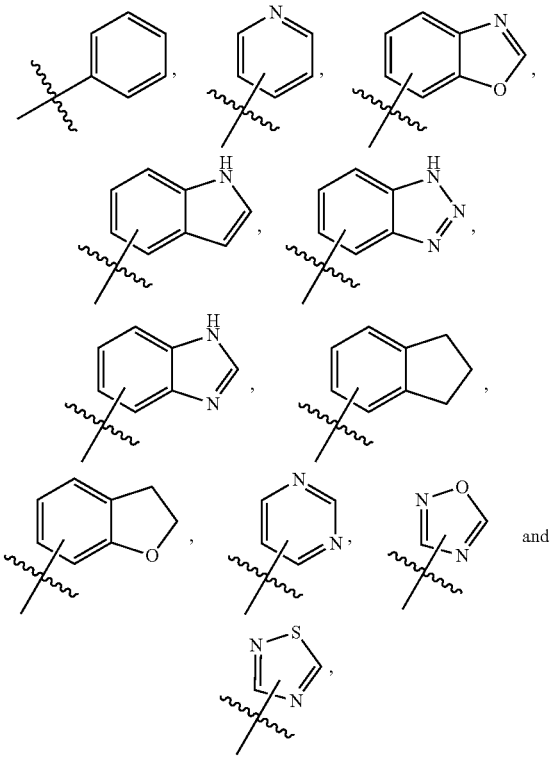

each of which is substituted with 1 to 3 substituents independently selected from $R^{10}$, or $R^{20}$ is selected from

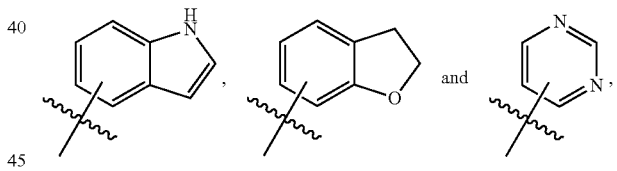

each of which is optionally substituted with 1 to 3 substituents independently selected from $R^{10}$;

n is 0, 1, 2, 3, 4, 5, 6 or 7; p is 1 or 2 and q is 1, 2, 3, 4, 5 or 6.

In certain embodiments, of such compounds of Formula (I):

$R^A$ is

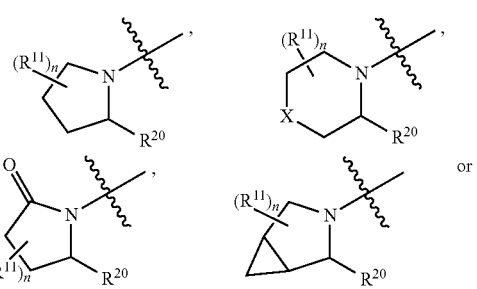

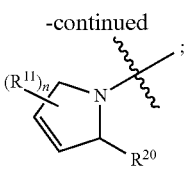

X is C(R³)₂, O or NR³;

R$^B$ is halo, —CN, —C(O)NH₂, -L¹R², -L²R⁷, —C(O)NHOR³, —C(O)NR³OR⁸, —C(O)NHNH₂, —NR³C(O)NR³R⁵,

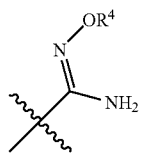

or —SO₂NR³R³;

L¹ is —C(O)NR³—, —C(O)NR³(CR⁴R⁴)$_q$—, —C(O)—, —C(O)NR³O(CR⁴R⁴)$_q$—, —C(O)O—, —C(O)—C₁-C₈alkylene or —C(O)—C₂-C₈alkenylene;

L² is —NR³C(O)(CR⁴R⁴)$_q$—;

each L³ is independently selected from a C₁-C₈alkylene and a C₁-C₈alkylene substituted with 1 to 3 substituents independently selected from C₁-C₆alkyl;

R² is selected from R⁹, —N(R³)₂, C₁-C₆alkyl, phenyl, C₁₀aryl, C₁₀aryl, C₃-C₈cycloalkyl, 4-6 membered heterocycloalkyl containing 1 to 2 heteroatoms selected from N, O and S, 5, 6, 9 or 10 membered heteroaryl containing 1 to 3 N heteroatoms and C₁-C₈alkyl substituted with 1 to 6 groups independently selected from halo, C₁-C₄alkyl, and —R⁶, or R² is selected from the phenyl, C₁₀aryl, C₁₄aryl, C₃-C₈cycloalkyl, a 4-6 membered heterocycloalkyl containing 1 to 2 heteroatoms selected from N, O and S, and a 5, 6, 9 or 10 membered heteroaryl containing 1 to 3 N heteroatoms, each of which is substituted with 1 to 3 substituents independently selected from halo, C₁-C₆alkyl, C₁-C₆alkyl substituted with 1 to 4 hydroxyl groups, 4-6 membered heterocycloalkyl containing 1 to 2 heteroatoms selected from N, O and S, —CN, —R⁸, —OR⁴, —C(O)R⁴, —C(O)OR⁴, —C(O)L³R⁶, —S(O)₂R⁴, and —S(O)₂NR⁴R⁴;

each R³ is independently selected from H, C₁-C₆alkyl;

each R⁴ is independently selected from H, C₁-C₆alkyl, and C₁-C₆alkyl substituted with 1 to 4 hydroxyl groups;

R⁵ is C₁-C₄haloalkyl or —OR³;

R⁶ is selected from —OC(O)R⁴, —NHC(O)OR⁴, —NR³R³, —C(O)N(R³R³), —S(O)₂R⁴, —S(O)₂NR⁴R⁴, —C(O)OR⁴ and —OR⁴;

R⁷ is halo, —OC(O)R¹², —OR¹², —CN, —NHC(O)OR¹², —NHC(O)R¹² or —NR³R³;

R⁸ is a 4-6 membered heterocycloalkyl containing 1 to 2 heteroatoms selected from N, O and S or 4-6 membered heterocycloalkyl containing 1 to 2 heteroatoms selected from N, O and S substituted with 1 to 4 substituents independently selected from halo, —OR⁴, C₁-C₆alkyl and C₁-C₆haloalkyl;

R⁹ is cyclohexyl having a C₁-C₆alkyl bridge,

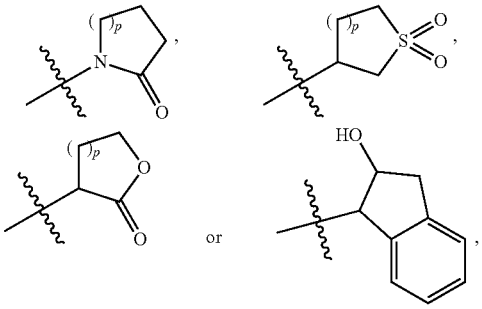

wherein each is optionally substituted with 1-3 substituents independently selected from halo, —CN, C₁-C₆alkyl, —R⁸, and —OR³;

each R¹⁰ is independently selected from halo, C₁-C₆alkyl, C₁-C₆haloalkyl, —C=NOR³, —CN, —(CR⁴R⁴)$_q$CN, —NR³R³, —C(O)OR⁴, —C(O)NR³R³, —(CR⁴R⁴)$_q$R⁶, —NR³C(O)NR³R³, —NR³S(O)₂R⁴, —NR³S(O)₂NR⁴R⁴, —S(O)₂NR⁴R⁴, —S(O)₂R⁴, —OR⁴, 4-6 membered heterocycloalkyl containing 1 to 2 heteroatoms selected from N, O and S and a 5 membered heteroaryl containing 1 to 4 N heteroatoms;

each R¹¹ is independently selected from halo, —OR³, deuterium, C₁-C₆alkyl, hydroxyl substituted C₁-C₆alkyl, C₁-C₆halolkyl;

R¹² is H, C₁-C₆alkyl, phenyl or phenyl substituted with 1 to 3 groups independently selected from halo, C₁-C₄alkyl, and —R⁶;

R²⁰ is selected from

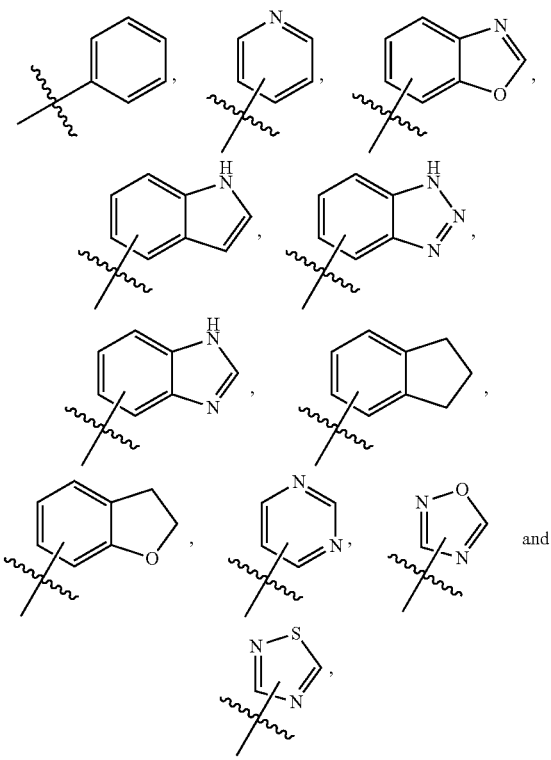

each of which is substituted with 1 to 3 substituents independently selected from R¹⁰, or $R^{20}$ is selected from

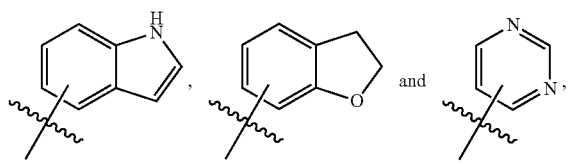

each of which is optionally substituted with 1 to 3 substituents independently selected from $R^{10}$;
n is 0, 1, 2, 3, 4, 5, 6 or 7; p is 1 or 2 and q is 1, 2, 3, 4, 5 or 6.

In certain embodiments, such compounds of Formula (I) are compounds having the structure of Formula (I-a):

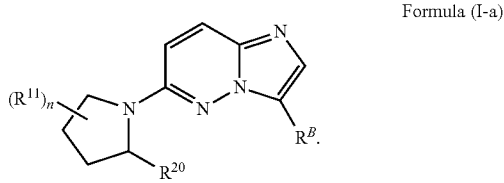

Formula (I-a)

In certain embodiments, such compounds of Formula (I) are compounds having the structure of Formula (II-a):

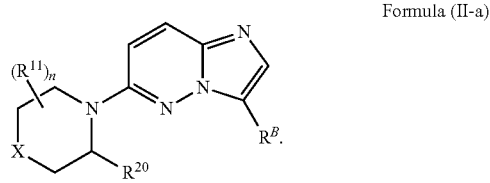

Formula (II-a)

In certain embodiments, such compounds of Formula (I) are compounds having the structure of Formula (III-a):

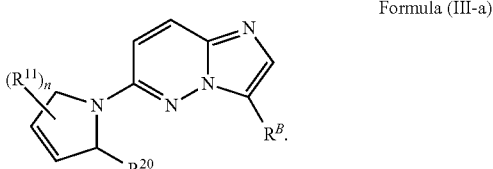

Formula (III-a)

In certain embodiments, such compounds of Formula (I-a) are compounds having the structure of Formula (I-b):

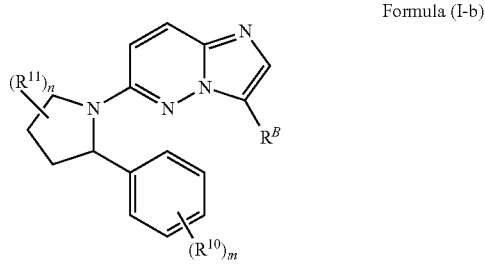

Formula (I-b)

wherein m is 1, 2 or 3.

In certain embodiments, such compounds of Formula (II-a) are compounds having the structure of Formula (II-b):

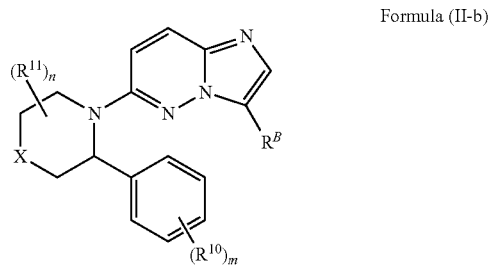

Formula (II-b)

wherein m is 1, 2 or 3.

In certain embodiments, such compounds of Formula (III-a) are compounds having the structure of Formula (III-b):

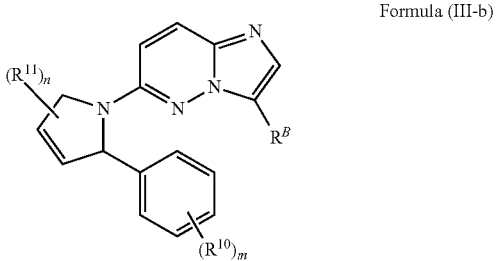

Formula (III-b)

wherein m is 1, 2 or 3.

In certain embodiments of compounds of Formula (I), Formula (I-a), Formula (II-a), Formula (III-a), Formula (I-b), Formula (II-b) and Formula (III-b), $R^B$ is —C(O)NH$_2$.

In other embodiments of compounds of Formula (I), Formula (I-a), Formula (II-a), Formula (III-a), Formula (I-b), Formula (II-b) and Formula (III-b), $R^B$ is -L$^1$R$^2$. In certain embodiments of such compounds of Formula (I), Formula (I-a), Formula (II-a), Formula (III-a), Formula (I-b), Formula (II-b) and Formula (III-b), L$^1$ is —C(O)NR$^3$—, —C(O)NR$^3$(CR$^4$R$^4$)$_q$— or —C(O)NR$^3$O(CR$^4$R$^4$)$_q$—. In other embodiments of such compounds of Formula (I), Formula (I-a), Formula (II-a), Formula (III-a), Formula (I-b), Formula (II-b) and Formula (III-b), L$^1$ is —C(O)— or —C(O)O—. In still other embodiments of such compounds of Formula (I), Formula (I-a), Formula (II-a), Formula (III-a), Formula (I-b), Formula (II-b) and Formula (III-b), L$^1$ is —C(O)—C$_1$-C$_8$alkylene or —C(O)—C$_2$-C$_8$alkenylene.

In certain embodiments of the aforementioned compounds of Formula (I), Formula (I-a), Formula (II-a), Formula (III-a), Formula (I-b), Formula (II-b) and Formula (III-b), $R^2$ is phenyl, cyclopropyl, cyclobutyl, cyclopentyl or cyclohexyl. In other embodiments of the aforementioned compounds of Formula (I), Formula (I-a), Formula (II-a), Formula (III-a), Formula (I-b), Formula (II-b) and Formula (III-b), $R^2$ is phenyl, cyclopropyl, cyclobutyl, cyclopentyl or cyclohexyl each of which is substituted with 1 to 3 substituents independently selected from halo, C$_1$-C$_6$alkyl, C$_1$-C$_6$alkyl substituted with 1 to 4 hydroxyl groups, 4-6 membered heterocycloalkyl containing 1 to 2 heteroatoms selected from N, O and S, —CN, —R$^8$, —OR$^4$, —C(O)R$^4$, —C(O)OR$^4$, —C(O)L$^3$R$^6$, —S(O)$_2$R$^4$, and —S(O)$_2$NR$^4$R$^4$.

In certain embodiments of the aforementioned compounds of Formula (I), Formula (I-a), Formula (II-a), Formula (III-a), Formula (I-b), Formula (II-b) and Formula (III-b), $R^2$ is tetrahydro-2H-pyranyl, tetrahydrofuranyl, piperidinyl, pyrrolidinyl, oxetanyl, morpholinyl, tetrahydro-2H-thiopyranyl, azetidinyl, piperazinyl, pyridyl, pyrazolyl, benzthiazolyl or pyrrolyl. In other embodiments of the aforementioned compounds of Formula (I), Formula (I-a), Formula (II-a), Formula (III-a), Formula (I-b), Formula (II-b) and Formula (III-b), $R^2$ is tetrahydro-2H-pyranyl, tetrahydrofuranyl, piperidinyl, pyrrolidinyl, oxetanyl, morpholinyl, tetrahydro-2H-thiopyranyl, azetidinyl, piperazinyl, pyridyl, pyrazolyl, benzthiazolyl or pyrrolyl, each of which is substituted with 1 to 3 substituents independently selected from halo, $C_1$-$C_6$alkyl, $C_1$-$C_6$alkyl substituted with 1 to 4 hydroxyl groups, 4-6 membered heterocycloalkyl containing 1 to 2 heteroatoms selected from N, O and S, —CN, —$R^8$, —$OR^4$, —$C(O)R^4$, —$C(O)OR^4$, —$C(O)L^3R^6$, —$S(O)_2R^4$, and —$S(O)_2NR^4R^4$.

In certain embodiments of compounds of Formula (I), Formula (I-a), Formula (II-a), Formula (III-a), Formula (I-b), Formula (II-b) and Formula (III-b), $R^B$ is —$C(O)NHOR^3$, —$C(O)NR^3OR^8$, —$C(O)NHNH_2$, —$NR^3C(O)NR^3R^5$ or

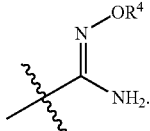

In certain embodiments of the aforementioned compounds of Formula (I), Formula (I-a), Formula (II-a), Formula (III-a), Formula (I-b), Formula (II-b) and Formula (III-b), $R^8$ is pyrrolidinyl, tetrahydro-2H-pyranyl, morpholinyl or piperidinyl. In certain embodiments of the aforementioned compounds of Formula (I), Formula (I-a), Formula (II-a), Formula (III-a), Formula (I-b), Formula (II-b) and Formula (III-b), $R^8$ is pyrrolidinyl, tetrahydro-2H-pyranyl, morpholinyl or piperidinyl, each of which is substituted with 1 to 2 —$OR^4$ groups.

In certain embodiments of the aforementioned compounds of Formula (I), Formula (I-a), Formula (II-a), Formula (III-a), Formula (I-b), Formula (II-b) and Formula (III-b), $R^2$ is $R^9$, —$N(R^3)_2$, methyl, ethyl, propyl, isopropyl, isobutene, t-butyl, or $C_1$-$C_8$alkyl substituted with 1 to 6 groups independently selected from halo, $C_1$-$C_4$alkyl, and —$R^6$.

In certain embodiments of the aforementioned compounds of Formula (I), Formula (I-a), Formula (II-a), Formula (III-a), Formula (I-b), Formula (II-b) and Formula (III-b), $R^9$ is cyclohexyl having a $C_1$alkyl bridge,

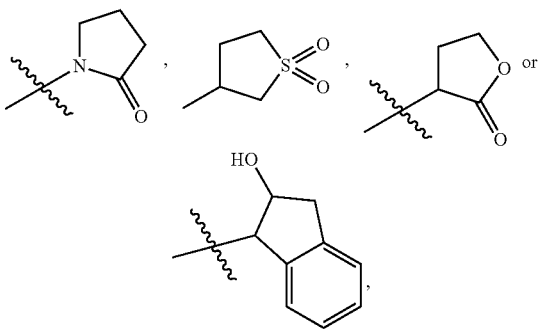

wherein each is optionally substituted with 1-3 substituents independently selected from $C_1$-$C_6$alkyl.

In certain embodiments of compounds of Formula (I), Formula (I-a), Formula (II-a), Formula (III-a), Formula (I-b), Formula (II-b) and Formula (III-b), $R^B$ is -$L^2R^7$.

In certain embodiments of compounds of Formula (I), Formula (I-a), Formula (II-a), Formula (III-a), Formula (I-b), Formula (II-b) and Formula (III-b), $R^B$ is —Br, —CN and —$SO_2NR^3R^3$.

In certain embodiments of the aforementioned compounds of Formula (I), Formula (I-a), Formula (II-a), Formula (III-a), Formula (I-b), Formula (II-b) and Formula (III-b), each $R^{10}$ is independently selected from F, Cl, methyl, —$CF_3$), —C=$NOR^3$, —CN, —$(CR^4R^4)_qCN$, —$NR^3R^3$, —C(O)$OR^4$, —C(O)$NR^3R^3$, —$(CR^4R^4)_qR^6$, —$NR^3C(O)NR^3R^3$, —$NR^3S(O)_2R^4$, —$NR^3S(O)_2NR^4R^4$, —$S(O)_2NR^4R^4$, —$S(O)_2R^4$, —$OR^4$, morpholinyl and tetrazolyl.

In certain embodiments of the aforementioned compounds of Formula (I), Formula (I-a), Formula (II-a), Formula (III-a), Formula (I-b), Formula (II-b) and Formula (III-b), each $R^{11}$ is independently selected from F, —$OR^3$, deuterium, methyl, hydroxyl substituted $C_1$-$C_6$alkyl or $C_1$-$C_6$haloalkyl.

In certain embodiments of the aforementioned compounds of Formula (I), Formula (I-a), Formula (II-a), Formula (III-a), Formula (I-b), Formula (II-b) and Formula (III-b), $R^6$ is selected from —OC(O)$R^4$, —NHC(O)$OR^4$, —$NR^3R^3$, —C(O)N($R^3R^3$), —$S(O)_2R^4$, —$S(O)_2NR^4R^4$, —C(O)$OR^4$ and —$OR^4$, and wherein each $R^4$ is independently selected from H, methyl, ethyl, propyl, isopropyl, t-butyl or a $C_1$-$C_6$alkyl substituted with 1 to 4 hydroxyl groups.

In certain embodiments of the aforementioned compounds of Formula (I), Formula (I-a), Formula (II-a), Formula (III-a), Formula (I-b), Formula (II-b) and Formula (III-b), $R^3$ is H, methyl or ethyl.

In certain embodiments of the aforementioned compounds of Formula (I), Formula (I-a), Formula (II-a), Formula (III-a), Formula (I-b), Formula (II-b) and Formula (III-b), q is 1, 2 or 3.

In certain embodiments compounds of Formula (I) are selected from: (2R)-1-{3-bromoimidazo[1,2-b]pyridazin-6-yl}-2-(3-fluorophenyl)pyrrolidine; 6-[(2R)-2-(3-fluorophenyl)pyrrolidin-1-yl]imidazo[1,2-b]pyridazine-3-carbonitrile; 6-[3-(3-fluorophenyl)morpholin-4-yl]imidazo[1,2-b]pyridazine-3-carbonitrile; 6-[(2R,4S)-3,3-difluoro-2-(3-fluorophenyl)-4-methylpyrrolidin-1-yl]imidazo[1,2-b]pyridazine-3-carbonitrile; 6-[2-(3-fluorophenyl)pyrrolidin-1-yl]imidazo[1,2-b]pyridazine-3-carboxamide; 6-[(2R)-2-(3-fluorophenyl)pyrrolidin-1-yl]imidazo[1,2-b]pyridazine-3-carboxamide; 6-[(2R,4S)-4-fluoro-2-(3-fluorophenyl)pyrrolidin-1-yl]imidazo[1,2-b]pyridazine-3-carboxamide; 6-[2-(3-fluorophenyl)-2-hydrogeniopyrrolidin-1-yl]imidazo[1,2-b]pyridazine-3-carboxamide; 6-[(2S)-2-(3-fluorophenyl)-2-hydrogeniopyrrolidin-1-yl]imidazo[1,2-b]pyridazine-3-carboxamide; 6-[(5S)-5-(3-fluorophenyl)-2,2-dihydrogeniopyrrolidin-1-yl]imidazo[1,2-b]pyridazine-3-carboxamide; 6-[(5R)-5-(3-fluorophenyl)-2,2-dihydrogeniopyrrolidin-1-yl]imidazo[1,2-b]pyridazine-3-carboxamide; 6-[5-(3-fluorophenyl)-2,2,3,3,4,4-hexahydrogeniopyrrolidin-1-yl]imidazo[1,2-b]pyridazine-3-carboxamide; 6-[2-(3-fluorophenyl)-2,3,3,4,4,5,5-heptahydrogeniopyrrolidin-1-yl]imidazo[1,2-b]pyridazine-3-carboxamide; 6-[(2R,4S)-4-fluoro-2-(3-fluorophenyl)pyrrolidin-1-yl]-N-(oxan-4-yl)imidazo[1,2-b]pyridazine-3-carboxamide; 6-[(2R)-2-(3-fluorophenyl)-2,5-dihydro-1H-pyrrol-1-yl]imidazo[1,2-b]pyridazine-3-carboxamide; 6-[3-(3-fluorophenyl)morpholin-4-yl]imidazo[1,2-b]pyridazine-3-carboxamide; 6-[(3R)-3-(3-fluorophenyl)morpholin-4-yl]imidazo[1,2-b]pyridazine-3-carboxamide; 6-[2-(3-fluorophenyl)piperidin-1-yl]imidazo[1,2-b]pyridazine-3- carboxamide; 6-[(2R)-2-(3-fluorophenyl)piperidin-1-yl]imidazo[1,2-b]pyridazine-3-carboxamide; 6-[(2R)-2-(3-fluorophenyl)pyrrolidin-1-yl]-N-(4-hydroxybutyl)imidazo[1,2-b]pyridazine-3-carboxamide; N-ethyl-6-[2-(3-fluorophenyl)pyrrolidin-1-yl]imidazo[1,2-b]pyridazine-3-carboxamide; N-(cyclobutylmethyl)-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-[2-(oxolan-2-yl)ethyl]imidazo[1,2-b]pyridazine-3-carboxamide; N-[(4-fluorophenyl)methyl]-6-[2-(3-fluorophenyl)pyrrolidin-1-yl]imidazo[1,2-b]pyridazine-3-carboxamide; 6-[(2R)-2-(3-fluorophenyl)pyrrolidin-1-yl]-N-{[6-(morpholin-4-yl)pyridin-2-yl]methyl}imidazo[1,2-b]pyridazine-3-carboxamide; 2-(4-fluorophenoxy)-N-{6-[(2R)-2-(3-fluorophenyl)pyrrolidin-1-yl]imidazo[1,2-b]pyridazin-3-yl}acetamide; N-[1-(ethanesulfonyl)piperidin-4-yl]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-[(1R,2S)-2-(hydroxymethyl)cyclohexyl]imidazo[1,2-b]pyridazine-3-carboxamide; 6-[(2R)-2-(3-fluorophenyl)pyrrolidin-1-yl]-N-(1-sulfamoylpiperidin-4-yl)imidazo[1,2-b]pyridazine-3-carboxamide; 6-[(2R)-2-(3-fluorophenyl)pyrrolidin-1-yl]-N-[(3S)-1-methanesulfonylpyrrolidin-3-yl]imidazo[1,2-b]pyridazine-3-carboxamide; 6-[(2R)-2-(3-fluorophenyl)pyrrolidin-1-yl]-N-[(3S)-1-(propane-2-sulfonyl)pyrrolidin-3-yl]imidazo[1,2-b]pyridazine-3-carboxamide; 6-[(2R)-2-(3-fluorophenyl)pyrrolidin-1-yl]-N-[1-(propane-2-sulfonyl)piperidin-4-yl]imidazo[1,2-b]pyridazine-3-carboxamide; (2S)-1-(4-{6-[(2R)-2-(3-fluorophenyl)pyrrolidin-1-yl]imidazo[1,2-b]pyridazine-3-amido}piperidin-1-yl)-1-oxopropan-2-yl acetate; 6-[(2R)-2-(3-fluorophenyl)pyrrolidin-1-yl]-N-{1-[(2S)-2-hydroxypropanoyl]piperidin-4-yl}imidazo[1,2-b]pyridazine-3-carboxamide; 6-[(2R)-2-(3-fluorophenyl)pyrrolidin-1-yl]-N-[1-(propane-1-sulfonyl)piperidin-4-yl]imidazo[1,2-b]pyridazine-3-carboxamide; N-[(5,5-dimethyloxolan-2-yl)methyl]-6-[(2R)-2-(3-fluorophenyl)pyrrolidin-1-yl]imidazo[1,2-b]pyridazine-3-carboxamide; N-[2-(4-fluorophenyl)ethyl]-6-[(2R)-2-(3-fluorophenyl)pyrrolidin-1-yl]imidazo[1,2-b]pyridazine-3-carboxamide; N-(1,3-benzothiazol-2-ylmethyl)-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-(propan-2-yl)imidazo[1,2-b]pyridazine-3-carboxamide; N-[3-(diethylamino)propyl]-6-[(2R)-2-(3-fluorophenyl)pyrrolidin-1-yl]imidazo[1,2-b]pyridazine-3-carboxamide; N-[1-(4-fluorophenyl)-2-methylpropan-2-yl]-6-[(2R)-2-(3-fluorophenyl)pyrrolidin-1-yl]imidazo[1,2-b]pyridazine-3-carboxamide; N-[1-(4-fluorophenyl)ethyl]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-methylimidazo[1,2-b]pyridazine-3-carboxamide; N-cyclopropyl-6-[(2R)-2-(3-fluorophenyl)pyrrolidin-1-yl]imidazo[1,2-b]pyridazine-3-carboxamide; N-tert-butyl-6-[(2R)-2-(3-fluorophenyl)pyrrolidin-1-yl]imidazo[1,2-b]pyridazine-3-carboxamide; N-cyclobutyl-6-[(2R)-2-(3-fluorophenyl)pyrrolidin-1-yl]imidazo[1,2-b]pyridazine-3-carboxamide; N-[(4-fluorophenyl)methyl]-6-[(2R)-2-(3-fluorophenyl)pyrrolidin-1-yl]imidazo[1,2-b]pyridazine-3-carboxamide; N-cyclopentyl-6-[(2R)-2-(3-fluorophenyl)pyrrolidin-1-yl]imidazo[1,2-b]pyridazine-3-carboxamide; N-cyclohexyl-6-[(2R)-2-(3-fluorophenyl)pyrrolidin-1-yl]imidazo[1,2-b]pyridazine-3-carboxamide; ethyl 4-{6-[(2R)-2-(3-fluorophenyl)pyrrolidin-1-yl]imidazo[1,2-b]pyridazine-3-amido}piperidine-1-carboxylate; 6-[(2R)-2-(3-fluorophenyl)pyrrolidin-1-yl]-N-(2-methoxyethyl)imidazo[1,2-b]pyridazine-3-carboxamide; 6-[(2R)-2-(3-fluorophenyl)pyrrolidin-1-yl]-N-[2-(morpholin-4-yl)ethyl]imidazo[1,2-b]pyridazine-3-carboxamide; 6-[(2R)-2-(3-fluorophenyl)pyrrolidin-1-yl]-N-(2,2,2-trifluoroethyl)imidazo[1,2-b]pyridazine-3-carboxamide; 6-[(2R)-2-(3-fluorophenyl)pyrrolidin-1-yl]-N-[(2S)-1-methoxypropan-2-yl]imidazo[1,2-b]pyridazine-3-carboxamide; N-ethyl-6-[(2R)-2-(3-fluorophenyl)pyrrolidin-1-yl]imidazo[1,2-b]pyridazine-3-carboxamide; N-[2-(dimethylamino)ethyl]-6-[(2R)-2-(3-fluorophenyl)pyrrolidin-1-yl]imidazo[1,2-b]pyridazine-3-carboxamide; N-[(6-chloropyridin-3-yl)methyl]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-[3-(morpholin-4-yl)propyl]imidazo[1,2-b]pyridazine-3-carboxamide; 6-[(2R)-2-(3-fluorophenyl)pyrrolidin-1-yl]-N-(thian-4-yl)imidazo[1,2-b]pyridazine-3-carboxamide; 6-[(2R)-2-(3-fluorophenyl)pyrrolidin-1-yl]-N-(2,2,3,3,3-pentafluoropropyl)imidazo[1,2-b]pyridazine-3-carboxamide; tert-butyl 3-{6-[(2R)-2-(3-fluorophenyl)pyrrolidin-1-yl]imidazo[1,2-b]pyridazine-3-amido}azetidine-1-carboxylate; tert-butyl (3R)-3-{6-[(2R)-2-(3-fluorophenyl)pyrrolidin-1-yl]imidazo[1,2-b]pyridazine-3-amido}pyrrolidine-1-carboxylate; tert-butyl 4-{6-[(2R)-2-(3-fluorophenyl)pyrrolidin-1-yl]imidazo[1,2-b]pyridazine-3-amido}piperidine-1-carboxylate; N-(1-acetylazetidin-3-yl)-6-[(2R)-2-(3-fluorophenyl)pyrrolidin-1-yl]imidazo[1,2-b]pyridazine-3-carboxamide; N-(3-cyanophenyl)-6-[(2R)-2-(3-fluorophenyl)pyrrolidin-1-yl]imidazo[1,2-b]pyridazine-3-carboxamide; N-[(3R)-1-acetylpyrrolidin-3-yl]-6-[(2R)-2-(3-fluorophenyl)pyrrolidin-1-yl]imidazo[1,2-b]pyridazine-3-carboxamide; N-(1-acetylpiperidin-4-yl)-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-(1-methanesulfonylazetidin-3-yl)imidazo[1,2-b]pyridazine-3-carboxamide; N-[(2-fluorophenyl)methyl]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-[(3R)-1-methanesulfonylpyrrolidin-3-yl]imidazo[1,2-b]pyridazine-3-carboxamide; 6-[(2R)-2-(3-fluorophenyl)pyrrolidin-1-yl]-N-(1-methanesulfonylpiperidin-4-yl)imidazo[1,2-b]pyridazine-3-carboxamide; 2-(4-{6-[(2R)-2-(3-fluorophenyl)pyrrolidin-1-yl]imidazo[1,2-b]pyridazine-3-amido}piperidin-1-yl)-2-oxoethyl acetate; N-[(3-fluorophenyl)methyl]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-[1-(2-hydroxyacetyl)piperidin-4-yl]imidazo[1,2-b]pyridazine-3-carboxamide; 6-[(2R)-2-(3-fluorophenyl)pyrrolidin-1-yl]-N-(3,3,3-trifluoropropyl)imidazo[1,2-b]pyridazine-3-carboxamide; N-(1-ethyl-1H-pyrazol-5-yl)-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-(2-hydroxyethyl)imidazo[1,2-b]pyridazine-3-carboxamide; 6-[(2R)-2-(3-fluorophenyl)pyrrolidin-1-yl]-N-(4-hydroxycyclohexyl)imidazo[1,2-b]pyridazine-3-carboxamide; 6-[(2R)-2-(3-fluorophenyl)pyrrolidin-1-yl]-N-[(1R,2R)-2-hydroxycyclopentyl]imidazo[1,2-b]pyridazine-3-carboxamide; 6-[(2R)-2-(3-fluorophenyl)pyrrolidin-1-yl]-N-[(1S,2S)-2-hydroxycyclohexyl]imidazo[1,2-b]pyridazine-3-carboxamide; 6-[(2R)-2-(3-fluorophenyl)pyrrolidin-1-yl]-N-(1-hydroxy-2-methylpropan-2-yl)imidazo[1,2-b]pyridazine-3-carboxamide; 6-[(2R)-2-(3-fluorophenyl)pyrrolidin-1-yl]-N-[(2R)-oxolan-2-ylmethyl]imidazo[1,2-b]pyridazine-3-carboxamide; 6-[(2R)-2-(3-fluorophenyl)pyrrolidin-1-yl]-N-[(2S)-oxolan-2-ylmethyl]imidazo[1,2-b]pyridazine-3- carboxamide; 6-[(2R)-2-(3-fluorophenyl)pyrrolidin-1-yl]-N-[2-(2-oxopyrrolidin-1-yl)ethyl]imidazo[1,2-b]pyridazine-3-carboxamide; methyl N-[(2S)-1-({6-[(2R)-2-(3-fluorophenyl)pyrrolidin-1-yl]imidazo[1,2-b]pyridazin-3-yl}formamido)propan-2-yl]carbamate; 6-((2R,4S)-4-fluoro-2-(3-fluorophenyl)pyrrolidin-1-yl)-N-(1,1-dioxo-tetrahydrothiophen-3-yl)imidazo[1,2-b]pyridazine-3-carboxamide; N-[(4-cyanophenyl)methyl]-6-[(2R)-2-(3-fluorophenyl)pyrrolidin-1-yl]imidazo[1,2-b]pyridazine-3-carboxamide; N-(cyclopropylmethyl)-6-[(2R)-2-(3-fluorophenyl)pyrrolidin-1-yl]imidazo[1,2-b]pyridazine-3-carboxamide; N-(2-cyclohexylethyl)-6-[(2R)-2-(3-fluorophenyl)pyrrolidin-1-yl]imidazo[1,2-b]pyridazine-3-carboxamide; N-(2,2-difluoroethyl)-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-(oxan-4-yl)imidazo[1,2-b]pyridazine-3-carboxamide; 6-[(2R)-2-(3-fluorophenyl)pyrrolidin-1-yl]-N-(2-methylpropyl)imidazo[1,2-b]pyridazine-3-carboxamide; N-(cyclohexylmethyl)-6-([2R)-2-(3-fluorophenyl)pyrrolidin-1-yl]imidazo[1,2-b]pyridazine-3-carboxamide; N-(2-fluoroethyl)-6-([2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-(oxan-3-yl)imidazo[1,2-b]pyridazine-3-carboxamide; methyl (2R)-2-({6-[(2R)-2-(3-fluorophenyl)pyrrolidin-1-yl]imidazo[1,2-b]pyridazin-3-yl}formamido)-3-hydroxypropanoate; 6-[(2R)-2-(3-fluorophenyl)pyrrolidin-1-yl]-N-({6-[(3R)-3-hydroxypyrrolidin-1-yl]pyridin-3-yl}methyl)imidazo[1,2-b]pyridazine-3-carboxamide; 6-[(2R)-2-(3-fluorophenyl)pyrrolidin-1-yl]-N-[(3R)-2-oxooxolan-3-yl]imidazo[1,2-b]pyridazine-3-carboxamide; N-[1,3-dihydroxy-2-(hydroxymethyl)propan-2-yl]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-[(2R)-1-hydroxy-3-methylbutan-2-yl]imidazo[1,2-b]pyridazine-3-carboxamide; 6-[(2R)-2-(3-fluorophenyl)pyrrolidin-1-yl]-N-[(2S)-1-hydroxy-3,3-dimethylbutan-2-yl]imidazo[1,2-b]pyridazine-3-carboxamide; 6-[(2R)-2-(3-fluorophenyl)pyrrolidin-1-yl]-N-[(2S)-1-hydroxy-4-methylpentan-2-yl]imidazo[1,2-b]pyridazine-3-carboxamide; N-[(2S)-2,3-dihydroxypropyl]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-[(1R,2R)-2-hydroxy-2,3-dihydro-1H-inden-1-yl]imidazo[1,2-b]pyridazine-3-carboxamide; 6-[(2R)-2-(3-fluorophenyl)pyrrolidin-1-yl]-N-[(2R)-1-hydroxy-4-methylpentan-2-yl]imidazo[1,2-b]pyridazine-3-carboxamide; N-(2-cyclopentylethyl)-6-[(2R)-2-(3-fluorophenyl)pyrrolidin-1-yl]imidazo[1,2-b]pyridazine-3-carboxamide; N-(cyclopentylmethyl)-6-[(2R)-2-(3-fluorophenyl)pyrrolidin-1-yl]imidazo[1,2-b]pyridazine-3-carboxamide; N-{[(1S,2R,5S)-6,6-dimethylbicyclo[3.1.1]heptan-2-yl]methyl}-6-[(2R)-2-(3-fluorophenyl)pyrrolidin-1-yl]imidazo[1,2-b]pyridazine-3-carboxamide; 6-[2-(3-fluorophenyl)pyrrolidin-1-yl]-N-(2,2,2-trifluoroethyl)imidazo[1,2-b]pyridazine-3-carboxamide; 6-[(2R,4S)-4-fluoro-2-(3-fluorophenyl)pyrrolidin-1-yl]-N-(2-fluoroethyl)imidazo[1,2-b]pyridazine-3-carboxamide; 6-[(2R,4S)-4-fluoro-2-(3-fluorophenyl)pyrrolidin-1-yl]-N-[2-(morpholin-4-yl)ethyl]imidazo[1,2-b]pyridazine-3-carboxamide; N-(2,2-difluoroethyl)-6-[(2R,4S)-4-fluoro-2-(3-fluorophenyl)pyrrolidin-1-yl]imidazo[1,2-b]pyridazine-3-carboxamide; tert-butyl 4-{6-[(2R,4S)-4-fluoro-2-(3-fluorophenyl)pyrrolidin-1-yl]imidazo[1,2-b]pyridazine-3-amido}piperidine-1-carboxylate; 6-((R)-2-(3-fluorophenyl)pyrrolidin-1-yl)-N-(1,1-dioxo-tetrahydrothiophen-3-yl)imidazo[1,2-b]pyridazine-3-carboxamide; 2-({6-[(2R,4S)-4-fluoro-2-(3-fluorophenyl)pyrrolidin-1-yl]imidazo[1,2-b]pyridazin-3-yl}formamido)acetamide; 6-[(2R,4S)-4-fluoro-2-(3-fluorophenyl)pyrrolidin-1-yl]-N-(2-sulfamoylethyl)imidazo[1,2-b]pyridazine-3-carboxamide; 6-[(2R,4S)-4-fluoro-2-(3-fluorophenyl)pyrrolidin-1-yl]-N-(2-hydroxyethyl)imidazo[1,2-b]pyridazine-3-carboxamide; 6-[(2R,4S)-4-fluoro-2-(3-fluorophenyl)pyrrolidin-1-yl]-N-(piperidin-4-yl)imidazo[1,2-b]pyridazine-3-carboxamide; 6-[(2R,4S)-4-fluoro-2-(3-fluorophenyl)pyrrolidin-1-yl]-N-(1-methanesulfonylpiperidin-4-yl)imidazo[1,2-b]pyridazine-3-carboxamide; (2E)-3-(6-bromopyridin-2-yl)-1-{6-[(2R)-2-(3-fluorophenyl)pyrrolidin-1-yl]imidazo[1,2-b]pyridazin-3-yl}prop-2-en-1-one; 1-{6-[(2R)-2-(3-fluorophenyl)pyrrolidin-1-yl]imidazo[1,2-b]pyridazin-3-yl}propan-1-one; 2,2-difluoro-1-{6-[(2R)-2-(3-fluorophenyl)pyrrolidin-1-yl]imidazo[1,2-b]pyridazin-3-yl}ethan-1-one; 1-{6-[(2R)-2-(3-fluorophenyl)pyrrolidin-1-yl]imidazo[1,2-b]pyridazin-3-yl}ethan-1-one; (2Z)-3-(3-fluorophenyl)-1-{6-[(2R)-2-(3-fluorophenyl)pyrrolidin-1-yl]imidazo[1,2-b]pyridazin-3-yl}prop-2-en-1-one; 3-(3-fluorophenyl)-1-{6-[(2R)-2-(3-fluorophenyl)pyrrolidin-1-yl]imidazo[1,2-b]pyridazin-3-yl}propan-1-one; (2E)-1-{6-[(2R)-2-(3-fluorophenyl)pyrrolidin-1-yl]imidazo[1,2-b]pyridazin-3-yl}-3-[6-(morpholin-4-yl)pyridin-2-yl]prop-2-en-1-one; 1-{6-[(2R)-2-(3-fluorophenyl)pyrrolidin-1-yl]imidazo[1,2-b]pyridazin-3-yl}-3-[6-(morpholin-4-yl)pyridin-2-yl]propan-1-one; (2E)-1-{6-[(2R)-2-(3-fluorophenyl)pyrrolidin-1-yl]imidazo[1,2-b]pyridazin-3-yl}-3-(1-methyl-1H-pyrrol-2-yl)prop-2-en-1-one; (2E)-1-{6-[(2R)-2-(3-fluorophenyl)pyrrolidin-1-yl]imidazo[1,2-b]pyridazin-3-yl}-3-(6-methoxypyridin-2-yl)prop-2-en-1-one; N-ethoxy-6-[(2R,4S)-4-fluoro-2-(3-fluorophenyl)pyrrolidin-1-yl]imidazo[1,2-b]pyridazine-3-carboxamide; N-(cyclopropylmethoxy)-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-(oxan-2-yloxy)imidazo[1,2-b]pyridazine-3-carboxamide; N-(tert-butoxy)-6-[(2R)-2-(3-fluorophenyl)pyrrolidin-1-yl]imidazo[1,2-b]pyridazine-3-carboxamide; N-[2-(dimethylamino)ethoxy]-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-(2-hydroxyethoxy)imidazo[1,2-b]pyridazine-3-carboxamide; 6-[(2R)-2-(3-fluorophenyl)pyrrolidin-1-yl]-N-(2-methoxyethoxy)imidazo[1,2-b]pyridazine-3-carboxamide; N-ethoxy-6-[(2R)-2-(3-fluorophenyl)pyrrolidin-1-yl]imidazo[1,2-b]pyridazine-3-carboxamide; 6-[(2R)-2-(3-fluorophenyl)pyrrolidin-1-yl]-N-hydroxyimidazo[1,2-b]pyridazine-3-carboxamide; 6-[(2R)-2-(3-fluorophenyl)pyrrolidin-1-yl]-N-methoxyimidazo[1,2-b]pyridazine-3-carboxamide; N-ethoxy-6-[2-(3-fluorophenyl)pyrrolidin-1-yl]imidazo[1,2-b]pyridazine-3-carboxamide; 6-[(2R,4S)-4-fluoro-2-(3-fluorophenyl)pyrrolidin-1-yl]-N-hydroxyimidazo[1,2-b]pyridazine-3-carboxamide; 6-[(2R)-2-(3-fluorophenyl)pyrrolidin-1-yl]-N-(4-methylpiperazin-1-yl)imidazo[1,2-b]pyridazine-3-carboxamide; 6-[(2R)-2-(3-fluorophenyl)pyrrolidin-1-yl]imidazo[1,2-b]pyridazine-3-carbohydrazide; ethyl 6-[2-(3-fluorophenyl)piperidin-1-yl]imidazo[1,2-b]pyridazine-3-carboxylate; methyl 6-[(2R)-2-(3-fluorophenyl)pyrrolidin-1-yl]imidazo[1,2-b]pyridazine-3-carboxylate; ethyl 6-[(2R)-2-(3-fluorophenyl)pyrrolidin-1-yl]imidazo[1,2-b]pyridazine-3-carboxylate; ethyl 6-[2-(3-fluorophenyl)-3-oxopyrrolidin-1-yl]imidazo[1,2-b]pyridazine-3-carboxylate; ethyl 6-[(2R,4R)-2-(3-fluorophenyl)-4-hydroxypyrrolidin-1-yl]imidazo[1,2-b]pyridazine-3-carboxylate; ethyl 6-[5-(3-fluorophenyl)-2,2,3,3,4,4-hexahydrogeniopyrrolidin-1-yl]imidazo[1,2-b]

pyridazine-3-carboxylate; ethyl 6-[2-(3-fluorophenyl)-2-hydrogeniopyrrolidin-1-yl]imidazo[1,2-b]pyridazine-3-carboxylate; ethyl 6-[2-(3-fluorophenyl)-2,3,3,4,4,5,5-heptahydrogeniopyrrolidin-1-yl]imidazo[1,2-b]pyridazine-3-carboxylate; ethyl 6-[(2S)-3,3,4,4-tetrafluoro-2-(3-fluorophenyl)pyrrolidin-1-yl]imidazo[1,2-b]pyridazine-3-carboxylate; ethyl 6-[(2R,4S)-4-fluoro-2-(3-fluorophenyl)pyrrolidin-1-yl]imidazo[1,2-b]pyridazine-3-carboxylate; ethyl 6-[(2S,4R)-4-fluoro-2-(3-fluorophenyl)pyrrolidin-1-yl]imidazo[1,2-b]pyridazine-3-carboxylate; 2-ethoxy-N-{6-[(2R)-2-(3-fluorophenyl)pyrrolidin-1-yl]imidazo[1,2-b]pyridazin-3-yl}acetamide; ({6-[(2R)-2-(3-fluorophenyl)pyrrolidin-1-yl]imidazo[1,2-b]pyridazin-3-yl}carbamoyl)methyl acetate; N-{6-[(2R)-2-(3-fluorophenyl)pyrrolidin-1-yl]imidazo[1,2-b]pyridazin-3-yl}-3-methoxypropanamide; 2-cyano-N-{6-[(2R)-2-(3-fluorophenyl)pyrrolidin-1-yl]imidazo[1,2-b]pyridazin-3-yl}acetamide; N-{6-[(2R)-2-(3-fluorophenyl)pyrrolidin-1-yl]imidazo[1,2-b]pyridazin-3-yl}-2-(4-methoxyphenoxy)acetamide; 1-({6-[(2R)-2-(3-fluorophenyl)pyrrolidin-1-yl]imidazo[1,2-b]pyridazin-3-yl}carbamoyl)-1-methylethyl acetate; tert-butyl N-[({6-[(2R)-2-(3-fluorophenyl)pyrrolidin-1-yl]imidazo[1,2-b]pyridazin-3-yl}carbamoyl)methyl]carbamate; 2-amino-N-{6-[(2R)-2-(3-fluorophenyl)pyrrolidin-1-yl]imidazo[1,2-b]pyridazin-3-yl}acetamide; N-{6-[(2R)-2-(3-fluorophenyl)pyrrolidin-1-yl]imidazo[1,2-b]pyridazin-3-yl}-2-methoxyacetamide; 2-acetamido-N-{6-[(2R)-2-(3-fluorophenyl)pyrrolidin-1-yl]imidazo[1,2-b]pyridazin-3-yl}acetamide; 2-amino-N-{6-[(2R)-4,4-difluoro-2-(3-fluorophenyl)pyrrolidin-1-yl]imidazo[1,2-b]pyridazin-3-yl}acetamide; 3-(2-chloroethyl)-1-{6-[(2R)-2-(3-fluorophenyl)pyrrolidin-1-yl]imidazo[1,2-b]pyridazin-3-yl}urea; 6-[2-(3-fluorophenyl)pyrrolidin-1-yl]-N'-hydroxyimidazo[1,2-b]pyridazine-3-carboximidamide; 6-[(2R)-2-(3-fluorophenyl)pyrrolidin-1-yl]-N'-hydroxyimidazo[1,2-b]pyridazine-3-carboximidamide; 6-[(2R)-2-(3-fluorophenyl)pyrrolidin-1-yl]-N'-methoxyimidazo[1,2-b]pyridazine-3-carboximidamide; 6-[(2R)-2-(3-fluorophenyl)pyrrolidin-1-yl]-N'-(2-hydroxyethoxy)imidazo[1,2-b]pyridazine-3-carboximidamide; tert-butyl N-{6-[(2R)-2-(3-fluorophenyl)pyrrolidin-1-yl]imidazo[1,2-b]pyridazin-3-yl}carbamate; propan-2-yl N-{6-[(2R)-2-(3-fluorophenyl)pyrrolidin-1-yl]imidazo[1,2-b]pyridazin-3-yl}carbamate; methyl N-{6-[(2R)-2-(3-fluorophenyl)pyrrolidin-1-yl]imidazo[1,2-b]pyridazin-3-yl}carbamate; ethyl N-{6-[(2R)-2-(3-fluorophenyl)pyrrolidin-1-yl]imidazo[1,2-b]pyridazin-3-yl}carbamate; N-ethyl-6-[(2R)-2-(3-fluorophenyl)pyrrolidin-1-yl]imidazo[1,2-b]pyridazine-3-sulfonamide; phenyl N-{6-[(2R)-4,4-difluoro-2-(3-fluorophenyl)pyrrolidin-1-yl]imidazo[1,2-b]pyridazin-3-yl}carbamate; ethyl 6-[(2R,4S)-2-(3,4-difluorophenyl)-4-fluoropyrrolidin-1-yl]imidazo[1,2-b]pyridazine-3-carboxylate; 6-[(2R,4S)-2-(3,4-difluorophenyl)-4-fluoropyrrolidin-1-yl]imidazo[1,2-b]pyridazine-3-carboxamide; 6-[(2R,4S)-2-(3,5-difluorophenyl)-4-fluoropyrrolidin-1-yl]imidazo[1,2-b]pyridazine-3-carboxamide; 6-[(2R,4S)-2-(2,5-difluorophenyl)-4-fluoropyrrolidin-1-yl]imidazo[1,2-b]pyridazine-3-carboxamide; ethyl 6-[(2R,4S)-2-(3-cyano-5-fluorophenyl)-4-fluoropyrrolidin-1-yl]imidazo[1,2-b]pyridazine-3-carboxylate; 6-[(2R,4S)-2-(3-cyano-5-fluorophenyl)-4-fluoropyrrolidin-1-yl]imidazo[1,2-b]pyridazine-3-carboxamide; (2R)-1-{3-bromoimidazo[1,2-b]pyridazin-6-yl}-4,4-difluoro-2-(3-fluorophenyl)pyrrolidine; 6-[(2R)-4,4-difluoro-2-(3-fluorophenyl)pyrrolidin-1-yl]imidazo[1,2-b]pyridazine-3-carboxamide; 6-[(2R)-4,4-difluoro-2-(3-fluorophenyl)pyrrolidin-1-yl]imidazo[1,2-b]pyridazine-3-carbonitrile; 6-(4,4-difluoro-2-{5-fluoro-2-[(propan-2-yl)carbamoyl]phenyl}pyrrolidin-1-yl)imidazo[1,2-b]pyridazine-3-carboxamide; {6-[(2R)-4,4-difluoro-2-(3-fluorophenyl)pyrrolidin-1-yl]imidazo[1,2-b]pyridazin-3-yl}carbonylurea, and methyl N-({6-[(2R)-4,4-difluoro-2-(3-fluorophenyl)pyrrolidin-1-yl]imidazo[1,2-b]pyridazin-3-yl}carbonyl)carbamate.

In a preferred embodiment a compound of Formula (I) is 6-[(2R)-4,4-difluoro-2-(3-fluorophenyl)pyrrolidin-1-yl]imidazo[1,2-b]pyridazine-3-carboxamide, while in another preferred embodiment a compound of Formula (I) is 6-[(2R,4S)-4-fluoro-2-(3-fluorophenyl)pyrrolidin-1-yl]imidazo[1,2-b]pyridazine-3-carboxamide. In another preferred embodiment a compound of Formula (I) is 6-[(2R,4S)-2-(3-cyano-5-fluorophenyl)-4-fluoropyrrolidin-1-yl]imidazo[1,2-b]pyridazine-3-carboxamide.

Another aspect provided herein are pharmaceutical compositions comprising a therapeutically effective amount of a compound of Formula (I) and a pharmaceutically acceptable carrier.

In certain embodiments of such pharmaceutical compositions, the pharmaceutical compositions are formulated for intravenous, oral administration, rectal administration inhalation, nasal administration, topical administration, ophthalmic administration or otic administration. In certain embodiments of such pharmaceutical compositions, the pharmaceutical composition is a tablet, a pill, a capsule, a liquid, an inhalant, a nasal spray solution, a suppository, a solution, an emulsion, an ointment, eye drop or ear drop.

Another aspect provided herein are medicaments for treating a TRK mediated disease or condition in a patient wherein the medicament comprises a therapeutically effective amount of a compound of Formula (I).

Another aspect provided herein is the use of a compound of Formula (I) in the manufacture of a medicament for treating a TRK mediated disease or condition. In certain embodiments of such methods, the disease or condition is cancer, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease. In certain embodiments of such methods, the disease or condition is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV or lupus. In certain embodiments of such uses, the disease or condition is condition is papillary thyroid carcinoma, pancreatic cancer, colon cancer, breast carcinoma, neuroblastoma pain, cachexia, dermatitis or asthma.

Another aspect provided herein is a method for inhibiting a TRK kinase comprising administering to a system or a subject in need thereof, a therapeutically effective amount of a compound of Formula (I), or pharmaceutically acceptable salts or pharmaceutical compositions thereof.

Another aspect provided herein is a method for treating a TRK kinase-mediated disease or condition, comprising administering to a system or subject in need of such treatment an effective amount of a compound of Formula (I), or pharmaceutically acceptable salts or pharmaceutical compositions thereof, wherein the disease or condition is selected from cancer, pain, cachexia, anorexia nervosa, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease, and wherein the compound is a compound of Formula (I). In certain embodiments the disease is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV, lupus, colon cancer or papillary thyroid carcinoma. In certain embodiments of such methods, the disease or condition is condition is papillary thyroid carcinoma, pancreatic cancer, colon cancer, breast carcinoma, neuroblastoma pain, cachexia, dermatitis or asthma.

Another aspect provided herein are methods for treating a cell-proliferative condition, comprising administering to a system or subject in need of such treatment an effective amount of a compound of Formula (I), or pharmaceutically acceptable salts or pharmaceutical compositions thereof; wherein the cell-proliferative condition is lymphoma, metastasis, anaplastic large-cell lymphoma, osteosarcoma, fibrosarcoma, melanoma, breast cancer, renal cancer, brain cancer, prostate cancer, colorectal cancer, thyroid cancer, papillary thyroid carcinoma, ovarian cancer, pancreatic cancer, neuronal cancer, neuroblastoma, lung cancer, uterine cancer or gastrointestinal cancer. In certain embodiments of such methods, the cell-proliferative condition is anaplastic large-cell lymphoma, pancreatic cancer, ovarian cancer and lung cancer.

Another aspect provided herein are compounds for use in a method of medical treatment, wherein the method of medical treatment is for treating a disease selected from cancer, pain, cachexia, anorexia nervosa, a proliferative diseases, a pain disorder, a dermatological disease, a metabolic disease, a muscle disease, a neurodegenerative disease, a neurological disease, an immunodeficiency disease, an immunologically-mediated disease, an autoimmune disease, an autoimmune mediated disease, a bone disease, an inflammatory disease, fibrosis, an ophthalmic disease, an infectious disease, a viral disease, wound repair, a respiratory disease, a pulmonary disease, a renal disease, a kidney disease, a liver disease, a cardiovascular disease, a vascular disease, heart disease, cell death and hyperplasiaan inflammatory disease, and wherein the compound is a compound of Formula (I). In certain embodiments the disease is asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, multiple sclerosis, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, HIV, lupus, colon cancer or papillary thyroid carcinoma. In certain embodiments the disease or condition is condition is papillary thyroid carcinoma, pancreatic cancer, colon cancer, breast carcinoma, neuroblastoma pain, cachexia, dermatitis or asthma.

Another aspect provided herein is a method of treating anorexia nervosa, comprising administering to a system or subject in need of such treatment an effective amount of a compound of Formula (I), or pharmaceutically acceptable salts or pharmaceutical compositions thereof.

DETAILED DESCRIPTION OF THE INVENTION

Definitions

The terms "alkenyl" and "alkene," as used herein, refers to a partially unsaturated branched or straight chain hydrocarbon having at least one carbon-carbon double bond. Atoms oriented about the double bond are in either the cis (Z) or trans (E) conformation. An alkenyl or alkene group can be optionally substituted. As used herein, the terms "$C_2$-$C_3$alkyenyl", "$C_2$-$C_4$alkyenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. Non-limiting examples of alkenyl groups, as used herein, include ethenyl, propenyl, butenyl, pentenyl, hexenyl, heptenyl, octenyl, nonenyl, decenyl and the like. As used herein, the terms "$C_2$-$C_3$alkene", "$C_2$-$C_4$alkene", "$C_2$-$C_5$alkene", "$C_2$-$C_6$alkene", "$C_2$-$C_7$alkene", and "$C_2$-$C_8$alkene" refer to an alkene group containing at least 2, and at most 3, 4, 5, 6, 7 or 8 carbon atoms, respectively. Non-limiting examples of alkene groups, as used herein, include ethene, propene, butene, pentene, hexene, heptene, octene, nonene, decene and the like.

The term "alkenylene," as used herein, refers to a partially unsaturated branched or straight chain divalent hydrocarbon radical derived from an alkenyl group. An alkenylene group can be optionally substituted. As used herein, the terms "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. An alkyl group can be optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. An alkylene group can be optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "aryl," as used herein, refers to monocyclic or fused bicyclic ring systems having a total of six, ten or fourteen carbon atom ring members. An aryl group can be optionally substituted with one or more substituents. Non-limiting examples of aryl groups, as used herein, include phenyl and naphthyl.

The term "arylene," as used means a divalent radical derived from an aryl group. An arylene group can be optionally substituted.

The term "cyano," as used herein, refers to a —CN group.

The term "cycloalkyl," as used herein, refers to a saturated monocyclic ring system or a saturated fused bicyclic ring system. As used herein, the terms "$C_3$-$C_5$ cycloalkyl", "$C_3$-$C_6$ cycloalkyl" and "$C_3$-$C_7$ cycloalkyl" refer to a cycloalkyl group wherein the saturated ring system contains at least 3, and at most 5, 6 or 7 carbon atoms. A cycloalkyl group can be optionally substituted. Non-limiting examples of cycloalkyl groups, as used herein, include cyclopropyl, cyclobutyl, cyclopentyl, cyclohexyl and cycloheptyl.

The terms "halo" or "halogen," as used herein, refers to fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different. By way of example ony, trifluoromethyl, pentafluoroethyl, and the like.

The term "heteroaryl," as used herein, refers to monocyclic or fused bicyclic ring systems having a total of 5, 6, 9 or 10 ring members, wherein at least one ring member is a heteroatom selected from nitrogen, oxygen and sulfur. A heteroaryl group can be optionally substituted with one or more substituents. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[b]furyl, benzo[b]thienyl, cinnolinyl, furazanyl, furyl, imidazolyl, indolyl, indolizinyl, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, thiazolyl, thiadiazolyl, thienyl, triazinyl, triazolyl and tetrazolyl.

The term "heteroarylene," as used means a divalent radical derived from a heteroaryl group. A heteroarylene group can be optionally substituted.

The term "heterocycloalkyl," as used herein, refers to a cycloalkyl, as defined herein, wherein one or more of the ring carbons are replaced by a moiety selected from —O—, —N═, —NR—, —C(O)—, —S—, —S(O)— or —S(O)2-, wherein R is hydrogen, $C_1$-$C_4$alkyl or a nitrogen protecting group. A heterocycloalkyl group can be optionally substituted. Non-limiting examples of heterocycloalkyl groups, as used herein, include morpholino, pyrrolidinyl, pyrrolidinyl-2-one, piperazinyl, piperazinyl-2-one, piperidinyl, piperidinylone, 1,3-dioxolanyl, imidazolidinyl, pyrazolidinyl, 1,4-dioxanyl, 1,4-dithianyl, thiomorpholinyl, azepanyl, hexahydro-1,4-diazepinyl, tetrahydrofuranyl, tetrahydrothienyl, tetrahydropyranyl, tetrahydrothiopyranyl, thioxanyl, azetidinyl, oxetanyl, thietanyl, oxepanyl, thiepanyl, dioxanyl, 1,3-dioxolanyl, dithianyl, dithiolanyl, imidazolidinyl, 3-azabicyclo[3.1.0]hexanyl, 2,5-diazabicyclo[2.2.1]heptane and 3-azabicyclo[4.1.0]heptanyl.

The term "heteroatom," as used herein, refers to an oxygen atom, sulfur atom, or nitrogen atom.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents, where proper valency is maintained, include, halo, —CN, ═O, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$, —NRS(O)$_2$, —NHS(O)$_2$R, —NRS(O)$_2$R, $C_1$-$C_8$alkyl, $C_1$-$C_8$alkoxy, aryl, heteroaryl, cycloalkyl, heterocycloalkyl, halo-substituted $C_1$-$C_8$alkyl, halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substitutent groups is done in accordance with the well-understood valence limitations of each group, for example ═O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound of the invention and prodrugs thereof to a subject in need of treatment.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, dermatitis, bullous disorders, collagenoses, contact dermatitis, eczema, Kawasaki Disease, rosacea, Sjogren-Larsso Syndrome, and urticaria.

The term "diluent" as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic", as used herein, means a condition, disorder, or disease created or worsened by medical or surgical therapy.

The term "inflammatory disorders", as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract (Disease,); skin (dermatitis); or multiple organs and tissues (systemic lupus erythematosus).

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system (brain and spinal cord).

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt", as used herein, refers to a formulation of a compound that does not cause significant irritation to an organism to which it is administered and does not abrogate the biological activity and properties of the compounds described herein.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a coagent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The term "pharmaceutical composition", as used herein, refers to a mixture of a compound described herein with other chemical components, such as carriers, stabilizers, diluents, dispersing agents, suspending agents, thickening agents, and/or excipients.

The term "prodrug", as used herein, refers to an agent that is converted into the parent drug in vivo. Prodrugs are often useful because, in some situations, they may be easier to administer than the parent drug. Prodrugs are bioavailable by oral administration whereas the parent is not. Prodrugs improve solubility in pharmaceutical compositions over the parent drug. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient", as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

The term "therapeutically effective amount", as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat", "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The terms "use" or "used," as used herein, are intended to include a compound of Formula (I) provided herein for use in the prophylactic and/or therapeutic treatment of one or more diseases provided herein, a method of use or a method of treatment comprising administering a compound of the Formula (I) to a person in need of such treatment in an effective amount for the prophylactic and/or therapeutic treatment of one or more diseases provided herein, the preparation or a method or preparation of a pharmaceutical formulation/preparation for use in the prophylactic and therapeutic treatment of one or more diseases provided herein, especially involving mixing a compound of the Formula (I) (as therapeutically active ingredient) with at least one pharma-ceutically acceptable carrier material, including making it ready for use in such treatment (e.g. adding an instruction insert (e.g. package leaflet or the like), formulation, appropriate preparation, adaptation for specific uses, customizing and the like), and the use of a compound of the Formula (I) for such preparation, and/or all other prophylactic or therapeutic uses mentioned herein.

Other objects, features and advantages of the methods and compositions described herein will become apparent from the following detailed description. It should be understood, however, that the detailed description and the specific examples, while indicating specific embodiments, are given by way of illustration only.

Compounds

Provided herein are compounds, pharmaceutically acceptable salts, solvates, N-oxides, prodrugs and isomers thereof, which are inhibitrs of TRKA, TRKB and TRKC kinase activity. Also provided herein are compounds, pharmaceutically acceptable salts, solvates, N-oxides, prodrugs and isomers thereof, pharmaceutical compositions, pharmaceutical combinations for the treatment diseases or conditions/disorders associated with TRKA, TRKB and TRKC kinase activity. Also provided herein are methods of treaing diseases or conditions/disorders associated with TRKA, TRKB and TRKC kinase activity, wherein the method includes administration of a therapeutically effective amount of a compound provided herein, pharmaceutically acceptable salts, solvates, N-oxides, prodrugs and isomers thereof, and pharmaceutical compositions containing such pharmaceutically acceptable salts, solvates, N-oxides, prodrugs and isomers thereof.

In certain embodiments, such diseases and/or disorders include, but are not limited to, cancer, proliferative diseases, pain, dermatological diseases and/or disorders, metabolic diseases and/or disorders, muscle diseases and/or disorders, neurodegenerative diseases and/or disorders, neurological diseases and/or disorders, inflammatory diseases, fibrosis, infectious diseases, respiratory diseases and/or disorders, pulmonary diseases and/or disorders and hyperplasia.

Such cancer and proliferative diseases include, but are not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes.

Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Such pain disorders include, but are not limited to, cancer-related pain, skeletal pain caused by tumor metastasis, osteoarthritis, visceral pain, inflammatory pain and neurogenic pain.

Such dermatological diseases and/or disorders include, but are not limited to, inflammatory or allergic conditions of the skin, dermatitis, eczema, psoriasis, dermatitis, atopic dermatitis, seborrhoeic dermatitis (Dandruff, Cradle cap), diaper rash, urushiol-induced contact dermatitis, contact dermatitis, erythroderma, lichen simplex chronicus, prurigo nodularis, itch, pruritus ani, nummular dermatitis, dyshidrosis, pityriasis alba, alopecia greata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, peritoneal and sub dermal adhesion and photoaging of the skin.

Such metabolic diseases and/or disorders and eating disorder include, but are not limited to, obesity, diabetes and anorexia.

Such muscle diseases and/or disorders include, but are not limited to, muscular atrophies (e.g. disuse), muscular dystrophies (e.g. Duchenne's muscle dystrophy, Becker's muscle dystrophy, Limb-Girdle muscle dystrophy), sarcopenia, cachexia, wasting and Facioscapulohumeral dystrophy.

Such neurological diseases and/or disorders and neurodegenerative disorders include, but are not limited to, impaired neurological function and Alzheimer's disease.

Such inflammatory diseases and/or disorders include, but are not limited to, uveitis, atherosclerosis, atherogenesis, glomerulonephritis, Kawasaki disease, inflammatory responses, polymyositis, arthritis, neurological inflammation, chronic arthritis inflammation and osteoarthritis.

Such fibrosis diseases and/or disorders include, but are not limited to, extracellular matrix accumulation and fibrosis, scleroderma, fibrosclerosis, radiation-induced fibrosis, kidney fibrosis, lung fibrosis and liver fibrosis, haemochromatosis, primary biliary cirrhosis, restenosis, retroperitoneal fibrosis, mesenteric fibrosis, endometriosis and keloids.

Such ophthalmic/ocular diseases and/or disorders include, but are not limited to, proliferative vitreoretinopathy, ocular scarring, corneal scarring, ocular disorders, corneal wounds, conjunctivitis, keratoconjunctivitis sicca, and vernal conjunctivitis.

Such infectious diseases and/or disorders include, but are not limited to, Chagas disease.

Such respiratory diseases and/or disorders and pulmonary disorders include, but are not limited to, asthma, bronchial asthma, allergic asthma, intrinsic (non-allergic) asthma, extrinsic (allergic) asthma, exercise-induced asthma, drug-induced asthma (including aspirin and NSAID-induced) and dust-induced asthma, chronic obstructive pulmonary disease (COPD); chronic obstructive airways disease (COAD), chronic obstructive lung disease (COLD), bronchitis, chronic bronchitis, acute bronchitis, dyspnea, arachidic bronchitis, catarrhal bronchitis, croupus bronchitis, phthinoid bronchitis, rhinitis, acute rhinitis, chronic rhinitis, rhinitis medicamentosa, vasomotor rhinitis, perennial and seasonal allergic rhinitis, rhinitis nervosa (hay fever), inflammatory or obstructive airways diseases, pulmonary hypertension, acute lung injury, adult/acute respiratory distress syndrome (ARDS), pulmonary fibrosis, idiopathic pulmonary fibrosis, chronic obstructive pulmonary disease, pulmonary disease due to infectious or toxic agents, emphysema, pneumoconiosis, aluminosis, anthracosis, asbestosis, chalicosis, ptilosis, siderosis, silicosis, tabacosis, byssinosis, acute lung injury (ALI), hypereosinophilia, Löffler's syndrome, eosinophilic pneumonia, parasitic (in particular metazoan) infestation (including tropical eosinophilia), bron-chopulmonary aspergillosis, polyarteritis nodosa (including Churg-Strauss syndrome), eosinophilic granuloma, eosinophil-related disorders affecting the airways occasioned by drug-reaction, pulmonary hypertension, primary pulmonary hypertension (PPH), secondary pulmonary hypertension (SPH), familial PPH, sporadic PPH, pre-capillary pulmonary hypertension, pulmonary arterial hypertension (PAH), pulmonary artery hypertension, idiopathic pulmonary hypertension, thrombotic pulmonary arteriopathy (TPA), plexogenic pulmonary arteriopathy, functional classes I to IV pulmonary hypertension, and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, hypoxemia, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

The aforementioned compounds and pharmaceutically acceptable salts, solvates, N-oxides, prodrugs and isomers thereof, are compounds having structures according to Formula (I):

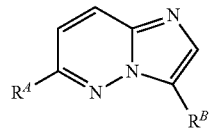

Formula (I)

wherein $R^A$ and $R^B$ are as defined herein.

In certain embodiments of the aforementioned compounds and pharmaceutically acceptable salts, solvates, N-oxides, prodrugs and isomers thereof, having structures according to Formula (I) are compounds having the structure of Formula (I-a):

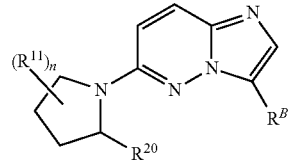

Formula (I-a)

wherein n, $R^{11}$, $R^{20}$ and $R^B$ are as defined herein.

In certain embodiments of the aforementioned compounds and pharmaceutically acceptable salts, solvates, N-oxides, prodrugs and isomers thereof, having structures according to Formula (I) are compounds having the structure of Formula (II-a):

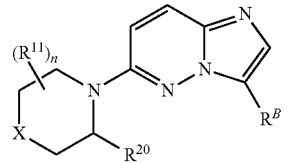

Formula (II-a)

wherein n, X, $R^{11}$, $R^{20}$ and $R^B$ are as defined herein.

In certain embodiments of the aforementioned compounds and pharmaceutically acceptable salts, solvates, N-oxides, prodrugs and isomers thereof, having structures according to Formula (I) are compounds having the structure of Formula (III-a):

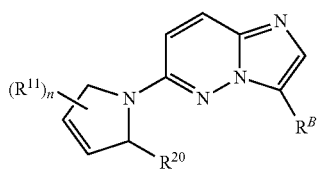

Formula (III-a)

wherein n, $R^{11}$, $R^{20}$ and $R^B$ are as defined herein.

In certain embodiments of the aforementioned compounds and pharmaceutically acceptable salts, solvates, N-oxides, prodrugs and isomers thereof, having structures according to Formula (I) are compounds having the structure of Formula (I-b):

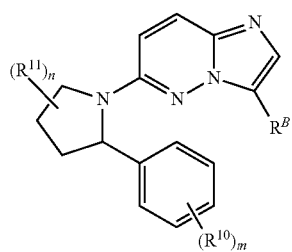

Formula (I-b)

wherein n, m, $R^{11}$, $R^{10}$ and $R^B$ are as defined herein.

In certain embodiments of the aforementioned compounds and pharmaceutically acceptable salts, solvates, N-oxides, prodrugs and isomers thereof, having structures according to Formula (I) are compounds having the structure of Formula (II-b):

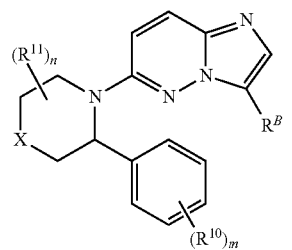

Formula (II-b)

wherein n, m, X, $R^{11}$, $R^{10}$ and $R^B$ are as defined herein.

In certain embodiments of the aforementioned compounds and pharmaceutically acceptable salts, solvates, N-oxides, prodrugs and isomers thereof, having structures according to Formula (I) are compounds having the structure of Formula (III-b):

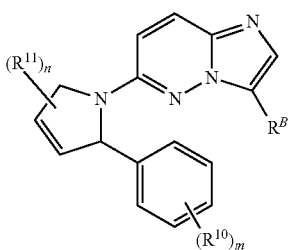

Formula (III-b)

wherein n, m, $R^{11}$, $R^{10}$ and $R^B$ are as defined herein.

The compounds, pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents. Isotopic variations of the compounds have the potential to change a compound's metabolic fate and/or create small changes in physical properties such as hydrophobicity, and the like. Isotopic variation have the potential to enhance efficacy and safety, enhance bioavailability and half-life, alter protein binding, change biodistribution, increase the proportion of active metabolites and/or decrease the formation of reactive or toxic metabolites.

Processes for Making Compounds of Formula (I)

General procedures for preparing compounds of Formula (I) are described in the Examples, infra. In the reactions described, reactive functional groups, for example hydroxyl, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) described herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) described herein is prepared by reacting the free acid form of the compound of Formula (I) with a pharmaceutically acceptable organic base or inorganic base. Alternatively, the salt forms of the compounds of Formula (I) described herein are prepared using salts of the starting materials or intermediates. In certain embodiments, the compounds of Formula (I) described herein are in the form of other salts including, but not limited to, oxalates and trifluoroacetates. In certain embodiments, hemisalts of acids and bases are formed, for example, hemisulphate and hemicalcium salts.

The pharmaceutically acceptable organic acid or inorganic acids used to form pharmaceutically acceptable acid addition salts of compounds of Formula (I) include, but are not limited to, hydrofluoric acid, hydrochloric acid, hydrobromic acid, hydroiodic acid, nitric acid, sulfuric acid, phosphoric acid, formic acid, acetic acid, trifluoroacetic acid, propionic acid, butyric acid, caprylic acid, dichloroacetic acid, hippuric acid, lactic acid, citric acid, tartaric acid, malic acid, gluconic acid, mandelic acid, maleic acid, succinic acid, adipic acid, aspartic acid, fumaric acid, glutamic acid, malonic acid, sebacic acid, salicylic acid, hexanoic acid, benzoic acid, p-chlorobenzoic acid, nicotinic acid, diphenylacetic acid, triphenylacetic acid, o-hydroxybenzoic acid, p-hydroxybenzoic acid, 1-hydroxynaphthalene-2-carboxylic acid or 3-hydroxynaphthalene-2-carboxylic acid, sulfonic acids, methanesulfonic acid, benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid and p-toluenesulfonic acid. Pharmaceutically acceptable solvates are generally hydrates.

Such pharmaceutically acceptable acid addition salts of compounds of Formula (I) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, orotate, oxalate, palmitate, pamoate, phosphate/hydrogen phosphate/dihydrogen phosphate, pyroglutamate, saccharate, stearate, tannate, tosylate, trifluoroacetate and xinofoate salts.

Such pharmaceutically acceptable base addition salt of a compound of Formula (I) include, but are not limited to, aluminium, ammonium, arginine, benzathine, calcium, choline, diethylamine, diolamine, glycine, lysine, magnesium, meglumine, olamine, potassium, sodium, tromethamine, ethanolamines, benzylamines, pyridine, benethamine, diethanolamine, 4-(2-hydroxy-ethyl)morpholine, 1-(2-hydroxyethyl)pyrrolidine, N-methyl glutamine, piperazine, triethanol-amine and zinc salts.

In certain embodiments, the free acid or free base forms of the compounds of Formula (I) described herein are prepared from the corresponding base addition salt or acid addition salt from, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

In certain embodiments, the compounds of Formula (I) described herein in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, prodrug derivatives of compounds Formula (I) described herein are prepared using methods known to those of ordinary skill in the art (e.g., for further details see Saulnier et al., (1994), Bioorganic and Medicinal Chemistry Letters, Vol. 4, p. 1985). For example, appropriate prodrugs are prepared by reacting a non-derivatized compound of Formula (I) with a suitable carbamylating agent (by way of example only, 1,1-acyloxyalkylcarbanochloridate, para-nitrophenyl carbonate, or the like).

In certain embodiments, the compounds of Formula (I) described herein are prepared as protected derivatives using methods known to those of ordinary skill in the art. A detailed description of the techniques applicable to the creation of protecting groups and their removal can be found in T. W. Greene, "Protecting Groups in Organic Chemistry," 3$^{rd}$ edition, John Wiley and Sons, Inc., 1999.

In certain embodiments, the compounds of Formula (I) described herein are prepared or formed, as solvates (e.g., hydrates). In certain embodiments, hydrates of compounds of Formula (I) are prepared by recrystallization from an aqueous/organic solvent mixture, using organic solvents such as dioxin, tetrahydrofuran or methanol.

In certain embodiments, the compounds of Formula (I) provided herein are prepared as a racemic mixture. In certain embodiments, the compounds of Formula (I) described herein are prepared as their individual stereoisomers. In certain embodiments, the compounds of Formula (I) provided herein are prepared as a racemic mixture and their individual stereoisomers are aobtained using chiral chromatography, including, but not limited to, chiral liquid chromatogtaphy. In other embodiments, the compounds of Formula (I) described herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are provided in substantially pure form. In certain embodiments compounds of Formula (I) are at least 60% pure. In certain embodiments compounds of Formula (I) are at least 75% pure. In certain embodiments compounds of Formula (I) are at 85% pure. In certain embodiments compounds of Formula (I) are at least 98% pure (% are on a weight for weight basis).

Compounds of Formula (I) are made by processes described herein and as illustrated in the Examples. Non-limiting examples of synthetic schemes used to make compounds of Formula (I) described herein are illustrated in reaction schemes (I)-(XXII), wherein n, m, p, q, X, $L^1$, $L^2$, $L^3$, $R^A$, $R^B$, $R^2$, $R^3$, $R^4$, $R^5$, $R^6$, $R^7$, $R^8$, $R^9$, $R^{10}$, $R^{11}$, $R^{12}$ and $R^{20}$ are as defined herein.

Reaction Scheme (I)

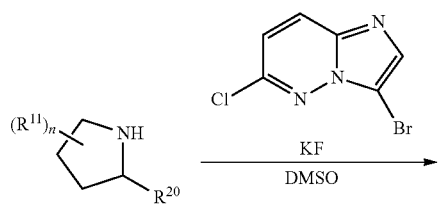

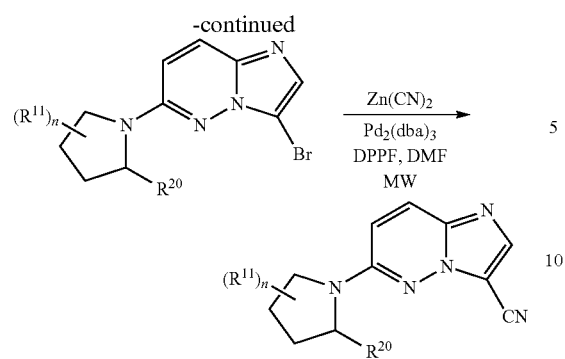
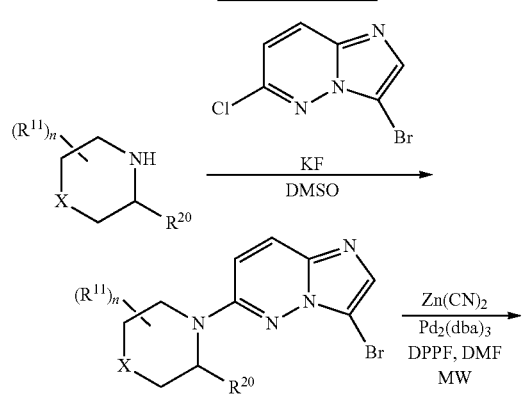
Reaction Scheme (II)
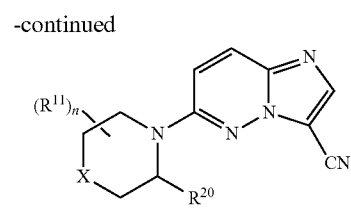
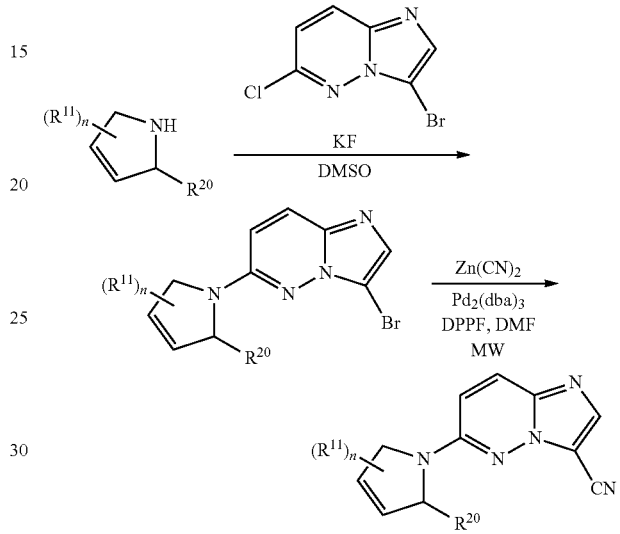
Reaction Scheme (III)
Reaction Scheme (IV)
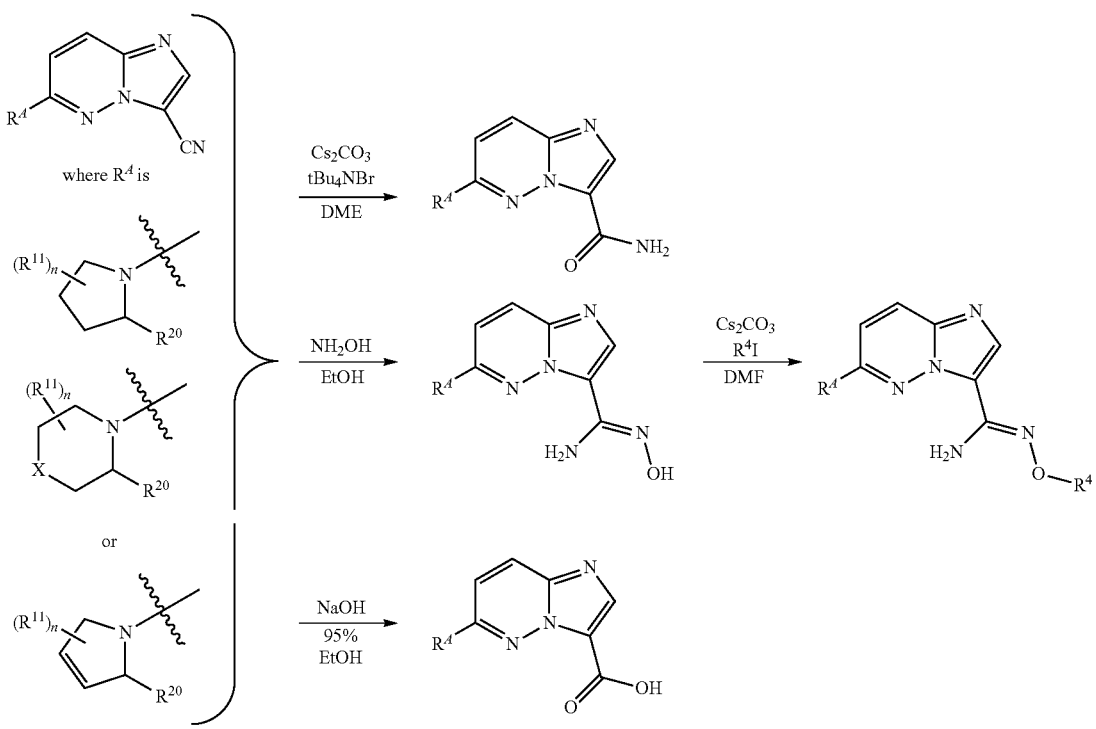

Reaction Scheme (V)
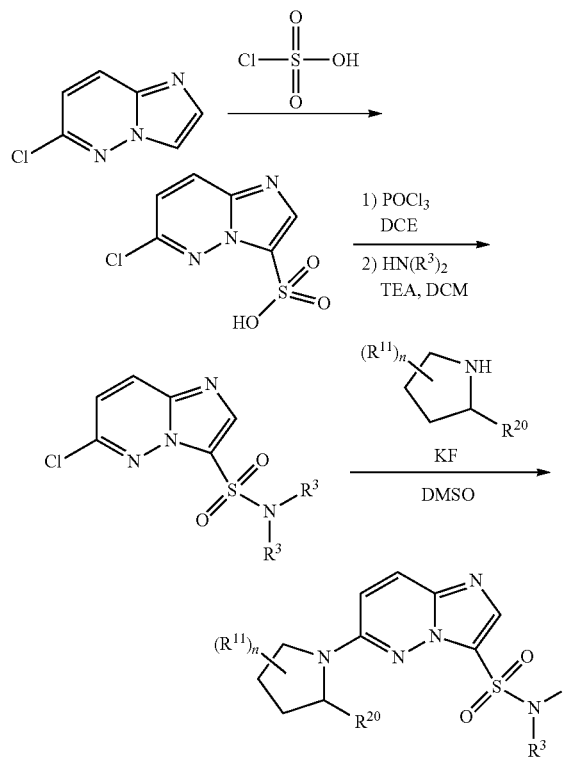
Reaction Scheme (VI)
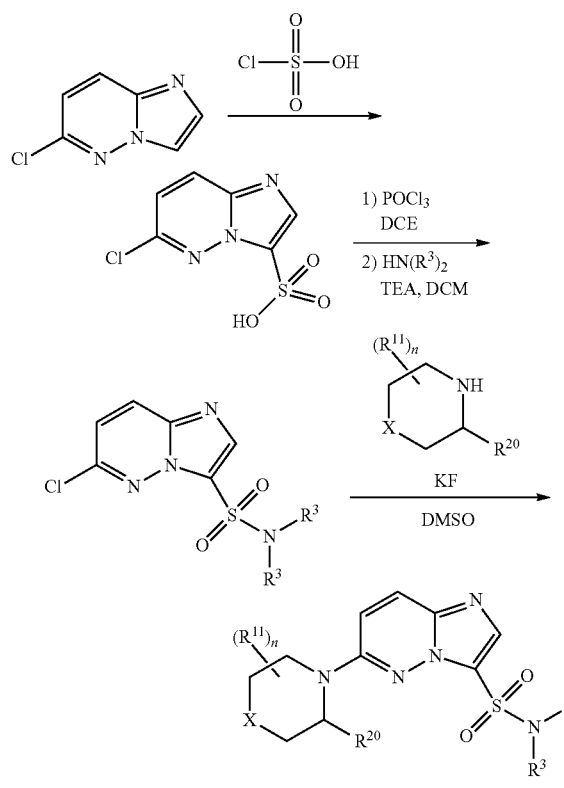
Reaction Scheme (VII)
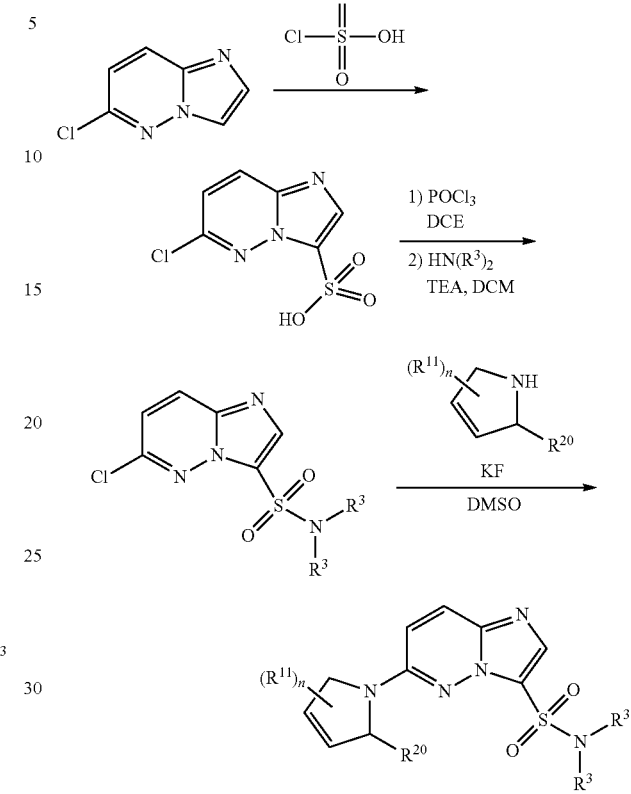
Reaction Scheme (VIII)
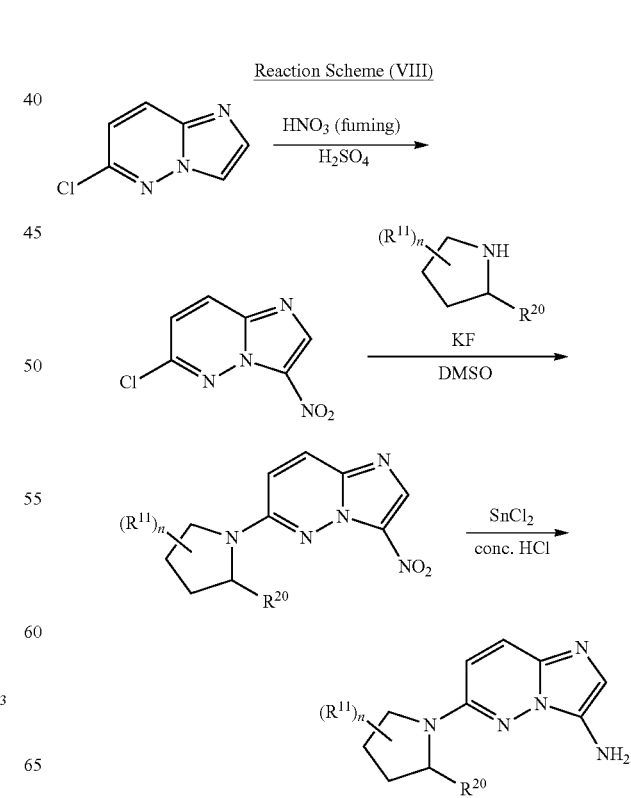

Reaction Scheme (IX)
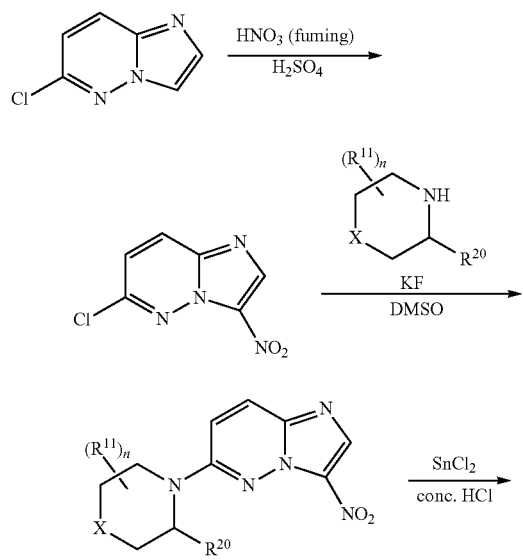
Reaction Scheme (XI)
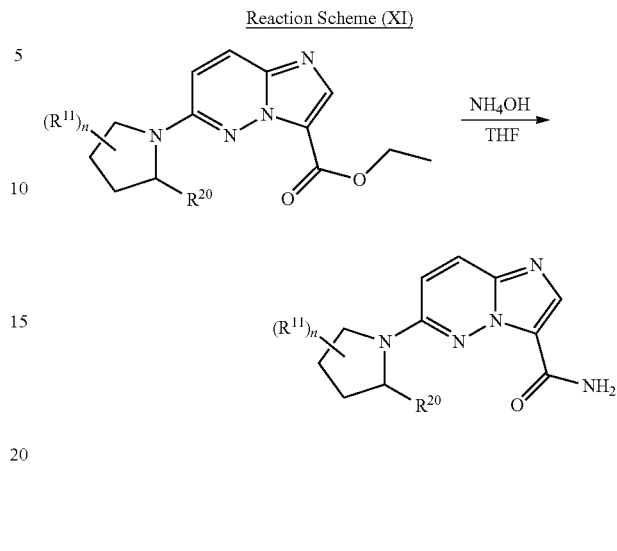
Reaction Scheme (XII)
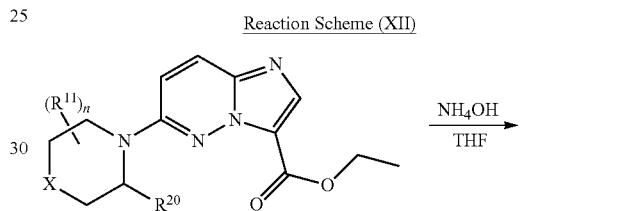
Reaction Scheme (X)
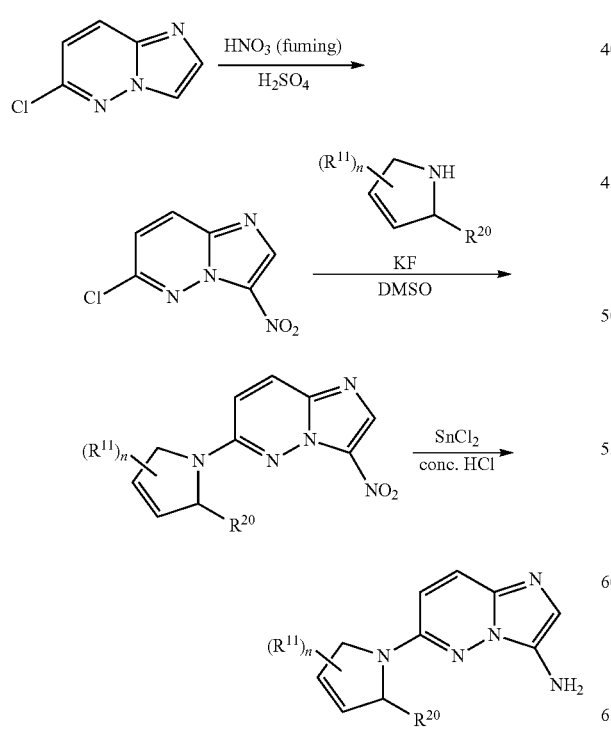
Reaction Scheme (XIII)
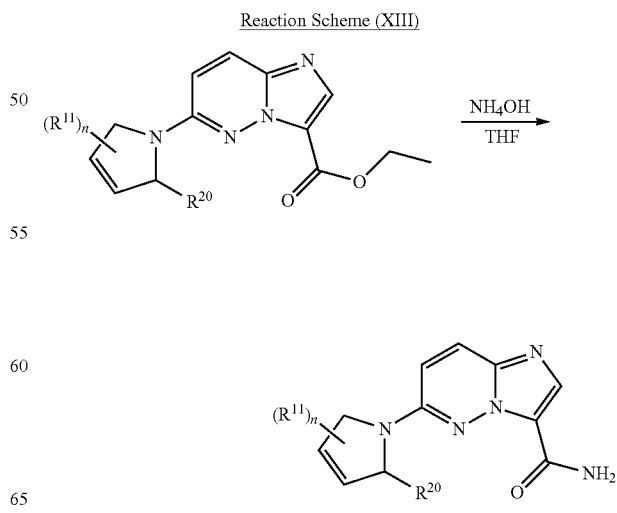

Reaction Scheme (XIV)
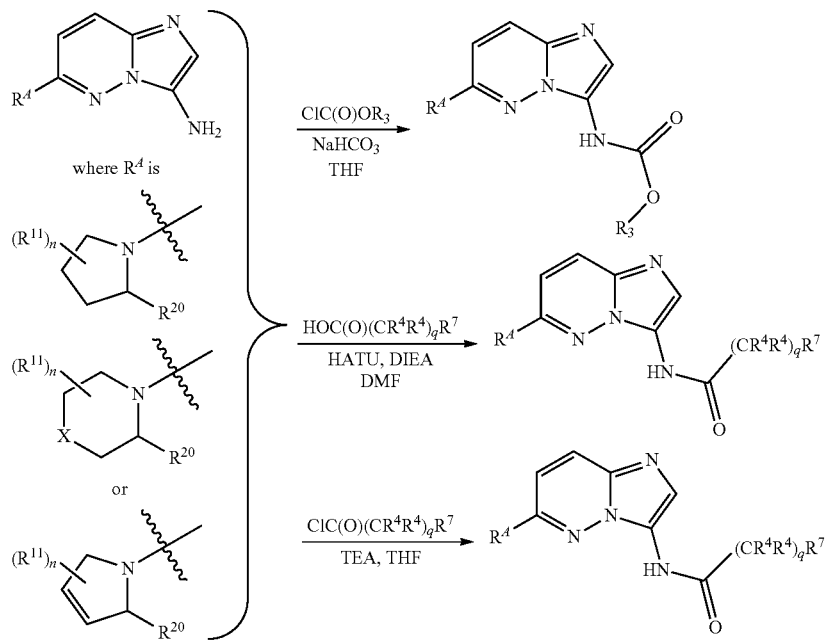
Reaction Scheme (XV)
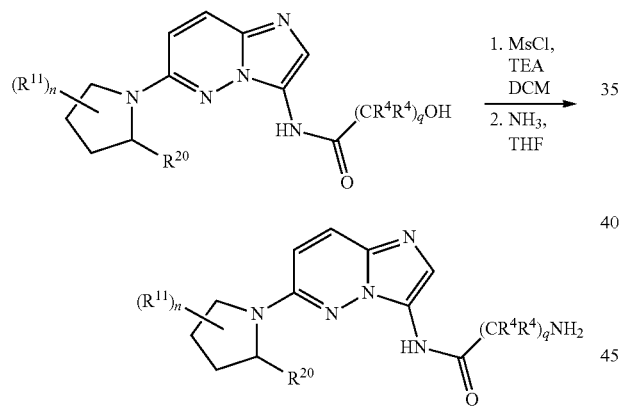
Reaction Scheme (XVII)
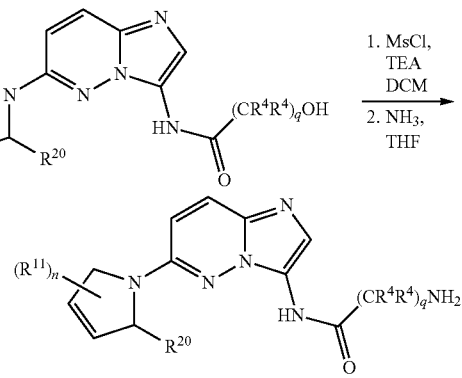
Reaction Scheme (XVI)
Reaction Scheme (XVIII)
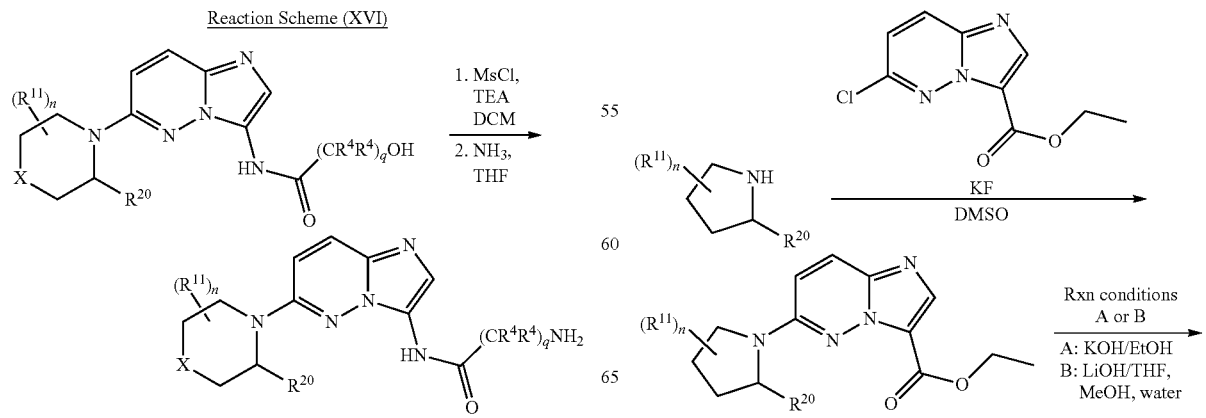

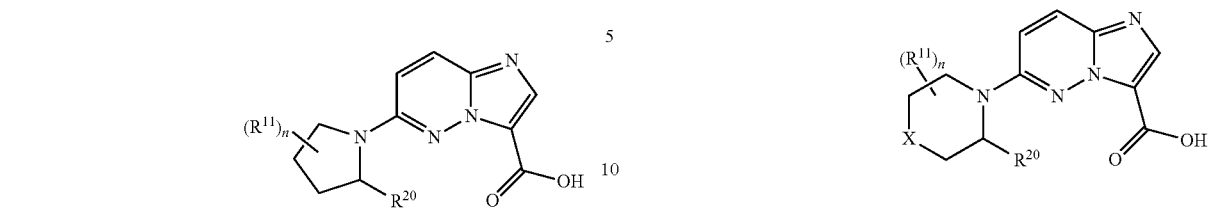
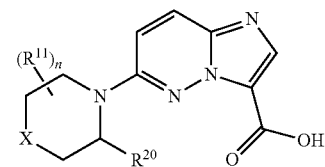
Reaction Scheme (XIX)
Reaction Scheme (XX)
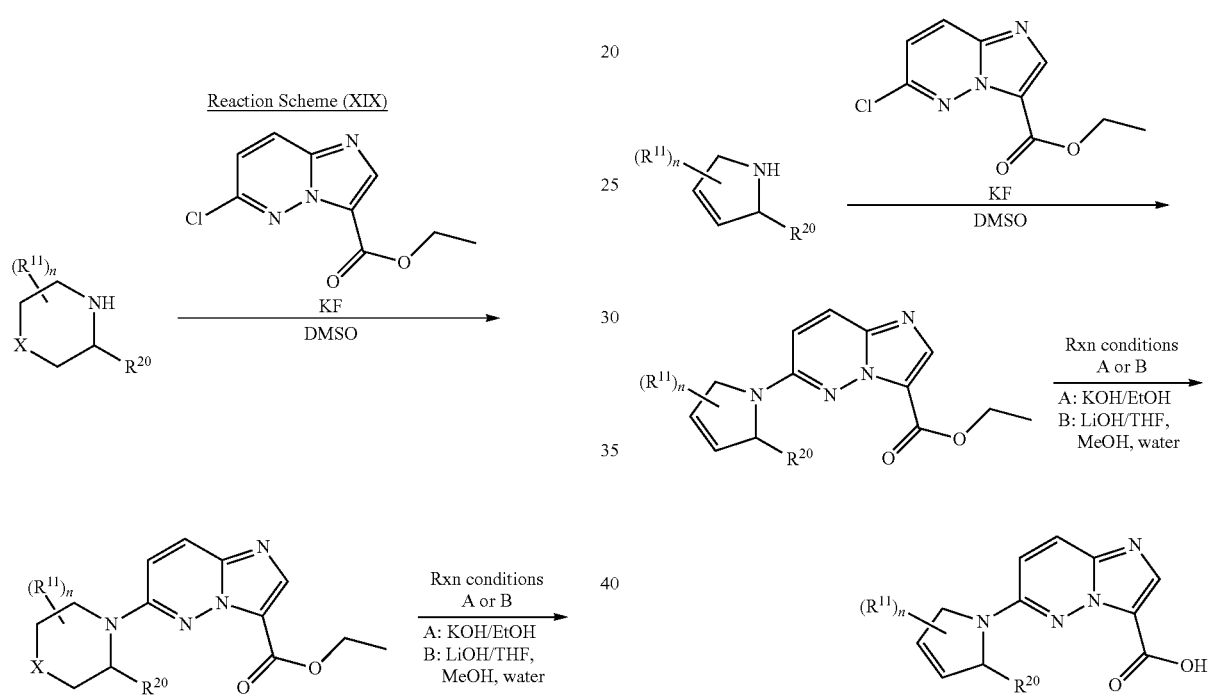
Reaction Scheme (XXI)
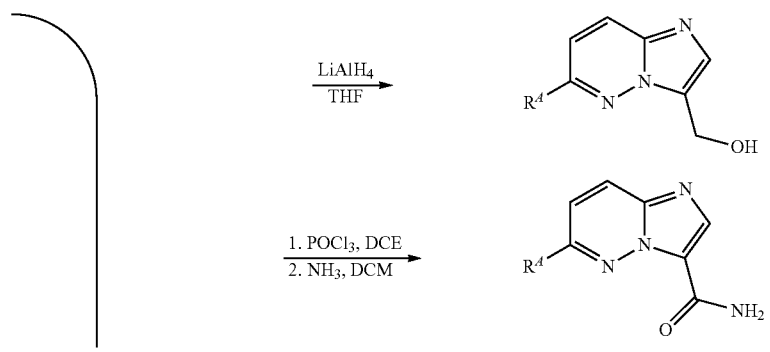

-continued
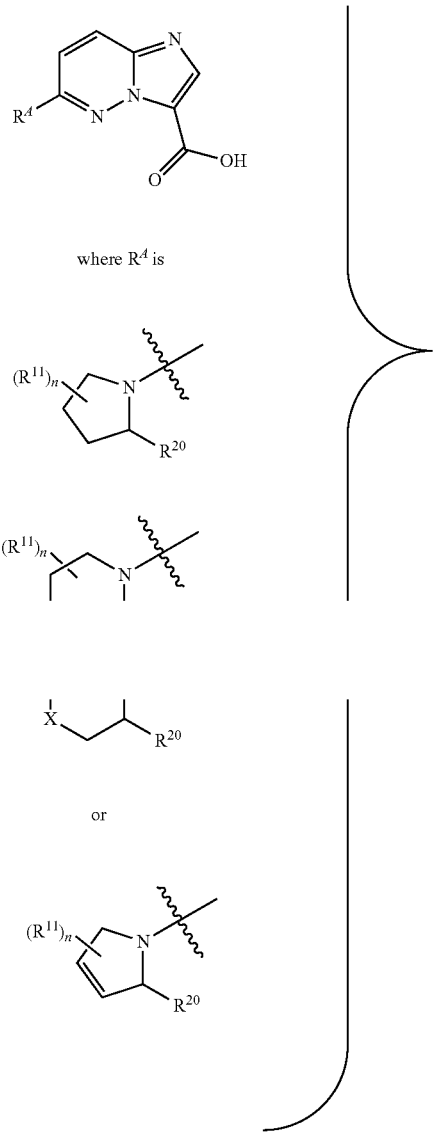
where R^A is
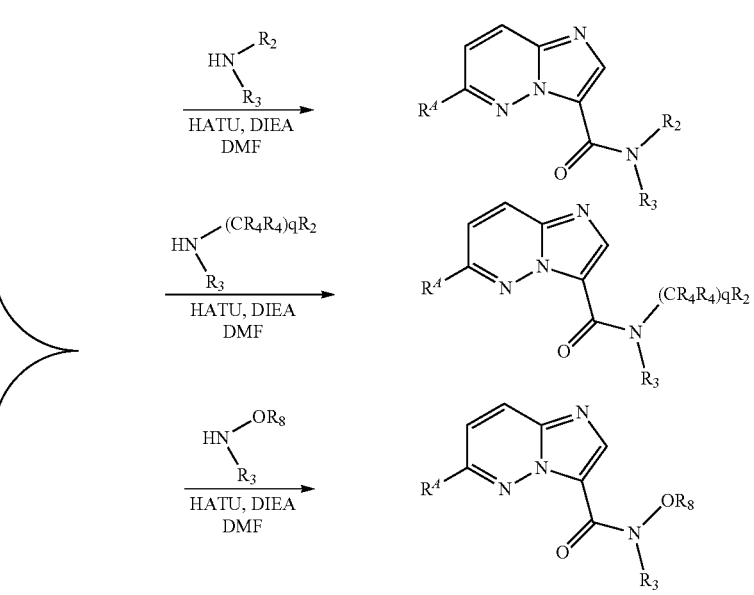
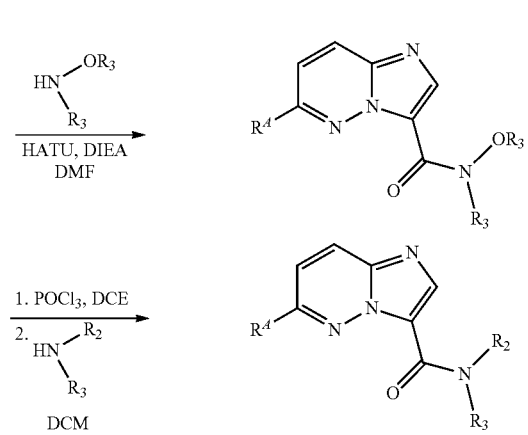

Reaction Scheme (XXII)
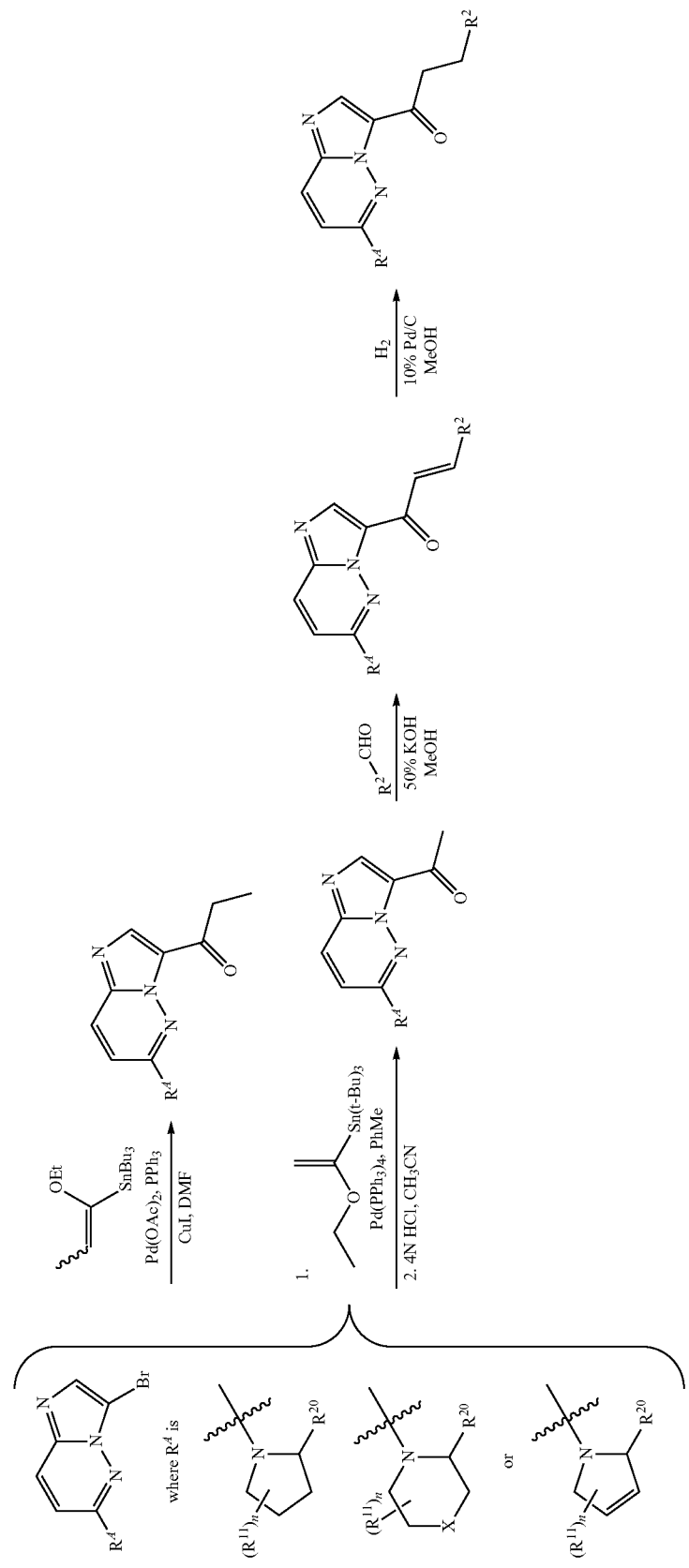

Non-limiting synthesis of the intermediates

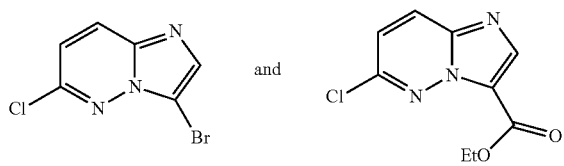 [SMILES: Clc1ccc2ncc(Br)n2n1 ; CCOC(=O)c1cnc2ccc(Cl)nn12]

are given in the example section below.

Pharmacology and Utility

Protein kinases (PTK) play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone-related diseases.

Examples of protein-tyrosine kinases include, but are not limited to, (a) tyrosine kinases such as Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB-4), FAK, FGF1R (also FGFR1 or FGR-1), FGF2R (also FGR-2), MET (also Met-I or c-MET), PDGFR (α and β), Tie-1, Tie-2 (also Tek-1 or Tek), VEGFR1 (also FLT-1), c-FMS, VEGFR2 (also KDR), FLT-3, FLT-4, c-KIT, JAK1, JAK2, JAK3, TYK2, LOK, RET, Ros, TRKA, TRKB, TRKC, PYK2, ALK (Anaplastic Lymphoma Kinase), EPHA (1-8), EPHB (1-6), RON, Fes, Fer or EPHB4 (also EPHB4-1), and (b) and serine/threonine kinases such as Aurora, c-RAF, SGK, MAP kinases (e.g., MKK4, MKK6, etc.), SAPK2α, SAPK2β, Ark, ATM (1-3), CamK (1-IV), CamKK, Chk1 and 2 (Checkpoint kinases), CKI, CK2, Erk, IKK-I (also IKK-ALPHA or CHUK), IKK-2 (also IKK-BETA), Ilk, Jnk (1-3), LimK (1 and 2), MLK3Raf (A, B and C), CDK (1-10), PKC (including all PKC subtypes), Plk (1-3), NIK, Pak (1-3), PDK1, PKR, RhoK, RIP, RIP-2, GSK3 (α and β), PKA, P38, Erk (1-3), PKB (including all PKB subtypes) (also AKT-1, AKT-2, AKT-3 or AKT3-1), IRAK1, FRK, SGK, TAK1 and Tp1-2 (also COT).

Phosphorylation modulates or regulates a variety of cellular processes such as proliferation, growth, differentiation, metabolism, apoptosis, motility, transcription, translation and other signaling processes. Aberrant or excessive PTK activity has been observed in many disease states including, but not limited to, benign and malignant proliferative disorders, diseases resulting from inappropriate activation of the immune system and diseases resulting from inappropriate activation of the nervous systems. Specific diseases and disease conditions include, but are not limited to, autoimmune disorders, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, obesity, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, rheumatoid arthritis, atherosclerosis, restenosis, auto-immune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

Tyrosine kinases can be broadly classified as receptor-type (having extracellular, transmembrane and intracellular domains) or the non-receptor type (being wholly intracellular) protein tyrosine kinases. Inappropriate or uncontrolled activation of many of these kinase (aberrant protein tyrosine kinase activity), for example by over-expression or mutation, results in uncontrolled cell growth. Many of the protein tyrosine kinases, whether a receptor or non-receptor tyrosine kinase have been found to be involved in cellular signaling pathways involved in numerous pathogenic conditions, including, but not limited to, immunomodulation, inflammation, or proliferative disorders such as cancer.

Compounds of the invention are inhibitors TrkA, TrkB and TrkC, and as such the compounds and pharmaceutical compositions provided herein are useful for treating diseases or disorders in which such kinases contribute to the pathology and/or symptomology of a disease or disorder associated with such kinases. Such diseases or disorders include, but are not limited to, cancer, pain, cachexia, anorexia nervosa, a proliferative diseases, a pain disorder, a dermatological disease, a metabolic disease, a muscle disease, neurodegenerative diseases and/or disorders, neurological diseases and/or disorders, an inflammatory disease, fibrosis, an infectious disease, a respiratory disease, a pulmonary disease and hyperplasiaan inflammatory disease, and wherein the compound is a compound of Formula (I). In certain embodiments the disease is asthma, chronic obstructive pulmonary disease (COPD), adult respiratory distress syndrome (ARDS), bronchitis, dermatitis, allergic rhinitis, psoriasis, scleroderma, lymphoma, metastasis, anaplastic large-cell lymphoma, osteosarcoma, fibrosarcoma, melanoma, breast cancer, renal cancer, brain cancer, prostate cancer, colorectal cancer, thyroid cancer, ovarian cancer, pancreatic cancer, neuronal cancer, neuroblastoma, lung cancer, uterine cancer, gastrointestinal cancer, colon cancer or papillary thyroid carcinoma.

Receptor Tyrosine Kinases (RTKs).

The Receptor Tyrosine Kinases (RTKs) comprise a large family of transmembrane receptors with diverse biological activities. A number of distinct RTK subfamilies have been identified including, but not limited to, ALK receptor family, EGF receptor family, the Insulin receptor family, the PDGF receptor family, the FGF receptor family, the VEGF receptor family, the HGF receptor family, the Trk receptor family, the EPH receptor family, the AXL receptor family, the LTK receptor family, the TIE receptor family, the ROR receptor family, the DDR receptor family, the RET receptor family, the KLG receptor family, the RYK receptor family and the MuSK receptor family.

Receptor tyrosine kinases have been shown to be not only key regulators of normal cellular processes but also to have a critical role in the development and progression of many types of cancer. The receptor tyrosine kinase (RTK) family includes receptors that are crucial for the growth and differentiation of a variety of cell types. The intrinsic function of RTK mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response such as, by way of example only, cell division, differentiation, metabolic effects, and changes in the extracellular microenvironment.

Tropomyosin-Receptor-Kinase (Trk) Family

The Trk family receptor tyrosine kinases (NTRK genes), TrkA (NTRK1), TrkB (NTRK2), and TrkC (NTRK3), are the signaling receptors that mediate the biological actions of the peptide hormones of the neurotrophin family. Trk receptors are membrane-bound receptors that, through several signal cascades, control neuronal growth and survival, and differentiation, migration and metastasis of tumor cells. The neurotrophin family of growth factors includes nerve growth factor (NGF), brain-derived neurotrophic factor (BDNF), and two neurotrophins (NT), NT-3, and NT-4. Neurotrophins are critical to the functioning of the nervous system, and the activation of Trk receptors by neurotrophin binding leads to activation of signal cascades resulting in promoting survival and other functional regulation of cells. Each type of neurotrophin has a different binding affinity toward its corresponding Trk receptor, and upon neurotrophin binding, the Trk receptors phosphorylates themselves and members of the MAPK pathway. The differences in the signaling initiated by these distinct types of receptors are important for generating diverse biological responses.

The Trk family kinase receptors promote tumorigenesis and are able to control tumor cell growth and survival as well as differentiation, migration and metastasis. The Trk receptors are implicated in the development and progression of cancer, through upregulation of either, the receptor, their ligand (NGF, BDNF, NT-3, and NT-4), or both. In many cases high Trk expression is associated with aggressive tumor behavior, poor prognosis and metastasis. Thus, diseases and disorders related to Trk receptors result from 1) expression of a Trk receptor(s) in cells which normally do not express such a receptor(s); 2) expression of a Trk receptor(s) by cells which normally do not express such a receptor(s); 3) increased expression of Trk receptor(s) leading to unwanted cell proliferation; 4) increased expression of Trk receptor(s) leading to adhesion independent cell survival; 5) mutations leading to constitutive activation of Trk receptor(s); 6) over stimulation of Trk receptor(s) due to abnormally high amount of, or mutations in, Trk receptor(s), and/or 7) abnormally high amount of Trk receptor(s) activity due to abnormally high amount of, or mutations in, Trk receptor(s).

Genetic abnormalities, i.e. point mutations and chromosomal rearrangements involving both the genes expressing TrkB and TrkC have been found in a variety of cancer types. In a kinome-wide approach to identify point mutants in tyrosine kinases, mutations in the genes expressing TrkB and TrkC were found in cell lines and primary samples from patients with colorectal cancer. In addition, chromosomal translocations involving the genes expressing TrkA and TrkB have been found in several different types of tumors. Gene rearrangements involving the genes expressing TrkA and a set of different fusion partners (TPM3, TPR, TFG) are a hallmark of a subset of papillary thyroid cancers. Moreover, secretary breast cancer, infant fibrosarcoma and congenital mesoblastic nephroma have been shown to be associated with a chromosomal rearrangement t(12;15) generating a ETV6-NTRK3 fusion gene that was shown to have constitutive kinase activity and transforming potential in several different cell lines including fibroblasts, hematopoietic cells and breast epithelial cells.

TrkA has the highest affinity to the binding nerve growth factor (NGF). NGF is important in both local and nuclear actions, regulating growth cones, motility, and expression of genes encoding the biosynthesis enzymes for neurotransmitters. Nocireceptive sensory neurons express mostly TrkA and not TrkB or TrkC.

TrkB serves as a receptor for both BDNF and NT-4, and is expressed in neuroendocrine-type cells in the small intestine and the colon, in the alpha cells of the pancreas, in the monocytes and macrophages of the lymph nodes and of the spleen, and in the granular layers of the epidermis. TrkB is also expressed in cancerous prostate cells but not in normal cells. The binding of BDNF to TrkB receptor causes activation of intercellular cascades which regulate neuronal development and plasticity, long-term potentiation, and apoptosis. BDNF promotes the proliferation, differentiation and growth and survival of normal neural components such as retinal cells and glial cells. In addition, TrkB activation is a potent and specific suppressor of anchorage independent cell death (anoikis), which is apoptosis induced by loss of attachment of a cell to its matrix. By way of example, activation of the Phosphatidylinositol-3-kinase/Protein Kinase B signaling axis by TrkB promotes the survival of non-transformed epithelial cells in 3-dimensional cultures and induces tumor formation and metastasis of those cells in immunocompromised mice. Anchorage independent cell survival is a metastatic process allowing tumor cells to migrate through the systemic circulation and grow at distant organs. Agonism of TrkB results in the failure of induced cell death by cancer treatments. Thus, TrkB modulation is a target for treatment of benign and malignant proliferative diseases, especially tumor diseases.

Diseases and disorders related to the TrkB receptor include, but are not limited to, cancers, such as, by way of example only, neuroblastoma progression, Wilm's tumor progression, breast cancer, pancreatic cancer, colon cancer, prostate cancer, and lung cancer. The TrkB receptor has been shown to be associated with Alzheimer's disease.

Additional research has discovered mutations in TrkB in humans that result in a partial loss of enzymatic activity of the receptor. This genetic legion results in an increase in apetite and obesity (hyperphagic obesity). Similar results have been obtained in mouse models, thus strengthening the hypothesis that lowering TrkB activity could serve to modulate feeding behavior, and would be useful in the treatment of disorders such as anorexia.

Other non-oncology indications for a Trk inhibitor include atopic dermatitis and psoriasis.

TrkC is activated by binding with NT-3 and is expressed by proprioceptive sensory neurons. The axons of these proprioceptive sensory neurons are much thicker than those of nocireceptive sensory neurons, which express TrkA. Signalling through TrkC leads to cell differentiation and development of proprioceptive neurons that sense body position. Mutations in this gene expressing TrkC is associated with medulloblastomas, secretory breast carcinomas and other cancers. In addition, high expression of TrkC is a hallmark of melanoma, especially in cases with brain metastasis.

Trk family members, especially NTRK1 and NTRK2, play a role in pancreatic cancer wherein: i) high expression of various members of the Trk family and their cognate ligands have been shown in tissue samples from patients with pancreatic cancer; ii) NTRK2 overexpression has been linked to a malignant, highly metastatic phenotype of pancreatic cancer; iii) high expression of NTRK1/NGF, has been correlated with enhanced proliferation, invasive behavior and pain in PC patients; and iv) nerve growth factor has been shown to increase the invasive potential of pancreatic cancer cell lines. Overexpression of TrkA in pancreatic cancer might be caused by methylation of negative regulatory AP-1 sites in the promoter region of TrkA.

Gene rearrangements involving NTRK1 are a hallmark of a subset of papillary thyroid cancers. Thyroid-specific TRK oncogenes are generated by rearrangements of the NTRK1 gene with three different activating genes, namely TPR, TPM3, and TFG.

Several loss of function mutations in thr TrkA are responsible for congenital insensitivity to pain with anhidrosis (CIPA), a disorder characterized by a lack of pain sensation and anhidrosis. More recently, an antagonistic TrkA antibody has been shown to be efficacious in inflammatory and neupathic pain animal models. In addition, TrkA and NGF have been implicated in eliciting cancer related pain. It was shown that NGF secreted by tumor cell and tumor invading macrophages secret NGF which directly stimulates TrkA located on peripheral pain fibers. Using various tumor models in both mouse and rats it was demonstrated that neutralizing NGF with a monoclonal antibody inhibits cancer related pain to a degree similar or superior to the highest tolerated dose of morphine. Therefore, a selective inhibitor of TrkA can be used in the treatment of pain associated with cancer.

High expression of Trk's are found in Wilm's tumor, prostate carcinoma and pancreatic cancers. High expression of TrkC is a hallmark of carcinoma. In neuroblastoma, high TRKB expression is correlated with an aggressive untreatable tumors and resistance to standard cytotoxic therapies. In mouse models of cancer metastasis, the NTRK2 gene (TrkB protein) can induce metastasis and removal of the gene reverses this metastatic potential. The bulk of evidence suggests that inhibition of Trk enzymes would block the growth and spread of various cancers where Trk is involved. Furthermore, activating mutations in Trk's are present in 7% of cancers.

Certain compounds, pharmaceutical compositions and pharmaceutical combination provided herein are inhibitors of Trk receptor tyrosine kinases (TrkA, TrkB, and TrkC), thus such compounds, pharmaceutical compositions and pharmaceutical combination are useful for the treatment of diseases and/or disorders that respond to inhibition of Trk receptor tyrosine kinases (TrkA, TrkB, and TrkC). In certain embodiments, such compounds, pharmaceutical compositions and pharmaceutical combination are useful in the treatment of cancer by inhibiting the development and/or progression of the cancer. In certain embodiments, such compounds, pharmaceutical compositions and pharmaceutical combination are useful in the treatment of diseases and/or disorders including, but are not limited to, neuroblastoma, Wilm's tumor, breast cancer, pancreatic cancer, colon cancer, prostate cancer, lung cancer, melanoma, anoerexia, atopic dermatitis, psoriasis and Alzheimer's disease.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Routes of Administration and Pharmaceutical Compositions

For the therapeutic uses of compounds of Formula (I), or pharmaceutically acceptable salts, solvates, N-oxides, prodrugs and isomers thereof, described herein, such compounds are administered in therapeutically effective amounts either alone or as part of a pharmaceutical composition. Accordingly, provided herein are pharmaceutical compositions, which comprise at least one compound of Formulas (I) described herein, pharmaceutically acceptable salts and/or solvates thereof, and one or more pharmaceutically acceptable carriers, diluents, or excipients. In addition, such compounds and compositions are administered singly or in combination with one or more additional therapeutic agents. The routes of administration of compounds of Formula (I) and pharmaceutical compositions include, but are not limited to, oral administration, intravitreal administration, rectal administration, parenteral, intravenous administration, intraperitoneal administration, intramuscular administration, inhalation, transmucosal administration, pulmonary administration, intestinal administration, subcutaneous administration, intramedullary administration, intrathecal administration, direct intraventricular, intranasal administration, topical administration, ophthalmic administration or otic administration.

In certain embodiments, compounds of Formula (I) or pharmaceutical compositions described herein are administered locally, while in other embodiments compounds of Formula (I) or pharmaceutical composite described herein are administered systemically. Local administration includes, but is not limited to, injection into an organ, optionally in a depot or sustained release formulation. Systemic administration includes, but is not limited to, oral administration or intravenous administration. In other embodiments, compounds of Formula (I) or pharmaceutical compositions described herein are administered in a targeted drug delivery system, such as, by way of example only, in a liposome coated with organ-specific antibody. The liposome is targeted to and taken up selectively by the organ. In other embodiments, compounds of Formula (I) or pharmaceutical compositions described herein are administered in the form of a rapid release formulation, while in other embodiments, compounds of Formula (I) or pharmaceutical compositions described herein are administered in the form of an extended release formulation. In other embodiments, compounds of Formula (I) or pharmaceutical compositions described herein are administered in the form of an intermediate release formulation.

The therapeutically effective amount will vary depending on, among others, the disease indicated, the severity of the disease, the age and relative health of the subject, the potency of the compound administered, the route of administration and the treatment desired. In certain embodiments, satisfactory results are indicated to be obtained at daily dosages daily dosage of a compound of Formula (I) from about 0.03 to 2.5 mg/kg per body weight. In certain embodiments, the daily dosage of a compound of Formula (I), administered orally, is in the range from 0.05 micrograms per kilogram body weight (μg/kg) to 100 micrograms per kilogram body weight (μg/kg). In certain embodiments, the daily dosage of a compound of Formula (I), administered topically, is in the range from 0.05 micrograms per kilogram body weight (μg/kg) to 100 micrograms per kilogram body weight (μg/kg). In other embodiments, the daily dosage of a compound of Formula (I), administered parenterally, is in the range from 0.05 micrograms per kilogram body weight (μg/kg) to 100 milligrams per kilogram body weight (mg/kg). In certain embodiments, the daily dosage of a compound of Formula (I), administered intrermuscularlly, is in the range from 0.05 micrograms per kilogram body weight (μg/kg) to 100 micrograms per kilogram body weight (μg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I).

Other aspects provided herein are processes for the preparation of pharmaceutical composition which comprise at least one compound of Formula (I) described herein. In certain embodiments, such processes include admixing a compound of Formula (I) described herein with one or more pharmaceutically acceptable carriers, diluents or excipients. In certain embodiments, the pharmaceutical compositions comprise a compound of Formula (I) in free form or in a pharmaceutically acceptable salt or solvate form. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, dissolving, granulating dragee-making, levigating, emulsifying, encapsulating, entrapping or compression processes and/or coating methods. In other embodiments, such compositions are optionally contain excipients, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, pills, dragees, granules, liquids, gels, syrups, flavored syrups, elixirs, slurries, solutions or suspensions in aqueous or non-aqueous liquids, edible foams or whips, and oil-in-water liquid emulsions or water-in-oil liquid emulsions. The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compound of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, physiological saline buffer, Ringer's Injection solution, Dextrose Injection, Dextrose and Sodium Chloride Injection, and Lactated Ringer's Injection solution; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments, a compound of Formula (I) or composition containing one or more compounds of Formula (I) is parenteral administration by bolus injection. In other embodiments, a compound of Formula (I) or composition containing one or more compounds of Formula (I) is parenteral administration by continuous infusion. Formulations for injection are presented in unit dosage form, by way of example only, in ampoules or formulations for injection are presented in multi-dose containers, with an added preservative. The compositions may take such forms as suspensions, solutions or emulsions in oily or aqueous vehicles, and may contain formulatory agents such as suspending, stabilizing and/or dispersing agents.

Transdermal Administration

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used. In certain embodiments transdermal administration is used to provide continuous, while in other embodiments transdermal administration is used to provide discontinuous infusion of a compound of Formula (I) in controlled amounts.

In certain embodiments, the rate of absorption is slowed by using rate-controlling membranes or by trapping the compound within a polymer matrix or gel. In certain embodiments, transdermal delivery is via a transdermal patch.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, the ionic strength, or tonicity are adjusted to improve delivery. In other embodiments, compounds such as stearates are added to advantageously alter the hydrophilicity or lipophilicity of one or more compound of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compound of Formula (I) are used to further adjust the properties of the resulting composition.

In other embodiments, transdermal delivery of the compound of Formula (I) is accomplished by means of iontophoretic patches and the like Topical Dosage Forms In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compound of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide;

dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Pulmonary Administration

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compound of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compound of Formula (I) are delivered to the lung using a liquid spray device, wherein such devices use extremely small nozzle holes to aerosolize liquid drug formulations that can then be directly inhaled into the lung. In other embodiments, compound of Formula (I) are delivered to the lung using a nebulizer device, wherein a nebulizers creates an aerosols of liquid drug formulations by using ultrasonic energy to form fine particles that can be readily inhaled. In other embodiments, compound of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

Rectal Administration

In certain embodiments pharmaceutical compositions containing at least one compound of Formula (I) are administered rectally in the form of suppositories, enemas, retention enemas ointment, creams rectal foams or rectal gels. In certain embodiments such suppositories are prepared from fatty emulsions or suspensions, cocoa butter or other glycerides.

Depot Administration

In certain embodiments pharmaceutical compositions containing at least one compound of Formula (I) are formulated as a depot preparation. Such long acting formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In certain embodiments injectable depot forms are made by forming microencapsulated matrices of the compound of Formula (I) in biodegradable polymers. The rate of compound of Formula (I) release is controlled by varying the ratio of compound of Formula (I) to polymer and the nature of the particular polymer employed. In other embodiments, depot injectable formulations are prepared by entrapping the compound of Formula (I) in liposomes or microemulsions.

Ophthalmic Administration

In certain embodiments, a compound of Formula (I) or pharmaceutical composition described herein are ophthalmically administered to the eye. Administration to the eye generally results in direct contact of the agents with the cornea, through which at least a portion of the administered agents pass. In certain embodiments, such compounds of Formula (I) or pharmaceutical compositions have an effective residence time in the eye of about 2 to about 24 hours. In certain embodiments, such compounds of Formula (I) or pharmaceutical compositions have an effective residence time in the eye of about 4 to about 24 hours. In certain embodiments, such compounds of Formula (I) or pharmaceutical compositions have an effective residence time in the eye of about 6 to about 24 hours.

Ophthalmic administration, as used herein, includes, but is not limited to, topical administration, intraocular injection, subretinal injection, intravitreal injection, periocular administration, subconjuctival injections, retrobulbar injections, intracameral injections (including into the anterior or vitreous chamber), sub-Tenon's injections or implants, ophthalmic solutions, ophthalmic suspensions, ophthalmic ointments, ocular implants and ocular inserts, intraocular solutions, use of iontophoresis, incorporation in surgical irrigating solutions, and packs (by way of example only, a saturated cotton pledget inserted in the formix). In certain embodiments, the compounds of Formula (I) or pharmaceutical composition described herein are formulated as an ophthalmic composition and are administered topically to the eye. Such topically administered ophthalmic compositions include, but are not limited to, solutions, suspensions, gels or ointments.

In certain embodiments the pharmaceutical compositions, comprising at least one compound of Formula (I) described herein, used for ophthalmic administration take the form of a liquid where the compositions are present in solution, in suspension or both. In some embodiments, a liquid composition includes a gel formulation. In other embodiments, the liquid composition is aqueous. In other embodiments, such liquid compositions take the form of an ointment. In certain embodiments pharmaceutical compositions containing at least one compound of Formula (I) are administered ophthamically as eye drops formulated as aqueous solutions that optionally contain solubilizers, stabilizers, tonicity enhancing agents, buffers and preservatives. A desired dosage is administered via a known number of drops into the eye. By way of example only, for a drop volume of 25 µl, administration of 1-6 drops delivers 25-150 µl of the composition. In certain embodiments, the aqueous compositions contain from about 0.01% to about 50% weight/volume of a compound of Formula (I). In other embodiments, the aqueous compositions contain from about 0.1% to about 20% weight/volume of a compound of Formula (I). In still other embodiments, the aqueous compositions contain from about 0.2% to about 10% weight/volume of a compound of Formula (I). In certain embodiments, the aqueous compositions contain from about 0.5% to about 5%, weight/volume of a compound of Formula (I).

In certain embodiments the aqueous compositions have an ophthalmically acceptable pH and osmolality. In certain embodiments the aqueous compositions include one or more ophthalmically acceptable pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an ophthalmically acceptable range.

In certain embodiments the compositions also include also include one or more ophthalmically acceptable salts in an amount required to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments the aqueous compositions also contain one or more polymers as suspending agents. Such polymers include, but are not limited to, water-soluble polymers such as cellulosic polymers described herein, (for example only, hydroxypropyl methylcellulose), and water-insoluble polymers described herein (for example only, cross-linked carboxyl-containing polymers). In certain embodiments, the aqueous compositions also include an ophthalmically acceptable mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In certain embodiments the compositions also include ophthalmically acceptable solubilizing agents to aid in the solubility of a compound of Formula (I). The term "solubilizing agent" generally includes agents that result in formation of a micellar solution or a true solution of the agent. In certain embodiments, ophthalmically acceptable nonionic surfactants including, but not limited to, polysorbate 80 are used as solubilizing agents. In other embodiments, ophthalmically acceptable glycols including, but not limited to, polyglycols, polyethylene glycol 400, and glycol ethers are used as solubilizing agents.

In certain embodiments the compositions also include one or more ophthalmically acceptable surfactants to enhance physical stability or for other purposes. Such nonionic surfactants include, but are not limited to, polyoxyethylene fatty acid glycerides and vegetable oils (by way of example only, polyoxyethylene (60) hydrogenated castor oil) and polyoxyethylene alkylethers and alkylphenyl ethers (by way of example only, octoxynol 10 and octoxynol 40).

In certain embodiments the compositions also include one or more ophthalmically acceptable preservatives to inhibit microbial activity. Such preservatives include, but are not limited to mercury-containing substances such as merfen and thiomersal; stabilized chlorine dioxide; and quaternary ammonium compounds such as benzalkonium chloride, cetyltrimethylammonium bromide and cetylpyridinium chloride.

In certain embodiments the compositions also include one or more antioxidants to enhance chemical stability where required. Such antioxidants include, but are not limited to, ascorbic acid and sodium metabisulfite.

In certain embodiments, the aqueous compositions provided herein are packaged in single-dose non-reclosable containers, while in other embodiments the aqueous compositions provided herein are packaged in multiple-dose reclosable containers wherein a preservative is included in the composition.

Otic Administration

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

Combination Therapies

In certain embodiments, a compound of Formula (I) provided herein, or a pharmaceutically acceptable salt or solvate thereof, or a pharmaceutical composition containing at least one compound of Formula (I), is administered alone (without an additional therapeutic agent) for the treatment of one or more of the disease and/or disorders associated TrkA, TrkB, and TrkC kinase activity.

In other embodiments, a compound of Formula (I) provided herein, or a pharmaceutically acceptable salt or solvate thereof, or a pharmaceutical composition containing at least one compound of Formula (I) provided herein, is administered in combination with one or more additional therapeutic agents, for the treatment of one or more of the disease and/or disorders associated with TrkA, TrkB, and TrkC kinase activity.

In other embodiments, a compound of Formula (I) provided herein, or a pharmaceutically acceptable salt or solvate thereof, or a pharmaceutical composition containing at least one compound of Formula (I) provided herein, is formulated in combination with one or more additional therapeutic agents and administered for the treatment of one or more of the disease and/or disorders associated with TrkA, TrkB, and TrkC kinase activity.

In another embodiment, a compound of Formula (I) provided herein, or a pharmaceutically acceptable salt or solvate thereof, or a pharmaceutical composition containing at least one compound of Formula (I) provided herein, is administered sequentially with one or more additional therapeutic agents, for the treatment of one or more of the disease and/or disorders associated with TrkA, TrkB, and TrkC kinase activity.

In other embodiments, the combination treatments provided herein include administration of a compound of Formula (I) provided herein, or a pharmaceutically acceptable salt or solvate thereof, or a pharmaceutical composition containing a compound of Formula (I) prior to administration of one or more additional therapeutic agents, for the treatment of one or more of the disease and/or disorders associated with TrkA, TrkB, and TrkC kinase activity.

In other embodiments, the combination treatments provided herein include administration of a compound of Formula (I) provided herein, or a pharmaceutically acceptable salt or solvate thereof, or a pharmaceutical composition containing a compound of Formula (I), subsequent to administration of one or more additional therapeutic agents, for the treatment of one or more of the disease and/or disorders associated with TrkA, TrkB, and TrkC kinase activity.

In other embodiments, the combination treatments provided herein include administration of a compound of Formula (I) provided herein, or a pharmaceutically acceptable salt or solvate thereof, or a pharmaceutical composition containing a compound of Formula (I), concurrently with administration of one or more additional therapeutic agents, for the treatment of one or more of the disease and/or disorders associated with TrkA, TrkB, and TrkC kinase activity.

In certain embodiments of the combination therapies described herein, the compounds of Formula (I) provided herein, or a pharmaceutically acceptable salts or solvates thereof, and the additional therapeutics agent(s) act additively. In certain embodiments of the combination therapies described herein, the compounds of Formula (I) provided herein, or a pharmaceutically acceptable salts or solvates thereof, and the additional therapeutics agent(s) act synergistically.

In other embodiments, a compound of Formula (I) provided herein, or a pharmaceutically acceptable salts or solvates thereof, or a pharmaceutical composition containing a compound of Formula (I), is administered to a patient who has not previously undergone or is not currently undergoing treatment with another therapeutic agent.

The additional therapeutic agents used in combination with at least one compound of Formula (I) provided herein, or a pharmaceutically acceptable salt or solvate thereof, include, but are not limited to chemotherapeutic agents, anti-inflammatory agents, bronchodilatory agents, antihistamine agents, decongestant agents, anti-tussive agents, antiproliferative agents, cytostatic agents, cytotoxic agents, inhibitors of polyamine biosynthesis, inhibitors of a protein kinase, inhibitors of a serine/threonine protein kinase, inhibitors of protein kinase C, inhibitors of a tyrosine protein kinase, inhibitors of EGF receptor tyrosine kinase, (e.g. Iressa®, inhibitors of VEGF receptor tyrosine kinase, (e.g. PTK787 or Avastin®), inhibitors of PDGF receptor tyrosine kinase, (e.g. STI571 (Glivec®)), a cytokine, a negative growth regulator, such as TGF-β or IFN-β, an aromatase inhibitor (e.g. letrozole (Femara®) or anastrozole), an inhibitor of the interaction of an SH2 domain with a phosphorylated protein, antiestrogens, bisphosphonates (e.g. AREDIA® or ZOMETA®) and monoclonal antibodies (e.g. against HER2, such as trastuzumab).

The anti-inflammatory agents used in combination with at least one compound of Formula (I) described herein, or a pharmaceutically acceptable salt or solvate thereof, include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide, leukotriene antagonists including, but not limited to, zileuton, aurothioglucose, gold sodium thiomalate and auranofin, steroids including, but not limited to, alclometasone diproprionate, amcinonide, beclomethasone dipropionate, betametasone, betamethasone benzoate, betamethasone diproprionate, betamethasone sodium phosphate, betamethasone valerate, budesonide, ciclesonide, clobetasol proprionate, clocortolone pivalate, hydrocortisone, hydrocortisone derivatives, desonide, desoximatasone, dexamethasone, flunisolide, flucoxinolide, flurandrenolide, fluticasone propionate, glucocorticosteroids, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

Other anti-inflammatory agents used in combination with at least one compound of Formula (I) described herein, or a pharmaceutically acceptable salt or solvate thereof, include, but are not limited to, steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248 and WO 05/05452; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, pranlukast, zafirlukast, accolate, SR2640, Wy-48,252, ICI 198615, MK-571, LY-171883, Ro 24-5913 and L-648051; dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)-benzothiazolone and pharmaceutically acceptable salts thereof (the hydrochloride being Viozan®—AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 99/16766, WO 01/13953, WO 03/104204, WO 03/104205, WO 04/000814, WO 04/000839 and WO 04/005258 (Merck), WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030212, WO 05/030725, WO 05/087744, WO 05/087745, WO 05/087749 and WO 05/090345 as well as those described in WO 98/18796 and WO 03/39544; A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

The bronchodilatory agents used in combination with at least one compound of Formula (I) described herein, or a pharmaceutically acceptable salt or solvate thereof, include, but are not limited to, beta-2 adrenoceptor agonists, anticholinergic agents, antimuscarinic agents, ipratropium bromide, oxitropium bromide, tiotropium salts, glycopyrrolate, CHF 4226 (Chiesi), SVT-40776, albuterol (salbutamol), metaproterenol, terbutaline, salmeterol, fenoterol, procaterol, formoterol, carmoterol, and GSK159797 and pharmaceutically acceptable salts thereof.

Other bronchodilatory agents used in combination with at least one compound of Formula (I) described herein, or a pharmaceutically acceptable salt or solvate thereof, include, but are not limited to, compounds (in free or salt or solvate form) of formula I of WO 0075114, preferably compounds of the Examples thereof, compounds (in free or salt or solvate form) of formula I of WO 04/16601 or of formula I of WO 04/087142, compounds, such as those described in EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897, WO 06/8173, EP 424021, U.S. Pat. Nos. 3,714, 357, 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Dual anti-inflammatory and bronchodilatory agents used in combination with at least one compound of Formula (I) described herein, or a pharmaceutically acceptable salt or solvate thereof, include, but are not limited to, dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

The antihistamine drug substances agents used in combination with at least one compound of Formula (I) described herein, or a pharmaceutically acceptable salt or solvate thereof, include, but are not limited to, cetirizine hydrochloride, levocetirizine, acetaminophen, clemastine fumarate, promethazine, loratidine, desloratidine, diphenhydramine and fexofenadine hydrochloride, activastine, astemizole, azelastine, dimetinden, ebastine, epinastine, levocabastine, mizolastine and tefenadine as well as those disclosed in WO 03/099807, WO 04/026841 and JP 2004107299.

In certain embodiments, the additional thereapeutic agent(s) used in the combination therapies described herein include, but are not limited to, non-selective cyclo-oxygenase COX-1/COX-2 inhibitors (by way of example only, piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (by way of example only, meloxicam, celecoxib, rofecoxib, valdecoxib, lumarocoxib, parecoxib and etoricoxib); glucocorticosteroids; methotrexate, lefunomide; hydroxychloroquine, d-penicillamine, auranofin or other parenteral or oral gold preparations.

Chemotherapeutic agents or other anti-proliferative agents used in combination with the compounds provided herein to treat proliferative diseases and cancer include, but are not limited to, surgery, radiotherapy (γ-radiation, neutron beam radiotherapy, electron beam radiotherapy, proton therapy, brachytherapy, and systemic radioactive isotopes), endocrine therapy, biologic response modifiers (interferons, interleukins, and tumor necrosis factor (TNF)), hyperthermia and cryotherapy, agents to attenuate any adverse effects (e.g., antiemetics), and other chemotherapeutic drugs, including, but not limited to, anthracyclines, alkyl sulfonates, aziridines, ethylenimines, methylmelamines, nitrogen mustards, nitrosoureas, folic acid analogs, dihydrofolate reductase inhibitor, purine analogs, pyrimidine analogs, podophyllotoxins, platinum-containing agents, interferons, interleukins, alkylating agents (mechlorethamine, chlorambucil, Cyclophosphamide, Melphalan, Ifosfamide), antimetabolites (Methotrexate, gemcitabine or capecitabine), purine antagonists and pyrimidine antagonists (6-Mercaptopurine, 5-Fluorouracil, Cytarabile, Gemcitabine), spindle poisons/microtubule active agents (Vinblastine, Vincristine, Vinorelbine, Paclitaxel, epothilone), topoisomerase I inhibitors, topoisomerase II inhibitors, podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), GLEEVEC™, adriamycin, dexamethasone, cyclophosphamide, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, methotrexate, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, teniposide, tenuazonic acid, triaziquone or combinations thereof.

Other agents used in combination with the compounds provided herein include, but are not limited to: treatments for asthma such as albuterol and SINGULAIR™; anti-inflammatory agents such as corticosteroids, TNF blockers, IL-1

RA, azathioprine, cyclophosphamide, and sulfasalazine; agents for treating blood disorders such as corticosteroids and anti-leukemic agents.

Treatment of Diseases Mediated by Kinase Activity

Compounds of Formula (I), pharmaceutically acceptable salts, solvates, N-oxides, prodrugs and isomers thereof, pharmaceutical compositions, and combination therapies provided herein are inhibitors of TrkA, TrkB, and TrkC kinase activity, and are useful in the treatment and/or prevention of diseases and/or disorders in which aberrant, abnormal or deregulated activity of TrkA, TrkB, and TrkC kinase contributes to the pathology and/or symptomology of such diseases and/or disorders. Such diseases and/or disorders mediated by TrkA, TrkB, and TrkC kinases are provided herein.

In certain embodiments, such diseases and/or disorders associated with TrkA, TrkB, and TrkC, kinases include, but are not limited to, cancer, proliferative diseases, pain, dermatological diseases and/or disorders, metabolic diseases and/or disorders, muscle diseases and/or disorders, neurodegenerative diseases and/or disorders, neurological diseases and/or disorders, inflammatory diseases, fibrosis, infectious diseases, respiratory diseases and/or disorders, pulmonary diseases and/or disorders and hyperplasia.

Such cancer and proliferative diseases include, but are not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gastrointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes.

Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Such pain disorders include, but are not limited to, cancer-related pain, skeletal pain caused by tumor metastasis, osteoarthritis, visceral pain, inflammatory pain and neurogenic pain.

Such dermatological diseases and/or disorders include, but are not limited to, inflammatory or allergic conditions of the skin, dermatitis, eczema, psoriasis, atopic dermatitis, seborrhoeic dermatitis (Dandruff, Cradle cap), diaper rash, urushiol-induced contact dermatitis, contact dermatitis, erythroderma, lichen simplex chronicus, prurigo nodularis, itch, pruritus ani, nummular dermatitis, dyshidrosis, pityriasis alba, alopecia greata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, peritoneal and sub dermal adhesion and photoaging of the skin.

Such metabolic diseases and/or disorders and eating disorder include, but are not limited to, obesity, diabetes and anoerexia.

Such muscle diseases and/or disorders include, but are not limited to, muscular atrophies (e.g. disuse), muscular dystrophies (e.g. Duchenne's muscle dystrophy, Becker's muscle dystrophy, Limb-Girdle muscle dystrophy), sarcopenia, cachexia, wasting and Facioscapulohumeral dystrophy.

Such neurological diseases and/or disorders and neurodegenerative disorders include, but are not limited to, impaired neurological function and Alzheimer's disease.

Such inflammatory diseases and/or disorders include, but are not limited to, uveitis, atherosclerosis, atherogenesis, glomerulonephritis, Kawasaki disease, inflammatory responses, polymyositis, arthritis, neurological inflammation, chronic arthritis inflammation and osteoarthritis.

Such fibrosis diseases and/or disorders include, but are not limited to, extracellular matrix accumulation and fibrosis, scleroderma, fibrosclerosis, radiation-induced fibrosis, kidney fibrosis, lung fibrosis and liver fibrosis, haemochromatosis, primary biliary cirrhosis, restenosis, retroperitoneal fibrosis, mesenteric fibrosis, endometriosis and keloids.

Such infectious diseases and/or disorders include, but are not limited to, Chagas disease.

Such respiratory diseases and/or disorders and pulmonary disorders include, but are not limited to, asthma, bronchial asthma, allergic asthma, intrinsic (non-allergic) asthma, extrinsic (allergic) asthma, exercise-induced asthma, drug-induced asthma (including aspirin and NSAID-induced) and dust-induced asthma, chronic obstructive pulmonary disease (COPD); chronic obstructive airways disease (COAD), chronic obstructive lung disease (COLD), bronchitis, chronic bronchitis, acute bronchitis, dyspnea, arachidic bronchitis, catarrhal bronchitis, croupus bronchitis, phthinoid bronchitis, rhinitis, acute rhinitis, chronic rhinitis, rhinitis medicamentosa, vasomotor rhinitis, perennial and seasonal allergic rhinitis, rhinitis nervosa (hay fever), inflammatory or obstructive airways diseases, pulmonary hypertension, acute lung injury, adult/acute respiratory distress syndrome (ARDS), pulmonary fibrosis, idiopathic pulmonary fibrosis, chronic obstructive pulmonary disease, pulmonary disease due to infectious or toxic agents, emphysema, pneumoconiosis, aluminosis, anthracosis, asbestosis, chalicosis, ptilosis, siderosis, silicosis, tabacosis, byssinosis, acute lung injury (ALI), hypereosinophilia, Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, pulmonary hypertension, primary pulmonary hypertension (PPH), secondary pulmonary hypertension (SPH), familial PPH, sporadic PPH, precapillary pulmonary hypertension, pulmonary arterial hypertension (PAH), pulmonary artery hypertension, idiopathic pulmonary hypertension, thrombotic pulmonary arteriopathy (TPA), plexogenic pulmonary arteriopathy, functional classes I to IV pulmonary hypertension, and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, hypoxemia, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, acute and chronic rhinitis including rhinitis medicamentosa, and vasomotor rhinitis; perennial and seasonal allergic rhinitis including rhinitis nervosa (hay fever).

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of dermatological disorders including, but not limited to, psoriasis, dermatitis, eczema, atopic dermatitis, contact dermatitis, urushiol-induced contact dermatitis, eczematous dermatoses, and delayed-type hypersensitivity reactions; phyto- and photodermatitis; seborrhoeic dermatitis, dermatitis herpetiformis, lichen simplex chronicus, lichen planus, lichen sclerosus et atrophica, discoid lupus erythematosus, diaper rash, erythroderma, prurigo nodularis, itch, pruritus ani, nummular dermatitis, dyshidrosis and pityriasis alba.

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of cancer including, but not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gas-trointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome.

In certain embodiments, the compounds of Formula (I), pharmaceutically acceptable salts, solvates, N-oxides, prodrugs and isomers thereof, pharmaceutical compositions, and/or combinations provided herein are used in the treatment and/or prevention of cancer including, but not limited to, hematopoietic disorders, hematopoietic malignancies, non-hematopoietic malignancies, benign or malignant tumors, tumors of the neck and head, brain cancer, kidney cancer, liver cancer, adrenal gland cancer, neuronal cancer, neuroblastoma, bladder cancer, breast cancer, secretory breast carcinoma, stomach cancer, gastric tumors, ovarian cancer, uterine cancer, colon cancer, rectal cancer, colorectal adenoma, prostate cancer, renal cancer, brain cancer, endometrial cancer, pancreatic cancer, lung cancer, non-small cell lung cancer, human adenoid cystic carcinoma, vaginal cancer, thyroid cancer, papillary thyroid carcinoma, sarcoma, congenital fibrosarcoma, osteolytic sarcoma, osteosarcoma, fibrosarcoma, myeloma, tumor metastasis to bone, congenital mesoblastic nephroma, glioblastomas, melanoma, multiple myeloma, gas-trointestinal cancer, gastrointestinal stromal tumors (GIST), mastocytosis, neuroblastoma, fibrotic cancers, tumor metastasis growth, epidermal hyperproliferation, psoriasis, metastasis, prostate hyperplasia, neoplasia, neoplasia of epithelial character, lymphomas, diffuse large B-cell lymphoma, B-cell lymphoma, mammary carcinoma, Wilm's tumor, Cowden syndrome, Lhermitte-Dudos disease and Bannayan-Zonana syndrome. Such hematopoietic disorders include, but are not limited to, myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes. Such hematological malignancies include, but are not limited to, leukemias, myeloid leukemias, hairy cell leukemia, lymphomas (non-Hodgkin's lymphoma), Hodgkin's disease (also called Hodgkin's lymphoma), and myeloma, including, but are not limited to, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma and acute promyelocytic leukemia (APL).

Compounds of Formula (I), pharmaceutically acceptable salts, solvates, N-oxides, prodrugs and isomers thereof, pharmaceutical compositions, and combination therapies provided herein are used in methods for inhibiting TrkA, TrkB, and TrkC kinase activity in a subject (human or other mammal) for the treatment and/or prevention of diseases and/or disorders associated with or mediated by TrkA, TrkB, and TrkC kinase activity. In certain embodiments, such methods include administering to a subject an effective amount of a compound of Formula (I), or a pharmaceutical composition containing a compound of Formula (I).

In certain embodiments, the methods for the treatment of a subject suffering from a disease and/or disorder associated with TrkA, TrkB, and TrkC kinase activity include administering to the subject an effective amount of a compound of Formula (I), or a pharmaceutically acceptable salt, solvate thereof, either alone or as part of a pharmaceutical composition as described herein.

In certain embodiments, a compound of Formula (I), or a pharmaceutically acceptable salt or solvate thereof, is used in the preparation of a medicament for the treatment of a disease or disorder associated with TrkA, TrkB, and TrkC kinase activity.

In accordance with the foregoing, provided herein are methods for preventing, treating and/or ameliorating the condition of any of the diseases or disorders described above in a subject in need of such treatment, which method comprises administering to said subject a therapeutically effective amount of a compound of Formula (I), or a pharmaceutically acceptable salt thereof. For any of the methods and uses provided herein, the required dosage will vary depending on the mode of administration, the particular condition to be treated and the effect desired.

EXAMPLES

The following examples are offered to illustrate, but not to limit, synthetic methods of compounds of Formula (I).

Synthesis of Intermediates

Synthesis of chloro-imidazo[1,2-b]pyridazine (I-1)

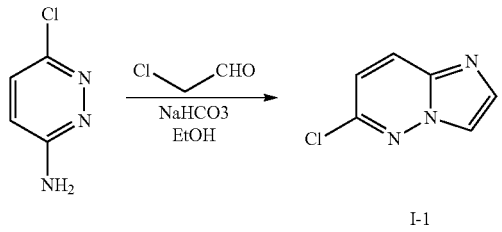

Chloracetaldehyde (55% in water, 126 mL, 880 mmol) was added to a solution of 6-chloro-pyridazin-3-ylamine (25.4 g, 196 mmol) and NaHCO₃ (28 g, 334 mmol) in EtOH (600 mL) and the reaction mixture was heated to reflux while stirring for 14 hours. The resulting dark brown reaction mixture was concentrated under vacuum and the resulting residue reconstituted with DCM. This solution was filtered through a Celite pad and the solid washed with DCM. The solvent was then removed to yield a dark brown oil. 2M HCl (290 mL) and water (300 mL) was added to the residue and the resulting slurry was stirred at room temperature for 15 minutes. The solution was filtered through a celite pad and the filter cake was washed with water. The filtrate was extracted with diethyl ether (3×200 mL). The aqueous layer was cooled to 0° C. (ice bath) and neutralized using NaOH (24 g). The resulting slurry was extracted with diethyl ether (6×300 mL), dried using sodium sulfate and the diethyl ether was removed via rotary evaporator to yield chloro-imidazo[1,2-b]pyridazine (I-1) as a light orange solid. ¹H NMR (400 MHz, CDCl₃) δ 7.94 (s, 1 H), 7.92 (d, J=9.6 Hz, 1 H), 7.79 (d, J=1.2 Hz, 1 H), 7.06 (d, J=9.6 Hz, 1 H). MS m/z 155.1 (M+1)⁺.

Synthesis of 3-bromo-6-chloroimidazo[1,2-b]pyridazine (I-2)

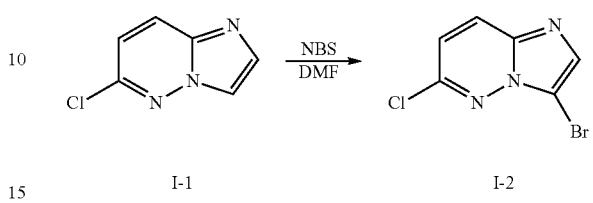

N-bromosuccinamide (19.2 g, 108 mmol) was added to a solution of chloro-imidazo[1,2-b]pyridazine (I-1) (15 g, 98 mmol) in DMF cooled to 0° C. The resulting solution was stirred at 0° C. for 1 hour and the reaction mixture was then poured into water (1.4 L) while stirring at room temperature. The resulting yellow heterogeneous solution was stirred at room temperature for 1 hour and the solid was filtered and washed with hexanes. The solid was dried under vacuum overnight to yield 3-bromo-6-chloroimidazo[1,2-b]pyridazine (I-2) as a yellow solid. ¹H NMR (400 MHz, CDCl3) δ 7.90 (d, J=9.6 Hz, 1 H), 7.78 (s, 1 H), 7.11 (d, J=9.6 Hz, 1 H). MS m/z 233.1, 235.1 (M+1)⁺.

Synthesis of 6-chloro-N-ethylimidazo[1,2-b]pyridazine-3-sulfonamide (I-4)

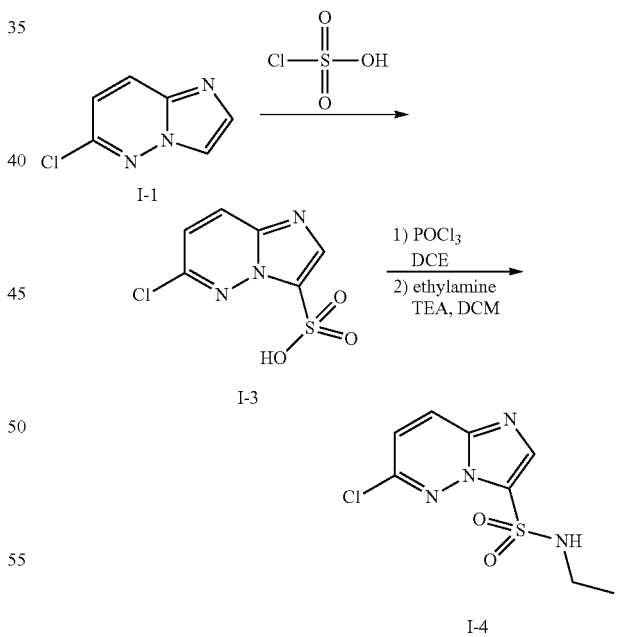

To 6-chloroimidazo[1,2-b]pyridazine (I-1) (3.0 g, 6.5 mmol) was added chlorosulfonic acid (30 mL, 450 mmol) and stirred at 100° C. for 48 hours. The excess chlorosulfonic acid was removed by distillation at 140° C. The remaining brown oil was poured into a stirring ice bath, resulting in a heterogeneous mixture. This mixture was stirred for 30 minutes and the solid was isolated by filtration and rinsed with hexanes. The beige solid was dried overnight in a vacuum oven (40° C.)

to yield 6-chloroimidazo[1,2-b]pyridazine-3-sulfonic acid (I-3). $^1$H NMR (400 MHz, MeOD-d$_4$) δ 8.51 (s, 1 H), 8.35 (d, J=9.6 Hz, 1 H), 7.76 (d, J=9.6 Hz, 1 H). MS m/z 234.0 (M+1)$^+$.

To a slurry of 6-chloroimidazo[1,2-b]pyridazine-3-sulfonic acid (I-3) (0.5 g, 2.1 mmol) in 1,2-dichloroethane (2 mL) was added phosphorus oxychloride (6 mL, 64 mmol) and stirred at 100° C. for 3 hours. The solvent was removed under vacuum and the excess POCl$_3$ was removed by azeotroping with DCM (3×50 mL) and diethyl ether (3×50 mL). The resulting beige residue was suspended in DCM (10 mL), cooled to 0° C. and triethylamine (0.88 mL, 6.3 mmol) was added. Ethylamine (2.5 mL of a 1 M solution in THF) was added drop wise and stirred for 20 minutes. The reaction mixture was diluted with DCM (40 mL) and extracted with brine (3×50 mL). The organic layer was dried over anhydrous sodium sulfate, filtered and reduced to dryness to yield 6-chloro-N-ethylimidazo[1,2-b]pyridazine-3-sulfonamide (I-4). $^1$H NMR (400 MHz, MeOD-d$_4$) δ 8.51 (s, 1 H), 8.22 (d, J=9.6 Hz, 1 H), 7.57 (d, J=9.6 Hz, 1 H), 3.12 (q, J=7.2 Hz, 2 H), 1.09 (t, J=7.2 Hz, 3 H). MS m/z 261.1 (M+1)$^+$.

Synthesis of ethyl
6-chloroimidazo[1,2-b]pyridazine-3-carboxylate
(I-7)

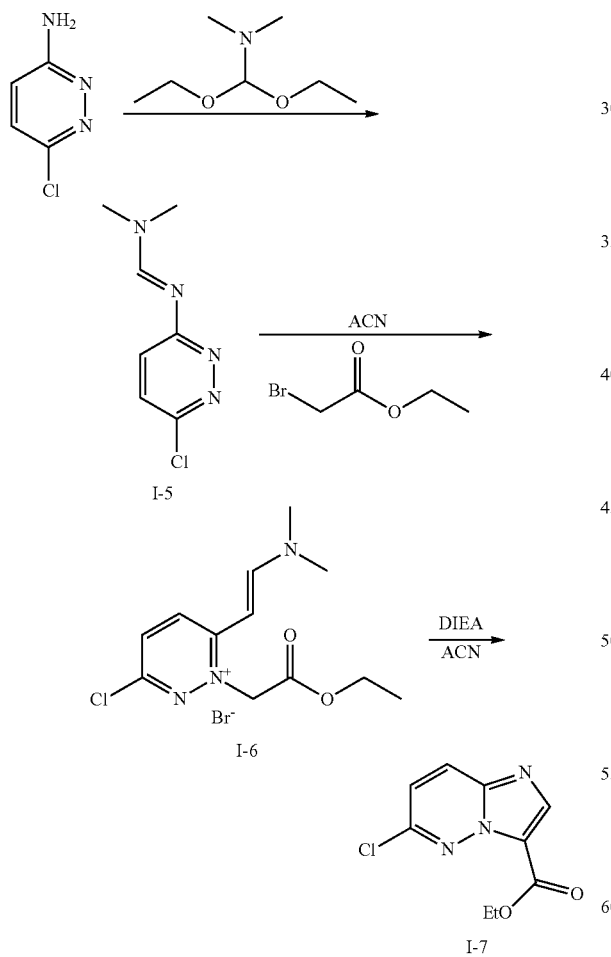

A mixture of 6-chloropyridazin-3-amine (5 g, 39 mmol) and N,N-diethylformamide dimethyl acetal (6.3 g, 43 mmol) was stirred at 110° C. for 1 hour. The mixture was then cooled to room temperature resulting in the homogeneous solution forming a solid cake. This was then treated with EtOAc (30 mL) and was sonicated for approximately 1 minute. The solid was isolated by filtration and dried under vacuum yielding N'-(6-chloropyridazin-3-yl)-N,N-dimethylformimidamide (I-5). MS m/z 185.1 (M+1)$^+$.

N'-(6-chloropyridazin-3-yl)-N,N-dimethylformimidamide (I-5) (4.2 g, 23 mmol) was dissolved in acetonitrile (50 mL) and ethylbromo acetate (7.6 mL, 69 mmol) was added in one portion. The resulting mixture was stirred for 3 hours at 85° C. The reaction mixture was cooled to room temperature resulting in precipitate formation. The solid was isolated by filtration, rinsed with diethyl ether and dried under vacuum to yield 3-chloro-6-(dimethylamino-methyleneamino)-1-ethoxycarbonylmethyl-pyridazin-1-ium bromide (I-6). MS m/z 351.0 (M+1)$^+$.

To a solution of 3-chloro-6-(dimethylamino-methyleneamino)-1-ethoxycarbonylmethyl-pyridazin-1-ium bromide (I-6) (3.4 g, 13 mmol) in ACN (60 mL) was added diisopropylethylamine (3 g, 26 mmol). The reaction mixture was stirred at room temperature for 3 hours. The solvent was removed and the residue was triturated with water and dried to yield ethyl 6-chloroimidazo[1,2-b]pyridazine-3-carboxylate (I-7). MS m/z 226.0 (M+1)$^+$. $^1$H NMR (400 MHz, CDCl$_3$) δ 8.36 (s, 1 H), 8.01 (d, J=9.6 Hz, 1 H), 7.26 (d, J=9.6 Hz, 1 H), 4.46 (q, J=7.2 Hz, 2 H), 1.43 (t, J=7.2 Hz, 3 H).

Synthesis of 4-(3-bromoimidazo[1,2-b]pyridazin-6-yl)-3-(3-fluorophenyl)morpholine (I-12)

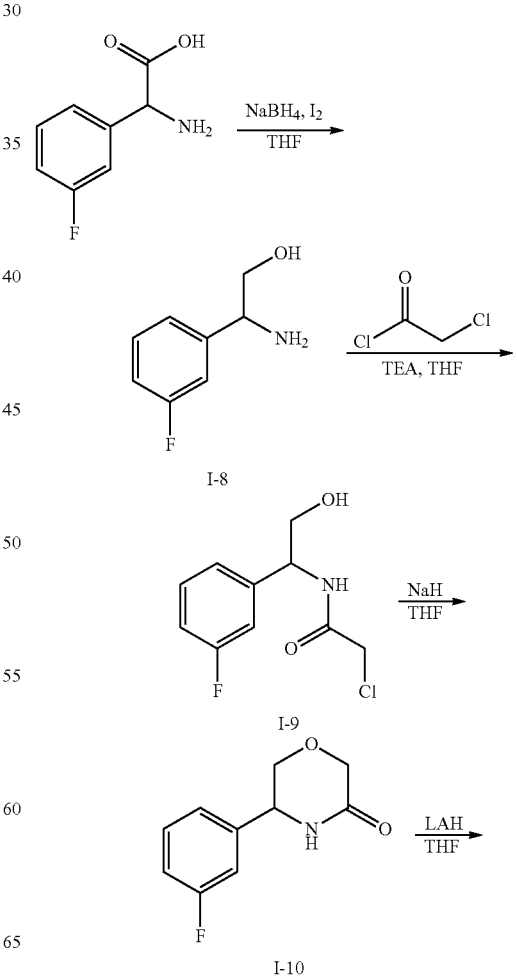

-continued

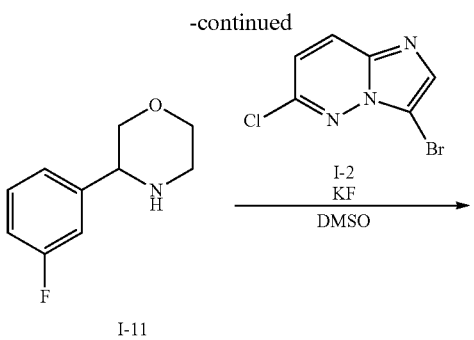

D,L-3-fluorophenylglycine (10 g, 59.2 mmol) was added to a suspension of NaBH₄ (5.37 g, 142 mmol) in THF (200 mL). The suspension was cooled to 0° C., and an iodine solution (15 g, 59.2 mmol) in THF was added drop wise. The resulting solution was heated while stirring overnight. This solution was cooled to room temperature, quenched with a 20% KOH solution (150 mL) and extracted with DCM (3×). The organics were combined, dried over MgSO₄ and the solvent was removed using a rotary evaporator. The product was purified by flash chromatography (0-10% MeOH/EtOAc) to yield 2-amino-2-(3-fluorophenyl)ethanol (I-8) as a white residue.

Triethylamine (8.15 mL, 58.6 mmol) was added to a solution of 2-amino-2-(3-fluorophenyl)ethanol (I-8) (7.57 g, 48.8 mmol) in THF at 0° C. and chloroacetyl chloride (5.08 mL, 58.6 mmol) was added drop wise. The mixture was cooled to 0° C. and stirred for 1 hour. The reaction mixture was quenched with water and the organic phase was washed with 0.5 N HCl, saturated NaHCO₃, brine, and dried over MgSO₄. The organic phase was concentrated and purified with flash chromatography (50% EtOAc/hexanes) to yield 2-chloro-N-(1-(3-fluorophenyl)-2-hydroxyethyl)acetamide (I-9) as a yellow solid.

A solution of 2-chloro-N-(1-(3-fluorophenyl)-2-hydroxyethyl)acetamide (I-9) (5.5 g, 24 mmol) in THF (150 mL) was slowly added to a suspension of NaH (1.05 g, 26 mmol) in THF (600 mL) at 0° C. The heterogeneous solution was warmed to room temperature and stirred overnight. The reaction mixture was quenched, concentrated and EtOAc was added to the residue. This solution was washed with water and brine and the organic phase was dried over MgSO₄, filtered and concentrated to yield 5-(3-fluorophenyl)morpholin-3-one (I-10).

A solution of 5-(3-fluorophenyl)morpholin-3-one (I-10) (4.56 g, 23.4 mmol) in THF at 0° C. was treated with lithium aluminum hydride (4.3 g, 107 mmol) in a single portion. The suspension was warmed to room temperature and stirred overnight. The reaction mixture was quenched with Na₂SO₄.10 H₂O and stirred for 4 hours. The heterogeneous solution was filtered through a celite pad and the filtrate was concentrated and purified with flash chromatography (5-10% methanol/EtOAc) to obtain 3-(3-fluorophenyl)morpholine (I-11) as a clear oil. ¹H NMR (400 MHz, CDCl₃) δ 7.28 (m, 1H), 7.13 (m, 2H), 6.97 (m, 1H), 3.93 (dd, J=6.5 Hz, 1H), 3.89 (m, 1H), 3.81 (dd, 1H), 3.64 (td, J=7.1 Hz, 1H), 3.35 (m, 1H), 3.12 (td, J=7.2 Hz, 1H), 3.02 (m, 1H).

A suspension of 3-(3-fluorophenyl)morpholine (I-11) (1.59 g, 6.9 mmol), 3-bromo-6-chloroimidazo[1,2-b]pyridazine (I-2) (1.5 g, 8.29 mmol) and potassium fluoride (1.6 g, 27.6 mmol) in DMSO (6 mL) was heated at 180° C. for 18 hours while stirring. The resulting solution was cooled to room temperature and purified by HPLC to yield 4-(3-bromoimidazo[1,2-b]pyridazin-6-yl)-3-(3-fluorophenyl)morpholine (I-12) as a yellow foam.

Synthesis of 2-(3-fluorophenyl)pyrrolidine (I-4)

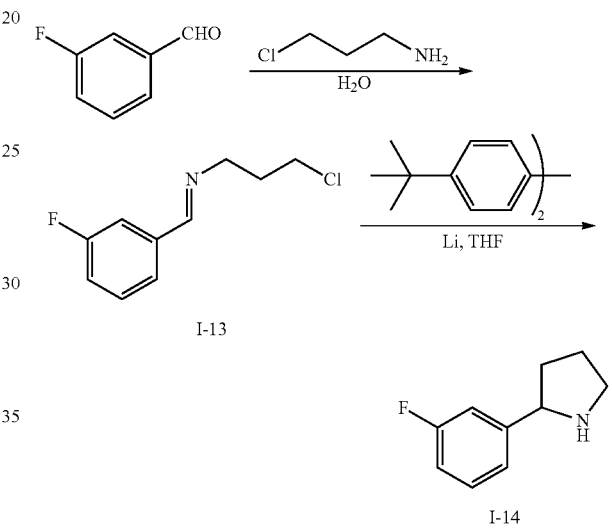

3-Chloropropan-1-amine hydrochloride (43 g, 331 mmol) was added to a suspension of 3-fluorobenzaldehyde (41 g, 331 mmol) and sodium carbonate (39 g, 364 mmol) in water (100 mL). The slurry was stirred overnight. The resulting solution was extracted with EtOAc (3×150 mL) and the organic layer was dried with sodium sulfate. The EtOAc was removed to yield 3-chloro-N-(3-fluorobenzylidene)propan-1-amine (I-13) as a light yellow oil. MS m/z 200.1 (M+1)⁺.

To a solution of lithium granules (5.5 g, 800 mmol) and 4,4'-di-tert-butylbiphenyl (5.7 g, 21 mmol) in THF (50 mL) at −78° C. was added 3-chloro-N-(3-fluorobenzylidene)propan-1-amine (I-13) (53 g, 266 mmol). The solution was stirred at −78° C. for 2 hours then quenched with water and warmed to 20° C. The solids were removed by filtration and the mother liquor was reduced to dryness. The resulting residue was reconstituted in EtOAc, washed with 1N HCl (3×25 mL). The combined aqueous layer was extracted with EtOAc. The aqueous layer was then neutralized with 1N NaOH solution and extracted with EtOAc (3×100 mL). The combined organic layers were dried with sodium sulfate, filtered and the solvent removed to yield 2-(3-fluorophenyl)pyrrolidine (I-14) as a light yellow oil. MS m/z 165.2 (M+1)⁺. Note: In some instances the hydrochloride salt of (R)-(3-fluorophenyl)pyrrolidine (I-14A) was purchased from NetChem Company, New Brunswick, N.J., USA.

Synthesis of (R)-6-(2-(3-fluorophenyl)pyrrolidin-1-yl)imidazo[1,2-b]pyridazin-3-amine (I-17)

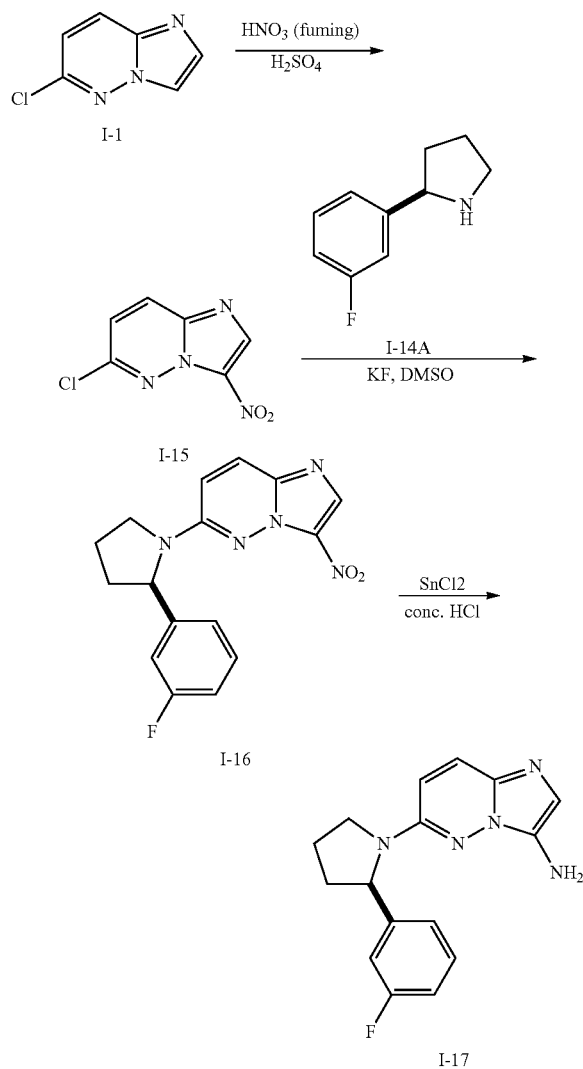

To a solution of 6-chloroimidazo[1,2-b]pyridazine (I-1) (2.5 g, 16.3 mmol) in conc. $H_2SO_4$ (2.5 mL) was added fuming $H_2NO_3$ (1.5 mL). The reaction was heated at 100° C. for 4 hours. The mixture was slowly poured onto ice and stirred at room temperature for 0.5 hour. The yellow solid formed was filtered and dried at 40° C. under vacuum overnight to yield 6-chloro-3-nitroimidazo[1,2-b]pyridazine (I-15). MS m/z 199.1 (M+1)$^+$.

To a solution of 6-chloro-3-nitroimidazo[1,2-b]pyridazine (I-15) (2.0 g, 10.1 mmol) in DMSO (20 mL) was added KF (2.9 g, 50.5 mmol) and (R)-2-(3-fluorophenyl)pyrrolidine (I-14A) (2.2 g, 11.1 mmol). The mixture was heated at 120° C. overnight. The mixture was poured into water and extracted with EtOAc. The organic layer was washed with brine, dried over sodium sulfate, filtered and concentrated. The crude was purified by column chromatography on silica gel with DCM/MeOH 0 to 10% gradient as eluant to yield (R)-6-(2-(3-fluorophenyl)pyrrolidin-1-yl)-3-nitroimidazo[1,2-b]pyridazine (I-16). MS m/z 328.1 (M+1)$^+$.

To (R)-6-(2-(3-fluorophenyl)pyrrolidin-1-yl)-3-nitroimidazo[1,2-b]pyridazine (I-16) (2.6 g, 7.94 mmol) in conc. HCl (20 mL) at 0° C. was slowly added $SnCl_2$ (9.0 g, 47.64 mmol) in portions. The ice bath was removed and replaced with an oil bath. The mixture was heated to 100° C. and stirred at 100° C. for 15 minutes. The reaction was cooled to 0° C. and quenched with water (20 mL). The pH of the reaction was made basic using 6N NaOH. The mixture was extracted with EtOAc (3×100 mL). The combined organic layer was washed with brine, separated, dried over sodium sulfate and concentrated. The crude was purified by column chromatography on silica gel with DCM/MeOH 0 to 10% gradient as eluant to yield (R)-6-(2-(3-fluorophenyl)pyrrolidin-1-yl)imidazo[1,2-b]pyridazin-3-amine (I-17). $^1$H NMR (400 MHz, DMSO-$d_6$) δ 7.52 (d, J=10 Hz, 1 H), 7.35 (td, J=6.0, 8.4 Hz, 1 H), 7.13-7.00 (m, 3 H), 6.75 (s, 1 H), 6.29 (d, J=10 Hz, 1 H), 5.13 (dd, J=8.0, 2.8 Hz, 1 H), 4.98 (bs, 2 H), 3.94-3.86 (m, 1 H), 3.67-3.58 (m, 1 H), 2.50-2.36 (m, 1 H), 2.05-1.90 (m, 2 H), 1.90-1.82 (m, 1H). MS m/z 298.10 (M+1)$^+$.

Synthesis of (S)-2,2,3,3-tetrafluoro-5-(3-fluorophenyl)pyrrolidine (I-22)

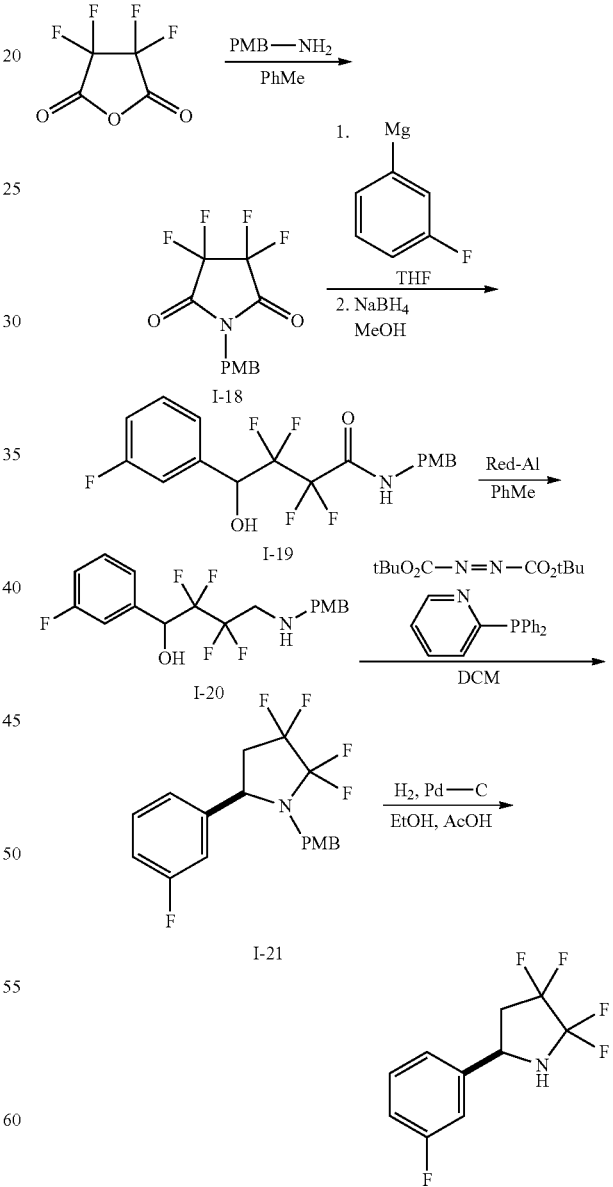

A solution of 3,3,4,4-tetrafluorodihydrofuran-2,5-dione (5.17 g, 30.0 mmol) and p-methoxybenzylamine (3.9 mL. 30.0 mmol) in toluene (30 mL) was heated to 80° C. for 16 hours. Subsequently, the reaction was reduced to dryness, triturated with Et₂O/hexanes and dried to yield 3,3,4,4-tetrafluoro-1-(4-methoxybenzyl)pyrrolidine-2,5-dione (I-18) as an off white solid. MS m/z 293.2 (M+1)⁺.

To a solution of 3,3,4,4-tetrafluoro-1-(4-methoxybenzyl) pyrrolidine-2,5-dione (I-18) (2.66 g, 9.1 mmol) in THF (15 mL) at 0° C. was added (3-fluorophenyl)magnesium bromide (10.9 mL of 1 M solution in THF) drop wise. The solution was stirred for 16 hours at room temperature and quenched at 0° C. with MeOH. NaBH₄ (0.52 g, 13.7 mmol) was added and stirred at room temperature for 2 hours. The reaction was quenched with aq. NH₄Cl and extracted with EtOAc (2×75 mL). The combined organic layer was dried over sodium sulfate, filtered and reduced to dryness. The crude product was purified on silica gel column chromatography with DCM/EtOAc gradient as eluant to yield 2,2,3,3-tetrafluoro-4-(3-fluorophenyl)-4-hydroxy-N-(4-methoxybenzyl)butanamide (I-19) as a colorless oil. MS m/z 390.1 (M+1)⁺.

To a solution of 2,2,3,3-tetrafluoro-4-(3-fluorophenyl)-4-hydroxy-N-(4-methoxybenzyl)butanamide (I-19) (2.0 g, 5.2 mmol) in toluene was added NaAlH₂(OCH₂CH₂OCH₃)₂ (4.37 mL of a 70% solution in toluene) and heated for 2 hours. Upon cooling the reaction was quenched with aq. NaOH and diluted with water. The mixture was extracted with EtOAc (2×75 mL). The combined organic layer was dried over magnesium sulfate, filtered and reduced to dryness. The crude product was purified on silica gel column chromatography with hexanes/EtOAc gradient as eluant to yield 2,2,3,3-tetrafluoro-1-(3-fluorophenyl)-4-((4-methoxybenzyl)amino) butan-1-ol (I-20) as a yellow oil. MS m/z 376.3 (M+1)⁺.

To a solution of 2,2,3,3-tetrafluoro-1-(3-fluorophenyl)-4-((4-methoxybenzyl)amino)butan-1-ol (I-20) (1.39 g, 3.7 mmol) and diphenyl-2-pyridylphosphine (1.17 g, 4.4 mmol) in DCM (15 mL) was added di-tert-butyl azodicarboxylate (1.02 g, 4.4 mmol). The reaction was stirred at room temperature for 20 hours then cold HCl (2 mL of a 1 M solution in Et₂O) was added and stirred for 30 minutes. Subsequently 1 N HCl (20 mL) was added and the reaction extracted with DCM (2×50 mL). The combined organic layer was dried over magnesium sulfate, filtered and reduced to dryness. The crude product was purified on silica gel column chromatography with hexanes/EtOAc gradient as eluant to yield 2,2,3,3-tetrafluoro-5-(3-fluorophenyl)-1-(4-methoxybenzyl)pyrrolidine as a pale yellow oil. MS m/z 358.3 (M+1)⁺. The racemic mixture was resolved on a 21×250 mm chiralpak AD-H column to yield (S)-2,2,3,3-tetrafluoro-5-(3-fluorophenyl)-1-(4-methoxybenzyl)pyrrolidine opticaly pure.

(S)-2,2,3,3-tetrafluoro-5-(3-fluorophenyl)-1-(4-methoxybenzyl)pyrrolidine (I-21) (0.45 g, 1.3 mmol) was dissolved in EtOH (5 mL) and AcOH (0.05 mL). 10% Pd/C (90 mg) was added and the reaciton was degassed and backfilled with hydrogen. The reaction was stirred at room temperature for 16 hours under a hydrogen atmosphere then filtered through a pad of celite and reduced to dryness to yield (S)-2,2,3,3-tetrafluoro-5-(3-fluorophenyl)pyrrolidine (I-22) as a clear colorless oil. MS m/z 238.1 (M+1)⁺.

Synthesis of 2-(3-fluorphenyl)pyrrolidine-2-d (I-25)

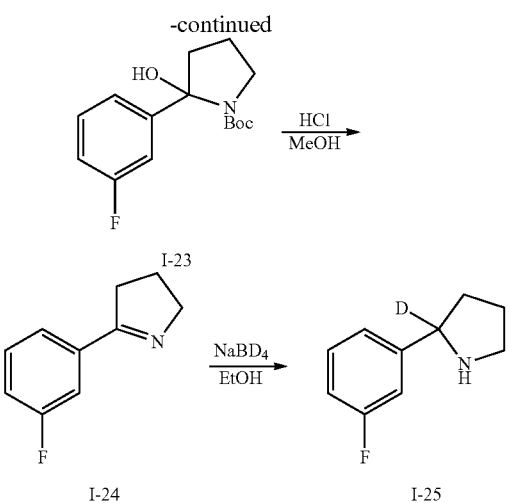

To a solution of tert-butyl 2-oxopyrrolidine-1-carboxylate (2 g, 10.8 mmol) in THF (30 mL) at 0° C. under argon was slowly added (3-fluorophenyl)magnesium bromide (14.5 mL of a 1 M solution in THF, 14.5 mmol). The resulting solution was warmed to room temperature and stirred for 3 hours. The reaction mixture was quenched with MeOH (50 mL) and stirred for 1 hour. The mixture was reduced to dryness and the resulting residue was reconstituted in EtOAc (150 mL). This solution was extracted with brine (3×100 mL) and saturated sodium bicarbonate solution (3×100 mL). The EtOAc was then dried over anhydrous sodium sulfate, filtered and reduced to dryness yielding the crude tert-butyl 2-(3-fluorophenyl)-2-hydroxypyrrolidine-1-carboxylate (I-23). MS m/z 226.1 (M−56)⁺.

To a solution of tert-butyl 2-(3-fluorophenyl)-2-hydroxypyrrolidine-1-carboxylate (I-23) (1.8 g, 3.5 mmol) in MeOH (30 mL) was added concentrated HCl (3 mL, 34.9 mmol). The resulting solution was stirred for 2 hours at 90° C. and then neutralized with a saturated sodium bicarbonate. The resulting mixture was extracted with EtOAc (3×100 mL). The combined organic layer was dried over anhydrous sodium sulfate, filtered and reduced to dryness to yield 5-(3-fluorophenyl)-3,4-dihydro-2H-pyrrole (I-24). MS m/z 164.1 (M+1)⁺.

To a solution of 5-(3-fluorophenyl)-3,4-dihydro-2H-pyrrole (I-24) (1.0 g, 6.1 mmol) in ethanol (30 mL) was added sodium borodeuteride (0.77 g, 18.3 mmol). The reaction mixture was stirred at room temperature for 72 hours then quenched with saturated sodium bicarbonate (50 mL) and extracted with EtOAc (3×50 mL). The combined organic layer was dried over anhydrous sodium sulfate, filtered and reduced to dryness to yield 2-(3-fluorophenyl)pyrrolidine-2-d (I-25). MS m/z 167.1 (M+1)⁺.

Synthesis of 2-(3-fluorophenyl)pyrrolidine-5,5-d2 (I-27)

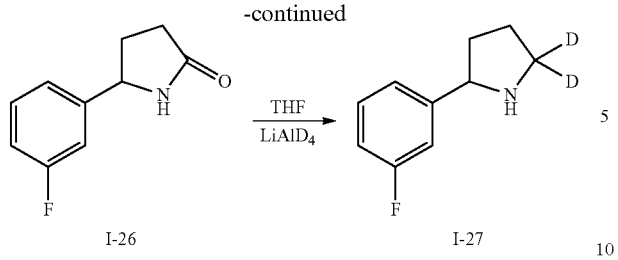

I-26 → I-27

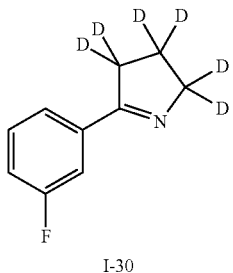

I-30

To (3-fluorophenyl)magnesium bromide in (100 mL of 1 M solution in THF, 100 mmol) cooled to −78° C. under argon was added a solution of pyrrolidine-2,5-dione (5 g, 50.5 mmol) in DCM (20 mL) over a period of 10 minutes. The resulting solution was slowly warmed to room temperature and stirred overnight. Sodium cyanoborohydride (3.8 g, 60.2 mmol) was then added to the reaction mixture and stirred for 1 hour. The pH was adjusted to 3-4 by the addition of HCl (20 mL of a 6 M aq. solution, 120 mmol) drop wise. After 1 hour the mixture was neutralized with sodium hydroxide (4.8 g, 120 mmol) in ethanol (50 mL) and water (10 mL) and extracted with DCM (3×100 mL). The combined organic layer was dried over anhydrous sodium sulfate, filtered and reduced to dryness to yield 5-(3-fluorophenyl)pyrrolidin-2-one (I-26). MS m/z 180.1 (M+1)$^+$.

To a solution of 5-(3-fluorophenyl)pyrrolidin-2-one (I-26) (1.0 g, 5.6 mmol) in THF (10 mL) was added lithium aluminum deuteride (28 mL of 1 M solution in THF) and stirred for 3 hours at room temperature. The reaction mixture was quenched with MeOH (50 mL) and stirred for 1 hour. The solvents were removed and the resulting residue was reconstituted in EtOAc (60 mL) and washed with a saturated sodium bicarbonate. The organic layer was dried over anhydrous sodium sulfate, filtered and reduced to dryness to yield 2-(3-fluorophenyl)pyrrolidine-5,5-d$_2$ (I-27) as a colorless oil. MS m/z 168.1 (M+1)$^+$.

Synthesis of 5-(3-fluorophenyl)-3,4-dihydro-2H-pyrrole-2,2,3,3,4,4-d6 (I-30)

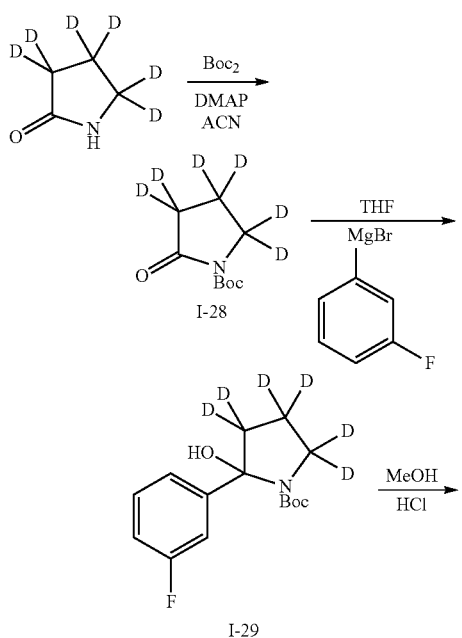

To a solution of 2-pyrrolidine-3,3,4,4,5,5-d$_6$ (0.5 g, 5.5 mmol) and N,N-dimethylpyridin-4-amine (70 mg, 0.6 mmol), in ACN (50 mL) at −5° C. was slowly added di-tert-butyl dicarbonate (2.4 g, 11 mmol) so not to exceed 0° C. The reaction mixture was stirred at room temperature for 3 hours then poured into water (200 mL). The resulting mixture was extracted with EtOAc (3×75 mL). The EtOAc fractions were combined and extracted with brine (3×50 mL), 1M HCl (1×50 mL), and saturated sodium bicarbonate (3×50 mL). The combined organic layer was dried over anhydrous sodium sulfate, filtered and reduced to dryness to yield tert-butyl-2-oxopyrrolidine-1-carboxylate-3,3,4,4,5,5-d$_6$ (I-28). MS m/z 136.1 (M−56)$^+$.

To a solution of tert-butyl-2-oxopyrrolidine-1-carboxylate-3,3,4,4,5,5-d$_6$ (I-28) (1.0 g, 5.2 mmol) in THF (30 mL) at 0° C. under argon gas was slowly added (3-fluorophenyl)magnesium bromide (10.5 mL of 1 M solution in THF, 10.5 mmol). The resulting solution was warmed to room temperature and stirred for 3 hours. The reaction mixture was diluted with MeOH (50 mL) and stirred for 1 hour. The solvents were removed and the resulting residue was reconstituted in EtOAc (150 mL). This solution was then extracted with brine (3×100 mL) and saturated sodium bicarbonate (3×100 mL). The combined organic layer was dried over anhydrous sodium sulfate, filtered and reduced to dryness to yield tert-butyl 2-(3-fluorophenyl)-2-hydroxypyrrolidine-1-carboxylate-3,3,4,4,5,5-d$_6$ (I-29). MS m/z 232.1 (M−56)$^+$.

To a solution of tert-butyl 2-(3-fluorophenyl)-2-hydroxypyrrolidine-1-carboxylate-3,3,4,4,5,5-d$_6$ (I-29) (1.0 g, 3.5 mmol) in MeOH (30 mL) was added concentrated HCl (2 mL, 23.3 mmol). The resulting solution was stirred for 2 hours at 90° C. then neutralized with saturated sodium bicarbonate. The resulting mixture was extracted with EtOAc (3×100 mL). The combined organic layer was dried over anhydrous sodium sulfate, filtered and reduced to dryness to yield 5-(3-fluorophenyl)-3,4-dihydro-2H-pyrrole-2,2,3,3,4,4-d$_6$ (I-30). MS m/z 170.1 (M+1)$^+$.

Synthesis of 2-(3-fluorophenyl)pyrrolidine-3,3,4,4,5,5-d6 (I-31)

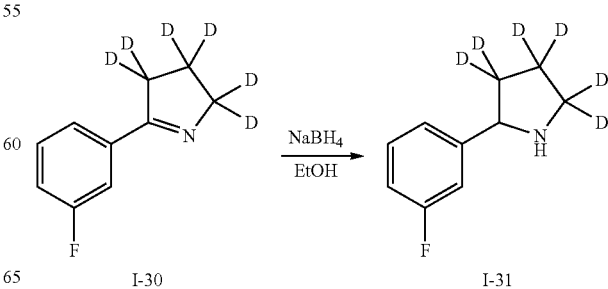

I-30 → I-31

To a solution of 5-(3-fluorophenyl)-3,4-dihydro-2H-pyrrole-2,2,3,3,4,4-$d_6$ (I-30) (0.4 g, 2.4 mmol) and ethanol (10 mL) was added sodium borohydride (0.4 g, 10.5 mmol). The reaction mixture was stirred at room temperature for 3 hours then quenched with saturated sodium bicarbonate (30 mL) and extracted with EtOAc (3×50 mL). The combined organic layer was dried over anhydrous sodium sulfate, filtered and reduced to dryness to yield 2-(3-fluorophenyl)pyrrolidine-3,3,4,4,5,5-$d_6$ (I-31). MS m/z 172.1 (M+1)$^+$.

Synthesis of 2-(3-fluorophenyl)pyrrolidine-2,3,3,4,4,5,5-d7 (I-32)

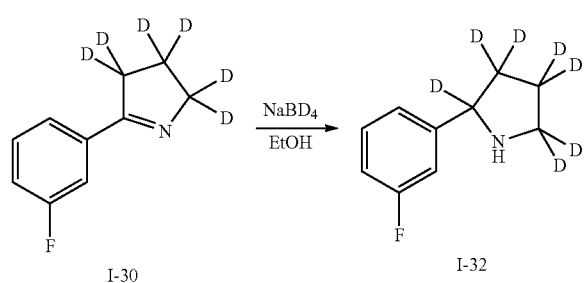

To a solution of 5-(3-fluorophenyl)-3,4-dihydro-2H-pyrrole-2,2,3,3,4,4-$d_6$ (I-30) (0.4 g, 2.4 mmol) and ethanol (10 mL) was added sodium borodeuteride (0.4 g, 9.5 mmol). The reaction mixture was stirred at room temperature overnight then quenched with saturated sodium bicarbonate (30 mL) and then extracted with EtOAc (3×50 mL). The EtOAc was dried over anhydrous sodium sulfate, filtered and reduced to dryness to yield 2-(3-fluorophenyl)pyrrolidine-2,3,3,4,4,5,5-$d_7$ (I-32). MS m/z 173.2 (M+1)$^+$.

Synthesis of (2S,4R)-3,3-difluoro-2-(3-fluorophenyl)-4-methylpyrrolidine (I-38)

To a suspension of NaH (3.0 g, 75 mmol) in DMF (100 mL) was added benzenethiol (5.1 mL, 50 mmol) at room temperature. The mixture was cooled to −60° C. and was added dibromodifluoromethane (14.0 mL, 150 mmol). The reaction was stirred at this temperature for 3 hours, quenched with water and extracted with hexanes. The organic layer was washed with brine, dried over sodium sulfate, filtered and reduced to dryness. The crude product was purified by silica gel column chromatography with hexanes as eluent to yield bromodifluoromethyl(phenyl)sulfane (I-33). MS m/z 240.1 (M+1)$^+$.

A mixture of TMSCl (2.0 g, 18.3 mmol) and magnesium (0.22 g, 9.2 mmol) in DMF (20 mL) was treated with bromodifluoromethyl(phenyl)sulfane (I-33) (1.1 g, 5.3 mmol) and stirred at room temperature for 1 hour. The reaction was reduced in volume to remove excess TMSCl then quenched with ice water and diluted with DCM. The organic layer was separated, washed with brine, dried over sodium sulfate, filtered and reduced to dryness. The crude product was purified by silica gel column chromatography with hexanes/EtOAc as eluent to yield (difluoro(phenylthio)methyl)trimethylsilane (I-34). MS m/z 233.1 (M+1)$^+$.

A mixture of (R)-2-methylpropane-2-sulfinamide (1.0 g. 8.3 mmol) and 3-fluorobenzaldehyde (0.93 g, 7.5 mmol) in toluene (20 mL) was treated with Ti(O-i-Pr)$_4$ (3.36 mL, 11.3 mmol) and heated at 50° C. for 18 hours. The reaciton was quenched with aq. NaHCO$_3$, extracted with toluene and the organic layer reduced to dryness. The crude product was purified by silica gel column chromatography with hexanes/EtOAc as eluent to yield (R)-(E)-N-(3-fluorobenzylidene)-2-methylpropane-2-sulfinamide (I-35). MS m/z 228.1 (M+1)$^+$.

To a mixture of (R)-(E)-N-(3-fluorobenzylidene)-2-methylpropane-2-sulfinamide (I-35) (0.21 g, 1.0 mmol) and (difluoro(phenylthio)methyl)trimethylsilane (I-34) (0.27 g, 1.1 mmol) in DMF (5 mL) at −40° C. was added tetrabutylammonium triphenyldifluorosilicate (TBAT) (0.27 g, 0.5 mmol) and stirred for 2 hours. The reaction was warmed to −20° C. for 4 hours and quenched at this temperature with aq. NH$_4$Cl. The reaction was extracted with EtOAc, washed with brine, dried over sodium sulfate, filtered and reduced to dryness. The crude product was purified by silica gel column chroma-

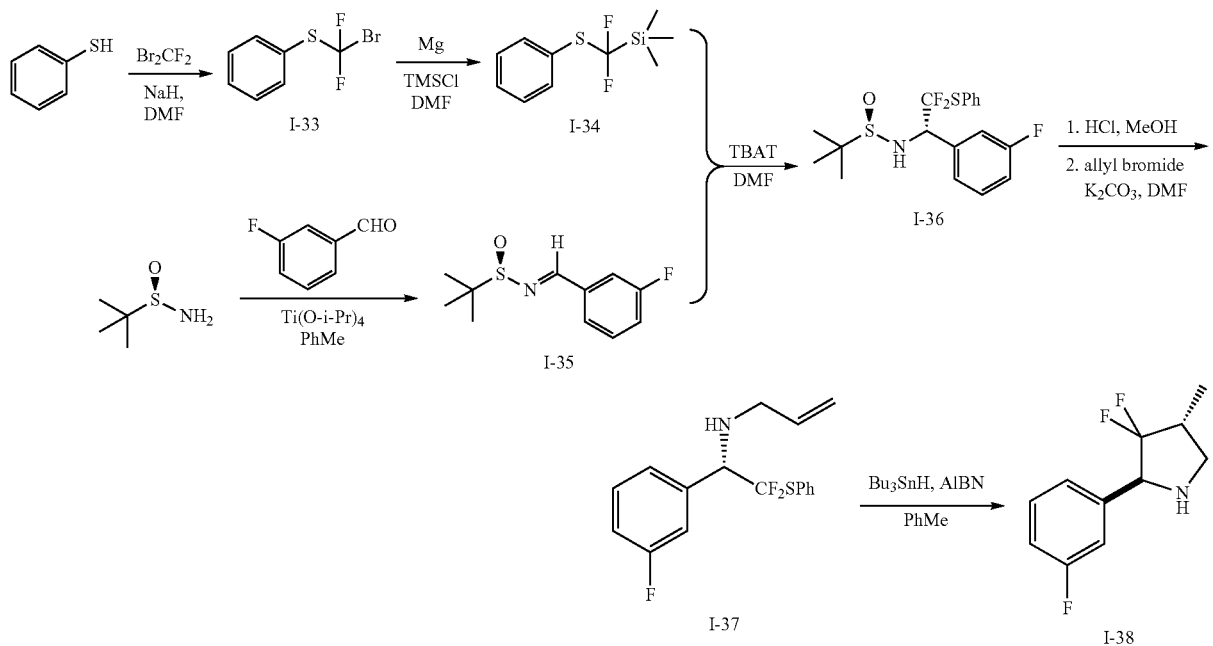

tography with hexanes/EtOAc as eluent to yield (R)-N-((S)-2,2-difluoro-1-(3-fluorophenyl)-2-(phenylthio)ethyl)-2-methylpropane-2-sulfinamide (I-36). MS m/z 388.1 (M+1)$^+$.

A solution of (R)-N-((S)-2,2-difluoro-1-(3-fluorophenyl)-2-(phenylthio)ethyl)-2-methylpropane-2-sulfinamide (I-36) (0.34 g, 0.9 mmol) in MeOH (10 mL) was treated with HCl (0.23 μL of 4 N solution in 1,4-dioxane) and stirred at room temperature for 1 hour. The reaction was reduced to dryness, re-dissolved in DMF (10 mL) and K$_2$CO$_3$ (0.25 g, 1.8 mmol) and allyl bromide (0.12 g, 1.0 mmol) were added. The mixture was stirred at room temperature for 18 hours then diluted with EtOAc. The organic layer was washed with aq. Na$_2$S$_2$O$_3$, brine, dried over sodium sulfate, filtered and reduced to dryness. The crude product was purified by silica gel column chromatography with hexanes/EtOAc as eluent to yield (S)-N-(2,2-difluoro-1-(3-fluorophenyl)-2-(phenylthio)ethyl)prop-2-en-1-amine (I-37). MS m/z 324.1 (M+1)$^+$.

A solution of (S)—N-(2,2-difluoro-1-(3-fluorophenyl)-2-(phenylthio)ethyl)prop-2-en-1-amine (I-37) (0.33 g, 1.0 mmol) and tributylstannane (41 μL, 1.5 mmol) in toluene (8 ml) was heated at 115° C. for 15 minutes then AIBN (20 mg) was added. The reaction was stirred for 16 hours at 115° C. then reduced to dryness. The crude product was purified by silica gel column chromatography with hexanes/EtOAc as eluent to yield (2S,4R)-3,3-difluoro-2-(3-fluorophenyl)-4-methylpyrrolidine (I-38). MS m/z 216.1 (M+1)$^+$.

Synthesis of (2R,4S)-4-fluoro-2-(3-fluorophenyl)pyrrolidine (I-44)

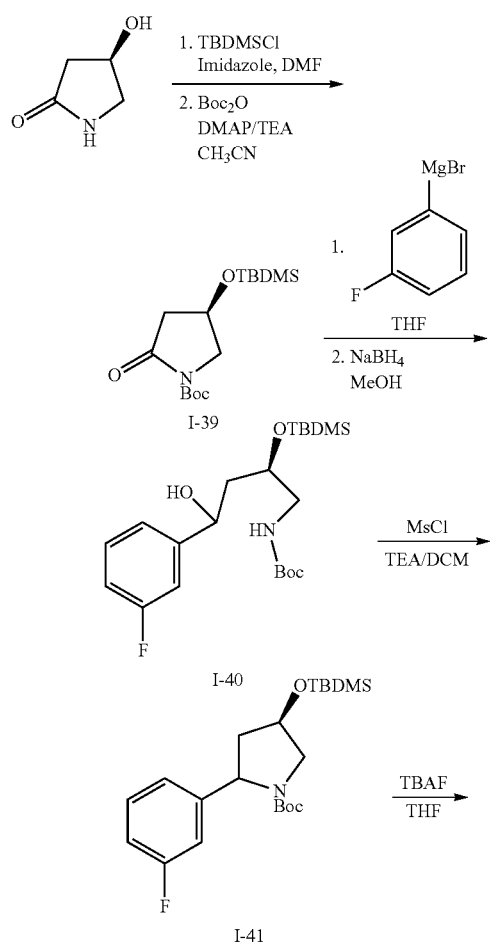

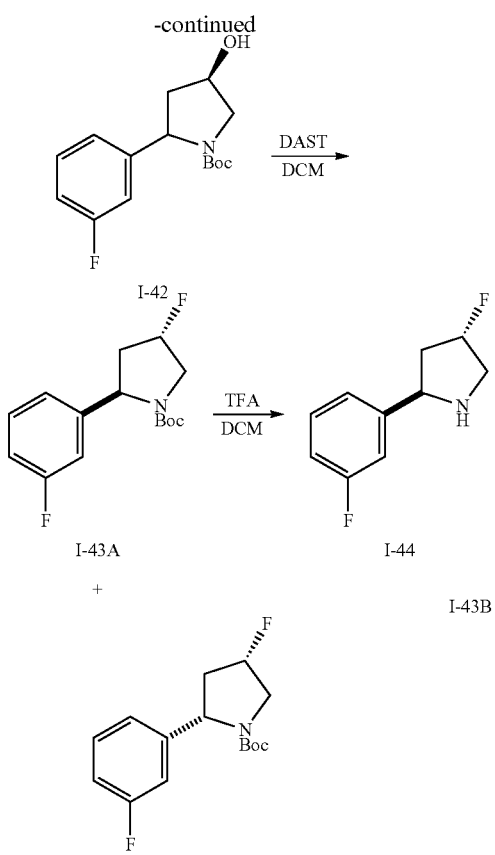

To a solution of (R)-4-hydroxypyrrolidin-2-one (5.0 g, 49.5 mmol) in DMF (25 mL) at 0° C. was added TBDMS-Cl (7.8 g, 52 mmol.) and imidazole (5.1 g, 74.25 mmol). The reaction was warmed to room temperature and stirred for 3 hours. The mixture was poured into water and the resulting precipitate was filtered and dried under vacuum overnight to yield (R)-tert-butyl 4-((tert-butyldimethylsilyl)oxy)-2-oxopyrrolidine-1-carboxylate. MS m/z 238.1 (M+23)$^+$. To a solution of this precipitate (10.9 g, 50.7 mmol) in CH$_3$CN (100 mL) at 0° C. under N$_2$ was added TEA (8.5 mL, 61 mmol), DMAP (3.1 g, 25.45 mmol) and di-tert-butyl dicarbonate (14.4 g, 66.2 mmol). The mixture was warmed to room temperature and stirred overnight. The mixture was poured into water and extracted with EtOAc. The organic layer was separated, washed with 1 N HCl, 1 N NaOH and brine, dried over sodium sulfate, filtered and concentrated to yield (R)-tert-butyl 4-(tert-butyldimethylsilyloxy)-2-oxopyrrolidine-1-carboxylate (I-39). MS m/z 338.1 (M+23)$^+$.

To a solution of (2R)-2-(tert-butyldimethylsilyloxy)-4-(3-fluorophenyl)-4-hydroxybutylcarbamate (I-39) (13.6 g, 43.2 mmol) in THF (100 mL) at 0° C. under N$_2$ was added slowly (3-fluorophenyl)magnesium bromide (52 mL of 1 M solution in THF, 51.84 mmol) over 1 hour. The reaction mixture was stirred at 0° C. for 1 hour. Methanol (80 mL) was added to the mixture followed by NaBH$_4$ (2.45 g, 64.8 mmol) at 0° C. The mixture was stirred at 0° C. for 1 hour then poured into 10% aq. NH$_4$Cl. The mixture was extracted with EtOAc, washed with brine, dried over sodium sulfate, filtered and concentrated. The crude was purified by column chromatography on silica gel with EtOAc/hexanes gradient as eluant to yield tert-butyl (2R)-2-(tert-butyldimethylsilyloxy)-4-(3-fluorophenyl)-4-hydroxybutylcarbamate (I-40). MS m/z 436.1 (M+23)$^+$.

To a solution of tert-butyl (2R)-2-(tert-butyldimethylsilyloxy)-4-(3-fluorophenyl)-4-hydroxybutylcarbamate (I-40) (15.8 g, 38.2 mmol) in DCM (120 mL) at −60° C. under N$_2$ was added TEA (16 mL, 114.6 mmol) and MsCl (3.3 mL, 42.0 mmol). The resulting mixture was stirred at −60° C. for 1 hour. The reaction was poured into water, washed with brine, dried over sodium sulfate, filtered and concentrated to yield the crude desired product (4R)-tert-butyl 4-(tert-butyldimethylsilyloxy)-2-(3-fluorophenyl)pyrrolidine-1-carboxylate (I-41). MS m/z 418.1 (M+23)⁺. The crude was used directly in the next step.

To a solution of (4R)-tert-butyl 4-(tert-butyldimethylsilyloxy)-2-(3-fluorophenyl)pyrrolidine-1-carboxylate (I-41) (18.1 g, 38.2 mmol) in THF (76 mL) at room temperature was added TBAF (50 mL of a 1.0 M in THF, 49.7 mmol). The mixture was stirred at room temperature for 2 hours then poured into water. The mixture was extracted with EtOAc, washed with water and brine, dried over sodium sulfate, filtered and concentrated. The mixture was purified by column chromatography on silica gel with EtOAc/hexanes gradient as eluant to yield (4R)-tert-butyl 2-(3-fluorophenyl)-4-hydroxypyrrolidine-1-carboxylate (I-42). MS m/z 304.1 (M+23)⁺. NOTE: In some instinces the two diastereomers were separated at this point by column chromatography on silica gel with EtOAc/hexanes gradient as eluant to yield (2R,4R)-tert-butyl 2-(3-fluorophenyl)-4-hydroxypyrrolidine-1-carboxylate (I-42A) and (2S,4R)-tert-butyl 2-(3-fluorophenyl)-4-hydroxypyrrolidine-1-carboxylate (I-42B). However, better resolution is achieved in the subsequent step.

To a solution of (4R)-tert-butyl 2-(3-fluorophenyl)-4-hydroxypyrrolidine-1-carboxylate (I-42) (2.7 g, 9.6 mmol) in DCM (25 mL) in a plastic bottle at −78° C. was added DAST (2.5 mL, 19.2 mmol). The mixture was stirred at −78° C. for 2 hours and then was warmed slowly to room temperature overnight. The mixture was added drop wise to aq. NaHCO₃ at 0° C. and was extracted with DCM. The organic layers were combined, washed with brine, dried over sodium sulfate, filtered and concentrated. The two diastereomers were separated by column chromatography on silica gel with EtOAc/hexanes gradient as eluant to yield (2R,4S)-tert-butyl 4-fluoro-2-(3-fluorophenyl)pyrrolidine-1-carboxylate (I-43A) (first eluting compound) and (2S,4S)-tert-butyl 4-fluoro-2-(3-fluorophenyl)pyrrolidine-1-carboxylate (I-43B). MS m/z 284.1 (M+1)⁺.

To a solution of (2R,4S)-tert-butyl 4-fluoro-2-(3-fluorophenyl)pyrrolidine-1-carboxylate (I-43A) (890 mg, 3.14 mmol) in DCM (5 mL) at room temperature was added TFA (5 mL). The mixture was stirred at room temperature for 2 hours. All the solvent was removed under reduced pressure. The crude was extracted with EtOAc, washed with aq. NHCO₃, brine, dried over sodium sulfate, filtered and concentrated to yield (2R,4S)-4-fluoro-2-(3-fluorophenyl)pyrrolidine (I-44). ¹H NMR (400 MHz, CDCl₃) δ 7.31-7.25 (m, 1 H), 7.15-7.10 (m, 2 H), 6.96-6.90 (m, 1 H), 5.29 (d, J=53.6 Hz 1 H), 4.50 (dd, J=9.6, 6.4 Hz, 1 H), 3.43-3.33 (m, 1 H), 3.31-3.28 (m, 1 H), 2.51 (ddd, J=21.2, 14.0, 6.4 Hz, 1 H), 2.23 (bs, 1 H), 1.79 (dddd, J=39.6, 14.4, 10.0, 4.4 Hz, 1 H). MS m/z 184.1 (M+1)⁺.

Synthesis of (2S,4R)-4-fluoro-2-(3-fluorophenyl) pyrrolidine (I-45)

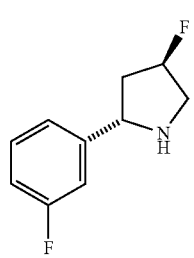

I-45

(2S,4R)-4-fluoro-2-(3-fluorophenyl)pyrrolidine (I-45) was prepared in the same manner as (2R,4S)-4-fluoro-2-(3-fluorophenyl)pyrrolidine (I-44) starting from (S)-4-hydroxypyrrolidin-2-one.

Synthesis of (2R,4R)-4-(tert-butyldimethylsilyloxy)-2-(3-fluorophenyl)pyrrolidine (I-46A)

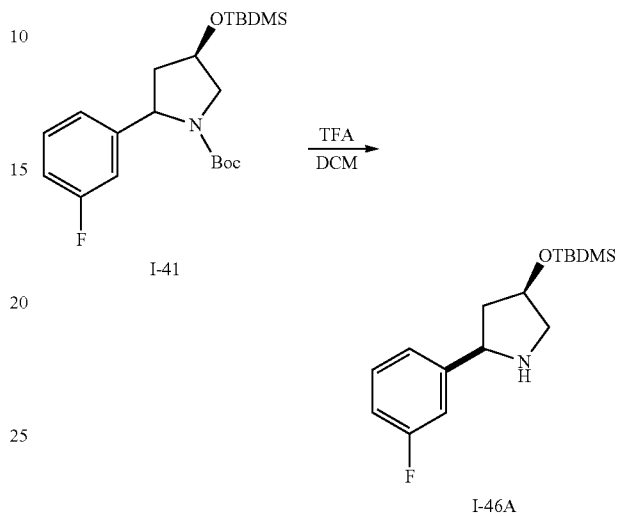

To a solution of (4R)-tert-butyl 4-(tert-butyldimethylsilyloxy)-2-(3-fluorophenyl)pyrrolidine-1-carboxylate (I-41) (400 mg, 1.01 mmol) in DCM (2 mL) at room temperature was added TFA (2 mL). The mixture was stirred at room temperature for 2 hours. All the solvent was removed under reduced pressure. The crude was purified by column chromatography on silica gel with EtOAc/hexanes gradient as eluant to yield (2R,4R)-4-(tert-butyldimethylsilyloxy)-2-(3-fluorophenyl)pyrrolidine (I-46A) (first eluting compound) and (2S,4R)-4-(tert-butyldimethylsilyloxy)-2-(3-fluorophenyl) pyrrolidine (I-46B) (second eluting compound). MS m/z 296.2 (M+1)⁺.

Synthesis of (R)-4,4-difluoro-2-(3-fluorophenyl) pyrrolidine (I-49)

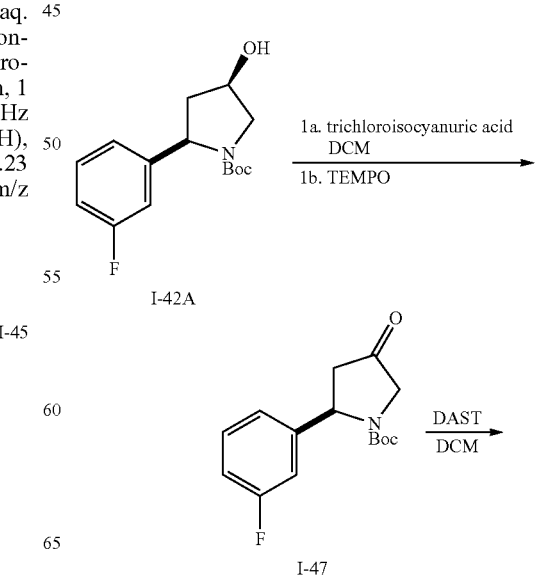

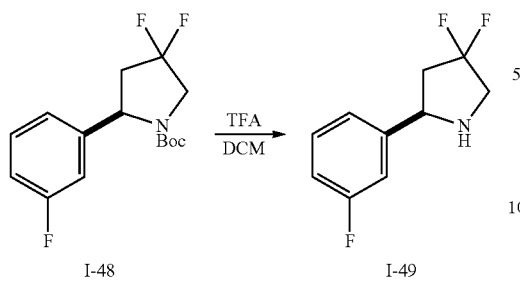

Synthesis of (R)-6-(4,4-difluoro-2-(3-fluorophenyl)pyrrolidin-1-yl)-3-nitroimidazo[1,2-b]pyridazine (I-50)

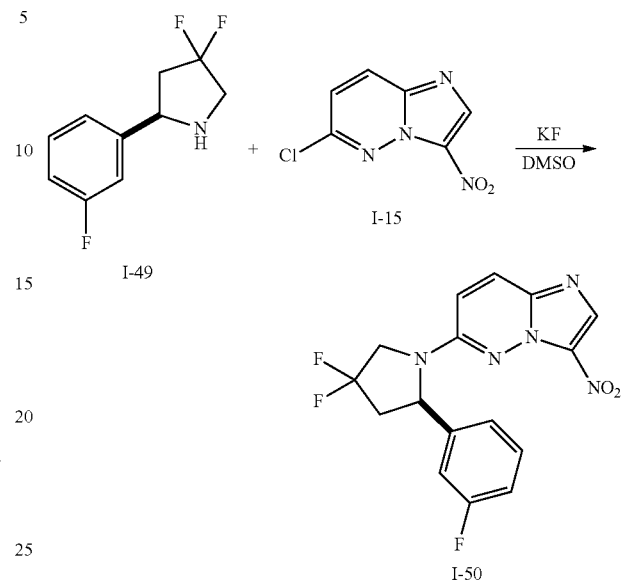

To a solution of (2R,4R)-tert-butyl 2-(3-fluorophenyl)-4-hydroxypyrrolidine-1-carboxylate (I-42A) (1.4 g, 5.0 mmol) and trichloroisocyanuric acid (1.2 g, 5.0 mmol) in DCM (70 mL) at −10° C. was added 2,2,6,6-tetramethylpiperidine-1-oxyl (TEMPO) (0.08 g, 0.5 mmol). The mixture was stirred at −10° C. for 15 minutes, then to room temperature over 1 hour and subsequently poured into cold saturated sodium bicarbonate solution containing ice while stirring. The organic layer was separated washed with brine, dried over anhydrous sodium sulfate, filtered and reduced to dryness to yield (R)-tert-butyl 2-(3-fluorophenyl)-4-oxopyrrolidine-1-carboxylate (I-47) as a light yellow oil. $^1$H NMR (400 MHz, MeOD-$d_4$) δ 7.40 (q, J=7.6 Hz, 1 H), 7.01 (d, J=7.6 Hz, 1 H), 7.03-6.99 (m, 2 H), 5.34 (bs, 1 H), 4.07-3.91 (m, 2 H), 3.30 (dd, J=18.8, 10.0 Hz, 1 H), 2.50 (dd, J=18.8, 3.2 Hz, 1 H), 1.31 (bs, 9H). MS m/z 224.1 (M−56)$^+$.

To a solution of (R)-tert-butyl 2-(3-fluorophenyl)-4-oxopyrrolidine-1-carboxylate (I-47) (1.3 g, 4.8 mmol) in DCM (15 mL) in a plastic bottle at −78° C. was added DAST (1.9 mL, 3 eq.) drop wise. The resulting orange homogeneous solution was stirred at −78° C. for 30 minutes. The solution was then warmed to room temperature and continued to stir for an additional 2 hours. The resulting solution was poured into stirring ice water (100 mL) and agitated for 15 minutes then extracted with DCM (3×50 mL). The DCM fractions were combined and dried over sodium sulfate, filtered and reduced to dryness yielding an orange film. The crude product was purified using a flash column chromatography on silica with hexanes/EtOAc gradient as eluant to yield (R)-tert-butyl 4,4-difluoro-2-(3-fluorophenyl)pyrrolidine-1-carboxylate (I-48) as a light yellow oil. $^1$H NMR (400 MHz, MeOD-$d_4$) δ 7.39 (q, J=7.6 Hz, 1 H), 7.11 (d, J=7.6 Hz, 1 H), 7.04-6.99 (m, 2 H), 5.03 (bs, 1 H), 4.02-3.89 (m, 2 H), 2.99-2.86 (m, 1 H), 2.39-2.28 (m, 1 H), 1.20 (bs, 9 H). MS m/z 246.1 (M−56)$^+$.

To a solution of (R)-tert-butyl 4,4-difluoro-2-(3-fluorophenyl)pyrrolidine-1-carboxylate (I-48) (0.9 g, 3.0 mmol) in DCM (20 mL) was added TFA (2 mL, 27 mmol) and stirred at room temperature for 2 hours. The reaction was cooled to 0° C. and a saturated sodium bicarbonate solution was added while rapidly stirring. The organic phase was washed with a saturated sodium bicarbonate solution, dried over anhydrous sodium sulfate, filtered and reduced to dryness yielding (R)-4,4-difluoro-2-(3-fluorophenyl)pyrrolidine (I-49) as a light yellow oil. $^1$H NMR (400 MHz, MeOD-$d_4$) δ 7.40 (q, J=1 H), 7.23 (d, J=8.8 Hz, 1 H), 7.20 (d, J=10.0 Hz, 1 H), 7.05 (dt, J=8.8, 2.4 Hz, 1 H), 4.41 (dd, J=10.4, 7.2 Hz, 1 H), 3.48 (q, J=12.0 Hz, 1 H), 3.30 (q, J=15.2 Hz, 1 H), 2.74-2.63 (m, 1 H), 2.29-2.14 (m, 1 H). MS m/z 202.1 (M+1)$^+$.

A mixture of (R)-4,4-difluoro-2-(3-fluorophenyl)pyrrolidine (I-49) (55 mg, 0.27 mmol), 6-chloro-3-nitroimidazo[1,2-b]pyridazine (I-15) (55 mg, 0.5 mmol) and spray dried potassium fluoride (80 mg, 1.4 mmol) in DMSO (2 mL) was heated at 85° C. overnight. The resulting orange-brown slurry was poured into stirring water (30 mL). This heterogeneous mixture was extracted with EtOAc (3×30 mL). The organic layers were combined and extracted with brine (3×50 mL), dried over anhydrous sodium sulfate, filtered and reduced to dryness. The crude product was purified using a flash column chromatography on silica gel with hexanes/EtOAc gradient as eluant to yield (R)-6-(4,4-difluoro-2-(3-fluorophenyl)pyrrolidin-1-yl)-3-nitroimidazo[1,2-b]pyridazine (I-50). MS m/z 364.1 (M+1)$^+$.

Synthesis of ethyl 6-((3S)-2-(3-fluorophenyl)-3-hydroxypyrrolidin-1-yl)imidazo[1,2-b]pyridazine-3-carboxylate (I-54)

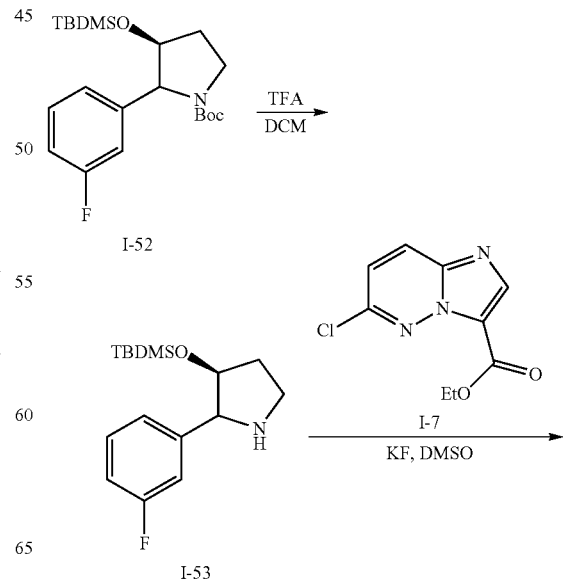

-continued

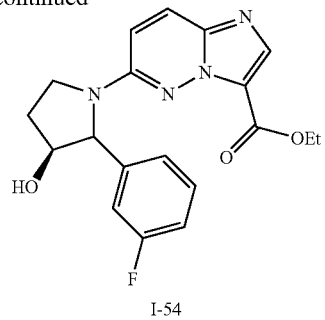

I-54

(3S)-tert-butyl 3-(tert-butyldimethylsilyloxy)-2-(3-fluorophenyl)pyrrolidine-1-carboxylate (I-52) was prepared in the same manner as (4R)-tert-butyl 4-(tert-butyldimethylsilyloxy)-2-(3-fluorophenyl)pyrrolidine-1-carboxylate (I-41) starting from commercially available (S)-3-hydroxypyrrolidin-2-one.

To a solution of (3S)-tert-butyl 3-(tert-butyldimethylsilyloxy)-2-(3-fluorophenyl)pyrrolidine-1-carboxylate (I-52) (660 mg, 1.67 mmol) in DCM (2.5 mL) at room temperature was added TFA (2.5 mL). The mixture was stirred at room temperature for 1 hour. All the solvents were removed under reduced pressure. The residue was dissolved in EtOAc, washed with saturated aq. NaHCO$_3$, water and brine, dried over sodium sulfate, filtered and concentrated. The crude was purified by column chromatography on silica gel with EtOAc/hexanes gradient as eluant to yield (3S)-3-(tert-butyldimethylsilyloxy)-2-(3-fluorophenyl)pyrrolidine (I-53). MS m/z 296.1 (M+1)$^+$.

To a suspension of ethyl 6-chloroimidazo[1,2-b]pyridazine-3-carboxylate (I-7) (128 mg, 0.565 mmol) in DMSO (2.5 mL) was added (3S)-3-(tert-butyldimethylsilyloxy)-2-(3-fluorophenyl)pyrrolidine (I-53) (167 mg, 0.565 mmol) and potassium floride (328 mg, 5.65 mmol). The mixture was heated at 120° C. overnight. The mixture was poured into water and extracted with EtOAc twice. The combined organic layers were washed with brine, dried over sodium sulfate, filtered and concentrated. The crude product was purified by column chromatography on silica gel with EtOAc/hexanes gradient as eluant to yield ethyl 6-((3S)-2-(3-fluorophenyl)-3-hydroxypyrrolidin-1-yl)imidazo[1,2-b]pyridazine-3-carboxylate (I-54). MS m/z 371.1 (M+1)$^+$.

Synthesis of (R)-6-(2-(3-fluorophenyl)pyrrolidin-1-yl)imidazo[1,2-b]pyridazine-3-carboxylic acid (I-55)

Protocol 1

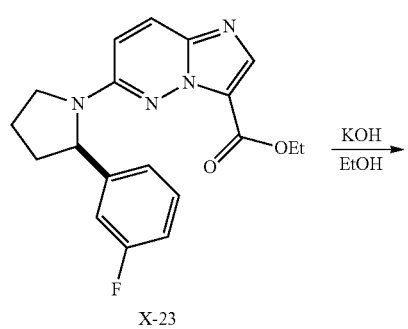

X-23

-continued

I-55

To a solution of potassium hydroxide (6.2 g, 110 mmol) in ethanol (150 mL) and water (5 mL) was added (R)-ethyl 6-(2-(3-fluorophenyl)pyrrolidin-1-yl)imidazo[1,2-b]pyridazine-3-carboxylate (X-23, vide infra) (7.8 g, 22 mmol). This solution was stirred at room temperature for 3 hours then evaporated to dryness. The residue was reconstituted in water (50 mL) and cooled to 0° C. The pH was adjusted to 6-7 with concentrated hydrochloric acid. The solid was filtered and the filtrate extracted with DCM. The DCM was dried over anhydrous sodium sulfate, filtered and evaporated to dryness. The resulting residue was combined with the filtered solid and dried in a vacuum oven overnight yielding (R)-6-(2-(3-fluorophenyl)pyrrolidin-1-yl)imidazo[1,2-b]pyridazine-3-carboxylic acid (I-55) as a white solid. $^1$H NMR (400 MHz, DMSO-d$_6$) δ 8.01 (s, 1 H), 7.89 (d, J=9.2 Hz, 1 H), 7.35 (t, J=7.6 Hz, 1 H), 7.16-7.09 (m, 2 H), 7.05 (t, J=8.4 Hz, 1 H), 6.80 (d, J=8.8 Hz, 1 H), 5.16 (d, J=6.0 Hz, 1 H), 3.98-3.86 (m, 1 H), 3.70-3.60 (m, 1 H), 2.50-2.40 (m, 1 H), 2.08-1.94 (m, 2 H), 1.92-1.84 (m, 1 H). MS m/z 327.1 (M+1)$^+$.

Protocol 2

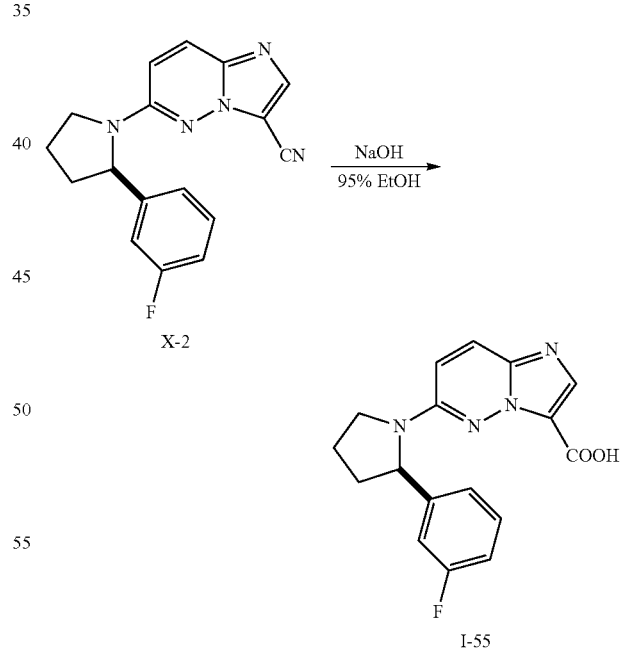

To a solution of (R)-6-(2-(3-fluorophenyl)pyrrolidin-1-yl)imidazo[1,2-b]pyridazine-3-carbonitrile (X-2, vide infra) (905 mg, 2.95 mmol) in EtOH was added NaOH (1.2 g, 29.5 mmol). The mixture was heated at reflux overnight. Upon cooling the solid that formed was filtered to yield (R)-6-(2-(3-fluorophenyl)pyrrolidin-1-yl)imidazo[1,2-b]pyridazine-3-carboxylic acid (I-55). $^1$H NMR (400 MHz, DMSO-d$_6$) δ 8.01 (s, 1 H), 7.89 (d, J=9.2 Hz, 1 H), 7.35 (t, J=7.6 Hz, 1 H), 7.16-7.09 (m, 2 H), 7.05 (t, J=8.4 Hz, 1 H), 6.80 (d, J=8.8 Hz, 1 H), 5.16 (d, J=6.0 Hz, 1 H), 3.98-3.86 (m, 1 H), 3.70-3.60 (m, 1 H), 2.50-2.40 (m, 1 H), 2.08-1.94 (m, 2 H), 1.92-1.84 (m, 1 H). MS m/z 327.1 (M+1)$^+$.

Synthesis of 6-((2R,4S)-4-fluoro-2-(3-fluorophenyl)pyrrolidin-1-yl)imidazo[1,2-b]pyridazine-3-carboxylic acid (I-56)

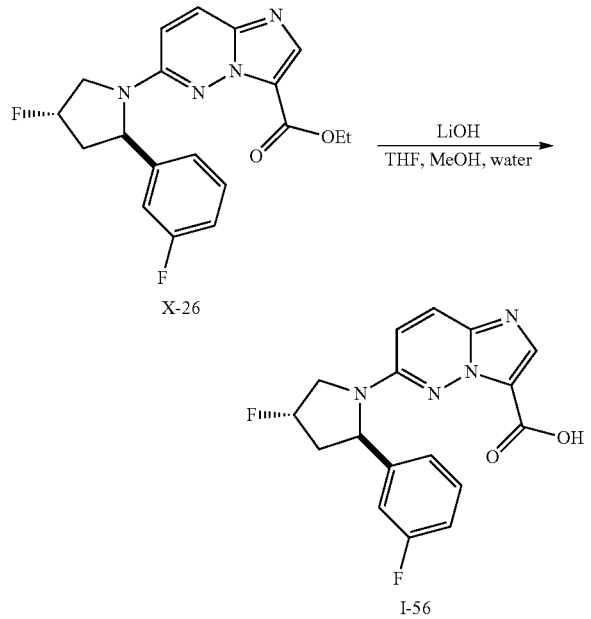

To a solution of ethyl 6-((2R,4S)-4-fluoro-2-(3-fluorophenyl)pyrrolidin-1-yl)imidazo[1,2-b]pyridazine-3-carboxylate (X-26, vide infra) (275 mg, 0.739 mmol) in THF/MeOH/H$_2$O (3:2:1, 6 mL) was added LiOH (155 mg, 3.7 mmol). The mixture was heated at 50° C. overnight. All the solvents were removed under reduced pressure. The crude was purified by column chromatography on silica gel with DCM/MeOH 0 to 20% gradient as eluant to yield 6-((2R,4S)-4-fluoro-2-(3-fluorophenyl)pyrrolidin-1-yl)imidazo[1,2-b]pyridazine-3-carboxylic acid (I-56). $^1$H NMR (400 MHz, DMSO-d$_6$) δ 7.90 (s, 1 H), 7.84 (d, J=10 Hz, 1 H), 7.40-7.24 (m, 3 H), 7.05 (td, J=8.0, 2.4 Hz, 1 H), 6.72 (d, J=9.6 Hz, 1 H), 5.50 (dd, J=52.8 Hz, 1 H), 5.22 (t, J=8.8 Hz, 1 H), 4.26-4.02 (m, 2 H), 2.88-2.74 (m, 1 H), 2.28-2.08 (m, 1 H). MS m/z 354.1 (M+1)$^+$.

Synthesis of (R)-6-(2-(3-fluorophenyl)pyrrolidin-1-yl)-N-(piperidin-4-yl)imidazo[1,2-b]pyridazine-3-carboxamide (I-57)

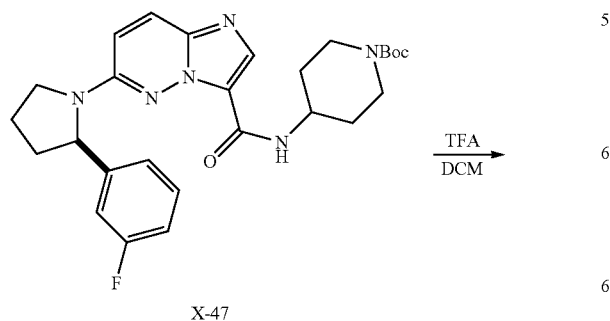

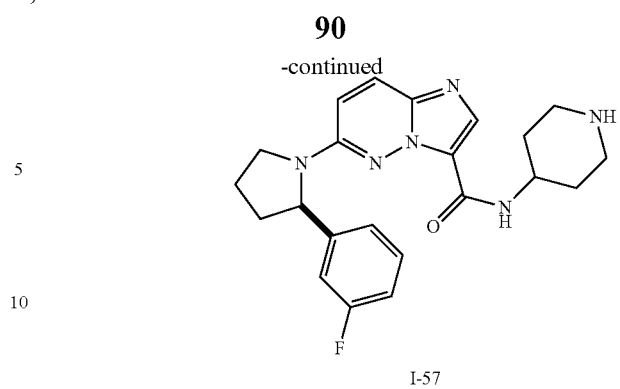

(R)-tert-Butyl-4-(6-(2-(3-fluorophenyl)pyrrolidin-1-yl)imidazo[1,2-b]pyridazine-3-carboxamido)piperidine-1-carboxylate (X-47) was prepared in the same manner as 6-(2-(3-fluorophenyl)pyrrolidin-1-yl)imidazo[1,2-b]pyridazine-3-carboxamide (X-8, vide infra) starting from (R)-6-(2-(3-fluorophenyl)pyrrolidin-1-yl)imidazo[1,2-b]pyridazine-3-carboxylic acid (I-55) and tert-butyl 4-aminopiperidine-1-carboxylate.

To a solution of (R)-tert-butyl-4-(6-(2-(3-fluorophenyl)pyrrolidin-1-yl)imidazo[1,2-b]pyridazine-3-carboxamido)piperidine-1-carboxylate (X-47) (0.25 g, 0.5 mmol) in DCM was added trifluoroacetic acid (2 mL, 27 mmol) and stirred at room temperature for 3 hours. The reaction mixture was quenched with saturated aq. sodium bicarbonate. The organic layer was extracted with a saturated aq. sodium bicarbonate (3×25 mL). The organic layer was dried over anhydrous sodium sulfate, filtered and reduced to dryness to yield (R)-6-(2-(3-fluorophenyl)pyrrolidin-1-yl)-N-(piperidin-4-yl)imidazo[1,2-b]pyridazine-3-carboxamide (I-57). MS m/z 409.2 (M+1)$^+$.

Synthesis of 3-bromo-6-((2S,4R)-3,3-difluoro-2-(3-fluorophenyl)-4-methylpyrrolidin-1-yl)imidazo[1,2-b]pyridazine (I-58)

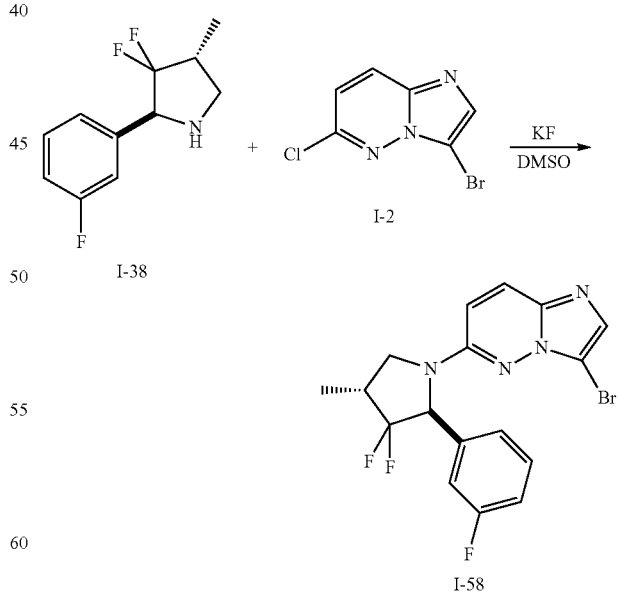

To a suspension of 3-bromo-6-chloroimidazo[1,2-b]pyridazine (I-2) (81 mg, 0.35 mmol) in DMSO (2 mL) was added (2S,4R)-3,3-difluoro-2-(3-fluorophenyl)-4-methylpyrrolidine (I-38) (90 mg, 0.42 mmol) and potassium floride (203 mg, 3.5 mmol). The mixture was heated at 120°

C. overnight. The mixture was poured into water and extracted with EtOAc several times. The combined organic layers were washed with brine, dried over sodium sulfate, filtered and concentrated. The crude was purified by column chromatography on silica gel with EtOAc/hexanes gradient as eluant to yield 3-bromo-6-((2S,4R)-3,3-difluoro-2-(3-fluorophenyl)-4-methylpyrrolidin-1-yl)imidazo[1,2-b]pyridazine (I-58). MS m/z 411.1 (M+1)$^+$.

Synthesis of (R)-(6-(2-(3-fluorophenyl)pyrrolidin-1-yl)imidazo[1,2-b]pyridazin-3-yl)methanol (I-59)

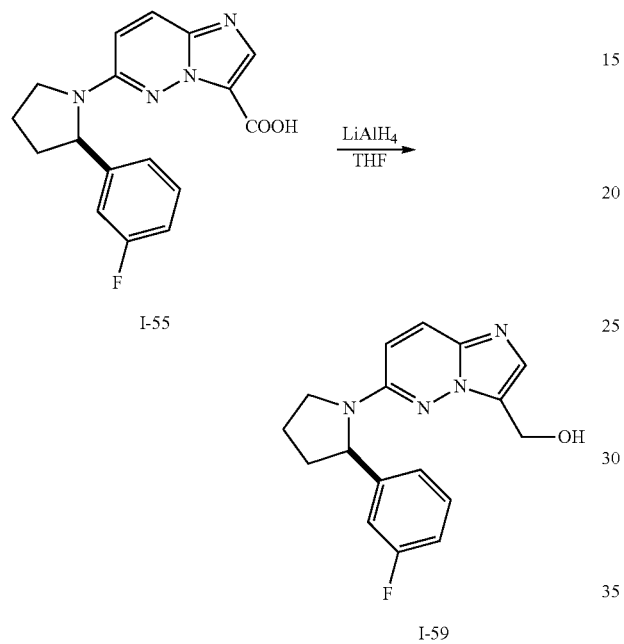

To a solution of (R)-6-(2-(3-fluorophenyl)pyrrolidin-1-yl)imidazo[1,2-b]pyridazine-3-carboxylic acid (I-55) (200 mg, 0.61 mmol) in THF (10 mL) at 0° C. was added LiAlH$_4$ (0.6 mL of a 2 M solution in THF, 1.23 mmol). The mixture was slowly warmed to room temperature and stirred for 4 hours. Saturated aq. Na$_2$SO$_4$ was added and the mixture was stirred for 1 hour. EtOAc was used to extract the mixture. The combined organic extracts were washed with brine, dried over sodium sulfate, filtered and concentrated. The crude was purified by column chromatography on silica gel with DCM/MeOH gradient as eluant to yield (R)-(6-(2-(3-fluorophenyl)pyrrolidin-1-yl)imidazo[1,2-b]pyridazin-3-yl)methanol (I-59). MS m/z 313.1 (M+1)$^+$.

Synthesis of 3-fluoro-5-((2R,4S)-4-fluoropyrrolidin-2-yl)benzonitrile (I-65)

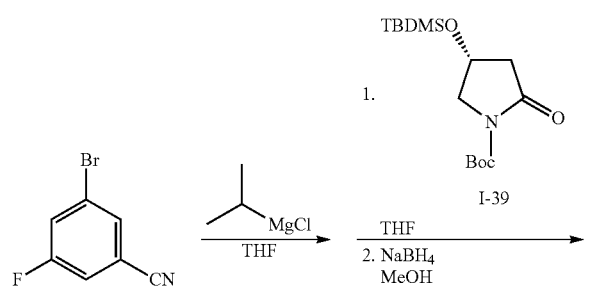

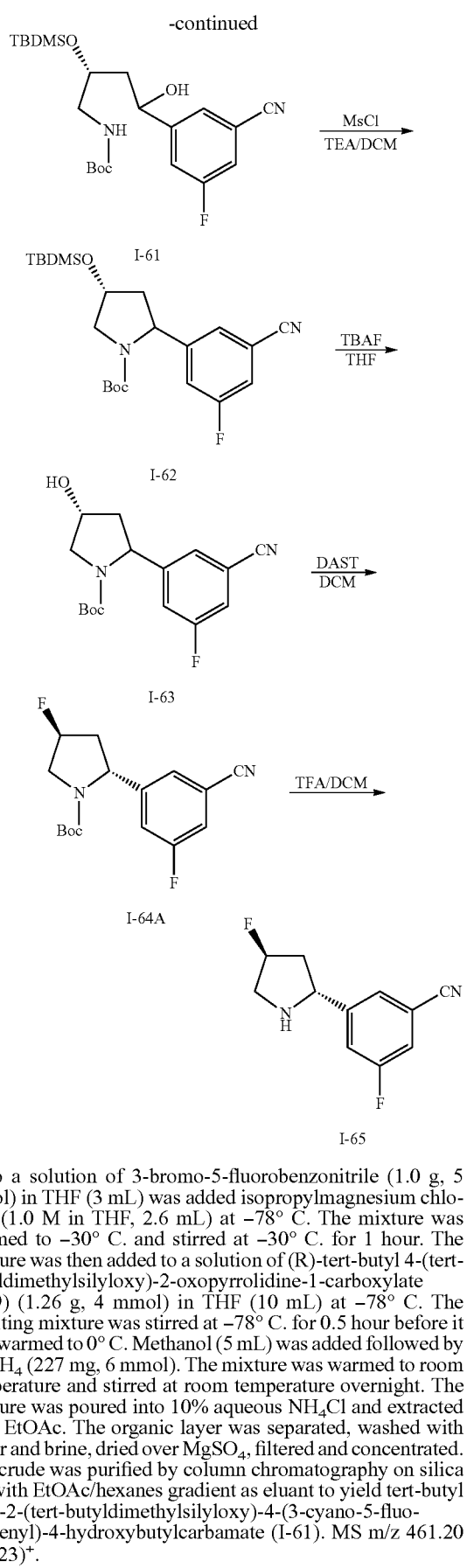

To a solution of 3-bromo-5-fluorobenzonitrile (1.0 g, 5 mmol) in THF (3 mL) was added isopropylmagnesium chloride (1.0 M in THF, 2.6 mL) at −78° C. The mixture was warmed to −30° C. and stirred at −30° C. for 1 hour. The mixture was then added to a solution of (R)-tert-butyl 4-(tert-butyldimethylsilyloxy)-2-oxopyrrolidine-1-carboxylate (I-39) (1.26 g, 4 mmol) in THF (10 mL) at −78° C. The resulting mixture was stirred at −78° C. for 0.5 hour before it was warmed to 0° C. Methanol (5 mL) was added followed by NaBH$_4$ (227 mg, 6 mmol). The mixture was warmed to room temperature and stirred at room temperature overnight. The mixture was poured into 10% aqueous NH$_4$Cl and extracted with EtOAc. The organic layer was separated, washed with water and brine, dried over MgSO$_4$, filtered and concentrated. The crude was purified by column chromatography on silica gel with EtOAc/hexanes gradient as eluant to yield tert-butyl (2R)-2-(tert-butyldimethylsilyloxy)-4-(3-cyano-5-fluorophenyl)-4-hydroxybutylcarbamate (I-61). MS m/z 461.20 (M+23)$^+$.

To a solution of tert-butyl (2R)-2-(tert-butyldimethylsilyloxy)-4-(3-cyano-5-fluorophenyl)-4-hydroxybutylcarbamate (I-61) (594 g, 1.35 mmol) in DCM (5 mL) at −60° C. was added TEA (0.56 mL, 4.05 mmol) and MsCl (0.11 mL, 1.42 mmol). The mixture was stirred at −60° C. for 2 hours. Then it was poured into water, extracted with DCM, washed with brine, dried over Na$_2$SO$_4$, filtered and concentrated. The crude was purified by column chromatography on silica gel with EtOAc/hexanes gradient as eluant to yield (4R)-tert-butyl 4-(tert-butyldimethylsilyloxy)-2-(3-cyano-5-fluorophenyl)pyrrolidine-1-carboxylate (I-62). MS m/z 443.10 (M+23)$^+$.

To a solution of (4R)-tert-butyl 4-(tert-butyldimethylsilyloxy)-2-(3-cyano-5-fluorophenyl)pyrrolidine-1-carboxylate (I-62) (523 mg, 1.24 mmol) in THF (5 mL) at room temperature was added TBAF (1.0 M in THF, 1.4 mL, 1.36 mmol). The mixture was stirred at room temperature for 1 hour then poured into water. The mixture was extracted with EtOAc, washed with water and brine, dried over sodium sulfate, filtered and concentrated. The mixture was purified by column chromatography on silica gel with EtOAc/hexanes gradient as eluant to yield (4R)-tert-butyl 2-(3-cyano-5-fluorophenyl)-4-hydroxypyrrolidine-1-carboxylate (I-63). MS m/z 304.1 (M+23)$^+$.

To a solution of (4R)-tert-butyl 2-(3-cyano-5-fluorophenyl)-4-hydroxypyrrolidine-1-carboxylate (I-63) (190 mg, 0.62 mmol) in DCM (2 mL) in a plastic bottle at −78° C. was added DAST (0.16 mL, 1.24 mmol). The mixture was stirred at −78° C. for 2 hours and then was warmed slowly to room temperature overnight. The mixture was loaded on the silica gel column. The two diasteromers were separated by column chromatography on silica gel with EtOAc/hexanes gradient as eluant to yield (2R,4S)-tert-butyl 2-(3-cyano-5-fluorophenyl)-4-fluoropyrrolidine-1-carboxylate (I-64A) and (2S,4S)-tert-butyl 2-(3-cyano-5-fluorophenyl)-4-fluoropyrrolidine-1-carboxylate (I-63B). MS m/z 331.1 (M+23)$^+$.

To a solution of (2R,4S)-tert-butyl 2-(3-cyano-5-fluorophenyl)-4-fluoropyrrolidine-1-carboxylate (I-64A) (47 mg, 0.152 mmol) in DCM (0.25 mL) at room temperature was added TFA (0.25 mL). The mixture was stirred at room temperature for 0.5 hour. All the solvent was removed under reduced pressure. The crude was extracted with EtOAc, washed with aqueous NaHCO$_3$, brine, dried over sodium sulfate, filtered and concentrated to yield 3-fluoro-5-((2R,4S)-4-fluoropyrrolidin-2-yl)benzonitrile (I-65). $^1$H NMR (400 MHz, CDCl$_3$) δ 7.51 (s, 1 H), 7.39 (d, 1 H), 7.18-7.22 (m, 1 H), 5.27 (dt, J=54, 3.6 Hz, 1 H), 4.55 (dd, J=9.6, 6.8 Hz, 1 H), 3.16-3.42 (m, 2 H), 3.31-3.28 (m, 1 H), 2.57 (ddd, J=20.8, 14.4, 6.8 Hz, 1 H), 2.20 (bs, 1 H), 1.71 (dddd, J=40, 14, 9.6, 4 Hz, 1 H). MS m/z 209.1 (M+1)$^+$.

Synthesis of (R)-6-(4,4-difluoro-2-(3-fluorophenyl)pyrrolidin-1-yl)imidazo[1,2-b]pyridazine (I-66)

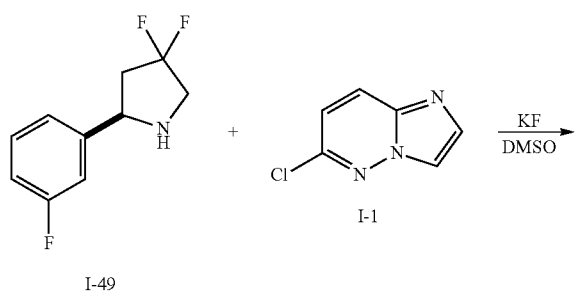

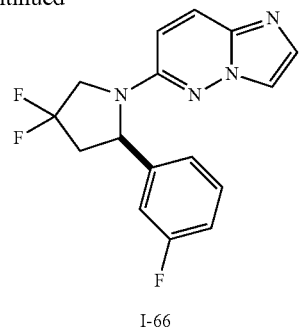

To a suspension of 6-chloroimidazo[1,2-b]pyridazine (I-1) (300 mg, 1.9 mmol) in DMSO (3 mL) was added (R)-4,4-difluoro-2-(3-fluorophenyl)pyrrolidine (I-49) (260 mg, 1.3 mmol) and potassium floride (375 mg, 6.5 mmol). The mixture was heated at 120° C. overnight. The mixture was poured into water and extracted with EtOAc several times. The combined organic layers were washed with brine, dried over sodium sulfate, filtered and concentrated. The crude was purified by column chromatography on silica gel with EtOAc/hexanes gradient as eluant to yield (R)-6-(4,4-difluoro-2-(3-fluorophenyl)pyrrolidin-1-yl)imidazo[1,2-b]pyridazine (I-66). $^1$H NMR (400 MHz, CD$_3$OD) δ 7.73 (s, 1 H), 7.61 (d, J=9.6 Hz, 1 H), 7.45 (s, 1 H), 7.33 (q, J=8.0 Hz, 1 H), 7.12 (d, J=8.0 Hz, 1 H), 7.07 (bd, J=10 Hz, 1 H), 6.97 (dt, J=8.4, 1.6 Hz, 1 H), 6.59 (d, J=10 Hz, 1 H), 5.33 (dd, J=8.8, 8.8 Hz, 1 H), 4.26-4.05 (m, 2 H), 3.16-3.02 (m, 1 H), 2.45 (qdd, J=12.8, 4.8, 1.2 Hz, 1 H). MS m/z 319.1 (M+1)$^+$.

Synthesis of 6-chloroimidazo[1,2-b]pyridazine-3-carbonitrile (I-68)

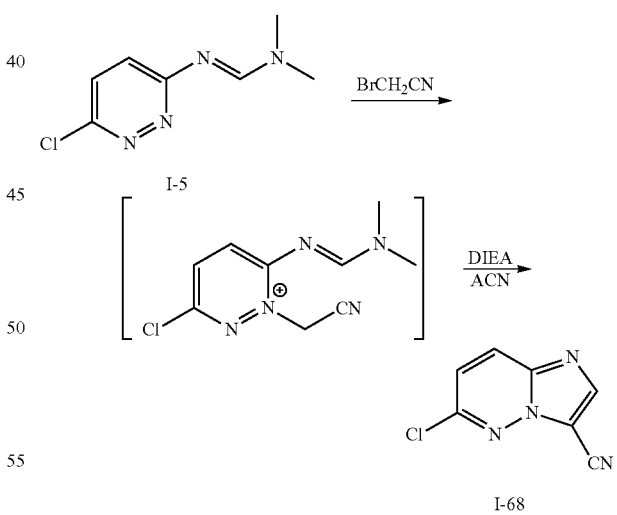

N'-(6-chloropyridazin-3-yl)-N,N-dimethylformimidamide (I-5) (1.00 g, 5.41 mmol) was dissolved in acetonitrile (15 mL) and bromoacetonitrile (1.13 mL, 16.25 mmol) was added. The reaction was stirred overnight at reflux. The solvent was removed in vacuo, the residue was dissolved in acetonitrile (15 mL) and diisopropylethylamine (6.0 mL, 35.60 mmol) was added. The mixture was stirred for 4 hours at room temperature and the solvent was removed in vacuo to give a residue that was purified by flash column chromatography on silica gel (ethyl acetate) to afford 6-chloro-imidazo[1,2-b]pyridazine-3-carbonitrile (I-68) as an off white solid. ¹H NMR (300 MHz, CDCls): 08.23 (1H, s), 8.02 (1H, d, J=9.5 Hz), 7.31 (1H, d, J=9.5 Hz). MS m/z 179.1 (M+1)+.

Synthesis of Synthesis of (R)-2-(4,4-difluoropyrrolidin-2-yl)-4-fluoro-N-isopropylbenzamide (I-91)

quenched by addition of saturated aqueous NH₄Cl (1 mL) and then allowed to warm to ambient temperature. The mixture was extracted with EtOAc (2×25 mL) and the combined extracts were washed with brine, dried over sodium sulfate and concentrated. The residue was purified by silica chromatography with EtOAc/Hex (25-50%) as eluent to afford a mixture of (S)-N-((R)-1-(2-bromo-5-fluorophenyl)but-3-en-

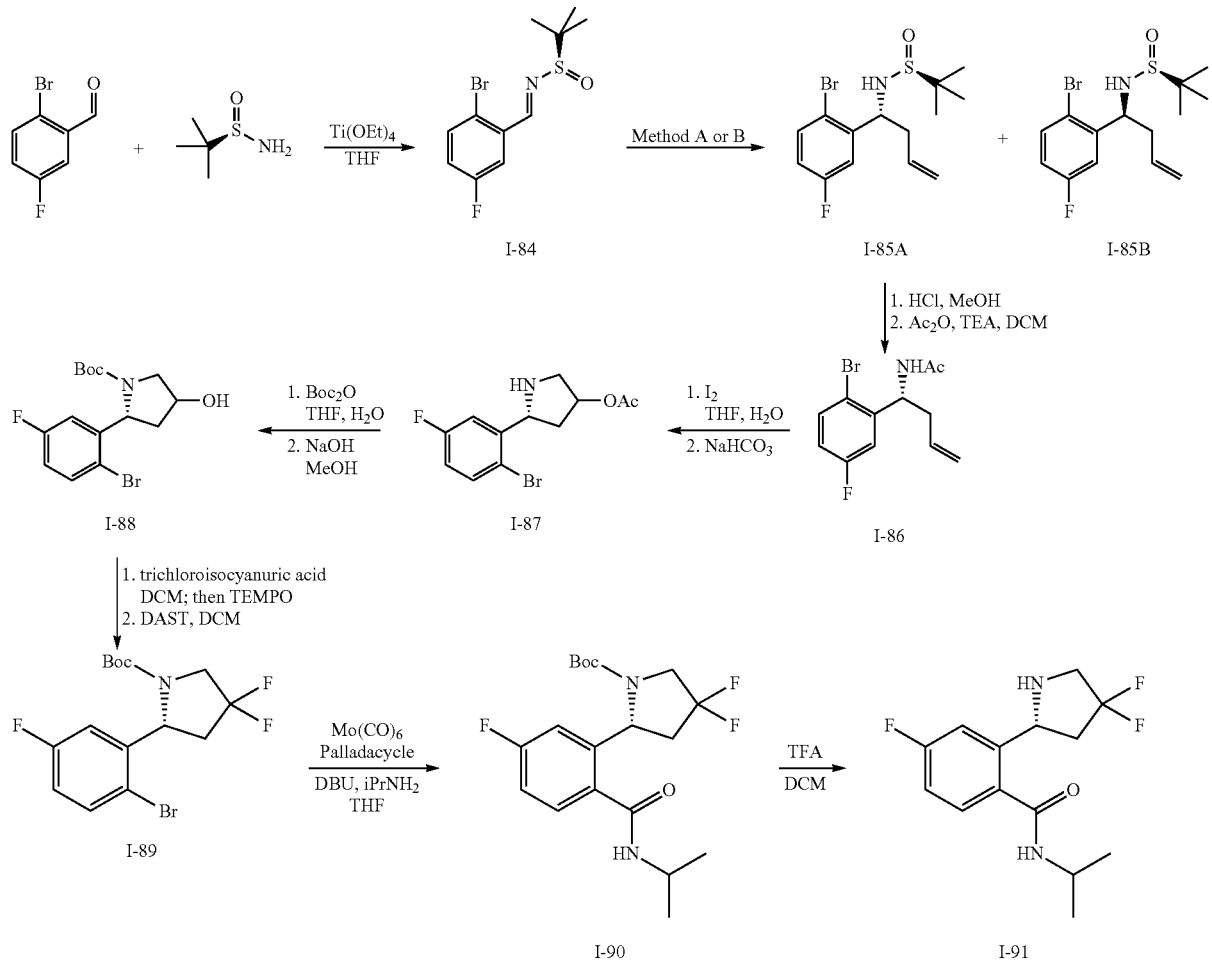

1-yl)-2-methylpropane-2-sulfinamide (I-85A) and (S)-N-((S)-1-(2-bromo-5-fluorophenyl)but-3-en-1-yl)-2-methylpropane-2-sulfinamide (I-85B) as a clear waxy solid. The latter has been assigned tentatively as the major product of the mixture after analysis of NMR and chiral HPLC data. ¹⁹F NMR (376 MHz, CDCl₃) δ −113.32, −113.87. MS m/z 348.0, 350.0 (M+1)⁺.

Method B

To a stirred suspension of (S,E)-N-(2-bromo-5-fluorobenzylidene)-2-methylpropane-2-sulfinamide (I-84) (153 mg, 0.50 mmol) and indium powder (230 mg, 2.0 mmol) in saturated NaBr (10 mL, aq) was added allyl bromide (169 μL, 2.0 mmol). After stirring 36 hours, the reaction mixture was charged with saturates aqueous NaHCO₃ and stirred 30 minutes. The mixture was extracted with EtOAc and combined extracts were washed with brine, dried over sodium sulfate and concentrated. The residue was purified by silica chromatography with EtOAc/Hex (5-35%) as eluent to yield the (S)-N-((R)-1-(2-bromo-5-fluorophenyl)but-3-en-1-yl)-2-methylpropane-2-sulfinamide (I-85A) as a clear oil. ¹H NMR (400 MHz, CDCl₃) δ 7.52 (dd, J=5.3, 8.8 Hz, 1 H), 7.14 (dd, To a solution of 2-bromo-5-fluorobenzaldehyde (2.44 g, 12.0 mmol) and (S)-(−)-2-methyl-2-propane-sulfinamide (1.45 g, 12.0 mmol) in THF (30 mL, anhyd) was added titanium tetraethoxide (2.8 mL, 13.2 mmol, tech) at ambient temperature. After stirring 16 hours, the reaction mixture was charged with brine (25 mL) and EtOAc (40 mL). After stirring 10 minutes, the mixture was filtered through a pad of Celite™. Combined filtrates were washed with water and brine, dried over sodium sulfate and concentrated. The residue was purified by silica chromatography with EtOAc/Hex (0-25%) as eluent to give (S,E)-N-(2-bromo-5-fluorobenzylidene)-2-methylpropane-2-sulfinamide (I-84) as a white solid. ¹H NMR (400 MHz, CDCl₃) δ 8.94 (d, J=2.2 Hz, 1 H), 7.77 (dd, J=3.1, 9.1 Hz, 1 H), 7.64 (dd, J=5.0, 8.8 Hz, 1 H), 7.12 (ddd, J=3.1, 7.5, 8.8 Hz, 1 H), 1.30 (s, 9 H).

Method A

To a solution of (S,E)-N-(2-bromo-5-fluorobenzylidene)-2-methylpropane-2-sulfinamide (I-84) (612 mg, 2.0 mmol) in DCM (6 mL) at −78° C. was added dropwise a solution of allylmagnesium chloride (2.0M in THF, 1.5 mL, 3.0 mmol). After stirring 5 hours at −78° C., the reaction mixture was J=3.1, 9.8 Hz, 1 H), 6.88 (ddd, J=3.1, 7.7, 8.7 Hz, 1 H), 5.77 (dddd, J=6.1, 8.2, 10.9, 16.6 Hz, 1 H), 5.28-5.16 (m, 2 H), 4.98-4.89 (m, 1 H), 3.74 (s, 1 H), 2.76-2.63 (m, 1 H), 2.39 (dt, J=8.3, 14.2 Hz, 1 H), 1.24 (s, 9 H). $^{19}$F NMR (376 MHz, CDCl$_3$) δ −113.87. MS m/z 348.0, 350.0 (M+1)$^+$.

To a solution of I-85A (1.95 g, 5.6 mmol) in MeOH (15 mL) at 0° C. was added 4N solution of HCl in MeOH (7.5 mL, 30 mmol). After stirring 45 min at ambient temperature, the reaction mixture was chilled to 0° C. and slowly made basic with 15% NaOH. The resulting mixture was concentrated to a minimum volume on a rotary evaporator and then partitioned in EtOAc and saturated aqueous NaHCO$_3$. The combined EtOAc extracts were washed with brine, dried over sodium sulfate and concentrated to yield the corresponding homoallylamine (1.4 g). MS m/z 244.0, 246.0 (M+1)$^+$. The amine was dissolved in DCM (20 mL), chilled to 0° C. and charged with triethylamine (0.98 mL, 7.0 mmol) and then acetic anhydride (0.57 mL, 6.05 mmol). After stirring 2 hour, the reaction mixture was washed successively with saturated aqueous NaHCO$_3$, water, 1N HCl and brine, then dried over sodium sulfate and concentrated to dryness to afford (R)-N-(1-(2-bromo-5-fluorophenyl)but-3-en-1-yl)acetamide (I-86) as a white solid. MS m/z 286.0, 288.0 (M+1)$^+$.

To a solution of (R)-N-(1-(2-bromo-5-fluorophenyl)but-3-en-1-yl)acetamide (I-86) (1.50 g, 5.24 mmol) in THF (12 mL) was added water (3 mL) followed by iodine (4.0 g, 15.7 mmol). After stirring 6 hours, the reaction mixture was poured into a mixture of saturated aqueous NaHCO$_3$ (30 mL) and saturated aqueous Na$_2$S$_2$O$_3$ (25 mL), extracted with EtOAc (2×40 mL), washed successively with saturated aqueous Na$_2$S$_2$O$_3$, water and brine, dried over sodium sulfate and concentrated to dryness to give (5R)-5-(2-bromo-5-fluorophenyl)pyrrolidin-3-yl acetate (I-87) as a pale amber oil, which was used without purification in the next step. MS m/z 302.0, 304.0 (M+1)$^+$.

To a mixture of (5R)-5-(2-bromo-5-fluorophenyl)pyrrolidin-3-yl acetate (I-87) (1.59 g, 5.24 mmol), dioxane (15 mL) and water (15 mL) was added a solution of di-tert-butyl dicarbonate (1M in THF, 6.6 mL, 6.6 mmol). Added 1N NaOH until pH 9 had been achieved. After 3 hours, the reaction mixture was partitioned into EtOAc/water and the combined extracts were washed with brine, dried over sodium sulfate and concentrated to dryness to afford the corresponding carbamate. MS m/z 424.0, 426.0 (M+23)$^+$.

The above carbamate was dissolved in MeOH (15 mL) and chilled to 0° C., and then charged dropwise with 1N NaOH (3.93 mL, 0.75 eq). After stirring 2 hours at ambient temperature, the reaction had not progressed to completion, as determined by LCMS analysis of an aliquot. Added another portion of 1N NaOH (0.75 eq). After hydrolysis was complete (approx. 1 hour), the reaction mixture was partitioned into EtOAc/brine. The combined EtOAc extracts were washed with brine, dried over sodium sulfate, and concentrated. The residue was purified by silica chromatography with EtOAc/Hex (25-50%) as eluent, to yield (2R)-tert-butyl 2-(2-bromo-5-fluorophenyl)-4-hydroxypyrrolidine-1-carboxylate (I-88) as a white foam. MS m/z 382.0, 384.0 (M+23)$^+$.

To a solution of (2R)-tert-butyl 2-(2-bromo-5-fluorophenyl)-4-hydroxypyrrolidine-1-carboxylate (I-88) (1.38 g, 3.83 mmol) in DCM (30 mL) at −10° C. was added trichloroisocyanuric acid (0.89 g, 3.8 mmol) followed by 2,2,6,6-tetramethylpiperidino-1-oxy (TEMPO) (60 mg, 0.38 mmol). After stirring 25 minutes at ambient temperature, the reaction mixture was poured into saturated aqueous NaHCO$_3$ and ice (2 g), then extracted with DCM. The combined extracts were washed with water (2×) and brine (2×), dried over sodium sulfate and concentrated to dryness to give the corresponding ketone as a pale yellow oil, which was used without purification in the next step. MS m/z 380.0, 382.0 (M+23)$^+$.

The above ketone was dissolved in DCM (8 mL), at −78° C. and then charged with diethylaminosulfur trifluoride (DAST) (1.0 mL, 2 eq). After stirring 12 hour at ambient temperature, the reaction mixture was added to cold water and extracted with DCM. The combined extracts were washed with water and brine, dried over sodium sulfate and concentrated to dryness to afford (R)-tert-butyl 2-(2-bromo-5-fluorophenyl)-4,4-difluoro-pyrrolidine-1-carboxylate (I-89) as a pale yellow, crystalline solid. $^1$H NMR (400 MHz, CDCl$_3$) δ 7.52 (dd, J=5.2, 8.7 Hz, 1 H), 7.06-6.85 (m, 2 H), 5.38-5.26 (m, 1 H), 4.16-4.01 (m, 1 H), 3.96 (q, J=12.4 Hz, 1 H), 3.06-2.88 (m, 1 H), 2.32-2.22 (m, 1 H), 1.49 (bs, 3 H), 1.23 (bs, 6 H). MS m/z 324.0, 326.0 (M−55)$^+$.

To a nitrogen-flushed microwave vial was added (R)-tert-butyl 2-(2-bromo-5-fluorophenyl)-4,4-difluoro-pyrrolidine-1-carboxylate (I-89) (304 mg, 0.80 mmol), molybdenum hexacarbonyl (211 mg, 0.80 mmol), trans-di-µ-acetatobis[2-di-o-tolylphosphino)benzyl]-dipalladium(II) (Palladacycle) (30 mg, 4 mol %), THF (1.6 mL), 1,8-diazabicyclo-[5.4.0] undec-7-ene (DBU) (239 µL, 1.6 mmol) and isopropylamine (171 µL, 2.0 mmol). The vial was capped and then heated at 150° C. for 30 minutes in a Biotage microwave reactor. The cooled reaction mixture was diluted with EtOAc and filtered through Celite. The combined filtrates were washed successively with saturated aqueous NH$_4$Cl, water, 2% citric acid and brine, then dried over sodium sulfate and concentrated. The residue was purified by silica chromatography with EtOAc/Hex (5-30%) as eluent, to yield (R)-tert-butyl 4,4-difluoro-2-(5-fluoro-2-(isopropylcarbamoyl)phenyl)pyrrolidine-1-carboxylate (I-90) as an off-white foam. $^1$H NMR (400 MHz, CDCl$_3$) δ 7.44 (bs, 1 H), 7.11 (bs, 1 H), 7.00 (td, J=2.5, 8.2 Hz, 1 H), 5.31 (t, J=7.7 Hz, 1 H), 4.23 (bs, 1 H), 4.09-3.87 (m, 2 H), 2.91 (bs, 1 H), 2.41 (bs, 1 H), 1.45 (bs, 6 H), 1.26 (d, J=6.5 Hz, 6 H), 1.19 (bs, 3 H). MS m/z 331.1 (M−55)$^+$.

To a solution of (R)-tert-butyl 4,4-difluoro-2-(5-fluoro-2-(isopropylcarbamoyl)phenyl)pyrrolidine-1-carboxylate (I-90) (203 mg, 0.525 mmol) in DCM (0.4 mL) was added TFA (1 mL). After stirring for 2 hours, the mixture was concentrated to dryness, diluted with DCM, washed with saturated aqueous NaHCO$_3$ and brine, dried over sodium sulfate and concentrated to dryness to give (R)-2-(4,4-difluoropyrrolidin-2-yl)-4-fluoro-N-isopropylbenzamide (I-91) as a pale brown solid. MS m/z 287.1 (M+H)$^+$. I-91 was also isolated as a racemic mixture using un-resolved I-85A and I-85B from Method A in the above sequence.

Synthesis of Example Compounds

Example 1

Synthesis of (R)-3-bromo-6-(2-(3-fluorophenyl)pyrrolidin-1-yl)imidazo[1,2-b]pyridazine (X-1)

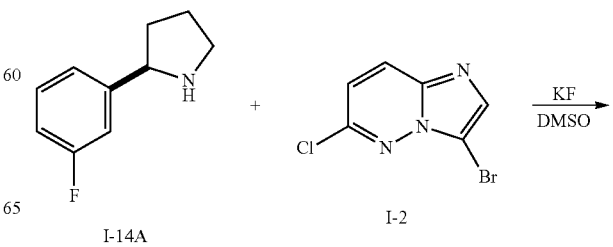

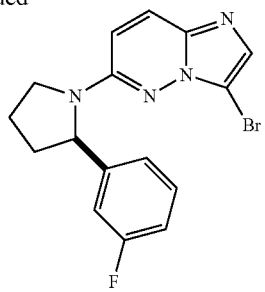

X-1

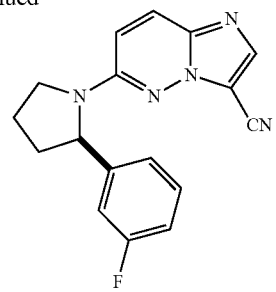

X-2

To a solution of sodium hydroxide (3.0 g, 75 mmol) in water (100 mL) was added (R)-2-(3-fluorophenyl)pyrrolidine hydrochloride (15.7 g, 68 mmol). This was stirred for 20 minutes and then extracted with EtOAc (3×100 mL). The EtOAc fractions were combined, dried over anhydrous sodium sulfate, filtered and reduced to dryness to yield (R)-2-(3-fluorophenyl)pyrrolidine (I-14A) as a light yellow oil. To this oil was added spray dried potassium fluoride (40 g, 680 mmol), 3-bromo-6-chloroimidazo[1,2-b]pyridazine (I-2) (15.7 g, 68 mmol) and DMSO (80 mL). The resulting heterogeneous mixture was then stirred at 100° C. for 72 hours. The reaction mixture was then poured into stirring water (500 mL) and stirred at room temperature for 30 minutes. This mixture was extracted with EtOAc (4×200 mL). The combined organic layers were washed with brine (4×100 mL), dried over anhydrous sodium sulfate, filtered and reduced to dryness to yield a yellow oil. The crude product was then purified using flash chromatography on silica with hexanes/EtOAc gradient to yield (R)-3-bromo-6-(2-(3-fluorophenyl)pyrrolidin-1-yl)imidazo[1,2-b]pyridazine (X-1). $^1$H NMR (400 MHz, MeOD-$d_4$) δ 7.48 (d, J=9.6 Hz, 1 H), 7.33 (s, 1 H), 7.24 (m, 1 H), 6.99 (d, J=7.6 Hz, 1 H), 6.92 (d, J=10 Hz, 1 H), 6.86 (dt, J=8.8, 2.8 Hz, 1 H), 6.60 (d, J=10 Hz, 1 H), 5.03 (dd, J=10, 3.2 Hz, 1 H), 3.88-3.82 (m, 1 H), 3.65 (q, J=7.6 Hz, 1 H), 2.46-2.36 (m, 1 H), 2.03-1.95 (m, 2 H), 1.91-1.85 (m, 1 H). MS m/z 361.1 (M+1)$^+$.

Example 2

Synthesis of (R)-6-(2-(3-fluorophenyl)pyrrolidin-1-yl)imidazo[1,2-b]pyridazine-3-carbonitrile (X-2)

To a solution of (R)-3-bromo-6-(2-(3-fluorophenyl)pyrrolidin-1-yl)imidazo[1,2-b]pyridazine (X-1) (1.08 g, 3 mmol) in DMF (5 mL) was added Zn(CN)$_2$ (423 mg, 4.2 mmol), Pd$_2$(dba)$_3$ (137 mg, 5% mol) and DPPF (116 mg, 7% mol). The mixture was heated at 150° C. for 1 hour using microwave irradiation. Then it was filtered through Celite and washed with EtOAc. The filtrate was collected, washed with water and brine, dried over sodium sulfate, filtered and concentrated. The crude was purified by column chromatography on silica gel with DCM/MeOH 0 to 10% gradient as eluant to yield (R)-6-(2-(3-fluorophenyl)pyrrolidin-1-yl)imidazo[1,2-b]pyridazine-3-carbonitrile (X-2). MS m/z 308.2 (M+1)$^+$.

Example 3

Synthesis of 6-(3-(3-fluorophenyl)morpholino)imidazo[1,2-b]pyridazine-3-carbonitrile (X-3)

A microwave vial was charged with 4-(3-bromoimidazo[1,2-b]pyridazin-6-yl)-3-(3-fluorophenyl)morpholine (I-12) (0.19 g, 0.5 mmol), Zn(CN)$_2$ (0.12 g, 1.0 mmol), Pd$_2$(dba)$_3$ (23 mg, 25 μmol), DPPF (14 mg, 25 μmol) and DMF (5 mL) under N$_2$. The vial was sealed and heated under microwave conditions at 150° C. for 15 minutes. Subsequently the reaction was diluted with aq. NH$_4$Cl and extracted with EtOAc (2×25 mL). The organic layers were combined and washed with brine, dried over magnesium sulfate, filtered and reduced to dryness. The crude product was purified on silica gel column chromotography with DCM 2% MeOH as eluant to yield 6-(3-(3-fluorophenyl)morpholino)imidazo[1,2-b]pyridazine-3-carbonitrile (X-3) as an amber oil. ¹H NMR (400 MHz, DMSO-d₆) δ 8.26 (s, 1 H), 8.07 (d, J=9.2 Hz, 1 H), 7.44 (d, J=10.0 Hz, 1 H), 7.38-7.36 (m, 1 H), 7.27-7.22 (m, 1 H), 7.09 (bt, J=8.4 Hz, 1 H), 5.35 (s, 1 H), 4.27 (d, J=12 Hz, 1 H), 4.05-3.97 (m, 3 H), 2.54 (bs, 2 H). MS m/z 324.1 (M+1)⁺.

Example 4

Synthesis of 6-((2S,4R)-3,3-difluoro-2-(3-fluorophenyl)-4-methylpyrrolidin-1-yl)imidazo[1,2-b]pyridazine-3-carbonitrile (X-4)

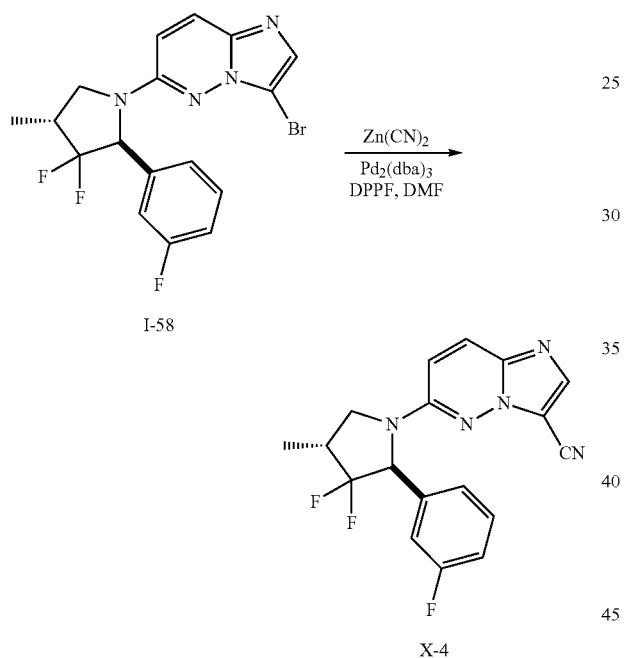

To a solution of 3-bromo-6-((2S,4R)-3,3-difluoro-2-(3-fluorophenyl)-4-methylpyrrolidin-1-yl)imidazo[1,2-b]pyridazine (I-58) (22 mg, 0.054 mmol) in DMF (0.5 mL) were added Zn(CN)₂ (8 mg, 0.064 mmol), Pd₂(dba)₃ (2 mg, 5% mol) and DPPF (2 mg, 7% mol). The mixture was heated at 150° C. for 1 hour using microwave irradiation. Then it was filtered through Celite and washed with EtOAc. The filtrate was collected, washed with water and brine, dried over sodium sulfate, filtered and concentrated. The crude was purified by column chromatography on silica gel with EtOAc/hexanes gradient as eluant to yield 6-((2S,4R)-3,3-difluoro-2-(3-fluorophenyl)-4-methylpyrrolidin-1-yl)imidazo[1,2-b]pyridazine-3-carbonitrile (X-4). ¹H NMR (400 MHz, CDCl₃) δ 7.99 (s, 1H), 7.71 (d, J=10.0 Hz, 1 H), 7.40 (td, J=8.0, 6.0 Hz, 1 H), 7.14 (d, J=7.6 Hz, 1 H), 7.11-7.05 (m, 1 H), 7.04-6.99 (m, 1 H), 6.50 (d, J=10 Hz, 1 H), 5.06 (d, J=17.6 Hz, 1 H), 4.22 (td, J=8.4, 10.8 Hz, 1 H), 3.49 (t, J=10.8 Hz, 1 H), 2.82-2.61 (m, 1 H), 1.26 (d, J=6.8 Hz, 3 H). MS m/z 358.2 (M+1)⁺.

Example 5

Synthesis of 6-(2-(3-fluorophenyl)pyrrolidin-1-yl)imidazo[1,2-b]pyridazine-3-carboxamide (X-5)

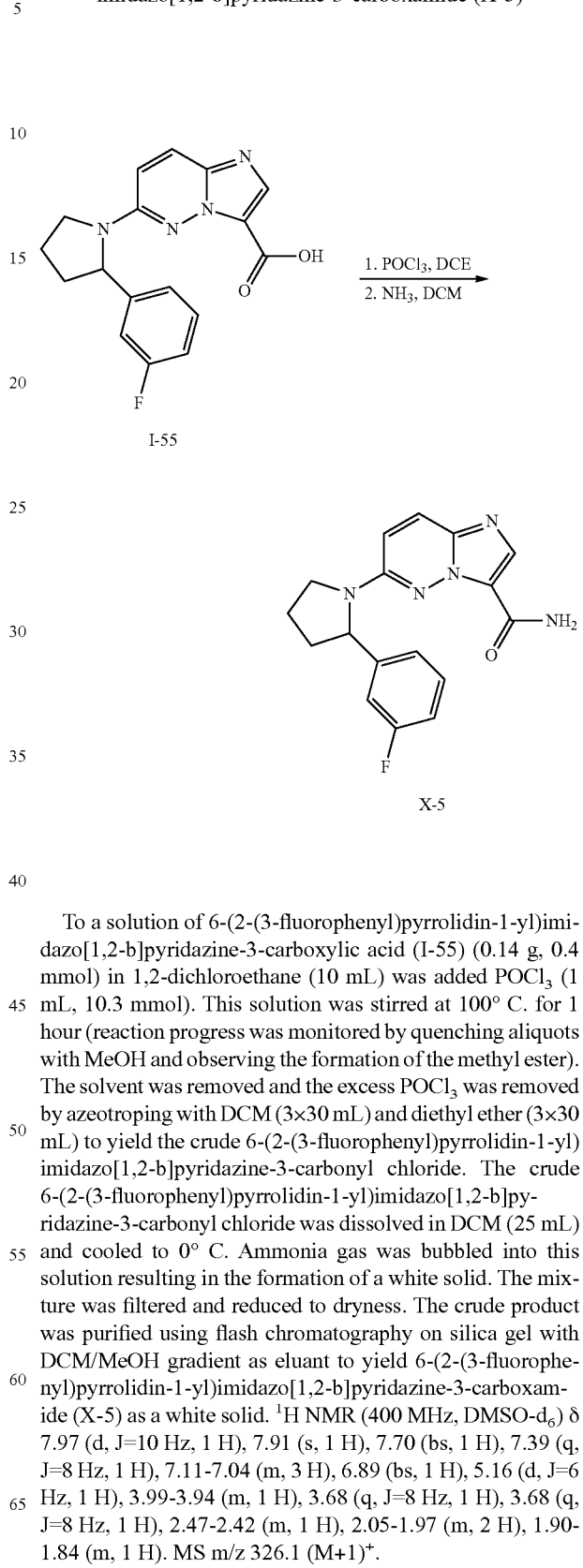

To a solution of 6-(2-(3-fluorophenyl)pyrrolidin-1-yl)imidazo[1,2-b]pyridazine-3-carboxylic acid (I-55) (0.14 g, 0.4 mmol) in 1,2-dichloroethane (10 mL) was added POCl₃ (1 mL, 10.3 mmol). This solution was stirred at 100° C. for 1 hour (reaction progress was monitored by quenching aliquots with MeOH and observing the formation of the methyl ester). The solvent was removed and the excess POCl₃ was removed by azeotroping with DCM (3×30 mL) and diethyl ether (3×30 mL) to yield the crude 6-(2-(3-fluorophenyl)pyrrolidin-1-yl)imidazo[1,2-b]pyridazine-3-carbonyl chloride. The crude 6-(2-(3-fluorophenyl)pyrrolidin-1-yl)imidazo[1,2-b]pyridazine-3-carbonyl chloride was dissolved in DCM (25 mL) and cooled to 0° C. Ammonia gas was bubbled into this solution resulting in the formation of a white solid. The mixture was filtered and reduced to dryness. The crude product was purified using flash chromatography on silica gel with DCM/MeOH gradient as eluant to yield 6-(2-(3-fluorophenyl)pyrrolidin-1-yl)imidazo[1,2-b]pyridazine-3-carboxamide (X-5) as a white solid. ¹H NMR (400 MHz, DMSO-d₆) δ 7.97 (d, J=10 Hz, 1 H), 7.91 (s, 1 H), 7.70 (bs, 1 H), 7.39 (q, J=8 Hz, 1 H), 7.11-7.04 (m, 3 H), 6.89 (bs, 1 H), 5.16 (d, J=6 Hz, 1 H), 3.99-3.94 (m, 1 H), 3.68 (q, J=8 Hz, 1 H), 3.68 (q, J=8 Hz, 1 H), 2.47-2.42 (m, 1 H), 2.05-1.97 (m, 2 H), 1.90-1.84 (m, 1 H). MS m/z 326.1 (M+1)⁺.

Example 6

Synthesis of 6-((2R,4S)-4-fluoro-2-(3-fluorophenyl)pyrrolidin-1-yl)imidazo[1,2-b]pyridazine-3-carboxamide (X-7)

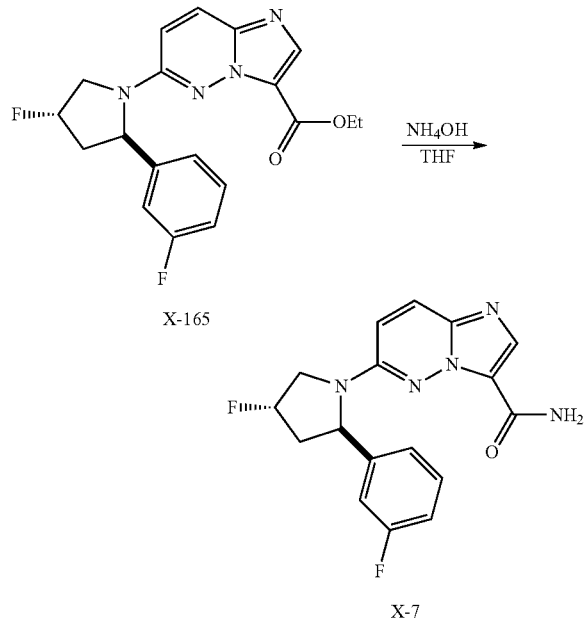

A sealed vial was charged with ethyl 6-((2R,4S)-4-fluoro-2-(3-fluorophenyl)pyrrolidin-1-yl)imidazo[1,2-b]pyridazine-3-carboxylate (X-165, vide infra) (55 mg, 0.148 mmol), NH$_4$OH (1 mL) and THF (0.1 mL). The mixture was heated at 50° C. for 3 hours. Upon cooling, the mixture was extracted with EtOAc, washed with water and brine, dried over sodium sulfate, filtered and concentrated. The crude was purified by column chromatography on silica gel with DCM/MeOH gradient as eluant to yield 6-((2R,4S)-4-fluoro-2-(3-fluorophenyl)pyrrolidin-1-yl)imidazo[1,2-b]pyridazine-3-carboxamide (X-7). $^1$H NMR (400 MHz, CDCl$_3$) δ 8.23 (s, 1 H), 7.84 (br s, 1 H), 7.79 (d, J=10.0 Hz, 1 H), 7.36 (td, J=8.0, 6.0 Hz, 1 H), 7.06 (d, J=8 Hz, 1 H), 7.02-6.93 (m, 2 H), 6.66 (d, J=9.6 Hz, 1 H), 5.55 (br s, 1 H), 5.42 (d, J=52.0 Hz, 1 H), 5.15 (dd, J=6.8, 10.0 Hz, 1 H), 4.22-4.16 (m, 1 H), 4.14-4.06 (m, 1 H), 2.90 (td, J=16.0, 6.8 Hz, 1 H), 2.14 (dddd, J=40.8, 14.0, 9.6, 3.6 Hz, 1 H). MS m/z 344.1 (M+1)$^+$. $^{19}$F NMR (400 MHz, CDCl$_3$) δ 176.50, 110.93.

Example 7

Synthesis of (R)-6-(2-(3-fluorophenyl)-2,5-dihydro-1H-pyrrol-1-yl)imidazo[1,2-b]pyridazine-3-carboxamide (X-15)

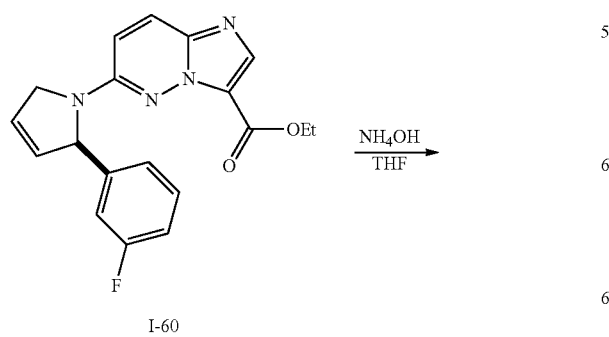

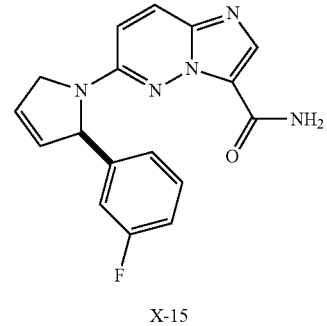

(R)-Ethyl 6-(2-(3-fluorophenyl)-2,5-dihydro-1H-pyrrol-1-yl)imidazo[1,2-b]pyridazine-3-carboxylate (I-60) was isolated as a minor product in the synthesis of 6-((2R,4S)-4-fluoro-2-(3-fluorophenyl)pyrrolidin-1-yl)imidazo[1,2-b]pyridazine-3-carboxylate (X-165, vide infra).

A vial charged with (R)-ethyl 6-(2-(3-fluorophenyl)-2,5-dihydro-1H-pyrrol-1-yl)imidazo[1,2-b]pyridazine-3-carboxylate (I-60) (20 mg, 0.0568 mmol), NH$_4$OH (1 mL) and THF (0.2 mL) was sealed and heated at 50° C. overnight. The mixture was extracted with EtOAc, washed with brine, dried over sodium sulfate, filtered and concentrated. The crude was purified by column chromatography on silica gel with DCM/MeOH gradient as eluant to yield (R)-6-(2-(3-fluorophenyl)-2,5-dihydro-1H-pyrrol-1-yl)imidazo[1,2-b]pyridazine-3-carboxamide (X-15). $^1$H NMR (400 MHz, CDCl$_3$) δ 8.21 (s, 1 H), 8.15-8.00 (bs, 1 H), 7.78 (d, J=10 Hz, 1 H), 7.37-7.30 (m, 1 H), 7.07 (s, 1 H), 7.01-6.92 (m, 2 H), 6.66 (d, J=10, Hz, 1 H), 6.07-6.02 (m, 1 H), 5.95-5.91 (m, 1 H), 5.80-5.68 (bs, 1 H), 5.68-5.64 (m, 1 H), 4.69-4.60 (m, 1 H), 4.58-4.50 (m, 1 H). MS m/z 324.1 (M+1)$^+$.

Example 8

Synthesis of (R)-6-(3-(3-fluorophenyl)morpholino)imidazo[1,2-b]pyridazine-3-carboxamide (X-17)

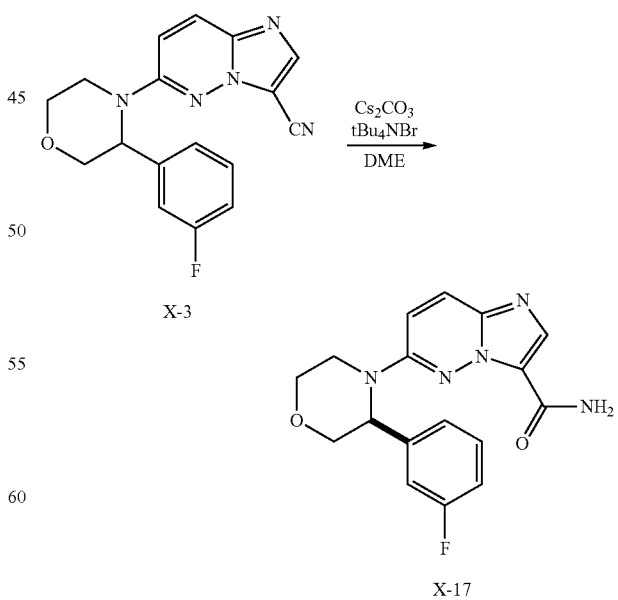

To a solution of 6-(3-(3-fluorophenyl)morpholino)imidazo[1,2-b]pyridazine-3-carbonitrile (X-3) (48 mg, 0.15 mmol) in DME (1 mL) was added Cs$_2$CO$_3$ (50 mg, 0.15 mmol) and tBu₄NBr (25 mg, 0.07 mmol). The reaction was heated at 55° C. in a sealed tube for 24 hours. Subsequently the reaction was diluted with aq. NH₄Cl and extracted with EtOAc (2×15 mL). The combined organic layers were washed with brine, dried over magnesium sulfate, filtered and reduced to dryness. The crude product was purified on silica gel preperative TLC with DCM 4% MeOH as eluant to yield 6-(3-(3-fluorophenyl)morpholino)imidazo[1,2-b]pyridazine-3-carboxamide (X-16). MS m/z 342.1 (M+1). The racemic mixture was resolved on a 21×250 mm chiralpak AD-H column using 80 g/minute 8/2 CO₂/MeOH at 35° C. to yield (R)-6-(3-(3-fluorophenyl)morpholino)imidazo[1,2-b]pyridazine-3-carboxamide (X-17) optically pure. $^1$H NMR (400 MHz, DMSO-d₆) δ 8.04 (d, J=8.0 Hz, 1 H), 7.99 (s, 1 H), 7.76 (s, 2 H), 7.39-7.33 (m, 2 H), 7.23-7.17 (m, 2 H), 7.08 (bt, J=8.4 Hz, 1 H), 5.30 (s, 1 H), 4.20 (d, J=12 Hz, 1 H), 4.05-3.92 (m, 3 H), 3.78-3.70 (m, 1 H), 3.60-3.56 (m, 1 H). MS m/z 342.1 (M+1)⁺.

Example 9

Synthesis of (R)-6-(2-(3-fluorophenyl)pyrrolidin-1-yl)-N-(1-sulfamoylpiperidin-4-yl)imidazo[1,2-b]pyridazine-3-carboxamide (X-29)

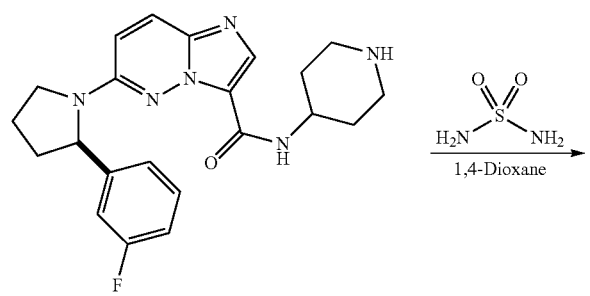

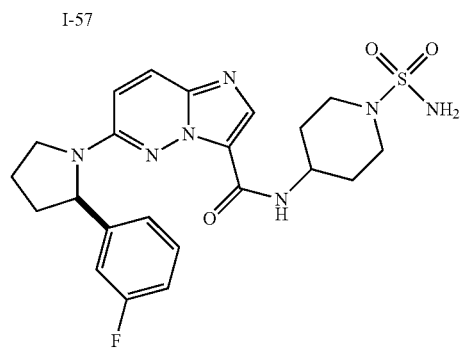

To a solution of (R)-6-(2-(3-fluorophenyl)pyrrolidin-1-yl)-N-(piperidin-4-yl)imidazo[1,2-b]pyridazine-3-carboxamide (I-57) (50 mg, 0.12 mmol) in 1,4-dioxane (10 mL) was added sulfamide (0.14 g, 1 mmol), heated to 110° C. and stirred for 72 hours. The reaction mixture was cooled to rt, and the solvents were removed. The crude product was purified using a preparative LCMS to yield (R)-6-(2-(3-fluorophenyl)pyrrolidin-1-yl)-N-(1-sulfamoylpiperidin-4-yl)imidazo[1,2-b]pyridazine-3-carboxamide (X-29). $^1$H NMR (400 MHz, MeOD-d₄) δ 8.30 (bs, 1 H), 7.99 (bs, 1 H), 7.44 (q, J=7.2 Hz, 1 H), 7.22 (bs, 1 H), 7.17 (d, J=8 Hz, 1 H), 7.05-7.00 (m, 2 H), 5.31 (d, J=7.6 Hz, 1 H), 4.04-3.99 (m, 2 H), 3.80-3.63 (m, 3 H), 2.88-2.76 (m, 2 H), 2.64-2.54 (m, 1 H), 2.29-2.00 (m, 5 H), 1.68 (bs, 2 H). MS m/z 488.2 (M+1)⁺.

Example 10

Synthesis of (R)-N-(3-cyanophenyl)-6-(2-(3-fluorophenyl)pyrrolidin-1-yl)imidazo[1,2-b]pyridazine-3-carboxamide (X-65)

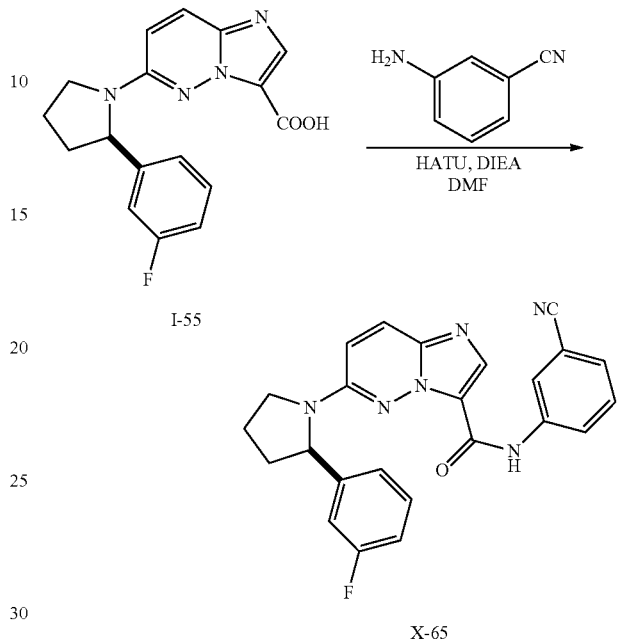

To a solution of (R)-6-(2-(3-fluorophenyl)pyrrolidin-1-yl)imidazo[1,2-b]pyridazine-3-carboxylic acid (I-55) (20 mg, 0.061 mmol) and 3-aminobenzonitrile (9 mg, 0.073 mmol) in DMF (3 mL) at room temperature was added DIEA (0.032 mL, 0.183 mmol) and HATU (23 mg, 0.061 mmol). The mixture was stirred at room temperature overnight. The resulting crude was diluted with EtOAc, washed with water and brine, dried over sodium sulfate, filtered and concentrated. The final product (R)-N-(3-cyanophenyl)-6-(2-(3-fluorophenyl)pyrrolidin-1-yl)imidazo[1,2-b]pyridazine-3-carboxamide (X-65) was isolated using column chromatography on silica gel with DCM/MeOH gradient. MS m/z 427.1 (M+1)⁺.

Example 11

Synthesis of (R)-6-(2-(3-fluorophenyl)pyrrolidin-1-yl)-N-(1-(methylsulfonyl)piperidin-4-yl)imidazo[1,2-b]pyridazine-3-carboxamide (X-71)

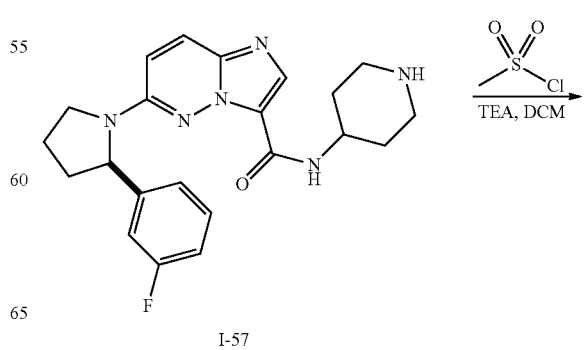

-continued

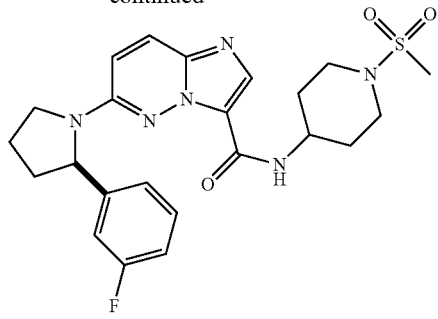

X-71

To a solution of (R)-6-(2-(3-fluorophenyl)pyrrolidin-1-yl)-N-(piperidin-4-yl)imidazo[1,2-b]pyridazine-3-carboxamide (50 mg, 0.12 mmol), triethylamine (I-57) (0.2 mL, 1.4 mmol) in DCM (3 mL) at 0° C. was added methane sulfonyl-chloride (30 mg, 0.26 mmol). The resulting solution was stirred at room temperature for 2 hours. The solvent was removed and the crude product was purified by preparative LCMS to yield (R)-6-(2-(3-fluorophenyl)pyrrolidin-1-yl)-N-(1-(methylsulfonyl)piperidin-4-yl)imidazo[1,2-b]pyridazine-3-carboxamide (X-71). MS m/z 487.2 $(M+1)^+$.

Example 12

Synthesis of (R)-2-(4-(6-(2-(3-fluorophenyl)pyrrolidin-1-yl)imidazo[1,2-b]pyridazine-3-carboxamido)piperidin-1-yl)-2-oxoethyl acetate (X-73)

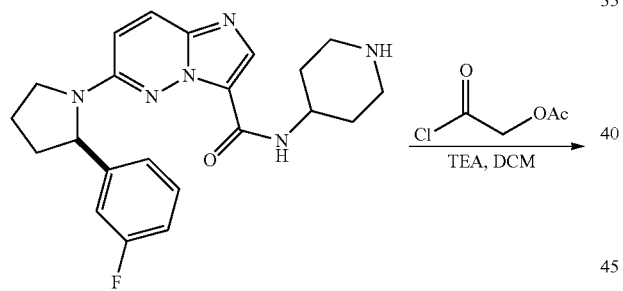

I-57

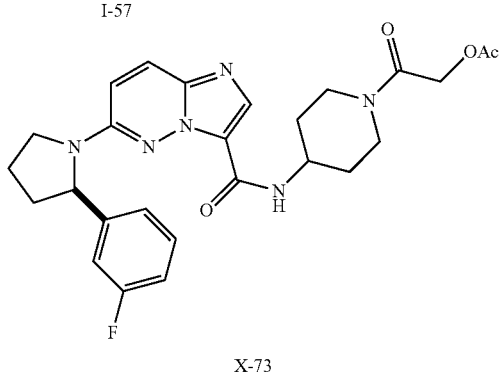

X-73

To a solution of (R)-6-(2-(3-fluorophenyl)pyrrolidin-1-yl)-N-(piperidin-4-yl)imidazo[1,2-b]pyridazine-3-carboxamide (I-57) (100 mg, 0.24 mmol), triethylamine (0.4 mL, 2.8 mmol) in DCM at 0° C. was added 2-chloro-2-oxoethyl acetate (80 mg, 0.59 mmol). The resulting solution was stirred at room temperature for 2 hours. The solvent was removed and the crude product was purified by preparative LCMS to yield (R)-2-(4-(6-(2-(3-fluorophenyl)pyrrolidin-1-yl)imidazo[1,2-b]pyridazine-3-carboxamido)piperidin-1-yl)-2-oxoethyl acetate (X-73). MS m/z 509.2 $(M+1)^+$.

Example 13

Synthesis of (R)-6-(2-(3-fluorophenyl)pyrrolidin-1-yl)-N-(1-(2-hydroxyacetyl)piperidin-4-yl)imidazo[1,2-b]pyridazine-3-carboxamide (X-75)

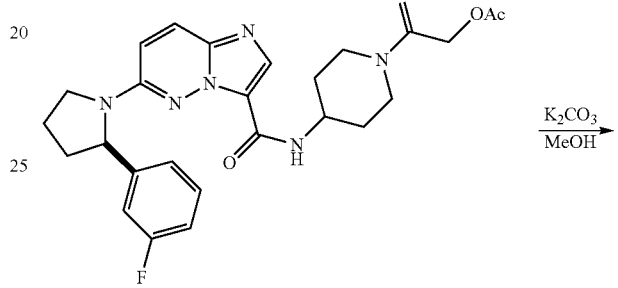

X-73

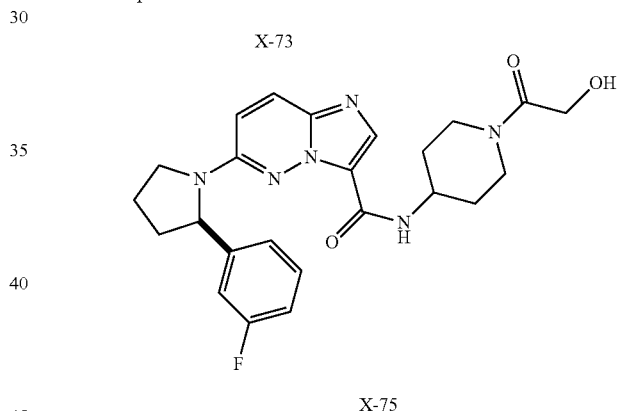

X-75

To a solution of (R)-2-(4-(6-(2-(3-fluorophenyl)pyrrolidin-1-yl)imidazo[1,2-b]pyridazine-3-carboxamido)piperidin-1-yl)-2-oxoethyl acetate (X-73) (50 mg, 0.1 mmol) in MeOH (3 mL) was added potassium carbonate (140 mg, 1.0 mmol). The resulting heterogeneous mixture was stirred at room temperature for 3 hours. The solids were removed by filtration and the mother liquor was reduced to dryness to yield the crude product. The crude product was then purified using preparative LCMS yielding (R)-6-(2-(3-fluorophenyl)pyrrolidin-1-yl)-N-(1-(2-hydroxyacetyl)piperidin-4-yl)imidazo[1,2-b]pyridazine-3-carboxamide (X-75). $^1$H NMR (400 MHz, MeOD-$d_4$) δ 8.00 (s, 1 H), 7.73 (d, J=10 Hz, 1 H), 7.27 (q, J=7.6 Hz, 1 H), 7.07 (t, J=6.4 Hz, 1 H), 6.92-6.87 (m, 3 H), 5.134 (d, J=7.6 Hz, 1 H), 4.49 (dd, J=38, 13.6 Hz, 1 H), 4.28-4.13 (m, 2 H), 4.02 (t, J=10.8 Hz, 1 H), 3.83 (t, J=8.4 Hz, 1 H), 3.74-3.56 (m, 2 H), 3.05 (q, J=14 Hz, 1 H), 2.74 (q, J=12.4 Hz, 1 H), 2.49-2.40 (m, 5 H), 1.33 (bs, 2 H). MS m/z 467.2 $(M+1)^+$.

Example 14

Synthesis of 6-((2R,4S)-4-fluoro-2-(3-fluorophenyl) pyrrolidin-1-yl)-N-(2-fluoroethyl)imidazo[1,2-b] pyridazine-3-carboxamide (X-112)

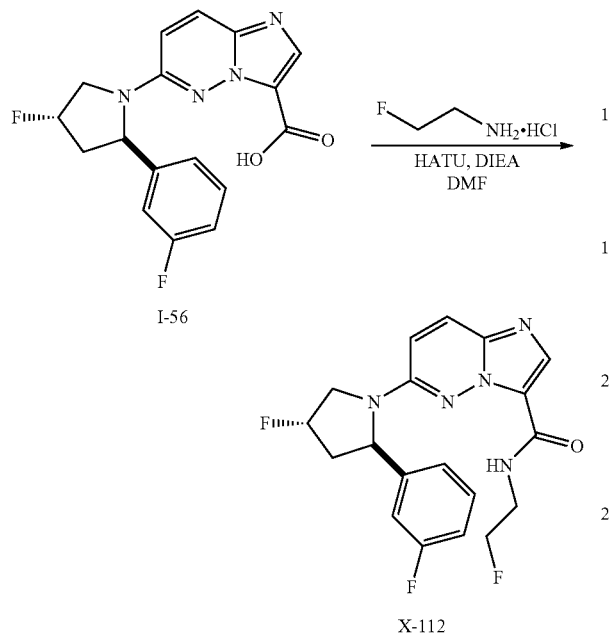

To a solution of 6-((2R,4S)-4-fluoro-2-(3-fluorophenyl) pyrrolidin-1-yl)imidazo[1,2-b]pyridazine-3-carboxylic acid (I-56) (18 mg, 0.063 mmol) and 2-fluoroethanamine hydrochloride (6 mg, 0.0749 mmol) in DMF (1 mL) at room temperature were added DIEA (0.027 mL, 0.156 mmol) and HATU (20 mg, 0.052 mmol). The mixture was stirred at room temperature overnight. The resulting crude was diluted with EtOAc, washed with water and brine, dried over sodium sulfate, filtered and concentrated. The final product 6-((2R, 4S)-4-fluoro-2-(3-fluorophenyl)pyrrolidin-1-yl)-N-(2-fluoroethyl)imidazo[1,2-b]pyridazine-3-carboxamide (X-112) was isolated using column chromatography on silica gel with DCM/MeOH gradient. $^1$H NMR (400 MHz, CDCl$_3$) δ 8.83 (br s, 1 H), 8.22 (s, 1 H), 7.72 (d, J=10.0 Hz, 1 H), 7.37-7.31 (m, 1 H), 7.06 (d, J=7.6, Hz, 1 H), 7.02-6.95 (m, 2 H), 6.57 (d, J=9.6 Hz, 1 H), 5.42 (d, J=52.4, 1 H), 5.18 (dd, J=9.2, 7.2 Hz, 1 H), 4.73-4.65 (m, 1 H), 4.61-4.53 (m, 1 H), 4.28-4.04 (m, 2 H), 4.01-3.84 (m, 1 H), 3.80-3.56 (m, 1 H), 2.98-2.86 (m, 1 H), 2.24-2.05 (m, 1 H). MS m/z 390.1 (M+1)$^+$.

Example 15

Synthesis of (R)-1-(6-(2-(3-fluorophenyl)pyrrolidin-1-yl)imidazo[1,2-b]pyridazin-3-yl)propan-1-one (X-123)

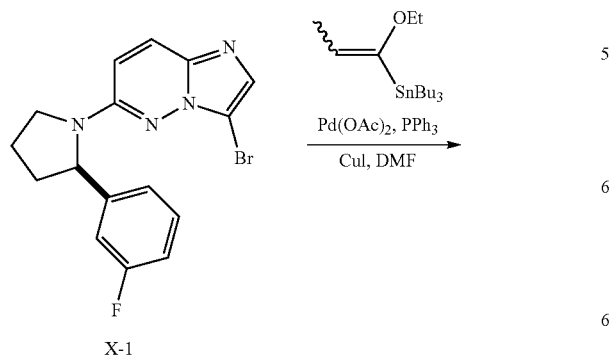

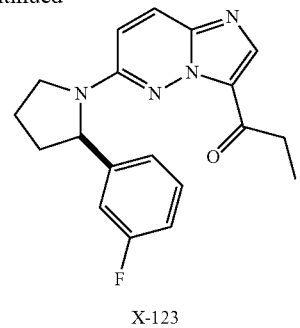

A microwave vial was charged with (R)-3-bromo-6-(2-(3-fluorophenyl)pyrrolidin-1-yl)imidazo[1,2-b]pyridazine (X-1) (90 mg, 0.25 mmol), Pd(OAc)$_2$ (3 mg, 13 μmol), PPh$_3$ (7 mg, 27 μmol), CuI (10 mg, 53 μmol), tributyl(1-ethoxyprop-1-en-1-yl)stannane (0.28 g, 0.75 mmol) and DMF (5 mL) under N$_2$. The vial was sealed and heated in an oil bath at 75° C. for 18 hours. Upon cooling the reaction was diluted with water and extracted with EtOAc (2×20 mL). The combined extracts were washed with brine, dried over magnesium sulfate, filtered and reduced to dryness. The crude residue was treated with HCl (4M in dioxane, 3 mL) and stirred at room temperature for 24 hours. The reaction was diluted with 3M NaOH and extracted with EtOAc (2×20 mL). The combined extracts were washed with brine, dried over magnesium sulfate, filtered and reduced to dryness. The crude residue was purified by silica gel column chromatography with DCM 5% MeOH to yield (R)-1-(6-(2-(3-fluorophenyl)pyrrolidin-1-yl)imidazo[1,2-b]pyridazin-3-yl)propan-1-one (X-123) as a white solid. MS m/z 339.1 (M+1)$^+$.

Example 16

Synthesis of (R)-1-(6-(2-(3-fluorophenyl)pyrrolidin-1-yl)imidazo[1,2-b]pyridazin-3-yl)ethanone (X-125)

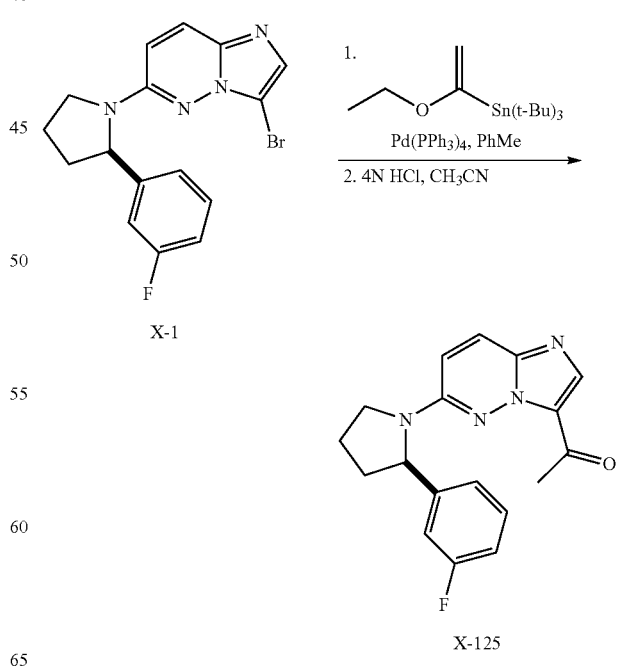

To a solution of (R)-3-bromo-6-(2-(3-fluorophenyl)pyrrolidin-1-yl)imidazo[1,2-b]pyridazine (X-1) (720 mg, 1.99 mmol) in toluene (20 mL) were added tri-tert-butyl(1-ethoxyvinyl)stannane (2.2 g, 6.09 mmol) and Pd(PPh₃)₄ (240 mg, 10% mmol). The mixture was heated at 110° C. overnight. The crude was concentrated and dissolved in CH₃CN (20 mL). To the above solution was added HCl (10 mL of a 4 M solution in 1,4-dioxane) and the resulting solution was stirred at room temperature overnight. All the solvent was removed under reduced pressure. The mixture was dissolved in DCM, washed with saturated aq. NaHCO3 and brine, dried over sodium sulfate, filtered and concentrated. The crude was purified by column chromatography on silica gel with DCM/MeOH gradient as eluant to yield (R)-1-(6-(2-(3-fluorophenyl)pyrrolidin-1-yl)imidazo[1,2-b]pyridazin-3-yl)ethanone (X-125). ¹H NMR (400 MHz, CDCl₃) δ 8.17 (s, 1 H), 7.68 (d, J=10.0 Hz, 1 H), 7.33-7.26 (m, 1 H), 7.00 (d, J=8.0 Hz, 1H), 6.97-6.87 (m, 2 H), 6.59 (d, J=9.6 Hz, 1 H), 5.04 (dd, J=8.4, 2.0 Hz, 1 H), 4.00-3.91 (m, 1 H), 3.79-3.69 (m, 1 H), 2.58 (s, 3 H), 2.55-2.45 (m, 1 H), 2.15-2.00 (m, 1 H). MS m/z 325.1 (M+1)⁺.

Example 17

Synthesis of (R)-3-(3-fluorophenyl)-1-(6-(2-(3-fluorophenyl)pyrrolidin-1-yl)imidazo[1,2-b]pyridazin-3-yl)prop-2-en-1-one (X-126)

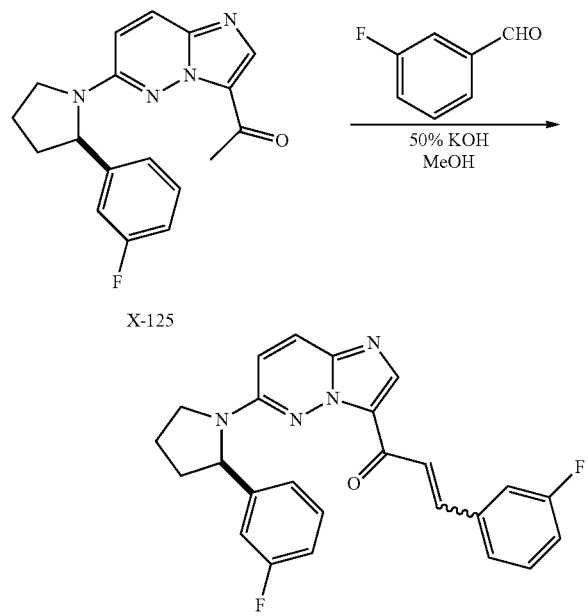

To a solution of (R)-1-(6-(2-(3-fluorophenyl)pyrrolidin-1-yl)imidazo[1,2-b]pyridazin-3-yl)ethanone (X-125) (162 mg, 0.5 mmol) in MeOH (5 mL) was added 3-fluorobenzaldehyde (62 mg, 0.5 mmol) and 50% aq. KOH (0.5 mL). The mixture was heated at 70° C. for 2 hours. Solid was formed upon cooling and was filtered to yield (R)-3-(3-fluorophenyl)-1-(6-(2-(3-fluorophenyl)pyrrolidin-1-yl)imidazo[1,2-b]pyridazin-3-yl)prop-2-en-1-one (X-126). MS m/z 431.1 (M+1)⁺.

Example 18

Synthesis of (R)-3-(3-fluorophenyl)-1-(6-(2-(3-fluorophenyl)pyrrolidin-1-yl)imidazo[1,2-k]pyridazin-3-yl)propan-1-one (X-127)

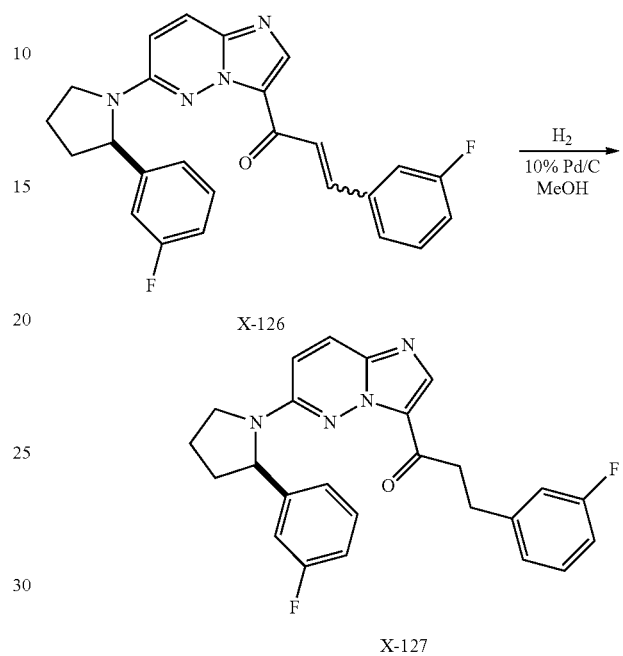

To a solution of (R)-3-(3-fluorophenyl)-1-(6-(2-(3-fluorophenyl)pyrrolidin-1-yl)imidazo[1,2-b]pyridazin-3-yl) prop-2-en-1-one (X-126) (30 mg, 0.07 mmol) in MeOH (1 mL) was added 10% Pd/C (6 mg). The mixture was stirred under a hydrogen atmosphere overnight. The catalyst was filtered and washed with MeOH. The filtrate was concentrated and purified by column chromatography on silica gel with DCM/MeOH gradient as eluant to yield (R)-3-(3-fluorophenyl)-1-(6-(2-(3-fluorophenyl)pyrrolidin-1-yl)imidazo[1,2-b]pyridazin-3-yl)propan-1-one (X-127). MS m/z 433.6 (M+1)⁺.

Example 19

Synthesis of N-ethoxy-6-((2R,4S)-4-fluoro-2-(3-fluorophenyl)pyrrolidin-1-yl)imidazo[1,2-k]pyridazine-3-carboxamide (X-142)

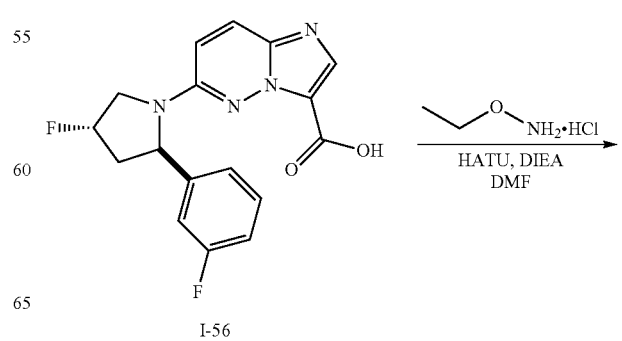

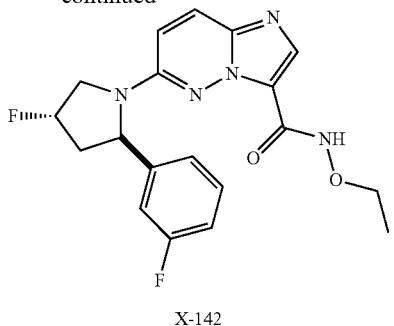

X-142

To a solution of 6-((2R,4S)-4-fluoro-2-(3-fluorophenyl)pyrrolidin-1-yl)imidazo[1,2-b]pyridazine-3-carboxylic acid (I-56) (33 mg, 0.1 mmol) and O-ethylhydroxylamine hydrochloride (10 mg, 0.1 mmol) in DMF (1 mL) at room temperature were added DIEA (0.052 mL, 0.3 mmol) and HATU (38 mg, 0.1 mmol). The mixture was stirred at room temperature overnight. The resulting crude was diluted with EtOAc, washed with water and brine, dried over sodium sulfate, filtered and concentrated. The crude was purified by column chromatography on silica gel with DCM/MeOH gradient as eluant to yield N-ethoxy-6-((2R,4S)-4-fluoro-2-(3-fluorophenyl)pyrrolidin-1-yl)imidazo[1,2-b]pyridazine-3-carboxamide (X-142). $^1$H NMR (400 MHz, CDCl$_3$) δ 10.29 (s, 1 H), 8.23 (s, 1 H), 7.79 (d, J=10.0 Hz, 1 H), 7.36 (td, J=7.6, 5.6 Hz, 1 H), 7.09 (d, J=7.6 Hz, 1 H), 7.03-6.95 (m, 2 H), 6.68 (d, J=10.0 Hz, 1 H), 5.43 (d, J=52.8, 1 H), 5.19 (dd, J=9.6, 7.2 Hz, 1 H), 4.24-4.05 (m, 3 H), 3.95-3.86 (m, 1 H), 2.92 (td, J=16.0, 6.8 Hz, 1 H), 2.15 (dddd, J=40.8, 14.0, 9.6, 3.6 Hz, 1 H), 1.36 (t, J=7.2 Hz, 3 H). MS m/z 388.10 (M+1)$^+$.

Example 20

Synthesis of N-ethoxy-6-(2-(3-fluorophenyl)pyrrolidin-1-yl)imidazo[1,2-b]pyridazine-3-carboxamide (X-152)

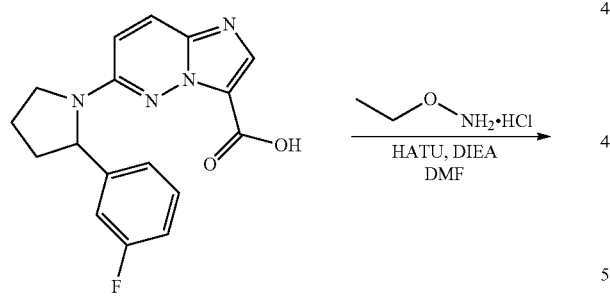

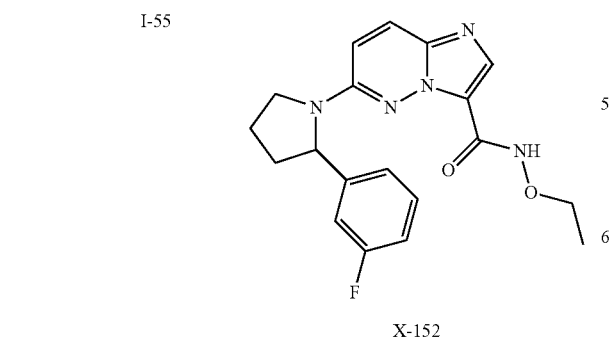

X-152

N-Ethoxy-6-(2-(3-fluorophenyl)pyrrolidin-1-yl)imidazo[1,2-b]pyridazine-3-carboxamide (X-152) was prepared in the same manner as N-ethoxy-6-((2R,4S)-4-fluoro-2-(3-fluorophenyl)pyrrolidin-1-yl)imidazo[1,2-b]pyridazine-3-carboxamide (X-142). Purified by preparative LCMS with ACN/water gradient. $^1$H NMR (400 MHz, MeOD-d$_4$) δ 8.04 (s, 1 H), 7.86 (d, J=9.6 Hz, 1 H), 7.41-7.36 (m, 1H), 7.14 (d, J=7.6 Hz, 1 H), 7.09 (d, J=9.6 Hz, 1 H), 7.01 (dt, J=8.8, 2.4 Hz, 1 H), 5.191 (dd, J=8, 2.8 Hz, 1 H), 4.04-3.94 (m, 2 H), 3.77 (q, J=8 Hz, 2 H), 2.63-2.53 (m, 1 H), 2.18-2.11 (m, 2 H), 2.04-1.98 (m, 1 H), 1.29 (t, J=3.8 Hz, 3 H). MS m/z 370.2 (M+1)$^+$.

Example 21

Synthesis of (R)-6-(2-(3-fluorophenyl)pyrrolidin-1-yl)-N-(4-methylpiperazin-1-yl)imidazo[1,2-b]pyridazine-3-carboxamide (X-154)

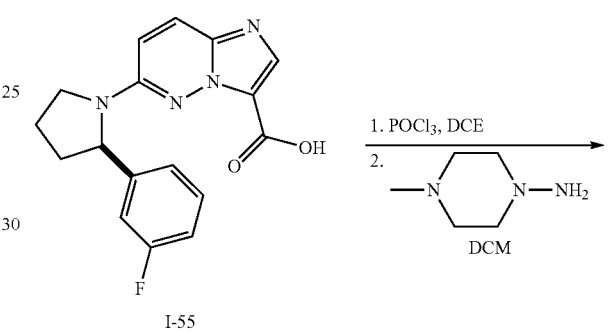

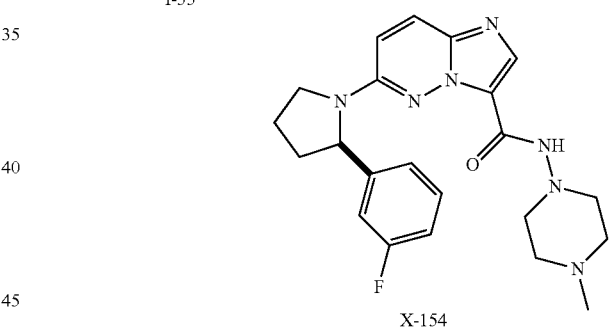

X-154

To a solution of (R)-6-(2-(3-fluorophenyl)pyrrolidin-1-yl)imidazo[1,2-b]pyridazine-3-carboxylic acid (I-55) (0.05 g, 0.15 mmol) in 1,2-dichloroethane (1.5 mL) was added POCl$_3$ (150 μL, 1.6 mmol). This solution was stirred at 100° C. for 30 minutes. The solvents were removed and the excess POCl$_3$ was removed by azeotroping with DCM (3×10 mL) and diethyl ether (3×10 mL) to yield the crude (R)-6-(2-(3-fluorophenyl)pyrrolidin-1-yl)imidazo[1,2-b]pyridazine-3-carbonyl chloride. This residue was dissolved in DCM (2 mL) and cooled to 0° C. and 4-methylpiperazin-1-amine (90 mg, 0.78 mmol) was added. This was warmed to room temperature and stirred for 1 hour. The crude product was purified by preparative LCMS to yield (R)-6-(2-(3-fluorophenyl)pyrrolidin-1-yl)-N-(4-methylpiperazin-1-yl)imidazo[1,2-b]pyridazine-3-carboxamide (X-154). MS m/z 424.2 (M+1)$^+$.

Example 22

Synthesis of ethyl 6-(2-(3-fluorophenyl)piperidin-1-yl)imidazo[1,2-b]pyridazine-3-carboxylate (X-156)

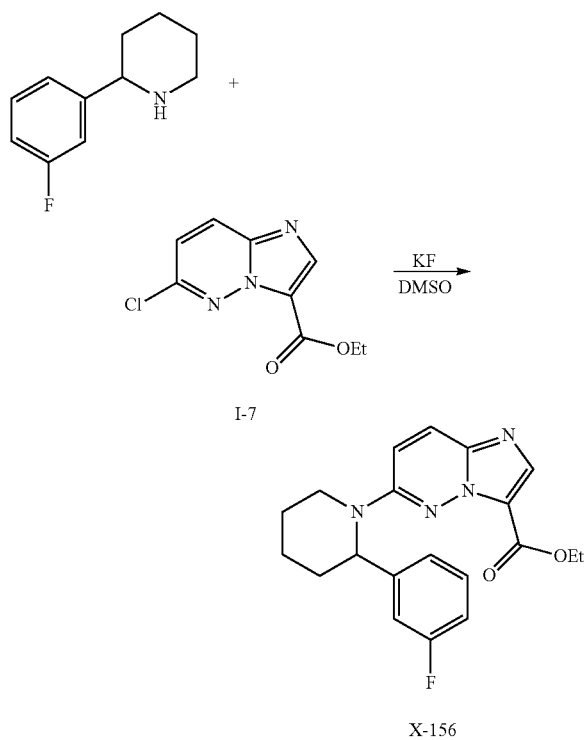

A heterogeneous mixture of 2-(3-fluorophenyl)piperidine (0.1 g, 0.6 mmol), spray dried potassium fluoride (0.12 g, 2.2 mmol) and ethyl 6-chloroimidazo[1,2-b]pyridazine-3-carboxylate (I-7) (0.1 g, 0.4 mmol) in DMSO (3 mL) was heated to 100° C. for 18 hours. The mixture was poured into water, extracted with EtOAc, washed with brine, dried over sodium sulfate, filtered and concentrated. The crude was purified by column chromatography on silica gel with DCM/MeOH gradient as eluant to yield ethyl 6-(2-(3-fluorophenyl)piperidin-1-yl)imidazo[1,2-b]pyridazine-3-carboxylate (X-156). $^1$H NMR (400 MHz, MeOD-d$_4$) δ 8.17 (s, 1 H), 8.01 (d, J=10 Hz, 1 H), 7.42-7.36 (m, 2 H), 7.13-7.05 (m, 3 H), 5.70 (s, 1 H), 2.02-1.94 (m, 1 H), 1.79-1.70 (m, 1 H), 1.63-1.57 (m, 2 H), 1.47-1.37 (m, 1 H), 1.29 (t, J=7.2 Hz, 3 H). MS m/z 369.2 (M+1)$^+$.

Example 23

Synthesis of (R)-ethyl 6-(2-(3-fluorophenyl)pyrrolidin-1-yl)imidazo[1,2-b]pyridazine-3-carboxylate (X-158)

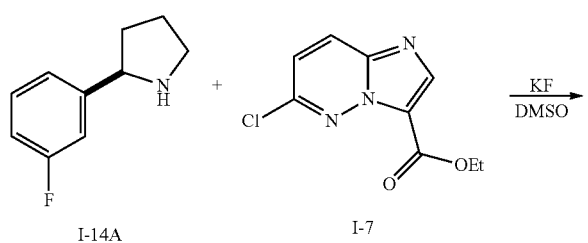

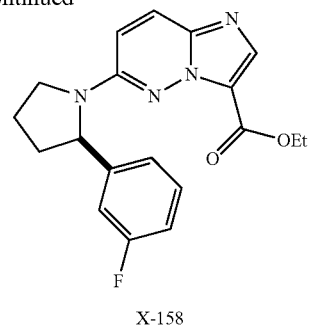

To (R)-2-(3-fluorophenyl)pyrrolidine (5.9 g, 35.5 mmol) was added spray dried potassium fluoride (6.4 g, 111 mmol), ethyl 6-chloroimidazo[1,2-b]pyridazine-3-carboxylate (I-7) (7.0 g, 30.9 mmol) and DMSO (30 mL). The resulting heterogeneous mixture was stirred at 100° C. for 18 hours. The reaction mixture was poured into water (250 mL) and stirred at room temperature for 20 minutes then extracted with EtOAc (3×150 mL). The combined extracts were washed with brine (3×100 mL), dried over anhydrous sodium sulfate, filtered and reduced to dryness to yield a yellow oil. The crude product was purified using a flash chromatography on silica with DCM/MeOH gradient as eluant to yield (R)-ethyl 6-(2-(3-fluorophenyl)pyrrolidin-1-yl)imidazo[1,2-b]pyridazine-3-carboxylate (X-158). MS m/z 355.2 (M+1)$^+$.

Example 24

Synthesis of ethyl 6-(2-(3-fluorophenyl)-3-oxopyrrolidin-1-yl)imidazo[1,2-b]pyridazine-3-carboxylate (X-159)

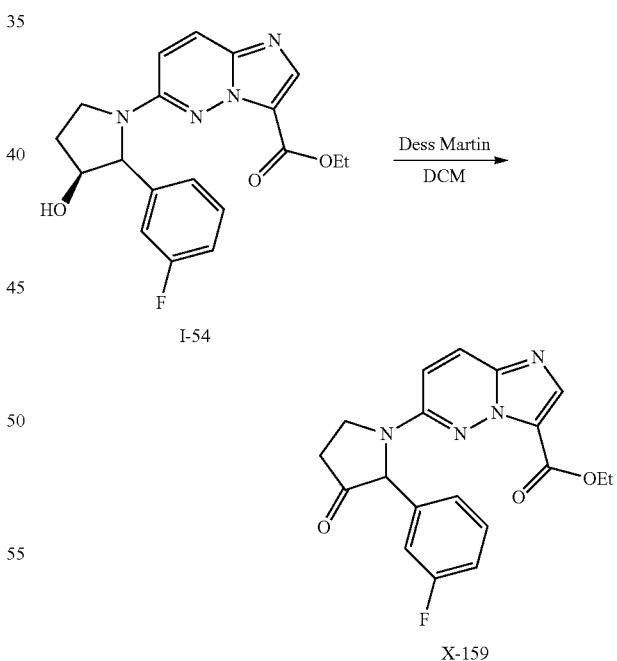

To a solution of ethyl 6-((3S)-2-(3-fluorophenyl)-3-hydroxypyrrolidin-1-yl)imidazo[1,2-b]pyridazine-3-carboxylate (I-54) (20 mg, 0.054 mmol) in DCM (1 mL) at 0° C. was added Dess-Martin periodinane (27 mg, 0.0648 mmol). The reaction was warmed to room temperature and stirred for 2 hours. The mixture was diluted with DCM, washed with brine, dried over sodium sulfate, filtered and concentrated. The crude was purified by column chromatography on silica gel with EtOAc/hexanes gradient as eluant to yield ethyl 6-(2-(3-fluorophenyl)-3-oxopyrrolidin-1-yl)imidazo[1,2-b]pyridazine-3-carboxylate (X-159). $^1$H NMR (400 MHz, CDCl$_3$) δ 8.09 (s, 1 H), 7.79 (d, J=10 Hz, 1 H), 7.44-7.35 (m, 1 H), 7.28-7.18 (m, 2 H), 7.16-7.08 (m, 1 H), 6.91 (d, J=9.6 Hz, 1 H), 5.26 (s, 1 H), 4.31 (q, J=7.2 Hz, 2 H), 4.26-4.18 (m, 1 H), 4.12-4.02 (m, 1 H), 3.03-2.80 (m, 2 H), 1.31 (t, J=7.2 Hz, 3H). MS m/z 396.1 (M+1)$^+$.

Example 25

Synthesis of ethyl 6-((2R,4R)-2-(3-fluorophenyl)-4-hydroxypyrrolidin-1-yl)imidazo[1,2-b]pyridazine-3-carboxylate (X-160)

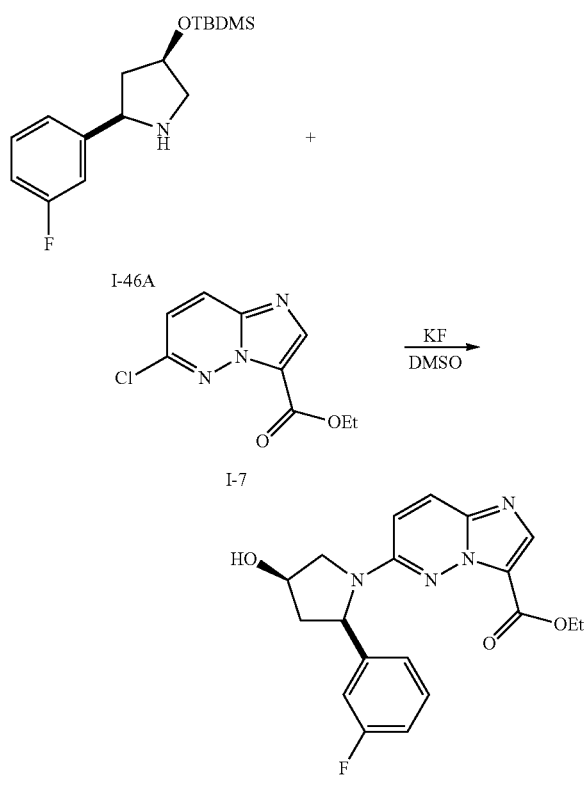

To a solution of (2R,4R)-4-(tert-butyldimethylsilyloxy)-2-(3-fluorophenyl)pyrrolidine (I-46A) (240 mg, 0.81 mmol) and ethyl 6-chloroimidazo[1,2-b]pyridazine-3-carboxylate (I-7) (184 mg, 0.81 mmol) in DMSO (4 mL) was added KF (236 mg, 4.07 mmol). The mixture was heated at 120° C. overnight. The mixture was poured into water, extracted with EtOAc, washed with brine, dried over sodium sulfate, filtered and concentrated. The crude was purified by column chromatography on silica gel with DCM/MeOH gradient as eluant to yield ethyl 6-((2R,4R)-2-(3-fluorophenyl)-4-hydroxypyrrolidin-1-yl)imidazo[1,2-b]pyridazine-3-carboxylate (X-160). $^1$H NMR (400 MHz, CDCl$_3$) δ 8.15 (s, 1 H), 7.64 (d, J=10 Hz, 1 H), 7.34-7.27 (m, 1 H), 7.15 (d, J=8 Hz, 1 H), 7.09 (d, J=10 Hz, 1 H), 6.72 (td, J=8.4, 2.0 Hz, 1 H), 6.49 (d, J=10 Hz, 1 H), 5.05 (dd, J=9.2, 2.8 Hz, 1 H), 4.68 (bs, 1 H), 4.41 (q, J=7.2 Hz, 2 H), 4.11-4.05 (m, 1 H), 4.05-3.98 (m, 1 H), 2.77 (ddd, J=5.2, 9.6, 14 Hz, 1 H), 2.23 (d, J=13.6 Hz, 1 H), 1.41 (t, J=7.2 Hz, 3H). MS m/z 371.1 (M+1)$^+$.

Example 26

Synthesis of (S)-ethyl 6-(3,3,4,4-tetrafluoro-2-(3-fluorophenyl)pyrrolidin-1-yl)imidazo[1,2-b]pyridazine-3-carboxylate (X-164)

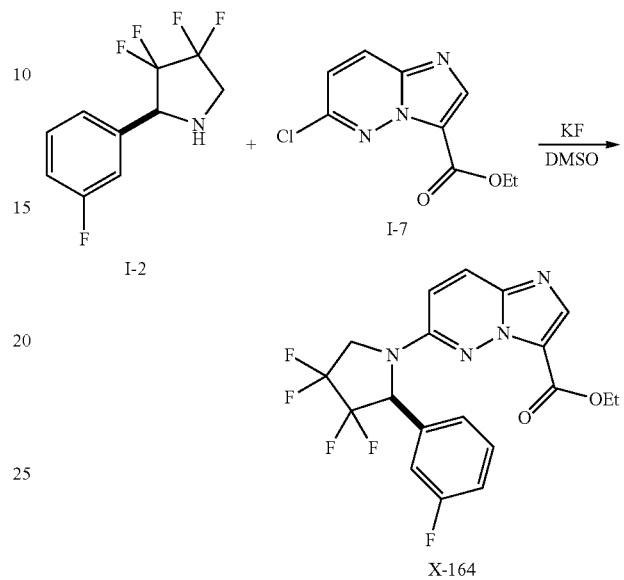

To a solution of (R)-2,2,3,3-tetrafluoro-5-(3-fluorophenyl)pyrrolidine (I-22) (0.27 g, 1.1 mmol) and ethyl 6-chloroimidazo[1,2-b]pyridazine-3-carboxylate (I-7) (0.23 g, 1.0 mmol) in DMF (3 mL) was added potassium fluoride (0.20 g, 3.4 mmol). The reaction was heated in a sealed flask at 120° C. for 4 hours. Upon cooling the reaction was diluted with brine and extracted with EtOAc (2×30 mL). The combined organic extracts were dried over magnesium sulfate, filtered and reduced to dryness. The crude material was purified on silica gel column chromatography with DCM/EtOAc gradient as eluant to yield (S)-ethyl 6-(3,3,4,4-tetrafluoro-2-(3-fluorophenyl)pyrrolidin-1-yl)imidazo[1,2-b]pyridazine-3-carboxylate (X-164). $^1$H NMR (400 MHz, DMSO-d$_6$) δ 8.36 (s, 1 H), 8.26 (d, J=7.6 Hz, 1 H), 7.45-7.39 (m, 1 H), 7.15-7.11 (m, 2 H), 7.05 (d, J=9.2 Hz, 1 H), 5.93 (d, J=8.0 Hz, 1 H), 5.30-5.27 (m, 1 H), 4.68-4.5 (m, 2 H), 4.37 (q, J=6.8 Hz, 2 H), 1.41 (t, J=7.2 Hz, 3 H). MS m/z 427.1 (M+1)$^+$.

Example 27

Synthesis of ethyl 6-((2R,4S)-4-fluoro-2-(3-fluorophenyl)pyrrolidin-1-yl)imidazo[1,2-b]pyridazine-3-carboxylate (X-165)

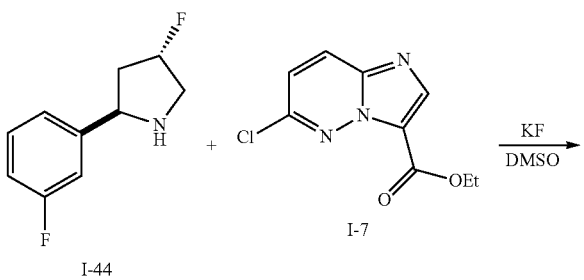

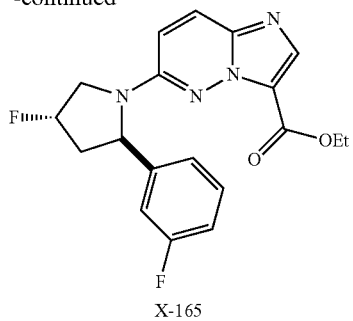

X-165

To a suspension of ethyl 6-chloroimidazo[1,2-b]pyridazine-3-carboxylate (I-7) (45 mg, 0.2 mmol) in DMSO (1 mL) were added (2R,4S)-4-fluoro-2-(3-fluorophenyl)pyrrolidine (I-44) (44 mg, 0.24 mmol) and potassium floride (116 mg, 2.0 mmol). The mixture was heated at 120° C. overnight. The mixture was poured into water and extracted with EtOAc. The organic layers were washed brine, dried over sodium sulfate, filtered and concentrated. The crude was purified by column chromatography on silica gel with EtOAc/hexanes gradient as eluant to yield ethyl 6-((2R,4S)-4-fluoro-2-(3-fluorophenyl)pyrrolidin-1-yl)imidazo[1,2-b]pyridazine-3-carboxylate (X-165). $^1$H NMR (400 MHz, CDCl$_3$) δ 8.14 (s, 1 H), 7.61 (d, J=10.0 Hz, 1 H), 7.32 (td, J=8.0, 5.6 Hz, 1 H), 7.09 (d, J=8.0 Hz, 1 H), 7.03-6.94 (m, 2 H), 6.47 (d, J=10.0 Hz, 1 H), 5.39 (d, J=52.4, 1 H), 5.12 (dd, J=9.2, 7.2 Hz, 1 H), 4.55-4.45 (m, 1 H), 4.42 (q, J=6.8 Hz, 2 H), 4.10 (ddd, J=37.2, 13.6, 2.0 Hz, 1 H), 2.95-2.83 (m, 1 H), 2.15 (dddd, J=41.2, 24.0, 9.6, 3.6 Hz, 1 H), 1.42 (t, J=7.2 Hz, 3 H). MS m/z 373.2 (M+1)$^+$.

Example 28

Synthesis of ethyl 6-((2S,4R)-4-fluoro-2-(3-fluorophenyl)pyrrolidin-1-yl)imidazo[1,2-b]pyridazine-3-carboxylate (X-166)

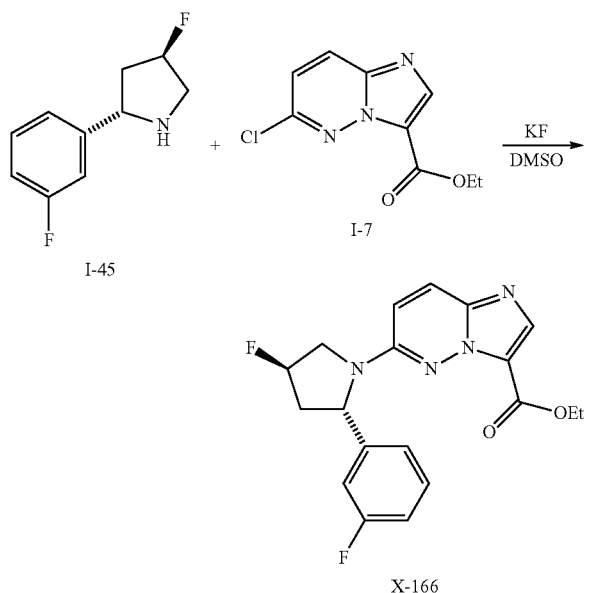

Ethyl 6-((2S,4R)-4-fluoro-2-(3-fluorophenyl)pyrrolidin-1-yl)imidazo[1,2-b]pyridazine-3-carboxylate (X-166) was synthesized in the same manner as ethyl 6-((2R,4S)-4-fluoro-2-(3-fluorophenyl)pyrrolidin-1-yl)imidazo[1,2-b]pyridazine-3-carboxylate (X-165) starting from (2S,4R)-4-fluoro-2-(3-fluorophenyl)pyrrolidine. $^1$H NMR (400 MHz, CDCl$_3$) δ 8.16 (s, 1 H), 7.66 (d, J=9.6 Hz, 1 H), 7.32-7.27 (m, 1 H), 7.12 (d, J=8 Hz, 1 H), 7.05 (d, J=10 Hz, 1 H), 6.95 (td, J=8.4, 2.4 Hz, 1 H), 6.50 (d, J=10 Hz, 1 H), 5.43 (dt, J=52.8, 4.0 Hz, 1 H), 5.10 (d, J=9.6 Hz, 1 H), 4.42 (q, J=7.2 Hz, 1 H), 4.35 (ddd, J=24.8 13.6, 2 Hz, 1 H), 4.03 (ddd, J=35.9, 14.0, 4.0 Hz, 1 H), 2.75 (dddd, J=41.2, 14.4, 10.0, 4.4 Hz, 1 H), 2.49 (dd, J=18.8, 14.4 Hz, 1 H), 1.42 (t, J=6.8 Hz, 3 H). MS m/z 373.1 (M+1)$^+$.

Example 29

Synthesis of (R)-2-ethoxy-N-(6-(2-(3-fluorophenyl)pyrrolidin-1-yl)imidazo[1,2-b]pyridazin-3-yl)acetamide (X-168)

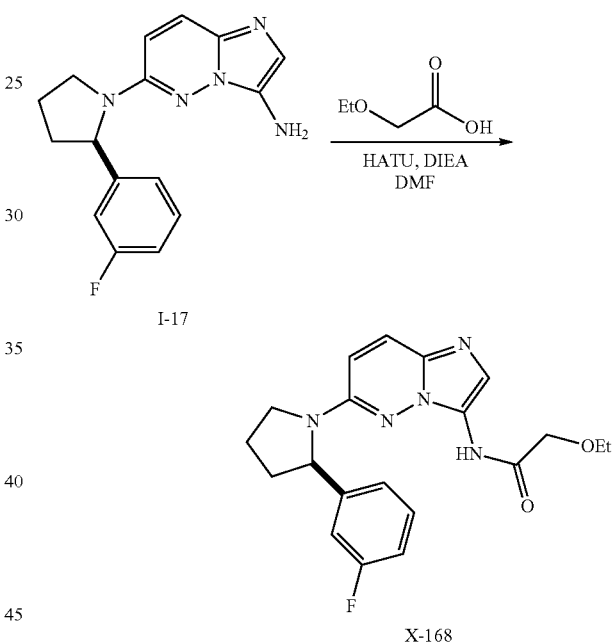

To a solution of (R)-6-(2-(3-fluorophenyl)pyrrolidin-1-yl)imidazo[1,2-b]pyridazin-3-amine (I-17) (30 mg, 0.1 mmol) and 2-ethoxyacetic acid (12 mg, 0.12 mmol) in DMF (1 mL) at room temperature were added DIEA (0.052 mL, 0.3 mmol) and HATU (38 mg, 0.1 mmol). The mixture was stirred at room temperature overnight. The reaction was diluted with EtOAc, washed with water and brine, dried over sodium sulfate, filtered and concentrated. The crude was purified by column chromatography on silica gel with DCM/MeOH gradient as gradient to yield (R)-2-ethoxy-N-(6-(2-(3-fluorophenyl)pyrrolidin-1-yl)imidazo[1,2-b]pyridazin-3-yl)acetamide (X-168). $^1$H NMR (400 MHz, CDCl$_3$) δ 8.65 (s, 1 H), 7.86 (s, 1 H), 7.60 (d, J=10 Hz, 1 H), 7.32-7.28 (m, 1 H), 7.03 (d, J=8 Hz, 1 H), 6.96-6.88 (m, 2 H), 6.46 (d, J=9.6 Hz, 1 H), 4.99 (dd, J=3.6, 8.2 Hz, 1 H), 3.95-3.88 (m, 1 H), 3.75-3.66 (m, 1 H), 2.55-2.44 (m, 1 H), 2.22-2.05 (m, 2 H), 2.05-1.98 (m, 1 H), 1.92 (t, J=19.6 Hz, 3 H). MS m/z 384.2 (M+1)$^+$.

Example 30

Synthesis of (R)-2-(6-(2-(3-fluorophenyl)pyrrolidin-1-yl)imidazo[1,2-b]pyridazin-3-ylamino)-2-oxoethyl acetate (X-172)

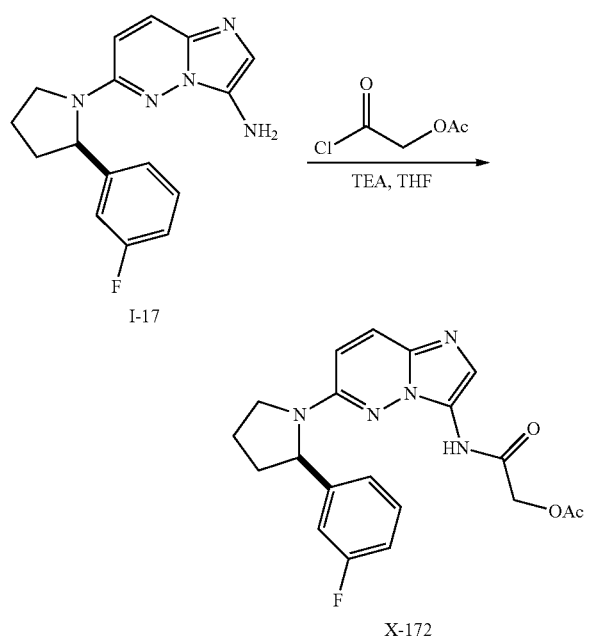

To a solution of (R)-6-(2-(3-fluorophenyl)pyrrolidin-1-yl)imidazo[1,2-b]pyridazin-3-amine (I-17) (30 mg, 0.092 mmol) in THF (0.5 mL) at room temperature was added 2-chloro-2-oxoethyl acetate (0.012 mL, 0.11 mmol) and TEA (0.026 mL, 0.184 mmol). The mixture was stirred at room temperature overnight. The mixture was diluted with EtOAc, washed with water and brine, dried over sodium sulfate, filtered and concentrated. The crude was purified by column chromatography on silica gel with EtOAc/hexanes gradient to yield (R)-2-(6-(2-(3-fluorophenyl)pyrrolidin-1-yl)imidazo[1,2-b]pyridazin-3-ylamino)-2-oxoethyl acetate (X-172). MS m/z 398.1 (M+1)$^+$.

Example 31

Synthesis of (R)-2-amino-N-(6-(4,4-difluoro-2-(3-fluorophenyl)pyrrolidin-1-yl)imidazo[1,2-b]pyridazin-3-yl)acetamide (X-204)

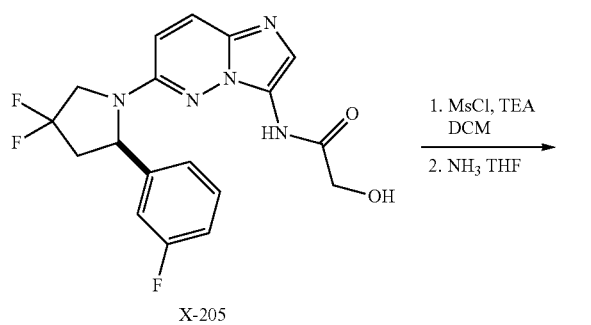

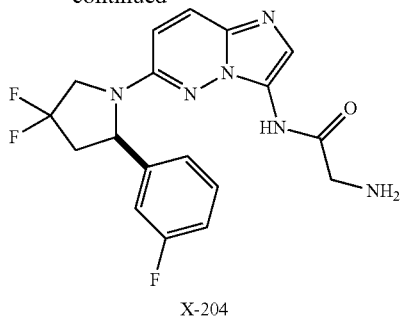

To a solution of (R)-N-(6-(4,4-difluoro-2-(3-fluorophenyl)pyrrolidin-1-yl)imidazo[1,2-b]pyridazin-3-yl)-2-hydroxyacetamide (X-205) (20 mg, 0.05 mmol) and triethylamine (20 µL, 0.15 mmol) in DCM (2 mL) at 0° C. was added methane sulfonyl chloride (10 µL, 0.1 mmol). The reaction was warmed to room temperature and stirred for 1 hour. The reaction was diluted with DCM (30 mL) and extracted with brine (3×30 mL). The organic layer was dried over anhydrous sodium sulfate, filtered and reduced to dryness to yield (R)-2-(6-(4,4-difluoro-2-(3-fluorophenyl)pyrrolidin-1-yl)imidazo[1,2-b]pyridazin-3-ylamino)-2-oxoethyl methanesulfonate. MS m/z 470.1 (M+1). (R)-2-(6-(4,4-difluoro-2-(3-fluorophenyl)pyrrolidin-1-yl)imidazo[1,2-b]pyridazin-3-ylamino)-2-oxoethyl methanesulfonate was immediately dissolved in THF (20 mL of an ammonia saturated solution) and transferred to a sealed tube. This mixture was heated to 60° C. while behind a blast shield and stirred for 18 hours. Upon cooling the reaction was reduced to dryness. The crude product was purified using preparative LCMS to yield (R)-2-amino-N-(6-(4,4-difluoro-2-(3-fluorophenyl)pyrrolidin-1-yl)imidazo[1,2-b]pyridazin-3-yl)acetamide (X-204). MS m/z 391.2 (M+1)$^+$.

Example 32

Synthesis of (R)-N-(6-(4,4-difluoro-2-(3-fluorophenyl)pyrrolidin-1-yl)imidazo[1,2-b]pyridazin-3-yl)-2-hydroxyacetamide (K-205)

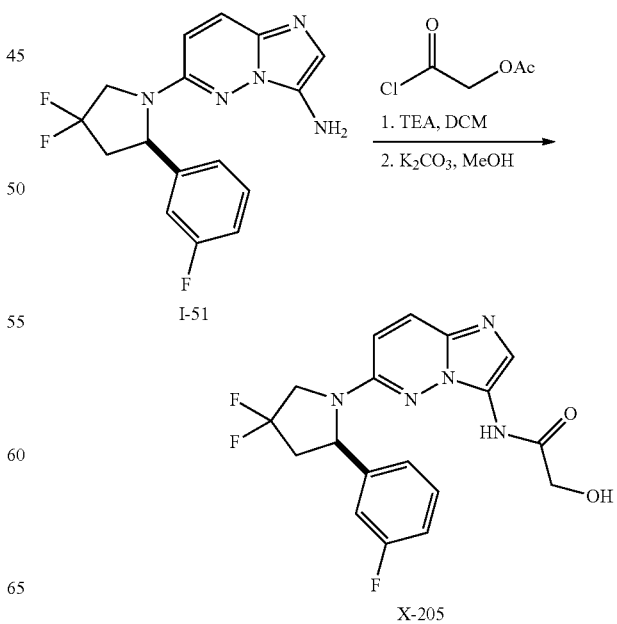

To a solution of (R)-6-(4,4-difluoro-2-(3-fluorophenyl) pyrrolidin-1-yl)imidazo[1,2-b]pyridazin-3-amine (I-51) (40 mg, 0.12 mmol) and triethylamine (50 µL, 0.36 mmol) in DCM (5 mL) at 0° C. was added 2-chloro-2-oxoethyl acetate (30 mg, 0.24 mmol) drop wise. This solution was warmed to room temperature and stirred for 1 hour. The reaction was extracted with brine, dried over anhydrous sodium sulfate, filtered and reduced to dryness. The residue was reconstituted in MeOH (10 mL) and to this was added potassium carbonate (100 mg, 0.9 mmol). The resulting yellow heterogeneous mixture was sonicated for 5 minutes, filtered, and solvent removed. The crude product was purified using preparative LCMS to yield (R)-N-(6-(4,4-difluoro-2-(3-fluorophenyl) pyrrolidin-1-yl)imidazo[1,2-b]pyridazin-3-yl)-2-hydroxyacetamide (X-205). $^1$H NMR (400 MHz, MeOD-d$_4$) δ 7.68 (s, 1 H), 7.65 (s, 1 H), 7.40-7.35 (m, 1 H), 7.23 (d, J=8 Hz, 1 H), 7.14 (d, J=10 Hz, 1 H), 7.00 (dt, J=8.4, 2 Hz, 1 H), 6.70 (d, J=9.6 Hz, 1 H), 5.38 (dd, J=8.8, 5.2 Hz, 1 H), 4.352 (q, J=12 Hz, 1 H), 4.25-4.15 (m, 3 H), 3.21-3.05 (m, 1 H), 2.51 (dq, J=13.2, 5.6 Hz, 1 H). MS m/z 392.1 (M+1)$^+$.

Example 33

Synthesis of (Z)-6-(2-(3-fluorophenyl)pyrrolidin-1-yl)-N'-hydroxyimidazo[1,2-b]pyridazine-3-carboximidamide (X-227)

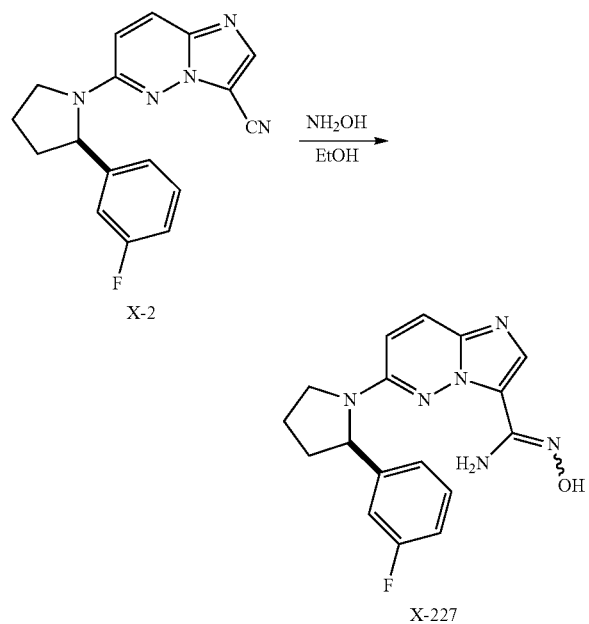

To a solution of 6-(2-(3-fluorophenyl)pyrrolidin-1-yl)imidazo[1,2-b]pyridazine-3-carbonitrile (X-2) (35 mg, 0.1 mmol) in EtOH (1 mL) was added NH$_2$OH (10 mL of a 50% aq. solution) and stirred at room temperature for 15 hours. The reaction was evaporated to dryness and purified on silica gel column chromatography with DCM 3% MeOH gradient as eluant to yield 6-(2-(3-fluorophenyl)pyrrolidin-1-yl)-N'-hydroxyimidazo[1,2-b]pyridazine-3-carboximidamide (X-227) as a yellow solid. $^1$H NMR (400 MHz, DMSO-d$_6$) δ 9.66 (s, 1 H), 7.89 (d, J=10.0 Hz, 1 H), 7.67 (s, 1 H), 7.46-7.41 (m, 1 H), 7.19-7.10 (m, 3 H), 6.78 (s, 1 H), 6.02 (s, 2 H), 5.17 (bd, J=8.0 Hz, 1 H), 4.00-3.98 (m, 1 H), 3.67 (q, J=8.4 Hz, 1 H), 2.52-2.48 (m, 1 H), 2.10-2.08 (m, 2 H), 1.93-1.90 (m, 1 H). MS m/z 341.1 (M+1)$^+$.

Example 34

Synthesis of (R)-6-(2-(3-fluorophenyl)pyrrolidin-1-yl)-N'-methoxyimidazo[1,2-b]pyridazine-3-carboximidamide (X-228)

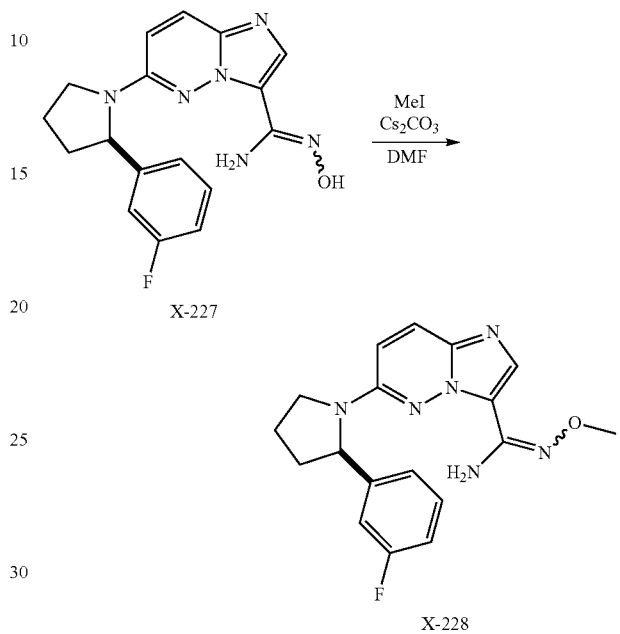

A solution of (R)-6-(2-(3-fluorophenyl)pyrrolidin-1-yl)-N'-hydroxyimidazo[1,2-b]pyridazine-3-carboximidamide (X-227) (25 mg, 0.07 mmol), Cs$_2$CO$_3$ (26 mg, 0.08 mmol) and MeI (5 µL, 0.07 mmol) in DMF (0.5 mL) was heated at 75° C. for 17 hours. Upon cooling the reaction was diluted with brine, extracted with DCM (2×10 mL), dried over magnesium sulfate, filtered and solvent removed. The crude product was purified on silica gel preparative TLC with DCM 5% MeOH as eluant to yield (R)-6-(2-(3-fluorophenyl)pyrrolidin-1-yl)-N'-methoxyimidazo[1,2-b]pyridazine-3-carboximidamide (X-228). MS m/z 355.1 (M+1)$^+$.

Example 35

Synthesis of (R)-ethyl 6-(2-(3-fluorophenyl)pyrrolidin-1-yl)imidazo[1,2-b]pyridazin-3-ylcarbamate (X-236)

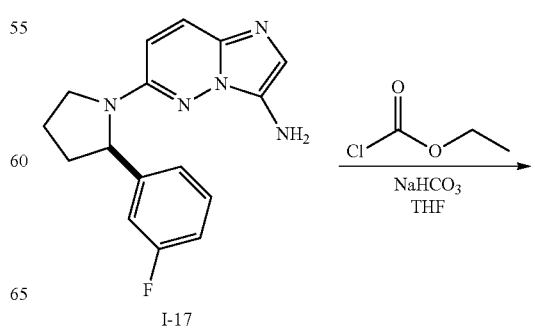

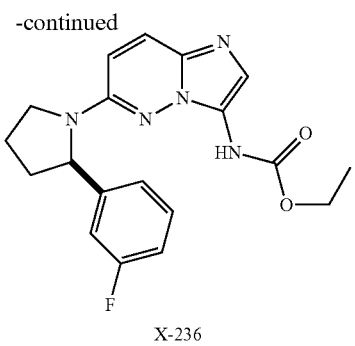

X-236

To a solution of (R)-6-(2-(3-fluorophenyl)pyrrolidin-1-yl)imidazo[1,2-b]pyridazin-3-amine (I-17) in THF (1 mL) at room temperature was added 1.0 N NaHCO$_3$ (0.3 mL) and ethyl chloroformate (20 mg, 0.2 mmol). The mixture was stirred at room temperature overnight. The mixture was extracted with EtOAc, washed with water and brine, dried over sodium sulfate, filtered and concentrated. The crude was purified by column chromatography on silica gel with DCM/MeOH gradient as eluant to yield (R)-ethyl 6-(2-(3-fluorophenyl)pyrrolidin-1-yl)imidazo[1,2-b]pyridazin-3-ylcarbamate (X-236). $^1$H NMR (400 MHz, CDCl$_3$) δ 7.64 (br s, 1 H), 7.52 (d, J=9.6 Hz, 1 H), 7.33-7.26 (m, 1 H), 7.01 (d, J=7.6 Hz, 1 H), 6.51 (d, J=7.6 Hz, 1 H), 6.97-6.88 (m, 2 H), 6.31 (d, J=10 Hz, 1 H), 4.97 (dd, J=3.2, 8.2 Hz, 1 H), 4.30 (q, J=7.2 Hz, 2 H), 3.93-3.85 (m, 1 H), 3.74-3.65 (m, 1 H), 2.54-2.42 (m, 1 H), 2.15-1.97 (m, 3 H), 1.37 (t, J=7.2 Hz, 3 H). MS m/z 370.10 (M+1)$^+$.

Example 36

Synthesis of (R)-N-ethyl-6-(2-(3-fluorophenyl)pyrrolidin-1-yl)imidazo[1,2-b]pyridazine-3-sulfonamide (X-237)

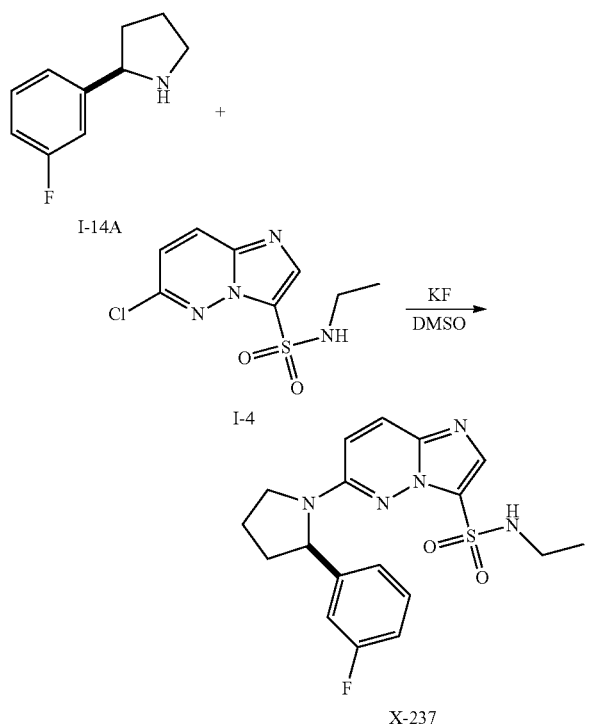

A slurry of (R)-2-(3-fluorophenyl)pyrrolidine (I-14A) (41 mg, 0.25 mmol), spray dried potassium fluoride (33 mg, 0.58 mmol), 6-chloro-N-ethylimidazo[1,2-b]pyridazine-3-sulfonamide (I-4) (30 mg, 0.12 mmol) and DMSO (2 mL) was stirred at 85° C. for 1 hour. The reaction mixture was then poured into water (20 mL) and stirred at room temperature for 10 minutes. The mixture was then extracted with EtOAc (3×30 mL). The combined organic fractions were washed with brine (3×30 mL), dried over anhydrous sodium sulfate, filtered and reduced to dryness. The crude product was purified preparative LCMS to yield (R)-N-ethyl-6-(2-(3-fluorophenyl)pyrrolidin-1-yl)imidazo[1,2-b]pyridazine-3-sulfonamide (X-237). MS m/z 390.2 (M+1)$^+$.

Example 37

Synthesis of (R)-3-bromo-6-(4,4-difluoro-2-(3-fluorophenyl)pyrrolidin-1-yl)imidazo[1,2-b]pyridazine (X-245)

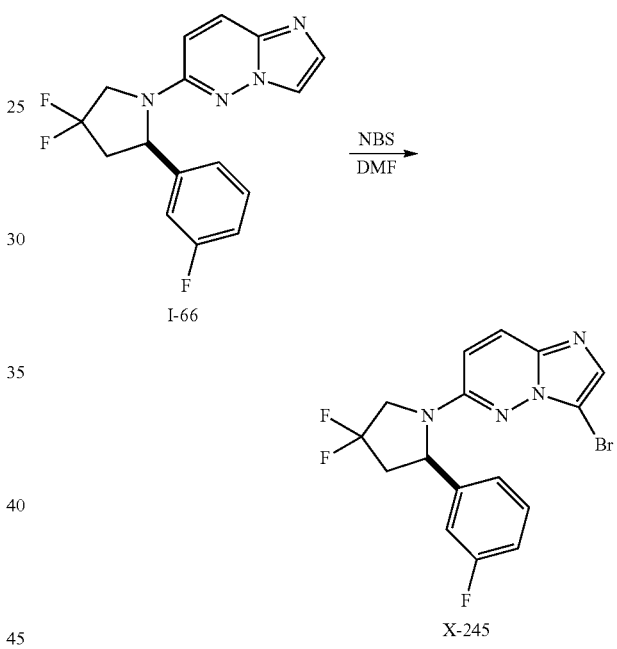

N-bromosuccinamide (118 mg, 0.7 mmol) was added to a solution of (R)-6-(4,4-difluoro-2-(3-fluorophenyl)pyrrolidin-1-yl)imidazo[1,2-b]pyridazine (I-66) (210 g, 0.7 mmol) in DMF (2 mL) at 0° C. The resulting solution was stirred at 0° C. for 1 hour and the reaction mixture was then poured into water while stirring at room temperature. The resulting yellow heterogeneous solution was stirred at room temperature for 1 hour and the solid was filtered and washed with hexanes. The solid was dried under vacuum then purified by column chromatography on silica gel with EtOAc/hexanes gradient as eluant to yield (R)-3-bromo-6-(4,4-difluoro-2-(3-fluorophenyl)pyrrolidin-1-yl)imidazo[1,2-b]pyridazine (X-245) as a yellow solid. $^1$H NMR (400 MHz, CD$_3$OD) δ 8.00 (s, 1 H), 7.96 (d, J=10 Hz, 1 H), 7.38 (q, J=6.8 Hz, 1 H), 7.24-7.15 (m, 3 H), 7.02 (dt, J=8.4, 2.4 Hz, 1 H), 5.46 (dd, J=8.8, 8.8 Hz, 1 H), 4.41 (q, J=12 Hz, 1 H), 4.27 (q, J=12 Hz, 1 H), 3.22-3.10 (m, 1 H), 2.58 (dq, J=13.2, 4.8 Hz, 1 H). MS m/z 397.1, 399.1 (M+1)$^+$.

Example 38

Synthesis of (R)-6-(4,4-difluoro-2-(3-fluorophenyl)pyrrolidin-1-yl)imidazo[1,2-b]pyridazine-3-carboxamide (X-247)

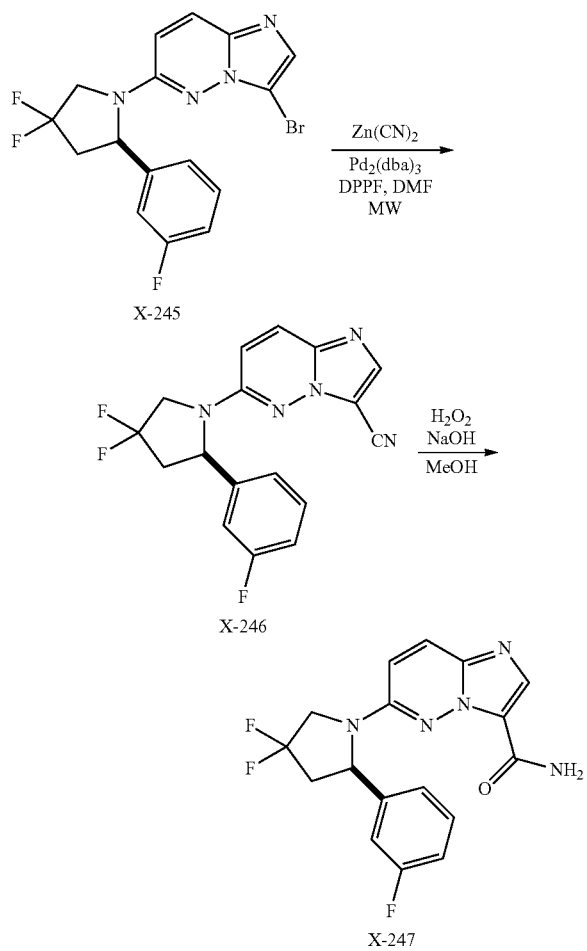

To a solution of (R)-3-bromo-6-(4,4-difluoro-2-(3-fluorophenyl)pyrrolidin-1-yl)imidazo[1,2-b]pyridazine (X-245) (100 mg, 0.25 mmol) in DMF (2 mL) was added $Zn(CN)_2$ (36 mg, 0.3 mmol), $Pd_2(dba)_3$ (12 mg, 0.01 mmol) and DPPF (10 mg, 0.02 mmol). The mixture was heated at 150° C. for 1 hour using microwave irradiation. The reaction was filtered through Celite and washed with EtOAc. The filtrate was collected, washed with water and brine, dried over sodium sulfate, filtered and concentrated. The crude was purified by column chromatography on silica gel with DCM/MeOH gradient as eluant to yield (R)-6-(4,4-difluoro-2-(3-fluorophenyl)pyrrolidin-1-yl)imidazo[1,2-b]pyridazine-3-carbonitrile (X-246). MS m/z 344.1 (M+1)+.

To a solution of (R)-6-(4,4-difluoro-2-(3-fluorophenyl)pyrrolidin-1-yl)imidazo[1,2-b]pyridazine-3-carbonitrile (X-246) (40 mg, 0.12 mmol) in MeOH (2 mL) was added 1 M NaOH (0.5 mL, 0.5 mmol) and 30% $H_2O_2$ (20 µL). The reaction was heated to 50° C. for 5 minutes then cooled to room temperature. The reaction mixture was filtered and purified by preparative HPLC to yield (R)-6-(4,4-difluoro-2-(3-fluorophenyl)pyrrolidin-1-yl)imidazo[1,2-b]pyridazine-3-carboxamide (X-247). 1H NMR (400 MHz, $CD_3OD$) δ 7.96 (s, 1 H), 7.79 (d, J=10 Hz, 1 H), 7.29 (q, J=8.0 Hz, 1 H), 7.08 (d, J=8.0 Hz, 1 H), 7.02 (d, J=9.6 Hz, 1 H), 6.95-6.89 (m, 2 H), 5.31 (dd, J=8.8, 8.8 Hz, 1 H), 4.30 (q, J=12 Hz, 1 H), 4.12 (q, J=12 Hz, 1 H), 3.11-3.98 (m, 1 H), 2.39 (dq, J=13.2, 4.8 Hz, 1 H). MS m/z 362.1 (M+1)+.

Example 39

Alternative Synthesis of (R)-6-(4,4-difluoro-2-(3-fluorophenyl)pyrrolidin-1-yl)imidazo[1,2-b]pyridazine-3-carboxamide (X-247)

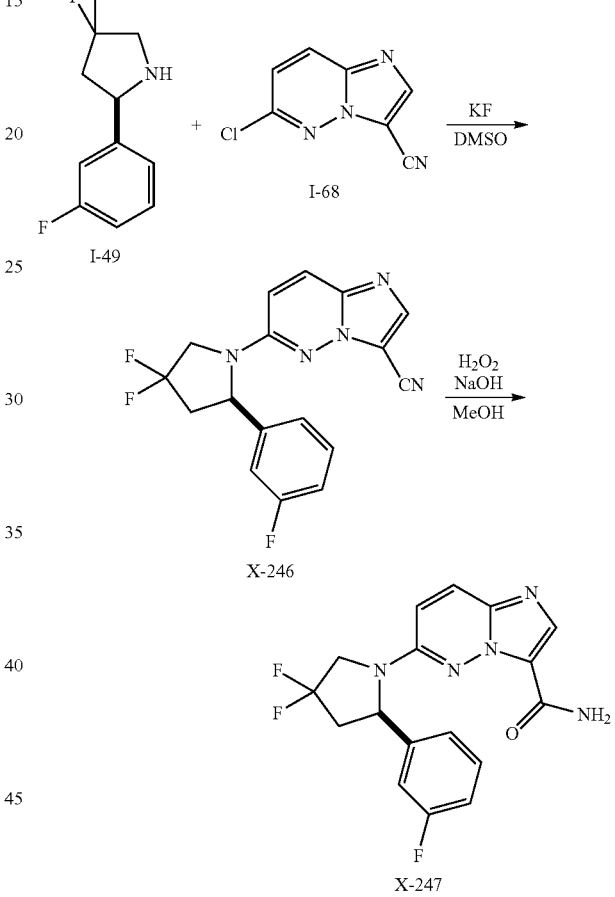

To a solution of (R)-4,4-difluoro-2-(3-fluorophenyl)pyrrolidine (I-49) (0.2 g, 1.0 mmol) in DMSO (5 mL) was added KF (0.17 g, 3.0 mmol) and 5-chloropyrazolo[1,5-a]pyrimidine-3-carboxamide (I-68) (0.18 g, 1.0 mmol). The reaction was heated at 105° C. for 6 hours then cooled to 0° C. The frozen reaction mixture was treated with water. The resulting white precipitate was filtered, washed with water and dried under vacuum. The crude product was purified by column chromatography on silica gel with DCM/MeOH gradient as eluant to yield (R)-6-(4,4-difluoro-2-(3-fluorophenyl)pyrrolidin-1-yl)imidazo[1,2-b]pyridazine-3-carbonitrile (X-246) as a white solid. 1H NMR (400 MHz, DMSO) δ 8.06 (d, J=10 Hz, 1 H), 7.96 (s, 1 H), 7.70 (s, 1 H), 7.59 (s, 1 H), 7.39 (dt, J=6.0, 8.0 Hz, 1 H), 7.22-7.19 (m, 2 H), 7.10 (dt, J=2.0, 8.0 Hz, 1 H), 6.92 (d, J=10 Hz, 1 H), 5.44 (dd, J=4.5, 9.0 Hz, 1 H), 4.48 (q, J=12.0 Hz, 1 H), 4.23 (q, J=12 Hz, 1 H), 3.23-3.09 (m, 1 H), 2.50-2.42 (m, 1 H). MS m/z 344.1 (M+1)+.

To a solution of (R)-6-(4,4-difluoro-2-(3-fluorophenyl)pyrrolidin-1-yl)imidazo[1,2-b]pyridazine-3-carbonitrile (X-246) (40 mg, 0.12 mmol) in MeOH (2 mL) at 0° C. was added 1 M NaOH (0.5 mL, 0.5 mmol) and 30% $H_2O_2$ (10 μL). The reaction was stirred to room temperature over 15 minutes. The reaction mixture was reduced to dryness and purified by column chromatography on silica gel with DCM/MeOH gradient as eluant to yield (R)-6-(4,4-difluoro-2-(3-fluorophenyl)pyrrolidin-1-yl)imidazo[1,2-b]pyridazine-3-carboxamide (X-247). $^1$H NMR (400 MHz, CD3OD) δ 7.96 (s, 1 H), 7.79 (d, J=10 Hz, 1 H), 7.29 (q, J=8.0 Hz, 1 H), 7.08 (d, J=8.0 Hz, 1 H), 7.02 (d, J=9.6 Hz, 1 H), 6.95-6.89 (m, 2 H), 5.31 (dd, J=8.8, 8.8 Hz, 1 H), 4.30 (q, J=12 Hz, 1 H), 4.12 (q, J=12 Hz, 1 H), 3.11-3.98 (m, 1 H), 2.39 (dq, J=13.2, 4.8 Hz, 1 H). MS m/z 362.1 (M+1)+. Chiral analytical analysis: 4.6× 100 mm ChiralPak AD-H with CO2/MeOH (5 to 50% in 8 minutes), 2 mL/min at 30° C.

Example 40

Synthesis of (R)-N-carbamoyl-6-(4,4-difluoro-2-(3-fluorophenyl)pyrrolidin-1-yl)imidazo[1,2-b]pyridazine-3-carboxamide (X-248)

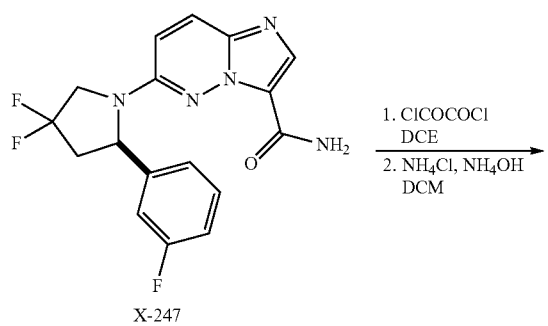

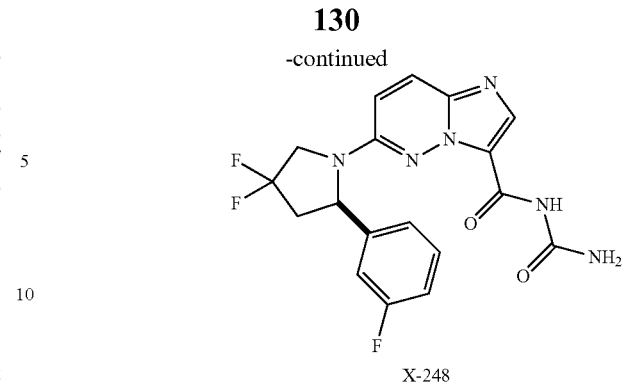

(R)-6-(4,4-difluoro-2-(3-fluorophenyl)pyrrolidin-1-yl)imidazo[1,2-b]pyridazine-3-carboxamide (X-247) (40 mg, 0.11 mmol), DCE (1 mL) and oxalyl chloride (0.048 mL, 0.55 mmol) were combined and heated to 90° C. for 30 minutes. The reaction was cooled to room temperature, concentrated and taken up in DCM (1 mL). A solution of NH4Cl (24 mg, 0.44 mmol) in NH4OH (0.1 mL) was added to the reaction and stirred for 10 minutes at room temperature. The reaction mixture was concentrated and purified by preparative LCMS to give (R)-6-(4,4-difluoro-2-(3-fluorophenyl)pyrrolidin-1-yl)imidazo[1,2-b]pyridazine-3-carboxamide (X-248) as a white solid. $^1$H NMR (400 MHz, CD3OD) δ 8.49 (bs, 1 H), 7.92 (bs, 1 H), 7.36 (dd, J=7.8, 6.1 Hz, 1 H), 7.22 (d, J=7.8 Hz, 1 H), 7.17 (d, J=9.8 Hz, 1 H), 7.0 (m, 2 H), 5.53 (dd, J=4.7, 4.2 Hz, 1 H), 4.44 (q, J=11.7 Hz, 1 H), 4.27 (q, J=13.1 Hz, 1 H), 3.19 (m, 1 H), 2.55 (m, 1 H). MS m/z 405.1 (M+1)+.

By repeating the procedures described in the above examples, using appropriate starting materials, the following compounds of Formula I, as identified in Table 1, were obtained.

TABLE 1

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-1 | 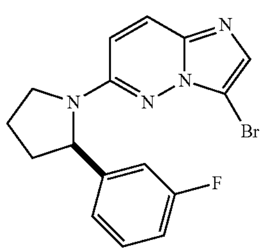 [SMILES: Fc1cccc([C@H]2CCCN2c2ccc3ncc(Br)n3n2)c1] | $^1$H NMR (400 MHz, MeOD-$d_4$) δ 7.48 (d, J = 9.6 Hz, 1 H), 7.33 (s, 1H), 7.24 (m, 1 H), 6.99 (d, J = 7.6 Hz, 1 H), 6.92 (d, J = 10 Hz, 1H), 6.86 (dt, J = 8.8, 2.8 Hz, 1 H), 6.60 d, J = 10 Hz, 1H), 5.03 (dd, J = 10, 3.2 Hz, 1 H), 3.88-3.82 (m, 1H), 3.65 (q, J = 7.6 Hz, 1H), 2.46-2.36 (m, 1H), 2.03-1.95 (m, 2H), 1.91-1.85 (m, 1H). MS m/z 361.1 (M + 1)+. | 0.128 | 0.316 | >10 |
| X-2 | 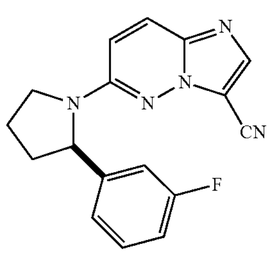 [SMILES: N#Cc1cnc2ccc(N3CCC[C@@H]3c3cccc(F)c3)nn12] | MS m/z 308.10 (M + 1)+. | 0.149 | 0.268 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-3 | 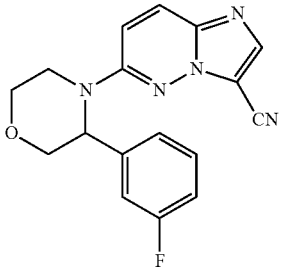 [SMILES: N#Cc1cnc2ccc(N3CCOCC3c3cccc(F)c3)nn12] | $^1$H NMR (400 MHz, DMSO-$d_6$) δ 8.26 (s, 1H), 8.07 (d, J = 9.2 Hz, 1H), 7.44 (d, J = 10.0 Hz, 1H), 7.38-7.36 (m, 1H), 7.27-7.22 (m, 1H), 7.09 (bt, J = 8.4 Hz, 1H), 5.35 (s, 1H), 4.27 (d, J = 12 Hz, 1H), 4.05-3.97 (m, 3H), 2.54 (bs, 2H). MS m/z 324.1 (M + 1)$^+$. | 0.779 | 0.957 | >10 |
| X-4 | 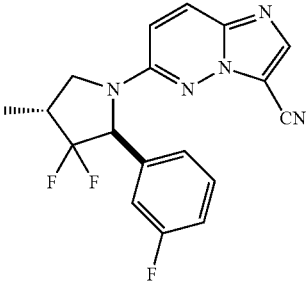 [SMILES: C[C@@H]1CN(c2ccc3ncc(C#N)n3n2)[C@@H](c2cccc(F)c2)C1(F)F] | $^1$H NMR (400 MHz, CDCl$_3$) δ 7.99 (s, 1H), 7.71 (d, J = 10.0 Hz, 1H), 7.40 (td, J = 8.0, 6.0 Hz, 1H), 7.14 (d, J = 7.6 Hz, 1H), 7.11-7.05 m, 1H), 7.04-6.99 (m, 1H), 6.50 (d, J = 10 Hz, 1H), 5.06 (d, J = 17.6 Hz, 1H), 4.22 (td, J = 8.4, 10.8 Hz, 1H), 3.49 (t, J = 10.8 Hz, 1H), 2.82-2.61 (m, 1H), 1.26 (d, J = 6.8 Hz, 3H). MS m/z 358.20 (M + 1)$^+$. | 0.034 | 0.155 | >10 |
| X-5 | 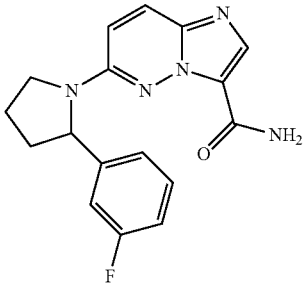 [SMILES: NC(=O)c1cnc2ccc(N3CCCC3c3cccc(F)c3)nn12] | $^1$H NMR (400 MHz, DMSO-$d_6$) δ 7.97 (d, J = 10 Hz, 1H), 7.91 (s, 1H), 7.70 (bs, 1H), 7.39 (q, J = 8 Hz, 1H), 7.11-7.04 (m, 3H), 6.89 (bs, 1H), 5.16 (d, J = 6 Hz, 1H), 3.99-3.94 (m, 1H), 3.68 (q, J = 8 Hz, 1H), 3.68 (q, J = 8 Hz, 1H), 2.47-2.42 (m, 1H), 2.05-1.97 (m, 2H), 1.90-1.84 (m, 1H). MS m/z 326.1 (M + 1)$^+$. | 0.057 | 0.117 | >10 |
| X-6 | 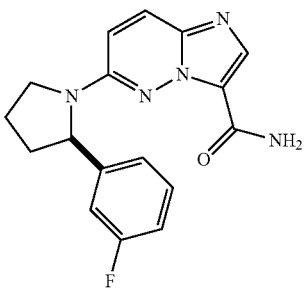 [SMILES: NC(=O)c1cnc2ccc(N3CCC[C@@H]3c3cccc(F)c3)nn12] | $^1$H NMR (400 MHz, CDCl$_3$) δ 8.20 (s, 1H), 8.13 (br s, 1H), 7.75 (d, J = 9.6 Hz, 1H), 7.34-7.28 (m, 1H), 7.01-6.93 (m, 2H), 6.89 (dt, J = 9.6, 2 Hz, 1H), 6.63 (d, J = 9.2 Hz, 1H), 5.61 (br s, 1H), 5.01 (dd, J = 8.2, 2.8 Hz, 1H), 3.95-3.87 (m, 1H), 3.74-3.66 (m, 1H), 2.58-2.47 (m, 1H), 2.21-2.09 (m, 2H), 2.09-2.00 (m, 1H). MS m/z 326.20 (M + 1)$^+$. | 0.03 | 0.051 | >10 |
| X-7 | 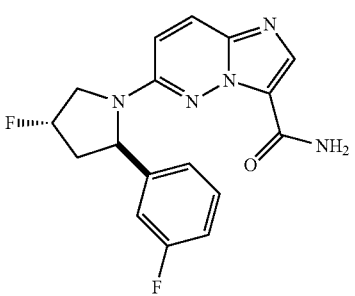 [SMILES: NC(=O)c1cnc2ccc(N3C[C@@H](F)C[C@@H]3c3cccc(F)c3)nn12] | $^1$H NMR (400 MHz, CDCl$_3$) δ 8.23 (s, 1H), 7.84 (br s, 1H), 7.79 (d, J = 10.0 Hz, 1H), 7.36 (td, J = 8.0, 6.0 Hz, 1H), 7.06 (d, J = 8 Hz, 1H), 7.02-6.93 (m, 2H), 6.66 (d, J = 9.6 Hz, 1H), 5.55 (br s, 1H), 5.42 (d, J = 52.0 Hz, 1H), 5.15 (dd, J = 6.8, 10.0 Hz, 1H), 4.22-4.16 (m, 1H), 4.14-4.06 (m, 1H), 2.90 (td, J = 16.0, 6.8 Hz, 1H), 2.14 (dddd, J = 40.8, 14.0, 9.6, 3.6 Hz, 1H). MS m/z 344.10 (M + 1)$^+$. | 0.005 | 0.005 | 3.56 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-8 | 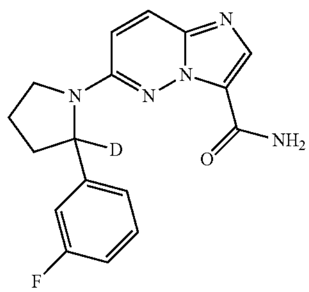 [SMILES: [2H]C1(c2cccc(F)c2)CCCN1c1ccc2ncc(C(N)=O)n2n1] | MS m/z 327.1 (M + 1)+. | 0.089 | 0.15 | >10 |
| X-9 | 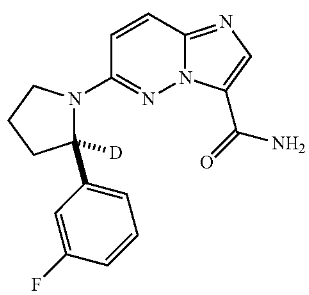 [SMILES: [2H][C@]1(c2cccc(F)c2)CCCN1c1ccc2ncc(C(N)=O)n2n1] | 1H NMR (400 MHz, MeOD-d4) δ 8.02 (s, 1H), 7.84 (d, J = 10 Hz, 1H), 7.40-7.34 (m, 1H), 7.12 (d, J = 8 Hz, 1H), 7.04-6.96 (m, 2H), 4.04-3.98 (m, 1H), 3.79-3.72 (m, 1H), 2.60-2.53 (m, 1H), 2.22-2.11 (m, 2 H), 2.04-1.97 (m, 1H), 2.22-2.11 (m, 2H), 2.04-1.97 (m, 1H). MS m/z 327.1 (M + 1)+. | 0.006 | 0.012 | >10 |
| X-10 | 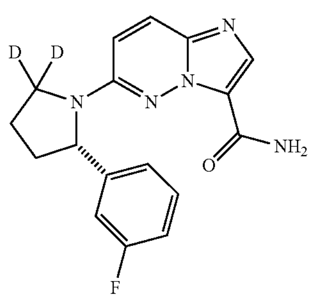 [SMILES: [2H]C1([2H])CC[C@@H](c2cccc(F)c2)N1c1ccc2ncc(C(N)=O)n2n1] | 1H NMR (400 MHz, MeOD-d4) δ 7.94 (bs, 1H), 7.71 (d, J = 9.6 Hz, 1H), 7.28 (q, J = 8 Hz, 1H), 6.92-6.85 (m, 3H), 5.03 (dd, J = 8.4, 3.2 Hz, 1H), 2.51-2.42 (m, 1 H), 2.07-1.98 (m, 2H), 1.94-1.85 (m, 1H). MS m/z 328.2 (M + 1)+. | 0.434 | 0.841 | >10 |
| X-11 | 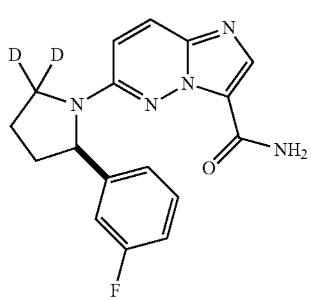 [SMILES: [2H]C1([2H])CC[C@H](c2cccc(F)c2)N1c1ccc2ncc(C(N)=O)n2n1] | 1H NMR (400 MHz, MeOD-d4) δ 7.92 (s, 1H), 7.73 (d, J = 10 Hz, 1H), 7.29 (q, J = 8 Hz, 1H), 7.01 (d, J = 7.6 Hz, 1H), 6.93-6.86 (m, 2 H), 5.05 (dd, J = 8.4, 3.2 Hz, 1H), 2.51-2.42 (m, 1 H), 2.08-1.97 (m, 2H), 1.92-1.86 (m, 1H). MS m/z 328.2 (M + 1)+. | 0.017 | 0.025 | >10 |
| X-12 | 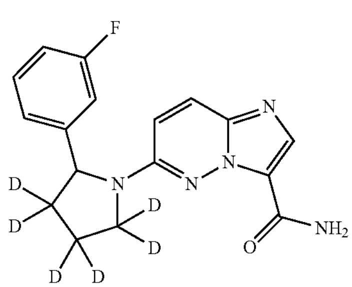 [SMILES: [2H]C1([2H])C(c2cccc(F)c2)N(c2ccc3ncc(C(N)=O)n3n2)C([2H])([2H])C1([2H])[2H]] | MS m/z 332.2 (M + 1)+. | 0.068 | 0.105 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-13 | 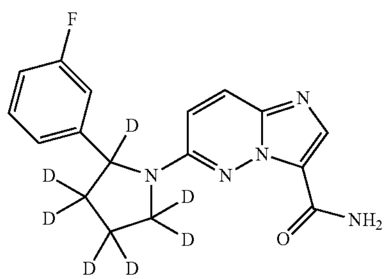 [SMILES: [2H]C1([2H])N(c2ccc3ncc(C(N)=O)n3n2)C([2H])(c2cccc(F)c2)C([2H])([2H])C1([2H])[2H]] | $^1$H NMR (400 MHz, DMSO-$d_6$) δ 7.96 (d, J = 10 Hz, 1H), 7.91 (s, 1H), 7.70 (bs, 1H), 7.39 (q, J = 8 Hz, 1H), 7.11-7.04 (M, 3 h), 6.88 (BS, 1 H). MS m/z 333.2 (M + 1)$^+$. | 0.068 | 0.11 | >10 |
| X-14 | 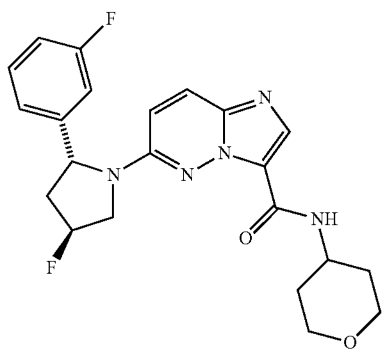 [SMILES: O=C(NC1CCOCC1)c1cnc2ccc(N3C[C@@H](F)C[C@@H]3c3cccc(F)c3)nn12] | MS m/z 382.20 (M + 1)$^+$. | 0.002 | 0.002 | 5.57 |
| X-15 | 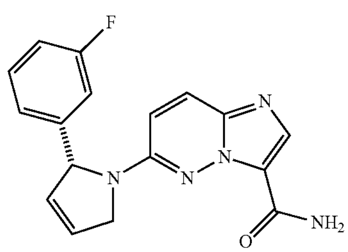 [SMILES: NC(=O)c1cnc2ccc(N3CC=C[C@@H]3c3cccc(F)c3)nn12] | $^1$H NMR (400 MHz, CDCl$_3$) δ 8.21 (s, 1H), 8.15-8.00 (bs, 1H), 7.78 (d, J = 10 Hz, 1H), 7.37-7.30 (m, 1 H), 7.07 (s, 1H), 7.01-6.92 (m, 2H), 6.66 (d, J = 10, Hz, 1H), 6.07-6.02 (m, 1H), 5.95-5.91 (m, 1 H), 5.80-5.68 (bs, 1H), 5.68-5.64 (m, 1H), 4.69-4.60 (m, 1H), 4.58-4.50 (m, 1H). MS m/z 324.10 (M + 1)$^+$. | 0.005 | 0.013 | 7.26 |
| X-16 | 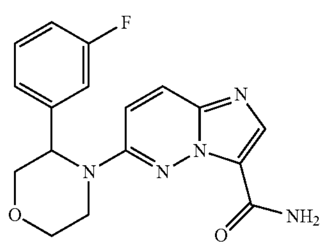 [SMILES: NC(=O)c1cnc2ccc(N3CCOCC3c3cccc(F)c3)nn12] | $^1$H NMR (400 MHz, DMSO-$d_6$) δ 8.04 (d, J = 8.0 Hz, 1H), 7.99 (s, 1H), 7.76 (s, 2H), 7.39-7.33 (m, 2H), 7.23-7.17 (m, 2H), 7.08 (bt, J = 8.4 Hz, 1H), 5.30 (s, 1H), 4.20 (d, J = 12 Hz, 1H), 4.05-3.92 (m, 3H), 3.78-3.70 (m, 1H), 3.60-3.56 (m, 1H). MS m/z 342.1 (M + 1)$^+$. | 0.454 | 0.614 | >10 |
| X-17 | 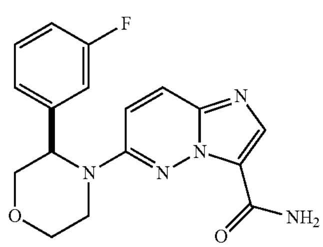 [SMILES: NC(=O)c1cnc2ccc(N3CCOC[C@H]3c3cccc(F)c3)nn12] | $^1$H NMR (400 MHz, DMSO-$d_6$) δ 8.04 (d, J = 8.0 Hz, 1H), 7.99 (s, 1H), 7.76 (s, 2H), 7.39-7.33 (m, 2H), 7.23-7.17 (m, 2H), 7.08 (bt, J = 8.4 Hz, 1H), 5.30 (s, 1H), 4.20 (d, J = 12 Hz, 1H), 4.05-3.92 (m, 3H), 3.78-3.70 (m, 1H), 3.60-3.56 (m, 1H). MS m/z 342.1 (M + 1)$^+$. | 0.047 | 0.328 | >10 |

TABLE 1-continued

| Compound No. | STRUCTURE | NMR and LC/MS | BaF3/TRKA-NGF (uM) | Ba/F3 Tel-TrkA (uM) | BAF 3/WT (uM) |
|---|---|---|---|---|---|
| X-18 | 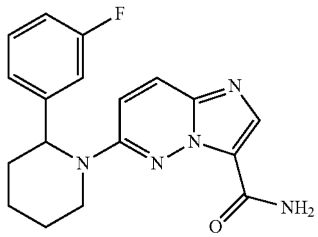 [SMILES: NC(=O)c1cnc2ccc(N3CCCCC3c3cccc(F)c3)nn12] | $^1$H NMR (400 MHz, MeOD-d$_4$) δ 8.09 (s, 1H), 8.05 (d, J = 11.2 Hz, 1H), 7.46 (d, J = 10.4 Hz, 1H), 7.39 (q, J = 7.6 Hz, 1H), 7.13-7.05 (m, 2H), 5.50 (t, J = 4.4 Hz, 1H), 4.16 (d, J = 9.6 Hz, 1H), 3.33 (dt, J = 14 Hz, 1H), 2.27-2.22 (m, 1H), 1.80-1.59 (m, 3H), 1.46-1.36 (m, 1H). MS m/z 340.2 (M + 1)$^+$. | 0.007 | 0.027 | >10 |
| X-19 | 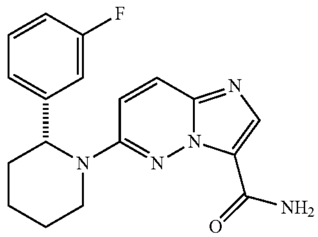 [SMILES: NC(=O)c1cnc2ccc(N3CCCC[C@@H]3c3cccc(F)c3)nn12] | $^1$H NMR (400 MHz, MeOD-d$_4$) δ 8.09 (s, 1H), 8.05 (d, J = 11.2 Hz, 1H), 7.46 (d, J = 10.4 Hz, 1H), 7.39 (q, J = 7.6 Hz, 1H), 7.13-7.05 (m, 2H), 5.50 (t, J = 4.4 Hz, 1H), 4.16 (d, J = 9.6 Hz, 1H), 3.33 (dt, J = 14 Hz, 1H), 2.27-2.22 (m, 1H), 1.80-1.59 (m, 3H), 1.46-1.36 (m, 1H). MS m/z 340.2 (M + 1)$^+$. | 0.027 | 0.079 | >10 |
| X-20 | 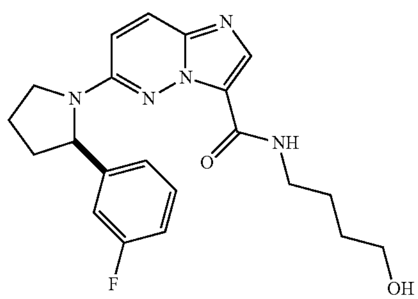 [SMILES: O=C(NCCCCO)c1cnc2ccc(N3CCC[C@@H]3c3cccc(F)c3)nn12] | MS m/z 398.2 (M + 1)$^+$. | 0.028 | 0.03 | >10 |
| X-21 | 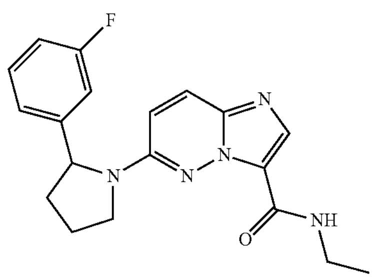 [SMILES: CCNC(=O)c1cnc2ccc(N3CCCC3c3cccc(F)c3)nn12] | $^1$H NMR (400 MHz, MeOD-d$_4$) δ 8.64 (bs, 1H), 8.00 (s, 1H), 7.83 (d, J = 10 Hz, 1H), 7.41 (q, J = 8 Hz, 1H), 7.13 (q, J = 8 Hz, 1H), 7.01-6.99 (m, 3H), 5.21 (dd, J = 8.4, 2 Hz, 1H), 4.02-3.96 (m, 1H), 3.76 (q, J = 8.8 Hz, 1H), 3.41 (bs, 2H), 2.63-2.53 (m, 1H), 2.15-2.09 (m, 2H), 2.07-2.01 (m, 1H), 1.12 (bs, 3H). MS m/z 354.2 (M + 1)$^+$. | 0.057 | 0.042 | >10 |
| X-22 | 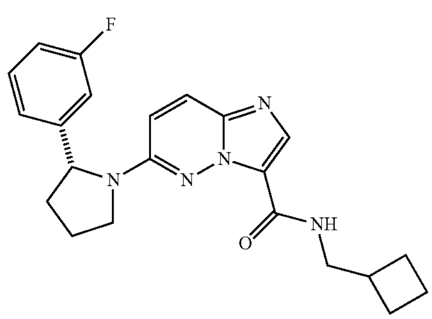 [SMILES: O=C(NCC1CCC1)c1cnc2ccc(N3CCC[C@@H]3c3cccc(F)c3)nn12] | MS m/z 394.2 (M + 1)$^+$. | 0.151 | 0.047 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-23 | 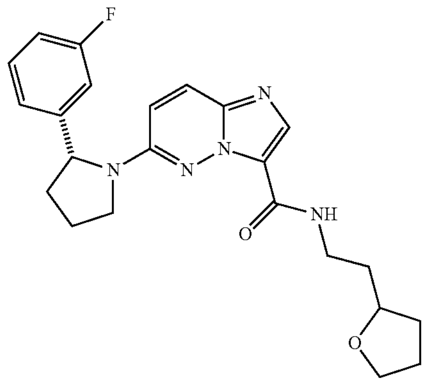 [SMILES: O=C(NCCC1CCCO1)c1cnc2ccc(N3CCC[C@@H]3c3cccc(F)c3)nn12] | MS m/z 424.2 (M + 1)+. | 0.053 | 0.092 | >10 |
| X-24 | 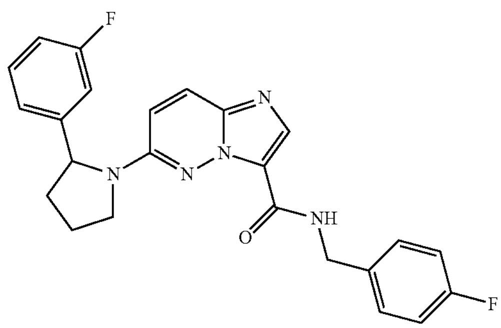 [SMILES: O=C(NCc1ccc(F)cc1)c1cnc2ccc(N3CCCC3c3cccc(F)c3)nn12] | ¹H NMR (400 MHz, CDCl₃) δ 8.78 (bs, 1H), 8.22 (s, 1 H), 7.73 (d, J = 9.6 Hz, 1 H), 7.35-7.27 (m, 2H), 7.25-7.18 (m, 1H), 6.88 (td, J = 8.4, 2.0 Hz, 1H), 6.84 (d, J = 8 Hz, 1H), 6.75 (d, J = 9.6 Hz, 1H), 6.57 (br d, J = 7.2 Hz, 1H), 4.95-4.90 (m, 1H), 4.66 (dd, J = 14.8, 6 Hz, 1H), 4.39 (bs, 1H), 3.59 (bs, 1 H), 3.40 (bs, 1H), 2.50-2.36 (m, 1H), 2.08-1.92 (m, 3H). MS m/z 434.10 (M + 1)+. | 0.209 | 0.236 | >10 |
| X-25 | 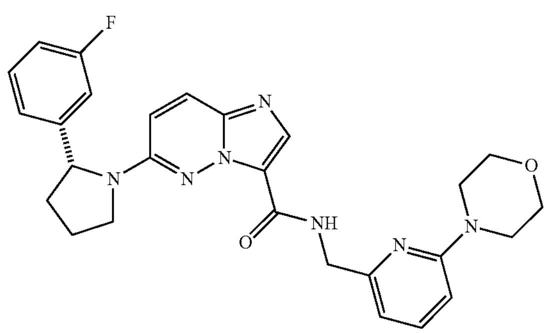 [SMILES: O=C(NCc1cccc(N2CCOCC2)n1)c1cnc2ccc(N3CCC[C@@H]3c3cccc(F)c3)nn12] | MS m/z 502.20 (M + 1)+. | 0.06 | 0.037 | >8.99 |
| X-26 | 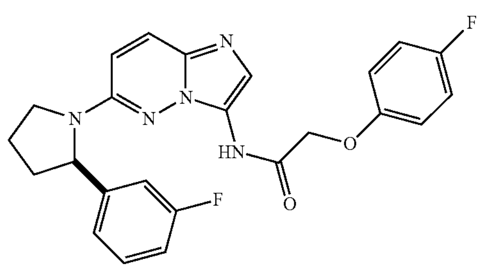 [SMILES: O=C(COc1ccc(F)cc1)Nc1cnc2ccc(N3CCC[C@@H]3c3cccc(F)c3)nn12] | ¹H NMR (400 MHz, CDCl₃) δ 9.09 (s, 1H), 7.95 (s, 1 H), 7.77 (d, J = 10.0 Hz, 1 H), 7.28-7.21 (m, 1H), 7.12-7.04 (m, 2H), 7.00-6.90 (m, 4H), 6.87 (dt, J = 9.6, 2.0 Hz, 1H), 6.69 (d, J = 9.6 Hz, 1H), 5.07 (dd, J = 8.4, 2.4 Hz, 1H), 4.70 (s, 2 H), 3.94-3.86 (m, 1H), 3.72-3.64 (m, 1H), 2.56-2.44 (m, 1H), 2.16-2.00 (m, 3H). MS m/z 450.10 (M + 1)+. | 0.079 | 0.085 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-27 | 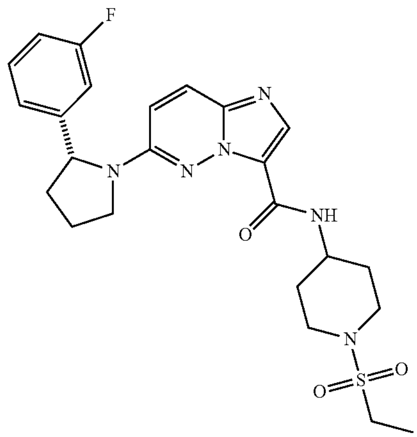 [SMILES: CCS(=O)(=O)N1CCC(NC(=O)c2cnc3ccc(N4CCC[C@@H]4c4cccc(F)c4)nn23)CC1] | MS m/z 501.2 (M + 1)+. | 0.021 | 0.017 | >10 |
| X-28 | 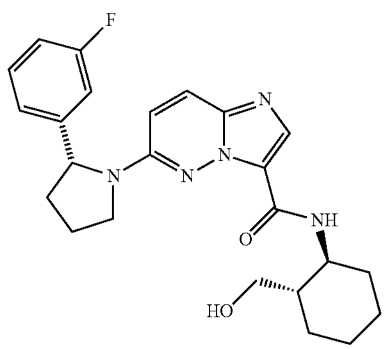 [SMILES: O=C(N[C@H]1CCCC[C@@H]1CO)c1cnc2ccc(N3CCC[C@@H]3c3cccc(F)c3)nn12] | $^1$H NMR (400 MHz, MeOD-d$_4$) δ 8.26 (s, 1H), 7.89 (dd, J = 10, 2.4 Hz, 1H), 7.40 (dq, J = 7.6, 1.6 Hz, 1H), 7.12 (d, J = 8 Hz, 1H), 7.06-6.98 (m, 3H), 5.28 (t, J = 8.8 Hz, 1H), 4.57 (bs, 1H), 4.06-4.00 (m, 1H), 3.87-3.78 (m, 1H), 3.60 (dq, J = 11.2, 7.6 Hz, 1H), 3.49-3.39 (m, 1H), 2.65-2.55 (m, 1H), 2.19-2.10 (m, 3H), 2.00-1.35 (m, 10H). MS m/z 438.2 (M + 1)+. | 0.155 | 0.112 | >10 |
| X-29 | 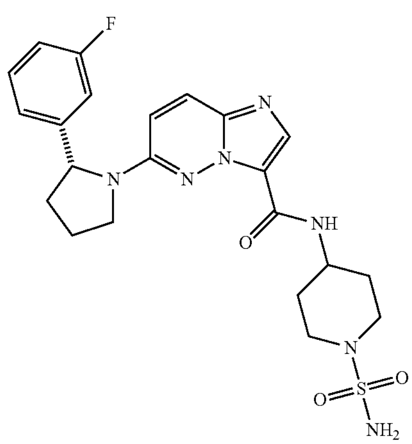 [SMILES: NS(=O)(=O)N1CCC(NC(=O)c2cnc3ccc(N4CCC[C@@H]4c4cccc(F)c4)nn23)CC1] | $^1$H NMR (400 MHz, MeOD-d$_4$) δ 8.30 (bs, 1H), 7.99 (bs, 1H), 7.44 (q, J = 7.2 Hz, 1H), 7.22 (bs, 1H), 7.17 (d, J = 8 Hz, 1H), 7.05-7.00 (m, 2H), 5.31 (d, J = 7.6 Hz, 1H), 4.04-3.99 (m, 2H), 3.80-3.63 (m, 3H), 2.88-2.76 (m, 2H), 2.64-2.54 (m, 1H), 2.29-2.00 (m, 5H), 1.68 (bs, 2H). MS m/z = 488.2 (M + 1). MS m/z 488.2 (M + 1)+. | 0.701 | 0.239 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-30 | 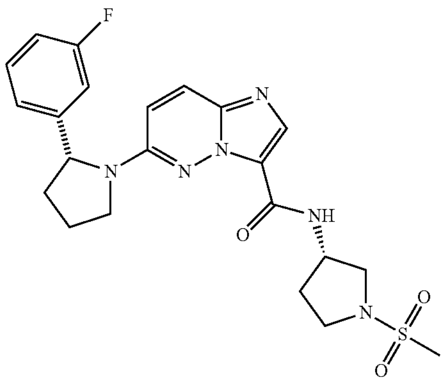 [SMILES: CS(=O)(=O)N1CC[C@H](NC(=O)c2cnc3ccc(N4CCC[C@@H]4c4cccc(F)c4)nn23)C1] | MS m/z 473.2 (M + 1)+. | 0.043 | 0.031 | >10 |
| X-31 | 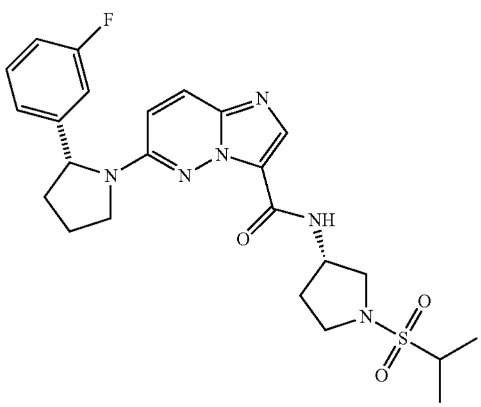 [SMILES: CC(C)S(=O)(=O)N1CC[C@H](NC(=O)c2cnc3ccc(N4CCC[C@@H]4c4cccc(F)c4)nn23)C1] | MS m/z 501.2 (M + 1)+. | 0.12 | 0.124 | >10 |
| X-32 | 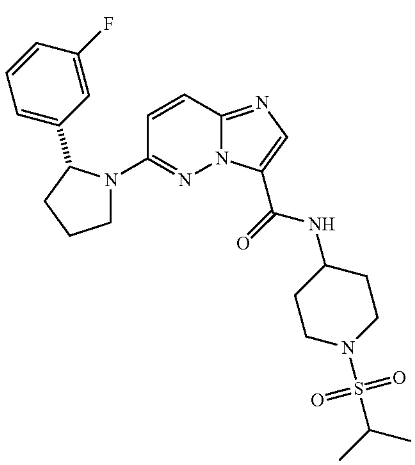 [SMILES: CC(C)S(=O)(=O)N1CCC(NC(=O)c2cnc3ccc(N4CCC[C@@H]4c4cccc(F)c4)nn23)CC1] | MS m/z 515.2 (M + 1)+. | 0.019 | 0.019 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-33 | 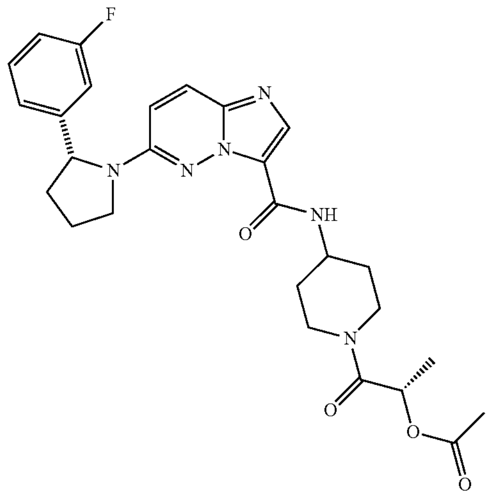 [SMILES: CC(=O)O[C@@H](C)C(=O)N1CCC(NC(=O)c2cnc3ccc(N4CCC[C@@H]4c4cccc(F)c4)nn23)CC1] | MS m/z 523.2 (M + 1)+. | 0.133 | 0.105 | >10 |
| X-34 | 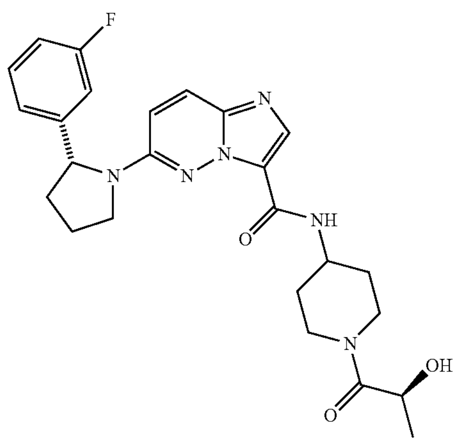 [SMILES: C[C@H](O)C(=O)N1CCC(NC(=O)c2cnc3ccc(N4CCC[C@@H]4c4cccc(F)c4)nn23)CC1] | MS m/z 481.2 (M + 1)+. | 0.106 | 0.076 | >10 |
| X-35 | 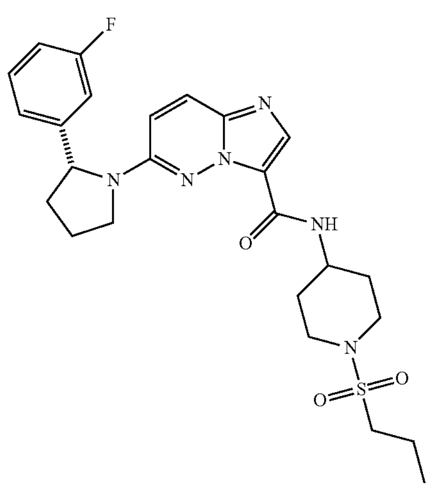 [SMILES: CCCS(=O)(=O)N1CCC(NC(=O)c2cnc3ccc(N4CCC[C@@H]4c4cccc(F)c4)nn23)CC1] | MS m/z 515.2 (M + 1)+. | 0.036 | 0.026 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-36 | 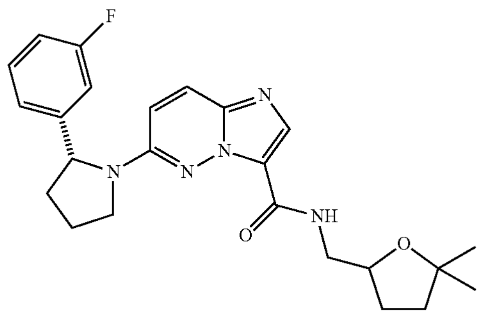 [SMILES: CC1(C)CCC(CNC(=O)c2cnc3ccc(N4CCC[C@@H]4c4cccc(F)c4)nn23)O1] | MS m/z 438.2 (M + 1)+. | 0.116 | 0.12 | >10 |
| X-37 | 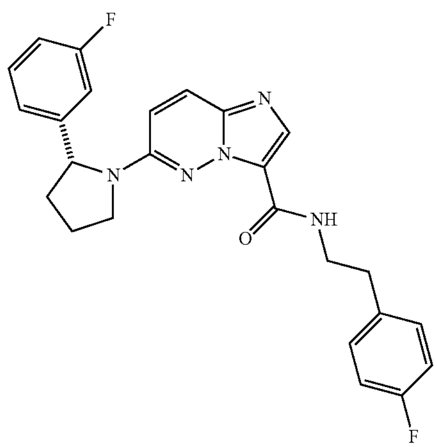 [SMILES: O=C(NCCc1ccc(F)cc1)c1cnc2ccc(N3CCC[C@@H]3c3cccc(F)c3)nn12] | MS m/z 448.10 (M + 1)+. | 0.047 | 0.137 | >10 |
| X-38 | 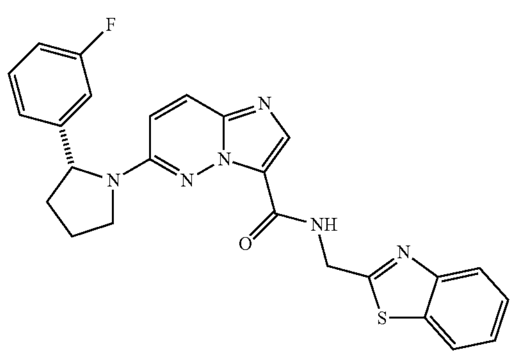 [SMILES: O=C(NCc1nc2ccccc2s1)c1cnc2ccc(N3CCC[C@@H]3c3cccc(F)c3)nn12] | MS m/z 473.10 (M + 1)+. | 0.09 | 0.196 | >10 |
| X-39 | 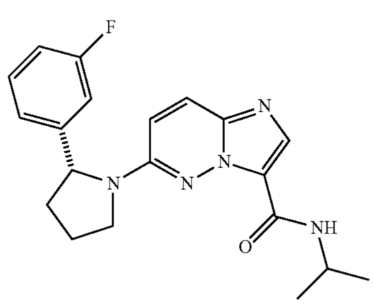 [SMILES: CC(C)NC(=O)c1cnc2ccc(N3CCC[C@@H]3c3cccc(F)c3)nn12] | MS m/z 368.10 (M + 1)+. | 0.009 | 0.014 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-40 | 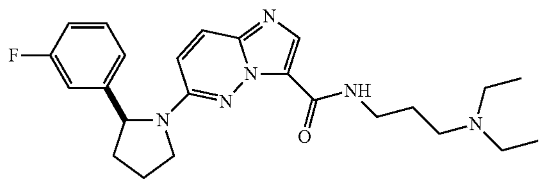 [SMILES: CCN(CC)CCCNC(=O)c1cnc2ccc(N3CCC[C@H]3c3cccc(F)c3)nn12] | MS m/z 439.20 (M + 1)+. | 0.204 | 0.951 | >10 |
| X-41 | 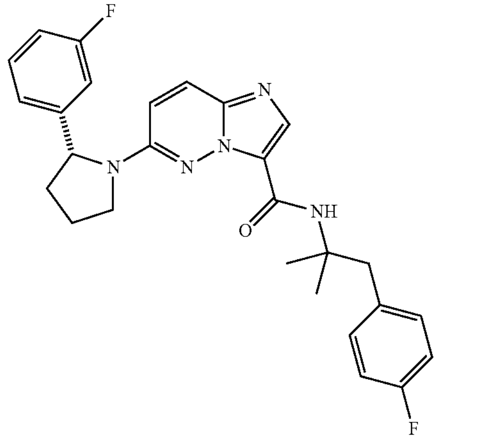 [SMILES: CC(C)(Cc1ccc(F)cc1)NC(=O)c1cnc2ccc(N3CCC[C@@H]3c3cccc(F)c3)nn12] | MS m/z 476.10 (M + 1)+. | 0.254 | 0.527 | 9.0 |
| X-42 | 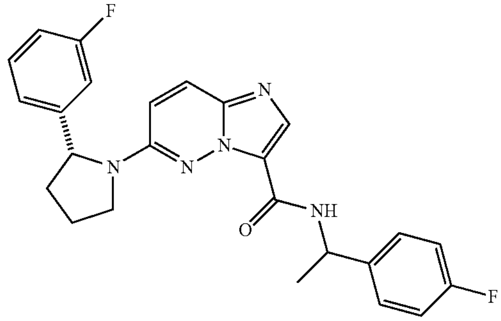 [SMILES: CC(NC(=O)c1cnc2ccc(N3CCC[C@@H]3c3cccc(F)c3)nn12)c1ccc(F)cc1] | MS m/z 448.10 (M + 1)+. | 0.049 | 0.127 | >9.57 |
| X-43 | 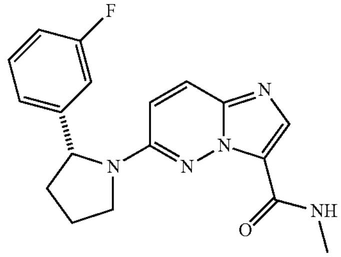 [SMILES: CNC(=O)c1cnc2ccc(N3CCC[C@@H]3c3cccc(F)c3)nn12] | ¹H NMR (400 MHz, MeOD-d₄) δ 8.19 (s, 1H), 8.01 (d, J = 10 Hz, 1H), 7.43 (q, J = 8 Hz, 1H), 7.35 (bs, 1H), 7.17 (d, J = 8 Hz, 1H), 7.10 (d, J = 9.6 Hz, 1H), 7.04 (dt, J = 8, 1.6 Hz, 1H), 5.25 (dd, J = 8, 2.8 Hz, 1H), 4.08-4.03 (m, 1H), 3.82 (q, J = 8 Hz, 1H), 2.84 (bs, 3H), 2.65-2.56 (m, 1H), 2.20-2.13 (m, 2H), 2.06-2.00 (m, 1H). MS m/z 340.2 (M + 1)+. | 0.04 | 0.046 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-44 | 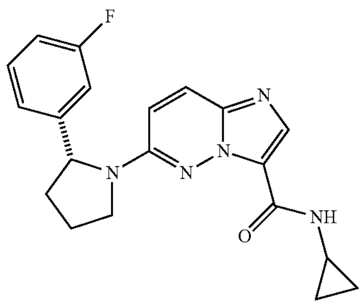 [SMILES: O=C(NC1CC1)c1cnc2ccc(N3CCC[C@@H]3c3cccc(F)c3)nn12] | $^1$H NMR (400 MHz, MeOD-d$_4$) δ 8.23 (s, 1H), 7.98 (d, J = 8.8 Hz, 1H), 7.41 (q, J = 8 Hz, 1H), 7.21 (bs, 1H), 7.13 (d, J = 7.6 Hz, 1H), 7.07-6.99 (m, 2H), 5.25 (d, J = 9.2 Hz, 1H), 4.02-3.97 (m, 1H), 3.78 (q, J = 8.8 Hz, 1H), 2.74 (bs, 1H), 2.67-2.55 (m, 1H), 2.20-2.06 (m, 3H), 0.88-0.82 (m, 2H), 0.80-0.75 (m, 1H). MS m/z 366.2 (M + 1)$^+$. | 0.008 | 0.011 | >10 |
| X-45 | 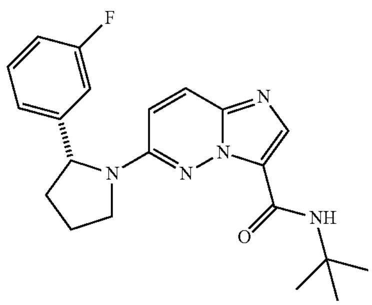 [SMILES: CC(C)(C)NC(=O)c1cnc2ccc(N3CCC[C@@H]3c3cccc(F)c3)nn12] | $^1$H NMR (400 MHz, MeOD-d$_4$) δ 8.25 (s, 1H), 7.95 (d, J = 10 Hz, 1H), 7.41 (q, J = 7.6 Hz, 1H), 7.11-7.00 (m, 4H), 5.29 (d, J = 8 Hz, 1H), 4.03-3.98 (m, 1H), 3.81-3.74 (m, 1H), 2.65-2.55 (m, 1H), 2.19-2.10 m, 3H), 1.51 (s, 9H). MS m/z 382.2 (M + 1)$^+$. | 0.032 | 0.022 | >10 |
| X-46 | 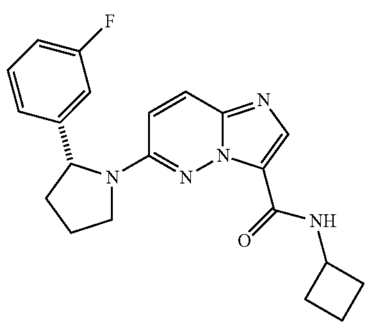 [SMILES: O=C(NC1CCC1)c1cnc2ccc(N3CCC[C@@H]3c3cccc(F)c3)nn12] | $^1$H NMR (400 MHz, MeOD-d$_4$) δ 8.20 (s, 1H), 7.97 (d, J = 8 Hz, 1H), 7.42 (q, J = 6 Hz, 1H), 7.18 (bs, 1H), 7.14 (d, J = 8 Hz, 1H), 7.09 (d, J = 9.6 Hz, 1H), 7.05 (dt, J = 8.4, 2.4 Hz, 1H), 5.32 (d, J = 7.6 Hz, 1H), 4.52 (p, J = 7.6 Hz, 1H), 4.05 (t, J = 8.4 Hz, 1H), 3.81-3.75 (m, 1H), 2.65-2.56 (m, 1H), 2.41-2.30 (m, 2H), 2.20-2.13 (m, 3H), 2.13-1.98 (m, 1H), 1.96-1.89 (m, 1H), 1.79 (bs, 2H). MS m/z 380.2 (M + 1)$^+$. | 0.031 | 0.02 | >10 |
| X-47 | 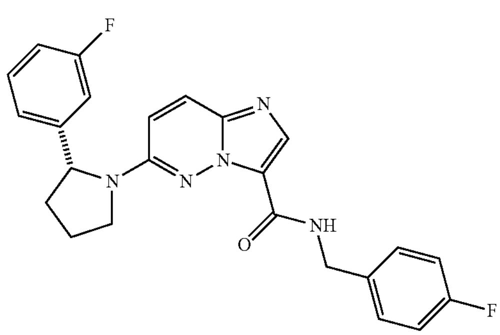 | MS m/z 434.10 (M + 1)$^+$. | 0.141 | 0.07 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-48 | 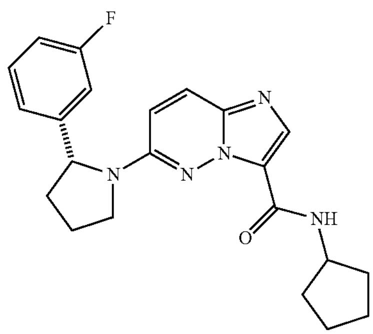 [SMILES: O=C(NC1CCCC1)c1cnc2ccc(N3CCC[C@@H]3c3cccc(F)c3)nn12] | ¹H NMR (400 MHz, MeOD-d₄) δ 8.20 (bs, 1H), 7.91 (d, J = 9.2 Hz, 1H), 7.41 (q, J = 8 Hz, 1H), 7.11-6.99 (m, 4H), 5.27 (d, J = 7.6 Hz, 1H), 4.32 (p, J = 6.4 Hz, 1H), 4.00-3.96 (m, 1 H), 3.77 (q, J = 9.6 Hz, 1 H), 2.64-2.54 (m, 1H), 2.22-2.01 (m, 5H), 1.81-1.57 (m, 6H). MS m/z 394.2 (M + 1)⁺. | 0.043 | 0.037 | >10 |
| X-49 | 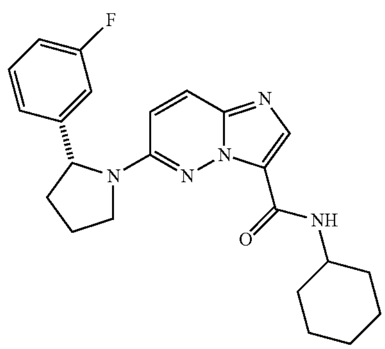 [SMILES: O=C(NC1CCCCC1)c1cnc2ccc(N3CCC[C@@H]3c3cccc(F)c3)nn12] | MS m/z 408.2 (M + 1)⁺. | 0.032 | 0.022 | >9.34 |
| X-50 | 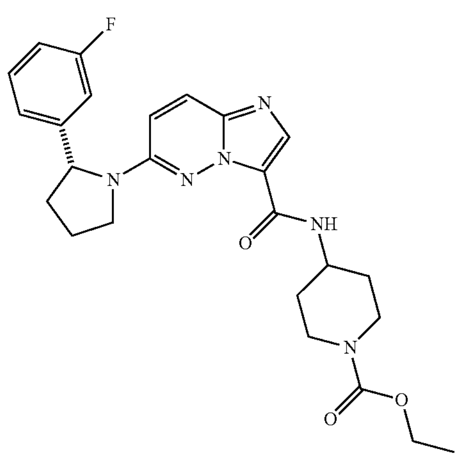 [SMILES: CCOC(=O)N1CCC(NC(=O)c2cnc3ccc(N4CCC[C@@H]4c4cccc(F)c4)nn23)CC1] | ¹H NMR (400 MHz, MeOD-d₄) δ 8.24 (s, 1H), 7.98 (bs, 1H), 7.39 (q, J = 8 Hz, 1 H), 7.22 (bs, 1H), 7.12 (d, J = 7.6 Hz, 1H), 7.05-6.98 (m, 2H), 5.28 (d, J = 7.6 Hz, 1H), 4.22-3.96 (m, 6 H), 3.77 (q, J = 9.6 Hz, 1 H), 2.93 (bs, 2H), 2.63-2.53 2.53 (m, 1H), 2.15 (bs, 2 H), 2.03 (bs, 2H), 1.83 (bs, 1H), 1.55-1.37 (m, 1H), 1.33 (t, J = 7.2 Hz, 3H), 1.28 (t, J = 7.2 Hz, 1H). MS m/z 481.2 (M + 1)⁺. | 0.031 | 0.04 | >10 |
| X-51 | 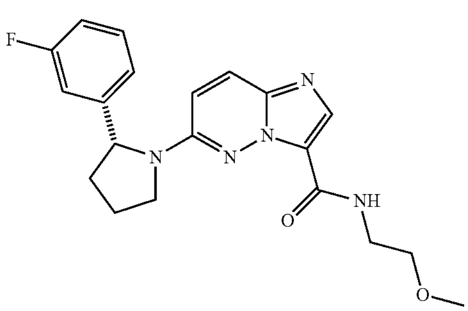 [SMILES: COCCNC(=O)c1cnc2ccc(N3CCC[C@@H]3c3cccc(F)c3)nn12] | ¹H NMR (400 MHz, MeOD-d₄) δ 8.26 (s, 1H), 7.97 (d, J = 9.6 Hz, 1H), 7.41 (q, J = 7.6 Hz, 1H), 7.18 (d, J = 7.6 Hz, 1H), 7.08 (d, J = 9.6 Hz, 1H), 7.04 (dt, J = 8.4, 2.8 Hz, 1H), 5.29 (d, J = 8 Hz, 1H), 4.08-4.02 (m, 1H), 3.83 (q, J = 8 Hz, 1H), 3.74-3.69 (m, 1H), 3.63-3.54 (m, 3H), 3.44 (s, 3H), 2.66-2.56 (m, 1 H), 2.19-2.14 (m, 2H), 2.09-2.05 (m, 1H). MS m/z 384.2 (M + 1)⁺. | 0.034 | 0.067 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-52 | 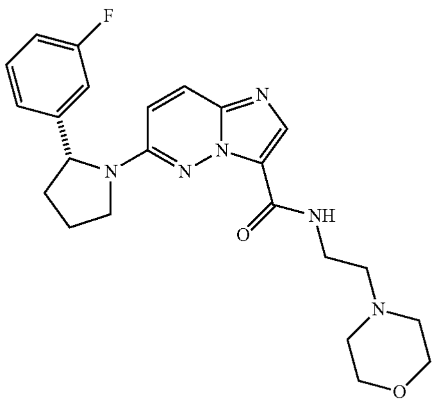 [SMILES: O=C(NCCN1CCOCC1)c1cnc2ccc(N3CCC[C@@H]3c3cccc(F)c3)nn12] | MS m/z 439.2 (M + 1)+. | 0.039 | 0.058 | >10 |
| X-53 | 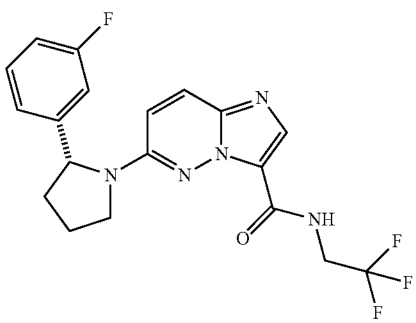 [SMILES: O=C(NCC(F)(F)F)c1cnc2ccc(N3CCC[C@@H]3c3cccc(F)c3)nn12] | 1H NMR (400 MHz, MeOD-d4) δ 7.97 (s, 1H), 7.74 (d, J = 10 Hz, 1H), 7.31 (q, J = 8 Hz, 1H), 7.01 (d, J = 7.6 Hz, 1H), 6.94-6.80 (m, 3 H), 5.10 (dd, J = 8.4, 2.0 Hz, 1H), 4.22-4.11 (m, 1 H), 3.92-3.87 (m, 1H), 3.75 (bs, 1H), 3.68 (q, J = 8.4 Hz, 1H), 2.53-2.43 (m, 1H), 2.05-1.99 (m, 2 H), 1.97-1.90 (m, 1H). MS m/z 408.1 (M + 1)+. | 0.005 | 0.003 | >10 |
| X-54 | 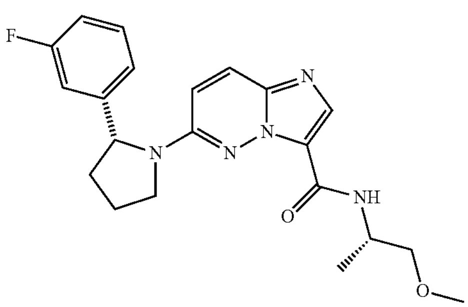 [SMILES: COC[C@H](C)NC(=O)c1cnc2ccc(N3CCC[C@@H]3c3cccc(F)c3)nn12] | MS m/z 398.2 (M + 1)+. | 0.043 | 0.053 | >10 |
| X-55 | 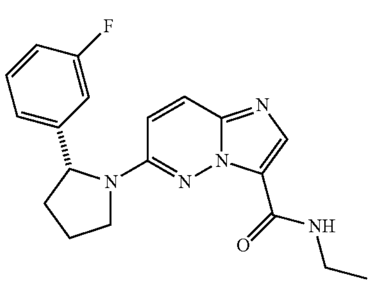 | MS m/z 354.2 (M + 1)+. | 0.007 | 0.007 | >9.62 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-56 | 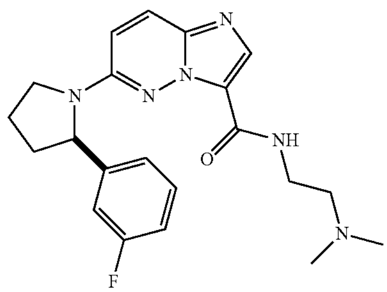 [SMILES: CN(C)CCNC(=O)c1cnc2ccc(N3CCC[C@@H]3c3cccc(F)c3)nn12] | MS m/z 397.2 (M + 1)+. | 0.211 | 0.676 | >10 |
| X-57 | 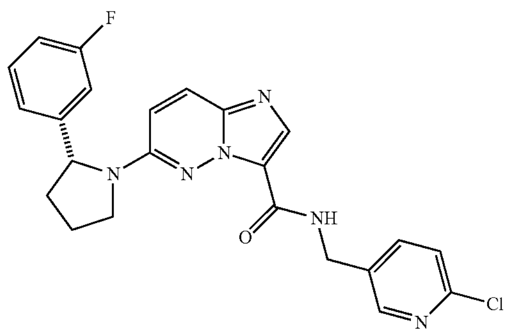 [SMILES: O=C(NCc1ccc(Cl)nc1)c1cnc2ccc(N3CCC[C@@H]3c3cccc(F)c3)nn12] | MS m/z 451.10 (M + 1)+. | 0.136 | 0.19 | >10 |
| X-58 | 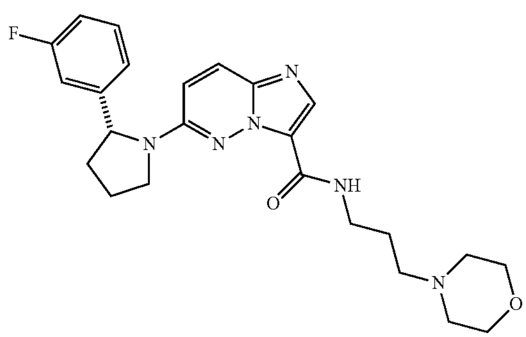 [SMILES: O=C(NCCCN1CCOCC1)c1cnc2ccc(N3CCC[C@@H]3c3cccc(F)c3)nn12] | MS m/z 453.2 (M + 1). | 0.167 | 0.39 | >10 |
| X-59 | 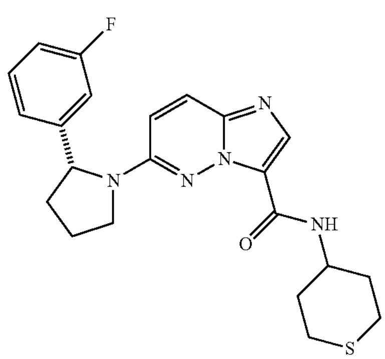 | $^1$H NMR (400 MHz, MeOD-d$_4$) δ 8.28 (s, 1H), 8.00 (d, J = 8.0 Hz, 1H), 7.44 (q, J = 8 Hz, 1H), 7.32 (bs, 1H), 7.16 (d, J = 8 Hz, 1H), 7.06-7.01 (m, 2H), 5.31 (d, J = 8 Hz, 1H), 4.04 (t, J = 8.4 Hz, 1H), 3.93 (bs, 1H), 3.81 (q, J = 9.6 Hz, 1H), 2.86 (q, J = 12 Hz, 2H), 2.76-2.57 (m, 4H), 2.31-2.27 (m, 1H), 2.19-2.08 (m, 4H), 1.79-1.66 (m, 1 H). MS m/z 426.2 (M + 1)+. | 0.107 | 0.036 | >10 |
| X-60 | 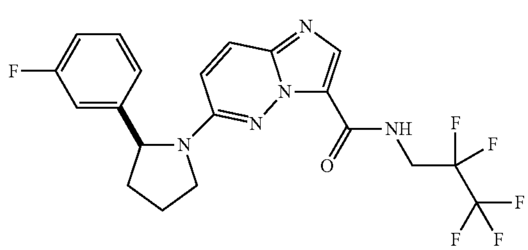 [SMILES: O=C(NCC(F)(F)C(F)(F)F)c1cnc2ccc(N3CCC[C@H]3c3cccc(F)c3)nn12] | MS m/z 458.1 (M + 1)+. | 0.069 | 0.035 | >10 |

TABLE 1-continued
| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-61 | 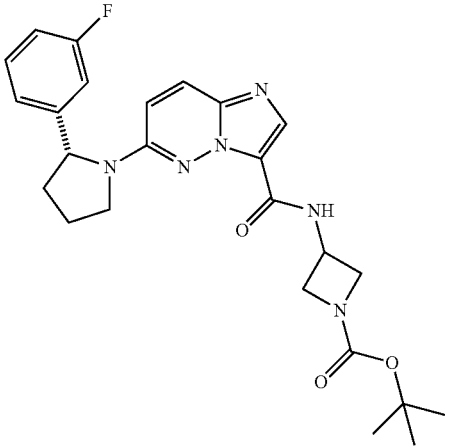 [SMILES: CC(C)(C)OC(=O)N1CC(NC(=O)c2cnc3ccc(N4CCC[C@@H]4c4cccc(F)c4)nn23)C1] | ¹H NMR (400 MHz, MeOD-d₄) δ 8.19 (s, 1H), 7.88 (d, J = 8.8 Hz, 1H), 7.43-7.36 (m, 1H), 7.14 (d, J = 7.6 Hz, 1H), 7.01-6.99 (m, 3H), 5.27 (dd, J = 8.4, 2.4 Hz, 1H), 4.37-4.25 (m, 4H), 4.08-4.00 (m, 1H), 3.93-3.91 (m, 1H), 3.83 (p, J = 9.2 Hz, 1H), 2.64-2.55 (m, 1H), 2.19-2.04 (m, 3H), 1.50 (s, 9H). MS m/z 425.1 (M − 56)⁺. | 0.171 | 0.144 | >10 |
| X-62 | 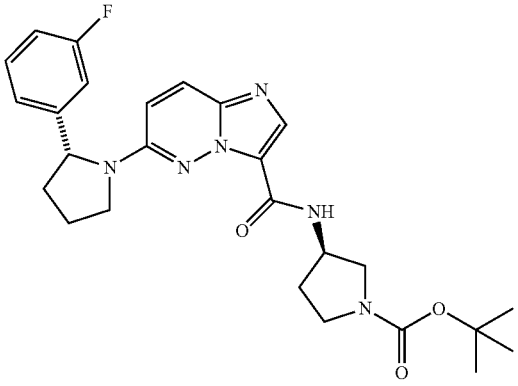 [SMILES: CC(C)(C)OC(=O)N1CC[C@@H](NC(=O)c2cnc3ccc(N4CCC[C@@H]4c4cccc(F)c4)nn23)C1] | ¹H NMR (400 MHz, MeOD-d₄) δ 8.17 (s, 1H), 7.91 (d, J = 9.6 Hz, 1H), 7.44 (q, J = 7.6 Hz, 1H), 7.15 (d, J = 8 Hz, 7.07-7.01 (m, 3H), 5.29 (d, J = 6.8 Hz, 1H), 4.54-4.40 (m, 1H), 4.05 (dt, J = 8, 2.4 Hz, 1H), 3.82 (q, J = 8.8 Hz, 1H), 3.63-3.52 (m, 2H), 3.47-3.36 (m, 2H), 2.61 (t, J = 7.6 Hz, 1H), 2.16-2.07 (m, 4H), 1.50 (s, 9H). MS m/z 439.2 (M − 56)⁺. | 0.711 | 0.91 | >10 |
| X-63 | 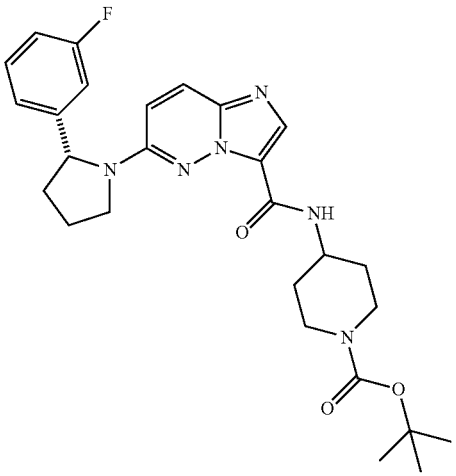 [SMILES: CC(C)(C)OC(=O)N1CCC(NC(=O)c2cnc3ccc(N4CCC[C@@H]4c4cccc(F)c4)nn23)CC1] | MS m/z 453.2 (M − 56)⁺. | 0.101 | 0.06 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-64 | 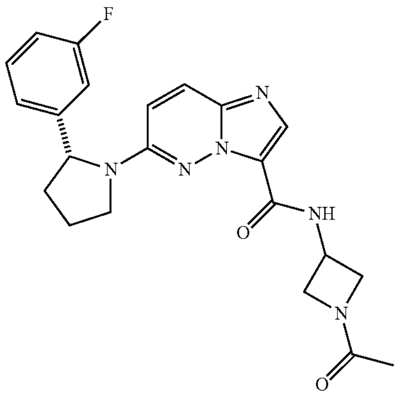 [SMILES: CC(=O)N1CC(NC(=O)c2cnc3ccc(N4CCC[C@@H]4c4cccc(F)c4)nn23)C1] | MS m/z 423.2 (M + 1)+. | 0.36 | 0.832 | >10 |
| X-65 | 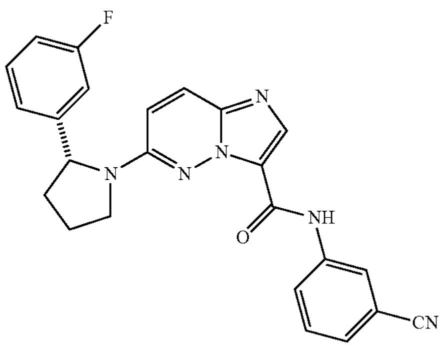 [SMILES: N#Cc1cccc(NC(=O)c2cnc3ccc(N4CCC[C@@H]4c4cccc(F)c4)nn23)c1] | MS m/z 427.20 (M + 1)+. | 0.105 | 0.092 | >9.51 |
| X-66 | 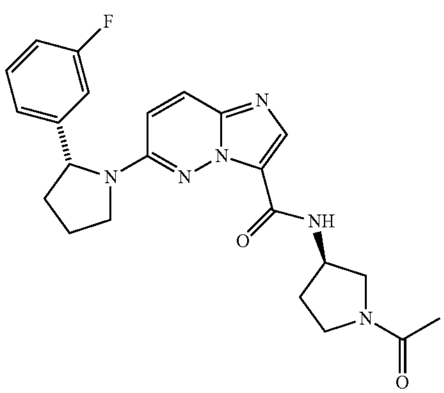 [SMILES: CC(=O)N1CC[C@@H](NC(=O)c2cnc3ccc(N4CCC[C@@H]4c4cccc(F)c4)nn23)C1] | MS m/z 437.1 (M + 1)+. | 0.475 | 0.737 | >10 |
| X-67 | 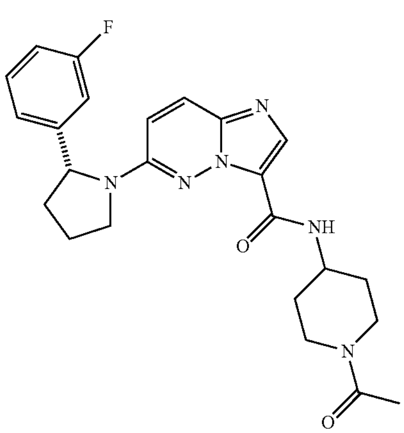 [SMILES: CC(=O)N1CCC(NC(=O)c2cnc3ccc(N4CCC[C@@H]4c4cccc(F)c4)nn23)CC1] | MS m/z 451.2 (M + 1)+. | 0.124 | 0.081 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-68 | 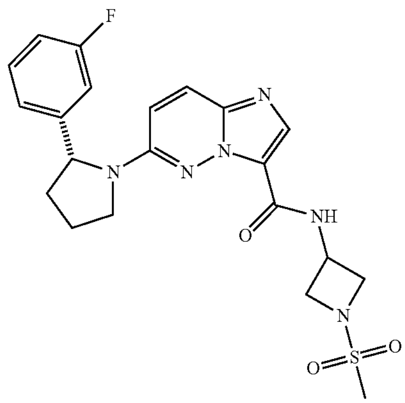 [SMILES: CS(=O)(=O)N1CC(NC(=O)c2cnc3ccc(N4CCC[C@@H]4c4cccc(F)c4)nn23)C1] | $^1$H NMR (400 MHz, MeOD-d$_4$) δ 7.94 (s, 1), 7.70 (d, J = 10 Hz, 1H), 7.31 (q, J = 8 Hz, 1H), 7.06 (d, J = 7.6 Hz, 1H), 6.95-6.88 (m, 2H), 6.79 (bs, 1H), 5.17 (d, J = 8 Hz, 1H), 4.67 (bs, 1H), 4.19-4.12 (m, 2H), 3.98-3.91 (m, 2H), 3.89 (t, J = 9.6 Hz, 1H), 3.71 (q, J = 8.4 Hz, 1H), 2.92 (s, 3H) 2.54-2.45 (m, 1H), 2.10-1.95 (m, 3H). MS m/z 459.2 (M + 1)$^+$. | 0.035 | 0.038 | >10 |
| X-69 | 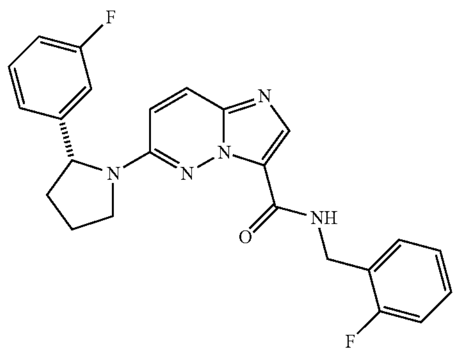 [SMILES: O=C(NCc1ccccc1F)c1cnc2ccc(N3CCC[C@@H]3c3cccc(F)c3)nn12] | MS m/z 434.10 (M + 1)$^+$. | 0.175 | 0.104 | >10 |
| X-70 | 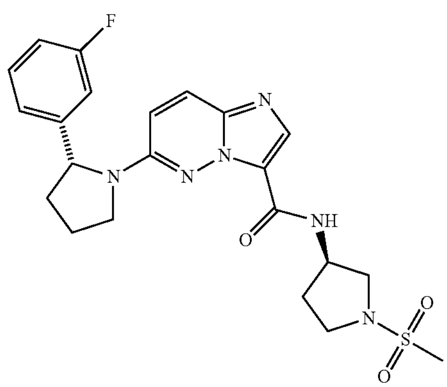 [SMILES: CS(=O)(=O)N1CC[C@@H](NC(=O)c2cnc3ccc(N4CCC[C@@H]4c4cccc(F)c4)nn23)C1] | $^1$H NMR (400 MHz, MeOD-d$_4$) δ 8.22 (s, 1H), 7.87 (d, J = 10 Hz, 2H), 7.41 (q, J = 8 Hz, 1H), 7.12 (d, J = 7.6 Hz, 1H), 7.06-6.90 (m, 3H), 5.26 (d, J = 8 Hz, 1H), 4.72 (bs, 1H), 4.05-3.99 (m, 1H), 3.82 (q, J = 8.8 Hz, 1H), 3.61-3.53 (m, 2H), 3.49-3.43 (m, 1H), 2.95 (s, 3H), 2.63-2.54 (m, 1H), 2.44-2.35 (m, 1H), 2.22-2.05 (m, 4H). MS m/z 473.2 (M + 1)$^+$. | 0.174 | 0.293 | >10 |
| X-71 | 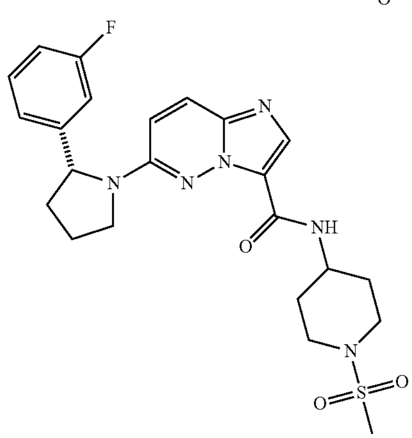 | MS m/z 487.2 (M + 1)$^+$. | 0.028 | 0.022 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-73 | 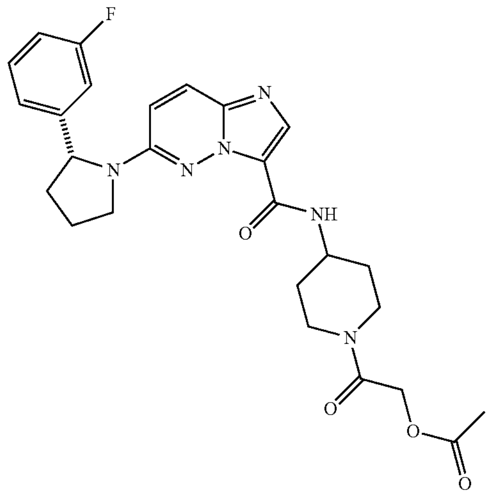 [SMILES: CC(=O)OCC(=O)N1CCC(NC(=O)c2cnc3ccc(N4CCC[C@@H]4c4cccc(F)c4)nn23)CC1] | MS m/z 509.2 (M + 1)+. | 0.059 | 0.109 | >10 |
| X-74 | 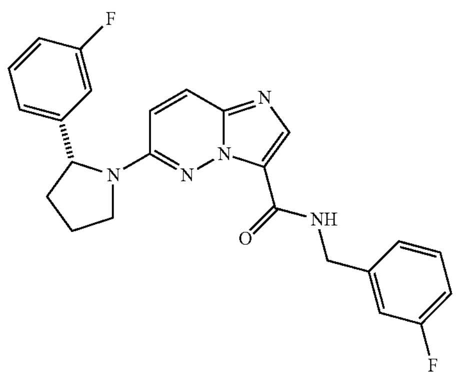 [SMILES: O=C(NCc1cccc(F)c1)c1cnc2ccc(N3CCC[C@@H]3c3cccc(F)c3)nn12] | MS m/z 434.10 (M + 1)+. | 0.039 | 0.07 | >10 |
| X-75 | 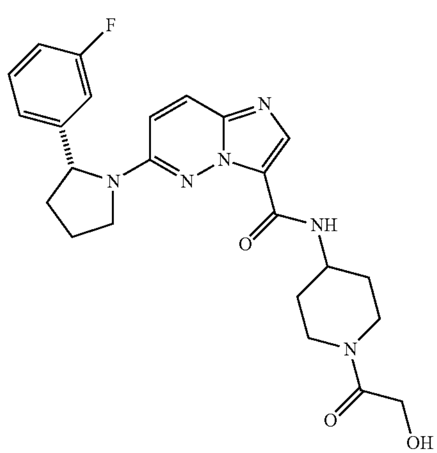 [SMILES: O=C(NC1CCN(C(=O)CO)CC1)c1cnc2ccc(N3CCC[C@@H]3c3cccc(F)c3)nn12] | 1H NMR (400 MHz, MeOD-d4) δ 8.00 (s, 1H), 7.73 (d, J = 10 Hz, 1H), 7.27 (q, J = 7.6 Hz, 1H), 7.07 (t, J = 6.4 Hz, 1H), 6.92-6.87 (m, 3H), 5.134 (d, J = 7.6 Hz, 1H), 4.49 (dd, J = 38, 13.6 Hz, 1H), 4.28-4.13 (m, 2H), 4.02 (t, J = 10.8 Hz, 1H), 3.836 (t, J = 8.4 Hz, 1H), 3.74-3.56 (m, 2H), 3.05 (q, J = 14 Hz, 1H), 2.74 (q, J = 12.4 Hz, 1H), 2.49-2.40 (m, 5H), 1.33 (bs, 2H). MS m/z 467.2 (M + 1)+. | 0.172 | 0.098 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-76 | 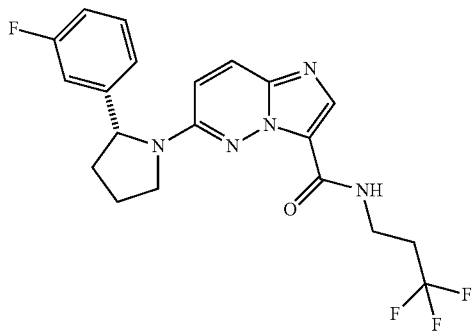 [SMILES: O=C(NCCC(F)(F)F)c1cnc2ccc(N3CCC[C@@H]3c3cccc(F)c3)nn12] | MS m/z 421.2 (M + 1)⁺. | 0.031 | 0.034 | >10 |
| X-77 | 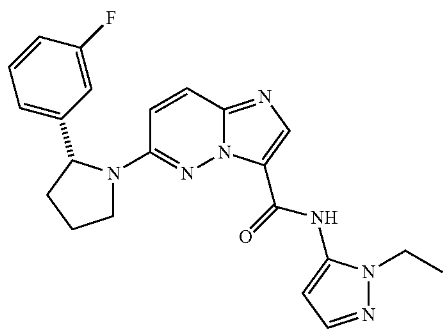 [SMILES: CCn1nccc1NC(=O)c1cnc2ccc(N3CCC[C@@H]3c3cccc(F)c3)nn12] | MS m/z 420.2 (M + 1)⁺. | 0.268 | 0.548 | >10 |
| X-79 | 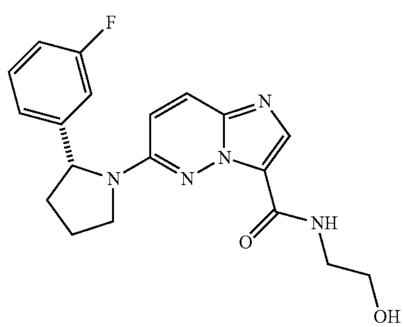 [SMILES: O=C(NCCO)c1cnc2ccc(N3CCC[C@@H]3c3cccc(F)c3)nn12] | ¹H NMR (400 MHz, MeOD-d₄) δ 7.92 (s, 1H), 7.70 (d, J = 10 Hz, 1H), 7.30-7.24 (m, 2H), 7.03 (d, J = 7.6 Hz, 1H), 6.97 (d, J = 10 Hz, 1H), 6.90 (dt, J = 8.8, 2.8 Hz, 1H), 6.83 (bs, 1H), 5.14 (dd, J = 7.6, 1.2 Hz, 1H), 3.95-3.90 (m, 1H), 3.67 (q, J = 8 Hz, 1H), 3.61-3.51 (m, 3H), 3.27 (bs, 1H), 2.51-2.41 (m, 1H), 2.05-1.97 (m, 2H), 1.94-1.88 (m, 2H). MS m/z 370.1 (M + 1)⁺. | 0.052 | 0.061 | >10 |
| X-80 | 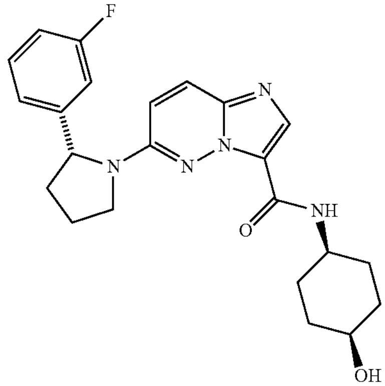 [SMILES: O=C(N[C@H]1CC[C@@H](O)CC1)c1cnc2ccc(N3CCC[C@@H]3c3cccc(F)c3)nn12] | MS m/z 424.2 (M + 1)⁺. | 0.015 | 0.006 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-81 | 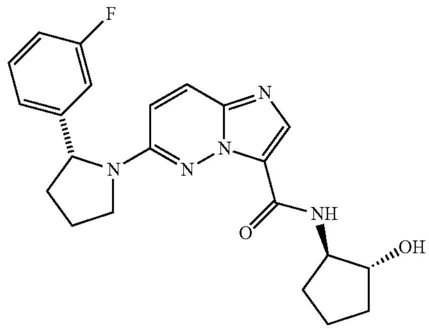 [SMILES: O=C(N[C@@H]1CCC[C@H]1O)c1cnc2ccc(N3CCC[C@@H]3c3cccc(F)c3)nn12] | ¹H NMR (400 MHz, MeOD-d₄) δ 7.95 (s, 1H), 7.70 (t, J = 7.6 Hz, 1H), 7.31-7.25 (m, 1H), 7.01 (d, J = 7.6 Hz, 1H), 6.96-6.85 (m, 2H), 6.80 (bs, 1H), 5.17-5.12 (m, 1H), 4.07-3.99 (m, 1H), 3.95-3.80 (m, 2H), 3.77-3.54 (m, 2H), 2.51-2.37 (m, 1H), 2.20-1.82 (m, 6H), 1.80-1.61 (m, 2H), 1.59-1.44 (m, 2H). MS m/z 410.1 (M + 1)⁺. | 0.014 | 0.012 | >10 |
| X-82 | 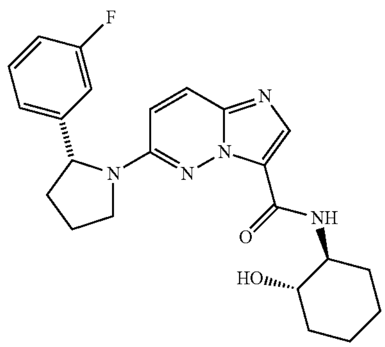 [SMILES: O=C(N[C@H]1CCCC[C@@H]1O)c1cnc2ccc(N3CCC[C@@H]3c3cccc(F)c3)nn12] | MS m/z 424.2 (M + 1)⁺. | 0.027 | 0.089 | >10 |
| X-83 | 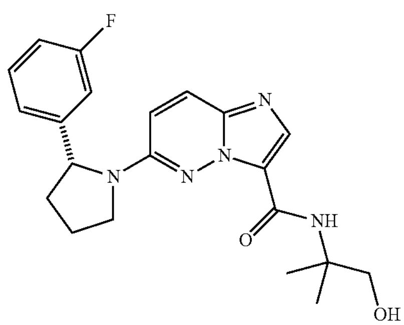 [SMILES: CC(C)(CO)NC(=O)c1cnc2ccc(N3CCC[C@@H]3c3cccc(F)c3)nn12] | ¹H NMR (400 MHz, MeOD-d₄) δ 8.77 (bs, 1H), 7.92 (s, 1H), 7.91 (d, J = 10 Hz, 1H), 7.39 (q, J = 7.6 Hz, 1H), 7.13-7.04 (m, 2H), 6.65 (d, J = 7.6 Hz, 1H), 5.28 (d, J = 7.6 Hz, 1H), 3.95 (t, J = 10.8 Hz, 1H), 3.68 (q, J = 8.4 Hz, 1H), 3.56-3.50 (m, 2H), 2.49-2.42 (m, 1H), 2.08-1.84 (m, 2H), 1.38 (s, 6H). MS m/z 398.2 (M + 1)⁺. | 0.015 | 0.02 | >10 |
| X-84 | 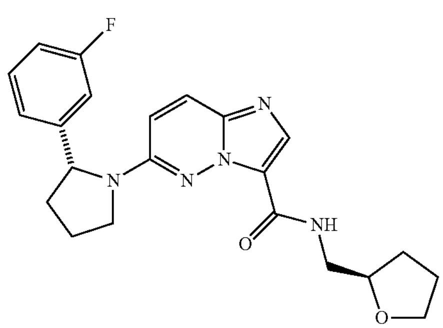 [SMILES: O=C(NC[C@H]1CCCO1)c1cnc2ccc(N3CCC[C@@H]3c3cccc(F)c3)nn12] | MS m/z 410.2 (M + 1)⁺. | 0.031 | 0.03 | >10 |

TABLE 1-continued
| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-85 | 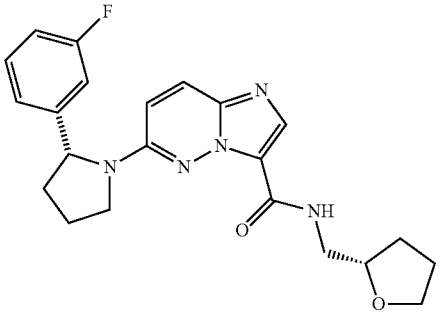 [SMILES: O=C(NC[C@@H]1CCCO1)c1cnc2ccc(N3CCC[C@@H]3c3cccc(F)c3)nn12] | MS m/z 410.1 (M + 1)+. | 0.042 | 0.054 | >10 |
| X-86 | 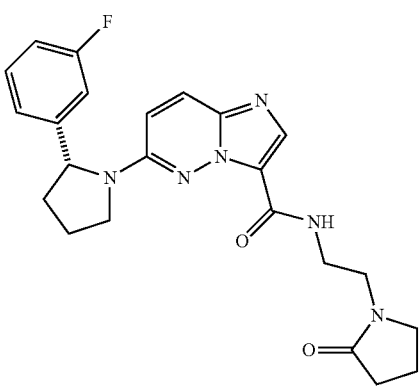 [SMILES: O=C(NCCN1CCCC1=O)c1cnc2ccc(N3CCC[C@@H]3c3cccc(F)c3)nn12] | MS m/z 437.2 (M + 1)+. | 0.276 | 0.191 | >10 |
| X-87 | 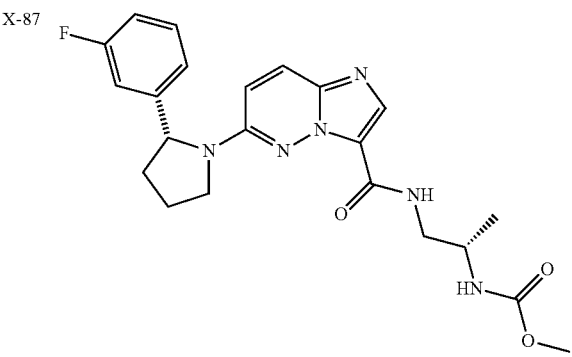 | MS m/z 441.2 (M + 1)+. | 0.071 | 0.076 | >10 |
| X-88 | 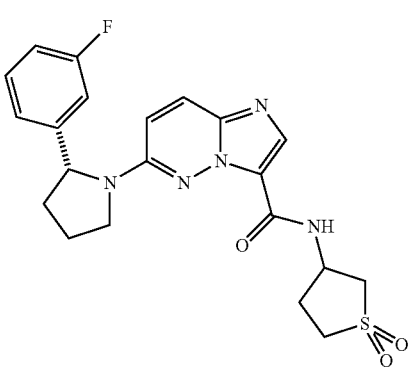 [SMILES: O=C(NC1CCS(=O)(=O)C1)c1cnc2ccc(N3CCC[C@@H]3c3cccc(F)c3)nn12] | $^1$H NMR (400 MHz, MeOD-d$_4$) δ 7.94 (s, 1H), 7.67 (d, J = 10 Hz, 1H), 7.32-7.26 (m, 1H), 7.04 (d, J = 7.6 Hz, 1H), 6.95-6.88 (m, 2H), 6.74 (bs, 1H), 5.17 (d, J = 7.6 Hz, 1H), 4.76-4.63 (m, 1H), 3.93 (t, J = 7.6, 1H), 3.69-3.62 (m, 1H), 3.50-3.37 (m, 1H), 3.18-3.02 (m, 2H), 2.84 (bs, 1H), 2.58-2.42 (m, 2H), 2.27-2.15 (m, 1H), 2.06-1.88 (m, 4H). MS m/z 444.1 (M + 1)+. | 0.037 | 0.053 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-89 | 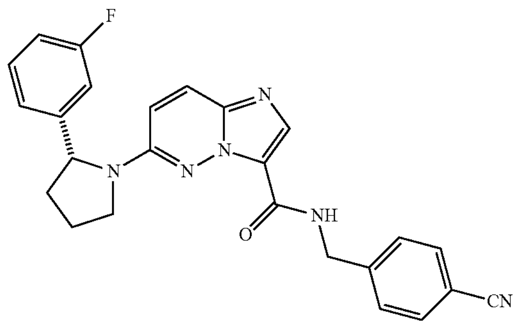 [SMILES: N#Cc1ccc(CNC(=O)c2cnc3ccc(N4CCC[C@@H]4c4cccc(F)c4)nn23)cc1] | MS m/z 441.10 ((M + 1)+. | 0.09 | 0.164 | >10 |
| X-90 | 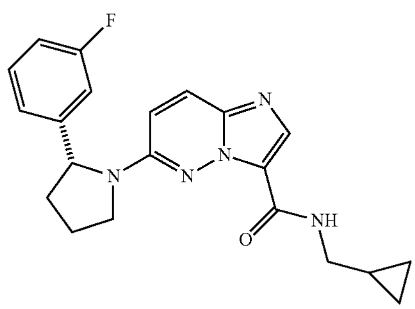 [SMILES: O=C(NCC1CC1)c1cnc2ccc(N3CCC[C@@H]3c3cccc(F)c3)nn12] | MS m/z 380.2 (M + 1)+. | 0.018 | 0.014 | >10 |
| X-91 | 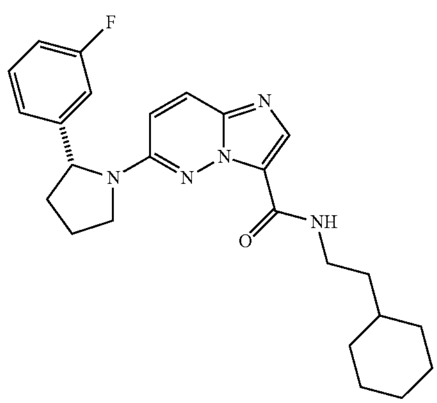 [SMILES: O=C(NCCC1CCCCC1)c1cnc2ccc(N3CCC[C@@H]3c3cccc(F)c3)nn12] | MS m/z 436.2 (M + 1)+. | 0.368 | 0.289 | 6.16 |
| X-92 | 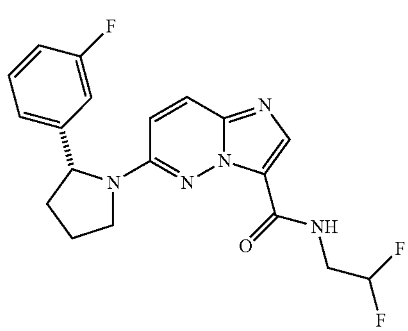 [SMILES: O=C(NCC(F)F)c1cnc2ccc(N3CCC[C@@H]3c3cccc(F)c3)nn12] | MS m/z 490.2 (M + 1)+. | 0.005 | 0.003 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-93 | 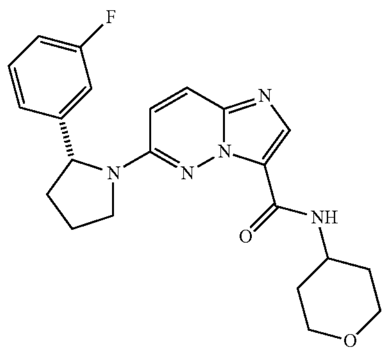 [SMILES: O=C(NC1CCOCC1)c1cnc2ccc(N3CCC[C@@H]3c3cccc(F)c3)nn12] | ¹H NMR (400 MHz, MeOD-d₄) δ 8.04 (s, 1H), 7.872 (d, J = 10 Hz, 1H), 7.40 (q, J = 7.6 Hz, 1H), 7.13 (d, J = 7.6 Hz, 1H), 7.06-6.99 (m, 2H), 6.92 (bs, 1H), 5.26 (d, J = 8 Hz, 1H), 4.14-4.09 (m, 1H), 4.04-3.95 (m, 3 H), 3.74 (dq, J = 7.2, 2.8 Hz, 1H), 3.55 (dq, J = 11.6, 1.6 Hz, 2H), 2.63 (m, 1H), 2.20-1.99 (m, 4H), 1.82 (bs, 1H), 1.63 (dq, J = 12, 3.6 Hz, 1H), 1.35 (bs, 1H). MS m/z 410.2 (M + 1)⁺. | 0.005 | 0.01 | >10 |
| X-94 | 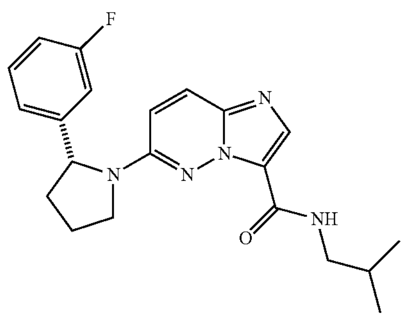 [SMILES: CC(C)CNC(=O)c1cnc2ccc(N3CCC[C@@H]3c3cccc(F)c3)nn12] | MS m/z 382.2 (M + 1)⁺. | 0.027 | 0.016 | >10 |
| X-95 | 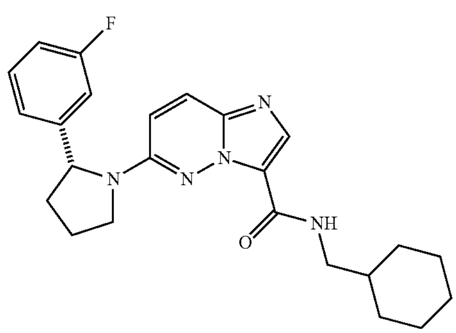 [SMILES: O=C(NCC1CCCCC1)c1cnc2ccc(N3CCC[C@@H]3c3cccc(F)c3)nn12] | MS m/z 422.2 (M + 1)⁺. | 0.113 | 0.118 | >10 |
| X-96 | 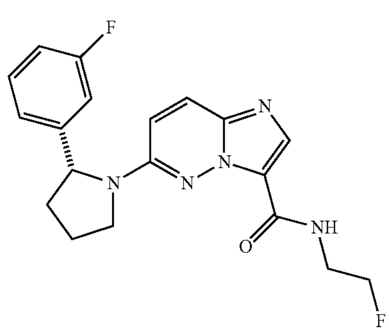 [SMILES: O=C(NCCF)c1cnc2ccc(N3CCC[C@@H]3c3cccc(F)c3)nn12] | MS m/z 372.1 (M + 1)⁺. | 0.006 | 0.007 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-97 | 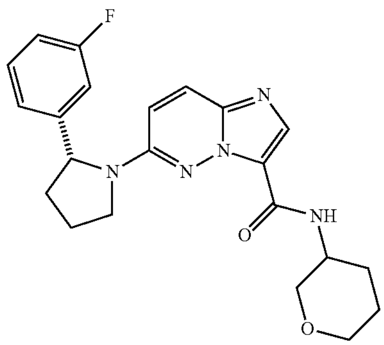 [SMILES: O=C(NC1CCCOC1)c1cnc2ccc(N3CCC[C@@H]3c3cccc(F)c3)nn12] | MS m/z 410.2 (M + 1)+. | 0.004 | 0.008 | >10 |
| X-98 | 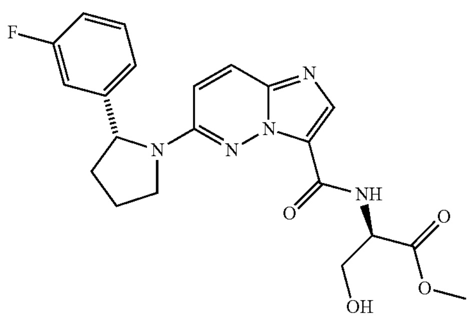 [SMILES: COC(=O)[C@@H](CO)NC(=O)c1cnc2ccc(N3CCC[C@@H]3c3cccc(F)c3)nn12] | MS m/z 428.2 (M + 1)+. | 0.248 | 0.354 | >10 |
| X-99 | 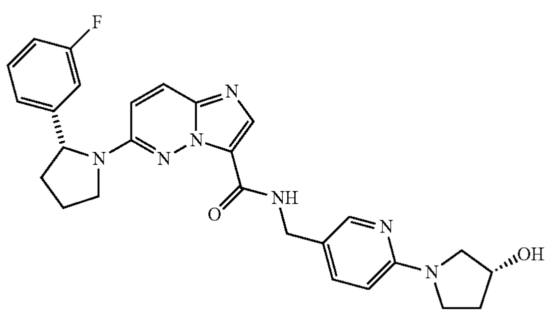 [SMILES: O=C(NCc1ccc(N2CC[C@@H](O)C2)nc1)c1cnc2ccc(N3CCC[C@@H]3c3cccc(F)c3)nn12] | MS m/z 502.30 (M + 1)+. | 0.4 | 0.731 | >10 |
| X-100 | 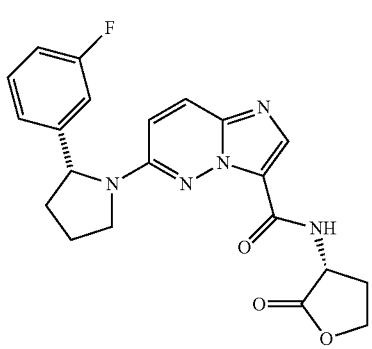 [SMILES: O=C(N[C@@H]1CCOC1=O)c1cnc2ccc(N3CCC[C@@H]3c3cccc(F)c3)nn12] | $^1$H NMR (400 MHz, MeOD-d$_4$) δ 7.93 (s, 1H), 7.72 (d, J = 9.6 Hz, 1H), 7.31 (q, J = 7.6 Hz, 1H), 7.03 (d, J = 7.6 Hz, 1H), 6.98-6.85 (m, 3H), 5.12 (dd, J = 8, 2.4 Hz, 1 H0, 4.45 (dt, J = 9.2, 2 Hz, 1H), 4.31 (q, J = 10.4 Hz, 1H), 3.94-3.85 (m, 1 H), 3.73-3.61 (m, 2H), 2.56-2.43 (m, 2H), 2.28-2.17 (m, 1H), 2.05-1.90 (m, 3H). MS m/z 410.1 (M + 1)+. | 0.016 | 0.027 | >10 |

TABLE 1-continued
| Compound No. | STRUCTURE | NMR and LC/MS | BaF3/TRKA-NGF (uM) | Ba/F3 Tel-TrkA (uM) | BAF 3/ WT (uM) |
|---|---|---|---|---|---|
| X-101 | 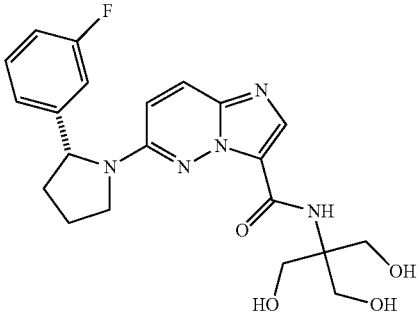 [SMILES: O=C(NC(CO)(CO)CO)c1cnc2ccc(N3CCC[C@@H]3c3cccc(F)c3)nn12] | MS m/z 430.2 (M + 1)+. | 0.198 | 0.452 | >10 |
| X-102 | 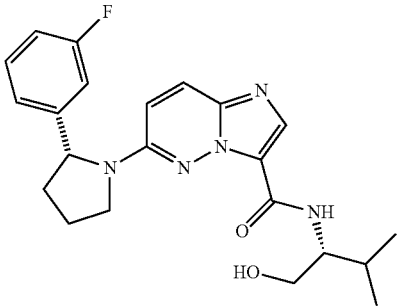 [SMILES: CC(C)[C@H](CO)NC(=O)c1cnc2ccc(N3CCC[C@@H]3c3cccc(F)c3)nn12] | MS m/z 412.2 (M + 1)+. | 0.029 | 0.031 | >10 |
| X-103 | 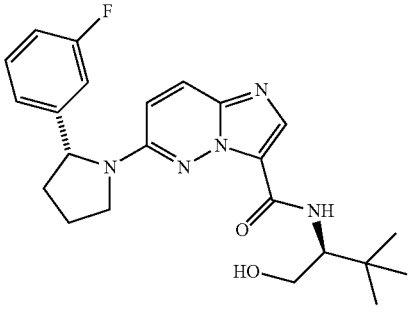 [SMILES: CC(C)(C)[C@@H](CO)NC(=O)c1cnc2ccc(N3CCC[C@@H]3c3cccc(F)c3)nn12] | MS m/z 426.2 (M + 1)+. | 0.359 | 0.379 | >10 |
| X-104 | 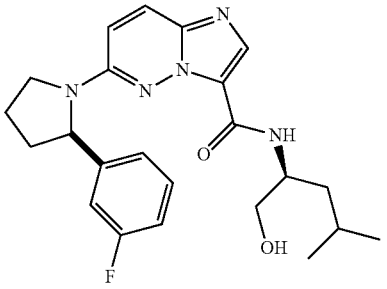 [SMILES: CC(C)C[C@@H](CO)NC(=O)c1cnc2ccc(N3CCC[C@@H]3c3cccc(F)c3)nn12] | MS m/z 426.2 (M + 1)+. | 0.15 | 0.697 | >10 |
| X-105 | 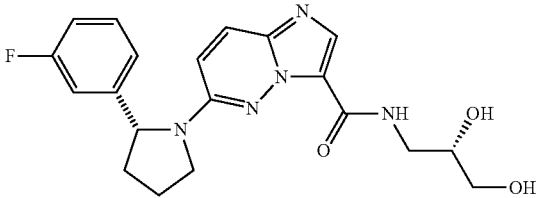 [SMILES: O=C(NC[C@H](O)CO)c1cnc2ccc(N3CCC[C@@H]3c3cccc(F)c3)nn12] | MS m/z 400.2 (M + 1)+. | 0.127 | 0.388 | >10 |

TABLE 1-continued
| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-106 | 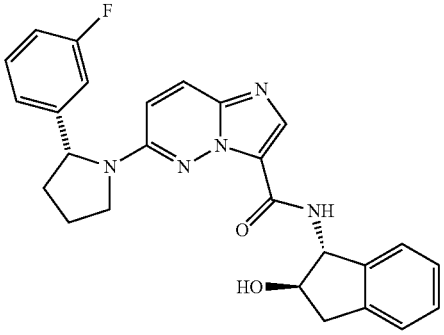 [SMILES: O=C(N[C@@H]1c2ccccc2C[C@H]1O)c1cnc2ccc(N3CCC[C@@H]3c3cccc(F)c3)nn12] | MS m/z 458.1 (M + 1)+. | 0.002 | 0.003 | >10 |
| X-107 | 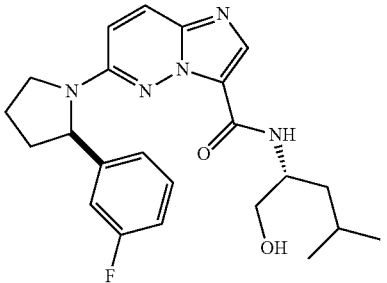 [SMILES: CC(C)C[C@H](CO)NC(=O)c1cnc2ccc(N3CCC[C@@H]3c3cccc(F)c3)nn12] | MS m/z 426.2 (M + 1)+. | 0.042 | 0.04 | >10 |
| X-108 | 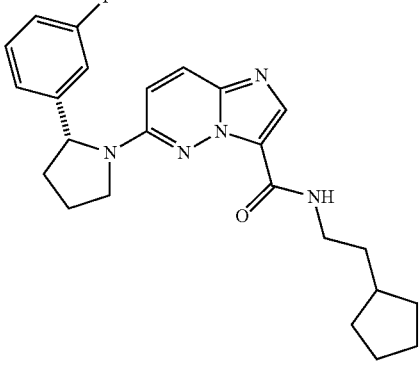 | MS m/z 422.2 (M + 1)+. | 0.311 | 0.191 | 6.48 |
| X-109 | 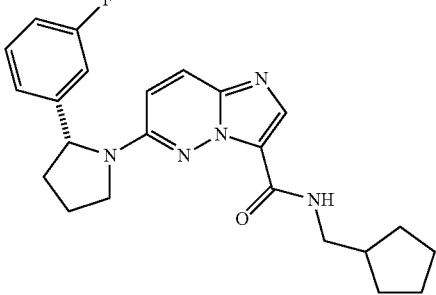 | MS m/z 408.1 (M + 1)+. | 0.068 | 0.04 | 7.96 |

TABLE 1-continued
| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-110 | 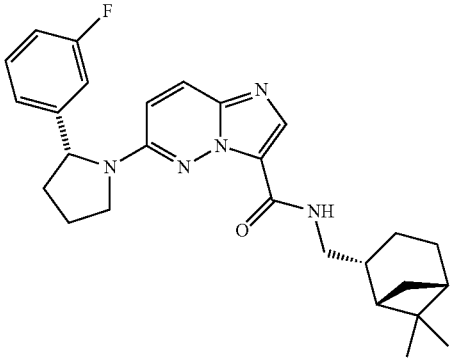 [SMILES: CC1(C)[C@H]2CC[C@@H](CNC(=O)c3cnc4ccc(N5CCC[C@@H]5c5cccc(F)c5)nn34)[C@@H]1C2] | MS m/z 462.3 (M + 1)+. | 0.163 | 0.207 | >9.76 |
| X-111 | 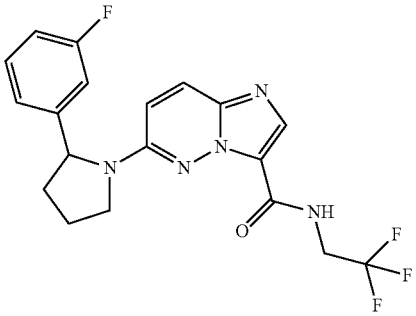 [SMILES: O=C(NCC(F)(F)F)c1cnc2ccc(N3CCCC3c3cccc(F)c3)nn12] | MS m/z 408.2 (M + 1)+. | 0.02 | 0.013 | >10 |
| X-112 | 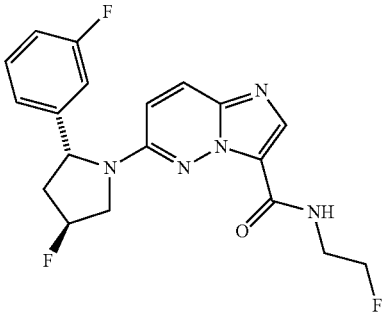 [SMILES: O=C(NCCF)c1cnc2ccc(N3C[C@@H](F)C[C@@H]3c3cccc(F)c3)nn12] | $^1$H NMR (400 MHz, CDCl$_3$) δ 8.83 (br s, 1H), 8.22 (s, 1 H), 7.72 (d, J = 10.0 Hz, 1 H), 7.37-7.31 (m, 1H), 7.06 (d, J = 7.6, Hz, 1H), 7.02-6.95 (m, 2H), 6.57 (d, J = 9.6 Hz, 1H), 5.42 (d, J = 52.4, 1H), 5.18 (dd, J = 9.2, 7.2 Hz, 1H), 4.73-4.65 (m, 1H), 4.61-4.53 (m, 1 H), 4.28-4.04 (m, 2H), 4.01-3.84 (m, 1H), 3.80-3.56 (m, 1H), 2.98-2.86 (m, 1H), 2.24-2.05 (m, 1 H). MS m/z 390.10 (M + 1). MS m/z 390.1 (M + 1)+. | <0.0003135 | 0.001 | 5.45 |
| X-113 | 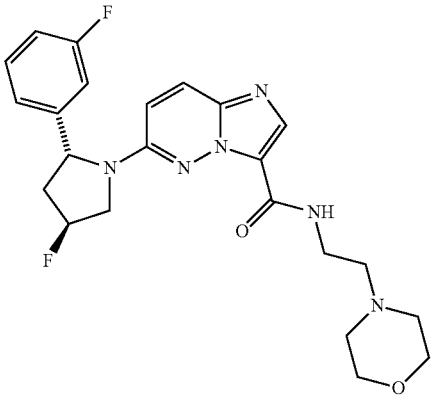 [SMILES: O=C(NCCN1CCOCC1)c1cnc2ccc(N3C[C@@H](F)C[C@@H]3c3cccc(F)c3)nn12] | MS m/z 457.20 (M + 1)+. | 0.005 | 0.009 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-114 | 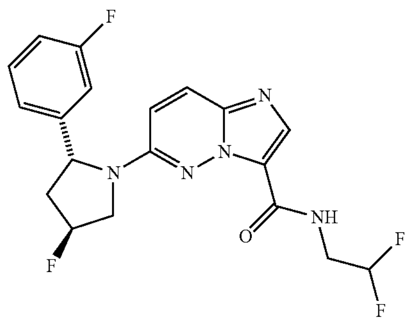 [SMILES: O=C(NCC(F)F)c1cnc2ccc(N3C[C@@H](F)C[C@@H]3c3cccc(F)c3)nn12] | MS m/z 408.1 (M + 1)+. | <0.0002766 | 0.001 | 7.49 |
| X-115 | 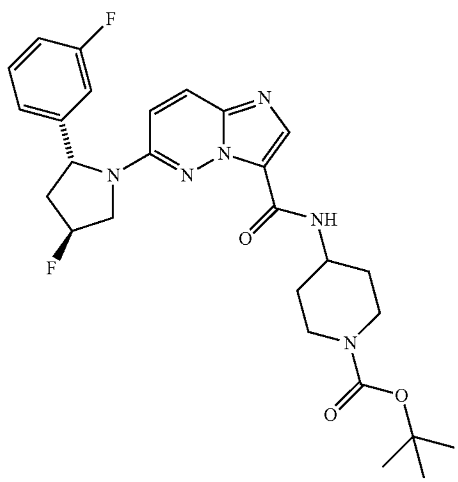 | MS m/z 470.2 (M − 56)+. | 0.0009 | 0.001 | 4.60 |
| X-116 | 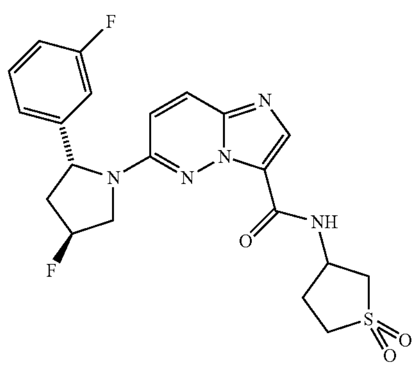 [SMILES: O=C(NC1CCS(=O)(=O)C1)c1cnc2ccc(N3C[C@@H](F)C[C@@H]3c3cccc(F)c3)nn12] | MS m/z 461.1 (M + 1)+. | 0.016 | 0.013 | >10 |
| X-117 | 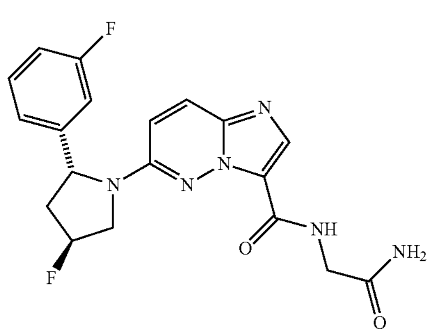 [SMILES: NC(=O)CNC(=O)c1cnc2ccc(N3C[C@@H](F)C[C@@H]3c3cccc(F)c3)nn12] | MS m/z 401.1 (M + 1)+. | 0.084 | 0.064 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-118 | 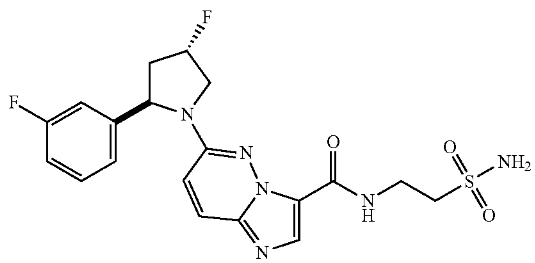 | MS m/z 451.1 (M + 1)+. | 0.062 | 0.054 | >10 |
| X-119 | 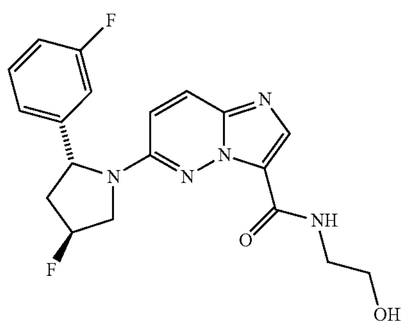 [SMILES: O=C(NCCO)c1cnc2ccc(N3C[C@@H](F)C[C@@H]3c3cccc(F)c3)nn12] | MS m/z 387.1 (M + 1)+. | 0.001 | 0.003 | >10 |
| X-120 | 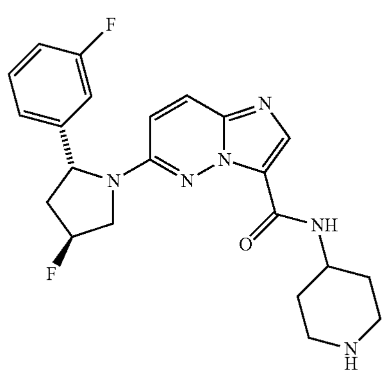 [SMILES: O=C(NC1CCNCC1)c1cnc2ccc(N3C[C@@H](F)C[C@@H]3c3cccc(F)c3)nn12] | MS m/z 427.2 (M + 1)+. | 0.308 | 0.331 | >10 |
| X-121 | 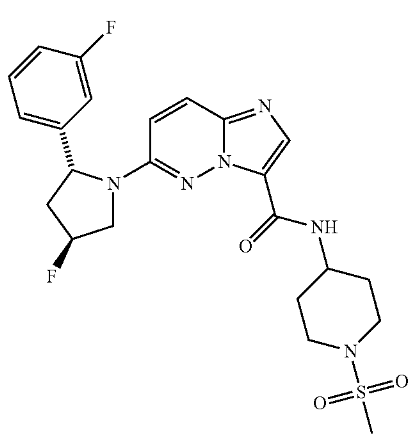 [SMILES: CS(=O)(=O)N1CCC(NC(=O)c2cnc3ccc(N4C[C@@H](F)C[C@@H]4c4cccc(F)c4)nn23)CC1] | MS m/z 505.2 (M + 1)+. | 0.003 | 0.002 | 5.14 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-122 | 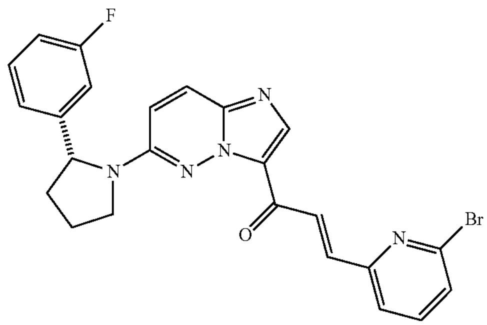 [SMILES: O=C(/C=C/c1cccc(Br)n1)c1cnc2ccc(N3CCC[C@@H]3c3cccc(F)c3)nn12] | MS m/z 493.10 (M + 1)+. | 0.104 | 0.045 | 1.124 |
| X-123 | 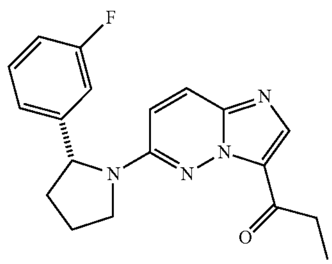 [SMILES: CCC(=O)c1cnc2ccc(N3CCC[C@@H]3c3cccc(F)c3)nn12] | MS m/z 339.1 (M + 1)+. | 0.162 | 0.097 | >10 |
| X-124 | 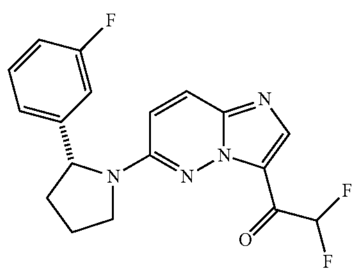 [SMILES: O=C(c1cnc2ccc(N3CCC[C@@H]3c3cccc(F)c3)nn12)C(F)F] | MS m/z 361.1 (M + 1)+. | 0.247 | 0.844 | >10 |
| X-125 | 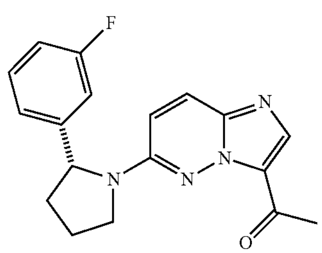 [SMILES: CC(=O)c1cnc2ccc(N3CCC[C@@H]3c3cccc(F)c3)nn12] | 1H NMR (400 MHz, CDCl3) δ 8.17 (s, 1H), 7.68 (d, J = 10.0 Hz, 1H), 7.33-7.26 (m, 1H), 7.00 (d, J = 8.0 Hz, 1H), 6.97-6.87 (m, 2H), 6.59 (d, J = 9.6 Hz, 1H), 5.04 (dd, J = 8.4, 2.0 Hz, 1H), 4.00-3.91 (m, 1H), 3.79-3.69 (m, 1H), 2.58 (s, 3H), 2.55-2.45 (m, 1H), 2.15-2.00 (m, 1H). MS m/z 325.10 (M + 1)+. | 0.164 | 0.219 | >10 |
| X-126 | 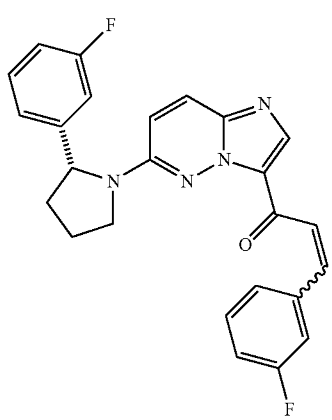 [SMILES: O=C(C=Cc1cccc(F)c1)c1cnc2ccc(N3CCC[C@@H]3c3cccc(F)c3)nn12] | MS m/z 431.10 (M + 1)+. | 0.079 | 0.022 | 1.092 |

TABLE 1-continued
| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-127 | 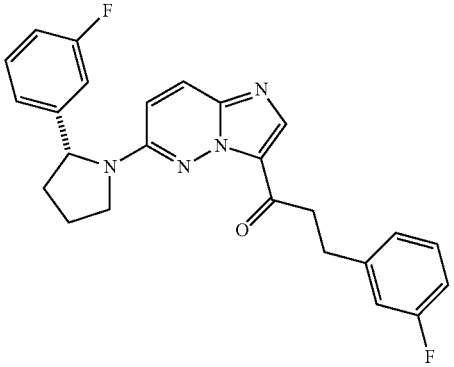 [SMILES: O=C(CCc1cccc(F)c1)c1cnc2ccc(N3CCC[C@@H]3c3cccc(F)c3)nn12] | MS m/z 433.10 (M + 1)+. | 0.057 | 0.038 | >10 |
| X-128 | 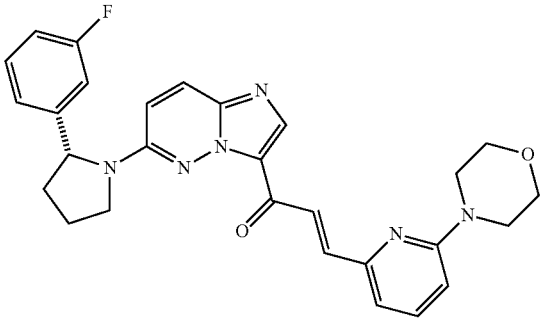 [SMILES: O=C(/C=C/c1cccc(N2CCOCC2)n1)c1cnc2ccc(N3CCC[C@@H]3c3cccc(F)c3)nn12] | MS m/z 499.10 (M + 1)+. | 0.088 | 0.174 | 1.394 |
| X-129 | 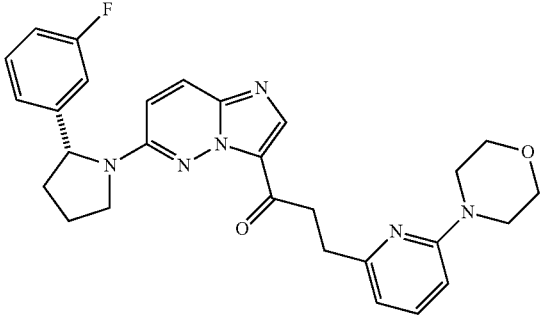 [SMILES: O=C(CCc1cccc(N2CCOCC2)n1)c1cnc2ccc(N3CCC[C@@H]3c3cccc(F)c3)nn12] | MS m/z 501.10 (M + 1)+. | 0.059 | 0.088 | >9.71 |
| X-130 | 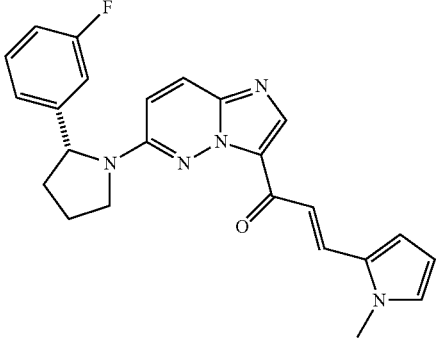 [SMILES: Cn1cccc1/C=C/C(=O)c1cnc2ccc(N3CCC[C@@H]3c3cccc(F)c3)nn12] | MS m/z 416.10 (M + 1)+. | 0.049 | 0.024 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-131 | 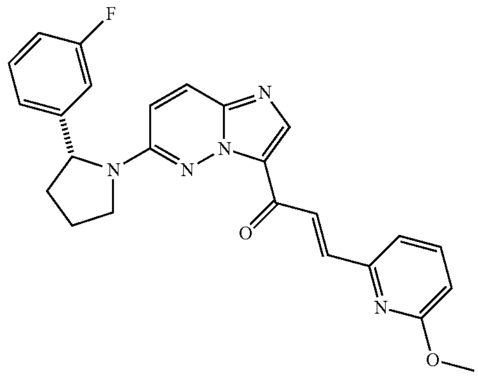 [SMILES: COc1cccc(/C=C/C(=O)c2cnc3ccc(N4CCC[C@@H]4c4cccc(F)c4)nn23)n1] | MS m/z 444.20 (M + 1)⁺. | 0.182 | 0.194 | 1.669 |
| X-142 | 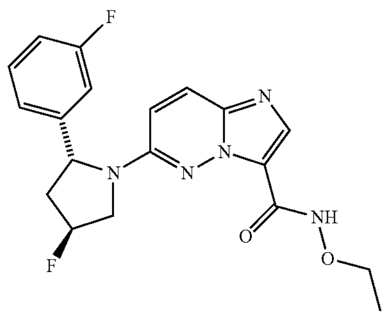 [SMILES: CCONC(=O)c1cnc2ccc(N3C[C@@H](F)C[C@@H]3c3cccc(F)c3)nn12] | ¹H NMR (400 MHz, CDCl₃) δ 10.29 (s, 1H), 8.23 (s, 1H), 7.79 (d, J = 10.0 Hz, 1H), 7.36 (td, J = 7.6, 5.6 Hz, 1H), 7.09 (d, J = 7.6 Hz, 1H), 7.03-6.95 (m, 2H), 6.68 (d, J = 10.0 Hz, 1H), 5.43 (d, J = 52.8, 1H), 5.19 (dd, J = 9.6, 7.2 Hz, 1H), 4.24-4.05 (m, 3H), 3.95-3.86 (m, 1H), 2.92 (td, J = 16.0, 6.8 Hz, 1H), 2.15 (dddd, J = 40.8, 14.0, 9.6, 3.6 Hz, 1H), 1.36 (t, J = 7.2 Hz, 3H). MS m/z 388.10 (M + 1)⁺. | 0.001 | 0.001 | 6.69 |
| X-143 | 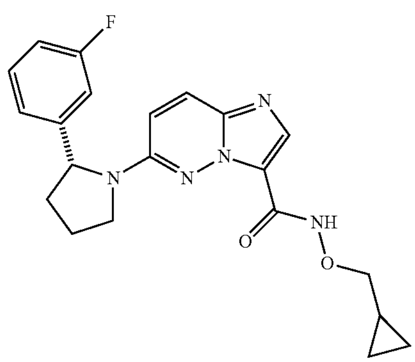 [SMILES: O=C(NOCC1CC1)c1cnc2ccc(N3CCC[C@@H]3c3cccc(F)c3)nn12] | MS m/z 396.2 (M + 1)⁺. | 0.055 | 0.045 | >10 |
| X-144 | 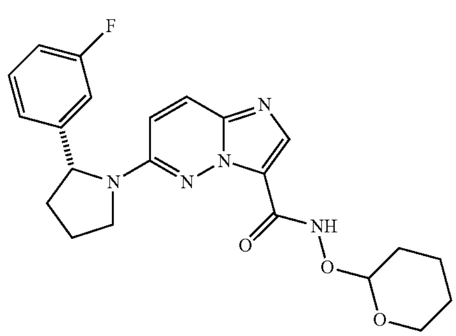 [SMILES: O=C(NOC1CCCCO1)c1cnc2ccc(N3CCC[C@@H]3c3cccc(F)c3)nn12] | ¹H NMR (400 MHz, MeOD-d₄) δ 8.22 (s, 1H), 7.98 (d, J = 9.6 Hz, 1H), 7.42 (q, J = 8 Hz, 1H), 7.28 (bs, 1H), 7.16 (d, J = 8 Hz, 1H), 7.07 (d, J = 9.6 Hz, 1H), 7.03-6.98 (m, 1H), 5.21(dd, J = 8, 3.2 Hz, 1H), 4.11-4.02 (m, 1H), 3.88-3.76 (m, 2H), 3.69 (d, J = 11.2, 1H), 3.58-3.49 (m, 1H), 2.65-2.55 (m, 1H), 2.26-2.11 (m, 2H), 2.09-1.99 (m, 1H), 1.95-1.74 (m, 2H), 1.64-1.63 (m, 2H), 1.62-1.50 (m, 2H). MS m/z 426.2 (M + 1)⁺. | 0.123 | 0.128 | >10 |

TABLE 1-continued
| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-145 | 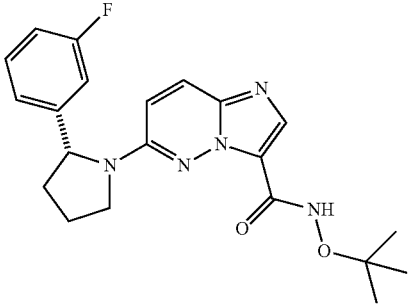 [SMILES: CC(C)(C)ONC(=O)c1cnc2ccc(N3CCC[C@@H]3c3cccc(F)c3)nn12] | MS m/z 398.2 (M + 1)⁺. | 0.041 | 0.033 | >10 |
| X-146 | 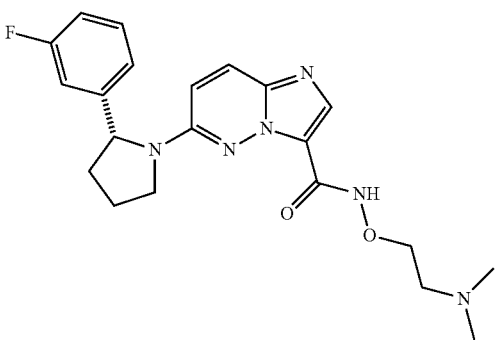 [SMILES: CN(C)CCONC(=O)c1cnc2ccc(N3CCC[C@@H]3c3cccc(F)c3)nn12] | MS m/z 413.2 (M + 1)⁺. | 0.134 | 0.302 | >10 |
| X-147 | 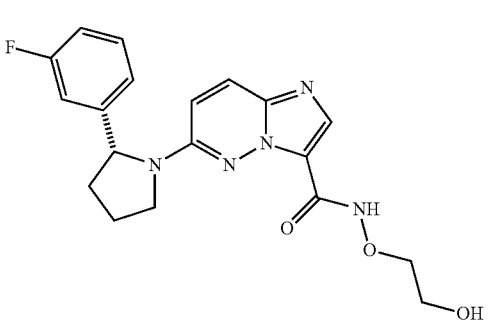 [SMILES: O=C(NOCCO)c1cnc2ccc(N3CCC[C@@H]3c3cccc(F)c3)nn12] | ¹H NMR (400 MHz, MeOD-d₄) δ 8.36 (bs, 1H), 8.03 (d, J = 8.0 Hz, 1H), 7.42 (q, J = 8 Hz, 1H), 7.38-7.26 (m, 1H), 7.18 (d, J = 7.6 Hz, 1H), 7.09 (d, J = 9.6 Hz, 1H), 7.02 (dt, J = 8.4, 2.4 Hz, 1H), 5.50 (s, 2H), 4.11-4.06 (m, 1H), 4.00 (bs, 1H), 3.86-3.79 (m, 2 H), 2.65-2.55 (m, 1H), 2.21-2.14 (m, 1H), 2.08-2.02 (m, 2H). MS m/z 386.2 (M + 1)⁺. | 0.021 | 0.031 | >10 |
| X-148 | 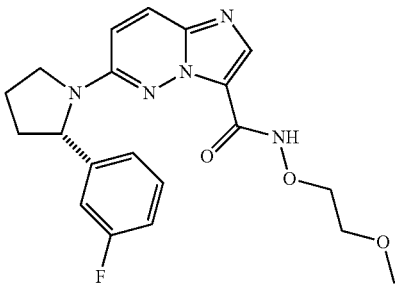 [SMILES: COCCONC(=O)c1cnc2ccc(N3CCC[C@H]3c3cccc(F)c3)nn12] | ¹H NMR (400 MHz, MeOD-d₄) δ 8.33 (s, 1H), 8.04 (bs, 1H), 7.43 (q, J = 8 Hz, 1 H), 7.17 (d, J = 7.6 Hz, 1 H), 7.13-6.95 (m, 3H), 5.50 (s, 2H), 5.28 (dd, J = 8.4, 2.8 Hz, 1H), 4.11-4.01 (m, 2H), 3.85-3.79 (m, 1H), 3.72 (t, J = 4.8 Hz, 1H), 3.44 (s, 3H), 2.66-2.53 (m, 1H), 2.25-2.12 (m, 2H), 2.08-2.02 (m, 2 H). MS m/z 400.2 (M + 1)⁺. | 0.026 | 0.028 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-149 | 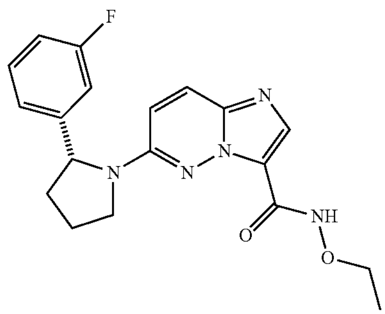 [SMILES: CCONC(=O)c1cnc2ccc(N3CCC[C@@H]3c3cccc(F)c3)nn12] | MS m/z 370.2 (M + 1)+. | 0.026 | 0.023 | >10 |
| X-150 | 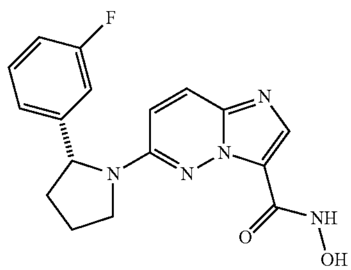 [SMILES: O=C(NO)c1cnc2ccc(N3CCC[C@@H]3c3cccc(F)c3)nn12] | ¹H NMR (400 MHz, DMSO-d₆) δ 10.24 (bs, 1H), 9.30 (bs, 1H), 7.97-7.90 (m, 2H), 7.31 (q, J = 8.4 Hz, 1H), 7.06-6.97 (m, 3H), 3.90 (bs, 1H), 5.11 (d, J = 6 Hz, 1H), 3.96-3.91 (m, 1H), 3.63-3.57 (m, 1H), 2.41 (m, 1H), 2.00-1.92 (m, 2H), 1.84-1.78 (m, 1H). MS m/z 341.1 (M + 1)+. | 0.212 | 0.21 | >10 |
| X-151 | 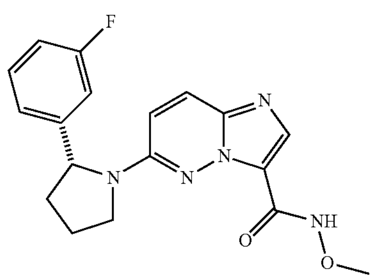 | MS m/z 356.1 (M + 1)+. | 0.055 | 0.045 | >10 |
| X-152 | 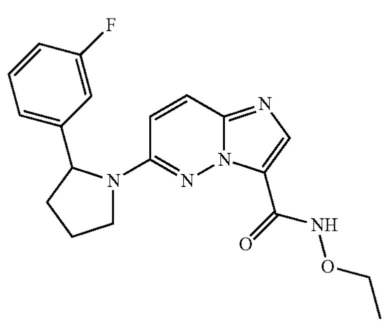 | ¹H NMR (400 MHz, MeOD-d₄) δ 8.04 (s, 1H), 7.86 (d, J = 9.6 Hz, 1H), 7.41-7.36 (m, 1H), 7.14 (d, J = 7.6 Hz, 1H), 7.09 (d, J = 9.6 Hz, 1H), 7.01 (dt, J = 8.8, 2.4 Hz, 1H), 5.19 (dd, J = 8, 2.8 Hz, 1H), 4.04-3.94 (m, 2H), 3.77 (q, 8 Hz, 2H), 2.63-2.53 (m, 1H), 2.18-2.11 (m, 2H), 2.04-1.98 (m, 1H), 1.29 (t, J = 3.8 Hz, 3H). MS m/z 370.2 (M + 1)+. | 0.044 | 0.042 | >10 |
| X-153 | 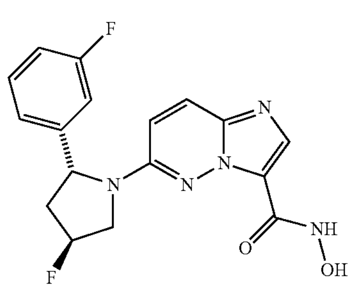 [SMILES: O=C(NO)c1cnc2ccc(N3C[C@@H](F)C[C@@H]3c3cccc(F)c3)nn12] | MS m/z 360.1 (M + 1)+. | 0.014 | 0.010 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-154 | 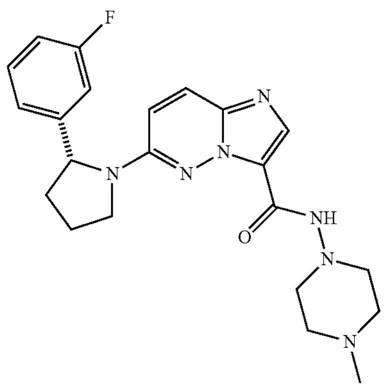 [SMILES: CN1CCN(NC(=O)c2cnc3ccc(N4CCC[C@@H]4c4cccc(F)c4)nn23)CC1] | MS m/z 424.2 (M + 1)+. | 0.093 | 0.153 | >10 |
| X-155 | 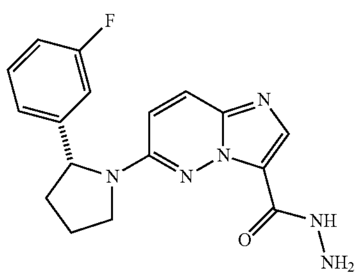 [SMILES: NNC(=O)c1cnc2ccc(N3CCC[C@@H]3c3cccc(F)c3)nn12] | ¹H NMR (400 MHz, MeOD-d₄) δ 8.23 (d, J = 9.6 Hz, 1 H), 7.98 (d, J = 10 Hz, 1H), 7.43 (q, J = 8 Hz, 1H), 7.08 (d, J = 7.2 Hz, 1H), 7.04-6.96 (m, 3H), 5.26 (dd, J = 8, 2.4 Hz, 1H), 4.10-4.03 (m, 1H), 3.85-3.77(m, 1 H), 2.66-2.55 (m, 1H), 2.21-2.13 (m, 2H), 1.99-1.98 (m, 1H). | 0.164 | 0.242 | >10 |
| X-156 | 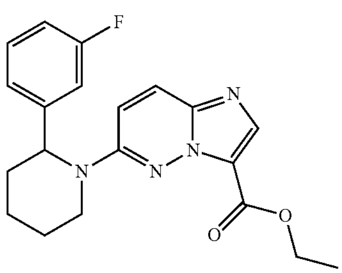 [SMILES: CCOC(=O)c1cnc2ccc(N3CCCCC3c3cccc(F)c3)nn12] | ¹H NMR (400 MHz, MeOD-d₄) δ 8.17 (s, 1H), 8.01 (d, J = 10 Hz, 1H), 7.42-7.36 (m, 2H), 7.13-7.05 (m, 3 H), 5.70 (s, 1H), 2.02-1.94 (m, 1H), 1.79-1.70 (m, 1 H), 1.63-1.57 (m, 2H), 1.47-1.37 (m, 1H), 1.29 (t, J = 7.2 Hz, 3H). MS m/z = 369.2 (M + 1)+. | 0.037 | 0.093 | >10 |
| X-157 | 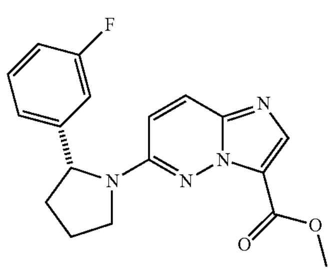 [SMILES: COC(=O)c1cnc2ccc(N3CCC[C@@H]3c3cccc(F)c3)nn12] | ¹H NMR (400 MHz, MeOD-d₄) δ 8.06 (s, 1H), 7.76 (d, J = 9.6 Hz, 1H), 7.36 (q, J = 8 Hz, 1H), 7.12 (d, J = 8 Hz, 1H), 6.98 (dt, J = 8.4, 2 Hz, 1H), 6.87 (d, J = 10 Hz, 1H), 5.21 (dd, J = 8.4, 2.8 Hz, 1H), 4.63 (bs, 1H), 4.03-3.98 (m, 1H), 3.90 (s, 3H), 3.80 (q, J = 8 Hz, 1 H), 2.59-2.49 (m, 1H), 2.15-2.07 (m, 1H), 2.04-1.97 (m, 1H). MS m/z 341.1 (M + 1)+. | 0.073 | 0.112 | >10 |
| X-158 | 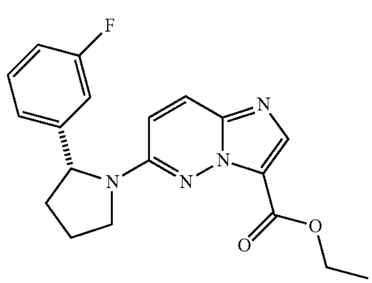 [SMILES: CCOC(=O)c1cnc2ccc(N3CCC[C@@H]3c3cccc(F)c3)nn12] | MS m/z 355.1 (M + 1)+. | 0.056 | 0.093 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-159 | 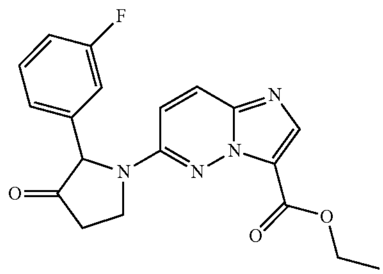 [SMILES: CCOC(=O)c1cnc2ccc(N3CCC(=O)C3c3cccc(F)c3)nn12] | $^1$H NMR (400 MHz, CDCl$_3$) δ 8.09 (s, 1H), 7.79 (d, J = 10 Hz, 1H), 7.44-7.35 (m, 1H), 7.28-7.18 (m, 2H), 7.16-7.08 (m, 1H), 6.91 (d, J = 9.6 Hz, 1H), 5.26 (s, 1H), 4.31 (q, J = 7.2 Hz, 2H), 4.26-4.18 (m, 1H), 4.12-4.02 (m, 1H), 3.03-2.80 (m, 2H), 1.31 (t, J = 7.2 Hz, 3H). MS m/z 369.10 (M + 1)$^+$. | 0.407 | 0.251 | >10 |
| X-160 | 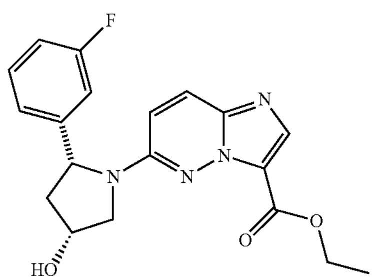 [SMILES: CCOC(=O)c1cnc2ccc(N3C[C@H](O)C[C@@H]3c3cccc(F)c3)nn12] | $^1$H NMR (400 MHz, CDCl$_3$) δ 8.15 (s, 1H), 7.64 (d, J = 10 Hz, 1H), 7.34-7.27 (m, 1H), 7.15 (d, J = 8 Hz, 1H), 7.09 (d, J = 10 Hz, 1H), 6.72 (td, J = 8.4, 2.0 Hz, 1H), 6.49 (d, J = 10 Hz, 1H), 5.05 (dd, J = 9.2, 2.8 Hz, 1H), 4.68 (bs, 1H), 4.41 (q, J = 7.2 Hz, 2H), 4.11-4.05 (m, 1H), 4.05-3.98 (m, 1H), 2.77 (ddd, J = 5.2, 9.6, 14 Hz, 1H), 2.23 (d, J = 13.6 Hz, 1H), 1.41 (t, J = 7.2 Hz, 3H). MS m/z 371.10 (M + 1)$^+$. | 0.026 | 0.073 | >10 |
| X-161 | 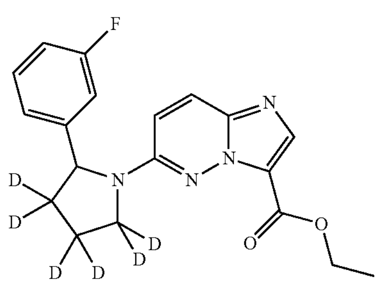 [SMILES: [2H]C1([2H])C(c2cccc(F)c2)N(c2ccc3ncc(C(=O)OCC)n3n2)C([2H])([2H])C1([2H])[2H]] | MS m/z 361.2 (M + 1)$^+$. | 0.068 | 0.063 | >10 |
| X-162 | 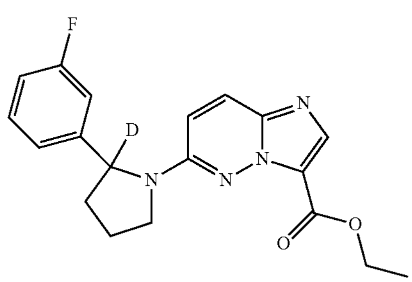 [SMILES: [2H]C1(c2cccc(F)c2)CCCN1c1ccc2ncc(C(=O)OCC)n2n1] | MS m/z 356.1 (M + 1)$^+$. | 0.063 | 0.08 | >10 |
| X-163 | 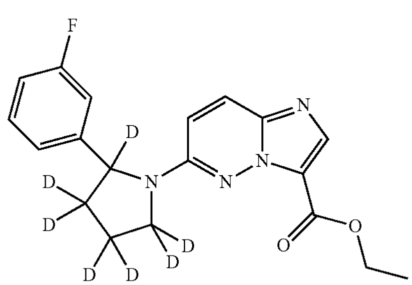 [SMILES: [2H]C1([2H])N(c2ccc3ncc(C(=O)OCC)n3n2)C([2H])(c2cccc(F)c2)C([2H])([2H])C1([2H])[2H]] | MS m/z 362.2 (M + 1)$^+$. | 0.073 | 0.079 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-164 | 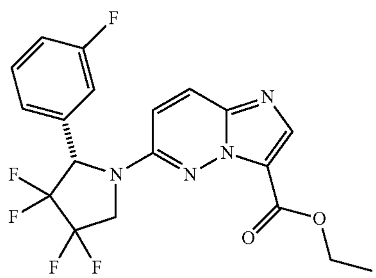 [SMILES: CCOC(=O)c1cnc2ccc(N3CC(F)(F)C(F)(F)[C@@H]3c3cccc(F)c3)nn12] | ¹H NMR (400 MHz, DMSO-d₆) δ 8.36 (s, 1H), 8.26 (d, J = 7.6 Hz, 1H), 7.45-7.39 (m, 1H), 7.15-7.11 (m, 2H), 7.05 (d, J = 9.2 Hz, 1H), 5.93 (d, J = 8.0 Hz, 1H), 5.30-5.27 (m, 1H), 4.68-4.5 (m, 2H), 4.37 (q, J = 6.8 Hz, 2H), 1.41 (t, J = 7.2 Hz, 3H). MS m/z 427.1 (M + 1)⁺. | 0.53 | 0.6 | >10 |
| X-165 | 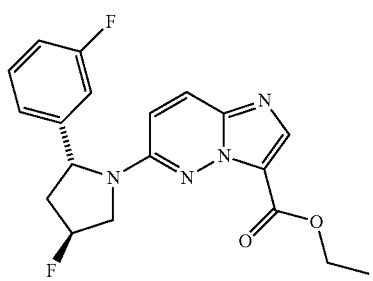 [SMILES: CCOC(=O)c1cnc2ccc(N3C[C@@H](F)C[C@@H]3c3cccc(F)c3)nn12] | ¹H NMR (400 MHz, CDCl₃) δ 8.14 (s, 1H), 7.61 (d, J = 10.0 Hz, 1H), 7.32 (td, J = 8.0, 5.6 Hz, 1H), 7.09 (d, J = 8.0 Hz, 1H), 7.03-6.94 (m, 2H), 6.47 (d, J = 10.0 Hz, 1H), 5.39 (d, J = 52.4, 1H), 5.12 (dd, J = 9.2, 7.2 Hz, 1H), 4.55-4.45 (m, 1H), 4.42 (q, J = 6.8 Hz, 2H), 4.10 (ddd, J = 37.2, 13.6, 2.0 Hz, 1H), 2.95-2.83 (m, 1H), 2.15 (dddd, J = 41.2, 24.0, 9.6, 3.6 Hz, 1H), 1.42 (t, J = 7.2 Hz, 3H). MS m/z 373.20 (M + 1)⁺. | 0.006 | 0.004 | >10 |
| X-166 | 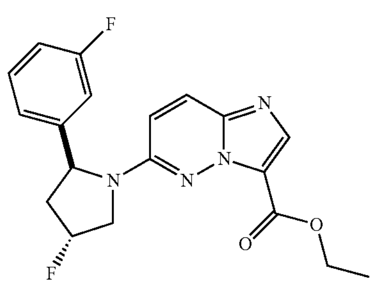 [SMILES: CCOC(=O)c1cnc2ccc(N3C[C@H](F)C[C@H]3c3cccc(F)c3)nn12] | ¹H NMR (400 MHz, CDCl₃) δ 8.16 (s, 1H), 7.66 (d, J = 9.6 Hz, 1H), 7.32-7.27 (m, 1H), 7.12 (d, J = 8 Hz, 1H), 7.05 (d, J = 10 Hz, 1H), 6.95 (td, J = 8.4, 2.4 Hz, 1H), 6.50 (d, J = 10 Hz, 1H), 5.43 (dt, J = 52.8, 4.0 Hz, 1H), 5.10 (d, J = 9.6 Hz, 1H), 4.42 (q, J = 7.2 Hz, 1H), 4.35 (ddd, J = 24.8 13.6, 2 Hz, 1H), 4.03 (ddd, J = 35.9, 14.0, 4.0 Hz, 1H), 2.75 (dddd, J = 41.2, 14.4, 10.0, 4.4 Hz, 1H), 2.49 (dd, J = 18.8, 14.4 Hz, 1H), 1.42 (t, J = 6.8 Hz, 3H). MS m/z 373.10 (M + 1)⁺. | 0.322 | 0.314 | >10 |
| X-168 | 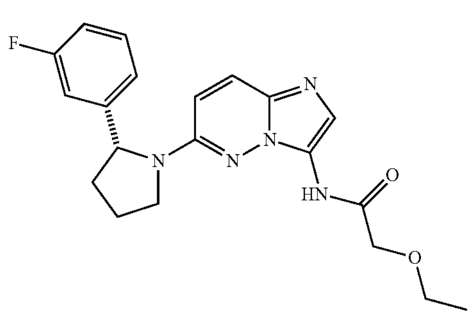 [SMILES: CCOCC(=O)Nc1cnc2ccc(N3CCC[C@@H]3c3cccc(F)c3)nn12] | ¹H NMR (400 MHz, CDCl₃) δ 8.65 (s, 1H), 7.86 (s, 1H), 7.60 (d, J = 10 Hz, 1H), 7.32-7.28 (m, 1H), 7.03 (d, J = 8 Hz, 1H), 6.96-6.88 (m, 2H), 6.46 (d, J = 9.6 Hz, 1H), 4.99 (dd, J = 3.6, 8.2 Hz, 1H), 3.95-3.88 (m, 1H), 3.75-3.66 (m, 1H), 2.55-2.44 (m, 1H), 2.22-2.05 (m, 2H), 2.05-1.98 (m, 1H), 1.92 (t, J = 19.6 Hz, 3H). MS m/z 384.2 (M + 1)⁺. | 0.032 | 0.017 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-172 | 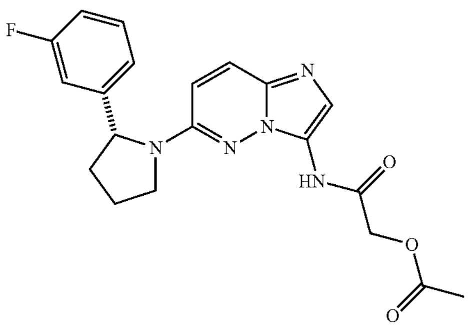 [SMILES: CC(=O)OCC(=O)Nc1cnc2ccc(N3CCC[C@@H]3c3cccc(F)c3)nn12] | MS m/z 398.10 (M + 1)⁺. | 0.036 | 0.038 | >10 |
| X-173 | 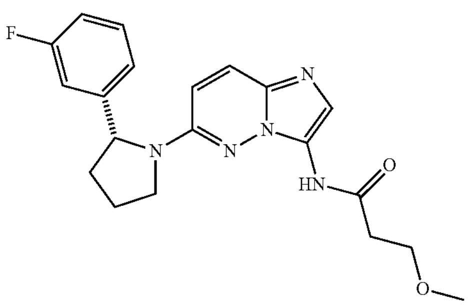 | ¹H NMR (400 MHz, CDCl₃) δ 9.18 (s, 1H), 7.89 (s, 1 H), 7.63 (d, J = 10.0 Hz, 1 H), 7.33-7.27 (m, 1H), 7.00 (d, J = 7.6 Hz, 1H), 6.98-6.88 (m, 1H), 6.42 (d, J = 9.6 Hz, 1H), 5.01 (dd, J = 8.4, 2.4 Hz, 1H), 3.96-3.89 (m, 1H), 3.78-(t, J = 5.6 Hz, 2H), 3.75-3.66 (m, 1H), 3.50 (s, 3H), 2.75 (t, J = 6 Hz, 2H), 2.55-2.45 (m, 1 H), 2.15-2.00 (m, 3H). MS m/z 384.10 (M + 1)⁺. | 0.279 | 0.229 | >10 |
| X-184 | 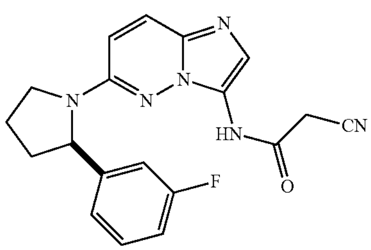 [SMILES: N#CCC(=O)Nc1cnc2ccc(N3CCC[C@@H]3c3cccc(F)c3)nn12] | MS m/z 365.10 (M + 1)⁺. | 0.109 | 0.291 | >10 |
| X-186 | 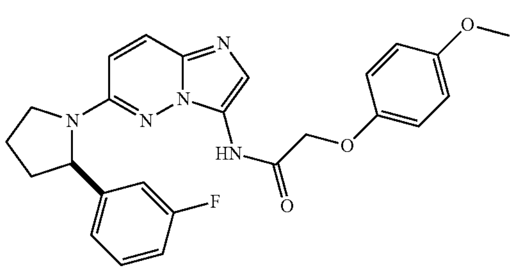 [SMILES: COc1ccc(OCC(=O)Nc2cnc3ccc(N4CCC[C@@H]4c4cccc(F)c4)nn23)cc1] | ¹H NMR (400 MHz, CDCl₃) δ 9.09 (s, 1H), 7.91 (s, 1 H), 7.58 (d, J = 10.0 Hz, 1 H), 7.25-7.20 (m, 1H), 6.99 (d, J = 8.0 Hz, 1H), 6.97-6.86 (m, 6H), 6.38 (d, J = 9.6 Hz, 1H), 5.02 (dd, J = 8.4, 2.4 Hz, 1H), 4.67 (s, 2H), 3.90-3.84 (m, 1H), 3.80 (s, 3H), 3.69-3.61 (m, 1H), 2.52 (d, J = 4 Hz, 2H), 2.55-2.42 (m, 1 H), 2.12-1.97 (m, 3H). MS m/z 462.10 (M + 1)⁺. | 0.118 | 0.078 | >10 |
| X-188 | 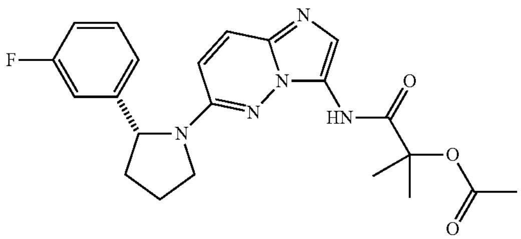 [SMILES: CC(=O)OC(C)(C)C(=O)Nc1cnc2ccc(N3CCC[C@@H]3c3cccc(F)c3)nn12] | ¹H NMR (400 MHz, CDCl₃) δ 8.63 (br s, 1H), 7.87 (s, 1 H), 7.57 (d, J = 9.6 Hz, 1 H), 7.32-7.27 (m, 1H), 7.02-6.86 (m, 3H), 6.37 (d, J = 8.8 Hz, 1H), 5.02 (d, J = 7.2 Hz, 1H), 3.94-3.86 (m, 1H), 3.74-3.64 (m, 1 H), 5.30 (s, 1H), 3.54 (s, 3 H), 2.55-2.42 (m, 1H), 2.16 (s, 3H), 2.12-1.98 (m, 3H), 1.74 (d, J = 10.4 Hz, 6 H). MS m/z 426.2 (M + 1)⁺. | 0.058 | 0.046 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-192 | 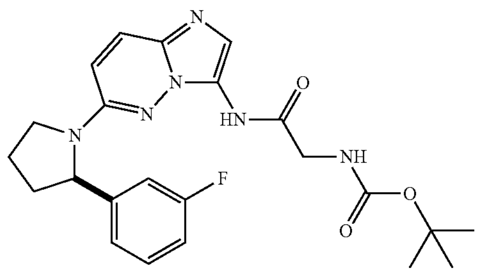 [SMILES: CC(C)(C)OC(=O)NCC(=O)Nc1cnc2ccc(N3CCC[C@@H]3c3cccc(F)c3)nn12] | MS m/z 455.20 (M + 1)+. | 0.124 | 0.127 | >10 |
| X-193 | 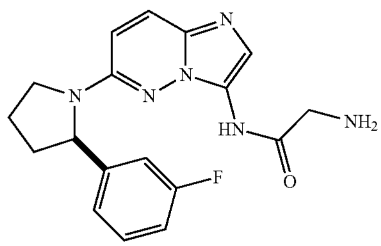 [SMILES: NCC(=O)Nc1cnc2ccc(N3CCC[C@@H]3c3cccc(F)c3)nn12] | MS m/z 355.10 (M + 1)+. | 0.147 | 0.118 | >10 |
| X-200 | 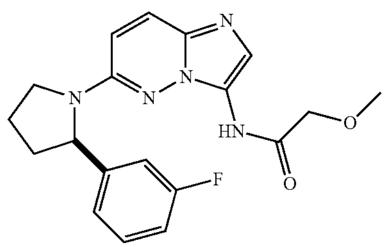 [SMILES: COCC(=O)Nc1cnc2ccc(N3CCC[C@@H]3c3cccc(F)c3)nn12] | ¹H NMR (400 MHz, CDCl₃) δ 8.93 (s, 1H), 7.89 (s, 1H), 7.70 (d, J = 8 Hz, 1H), 7.31-7.24 (m, 2H), 7.01 (d, J = 7.6 Hz, 1H), 6.51 (d, J = 9.6 Hz, 1H), 5.06 (dd, J = 2.8, 8 Hz, 1H), 4.10 (dd, J = 15.2, 22.6 Hz, 2H), 3.96-3.89 (m, 1H), 3.74-3.66 (m, 1H), 5.30 (s, 1H), 3.54 (s, 3H), 2.54-2.43 (m, 1H), 2.20-2.06 (m, 2H), 2.06-1.97 (m, 1H). MS m/z 370.2 (M + 1)+. | 0.071 | 0.023 | >8.83 |
| X-201 | 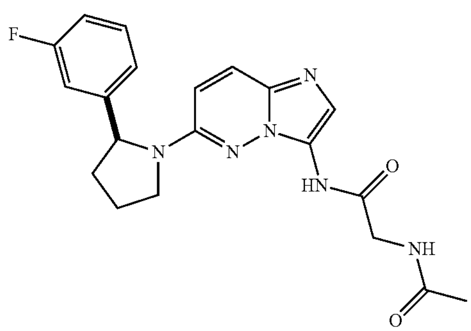 [SMILES: CC(=O)NCC(=O)Nc1cnc2ccc(N3CCC[C@H]3c3cccc(F)c3)nn12] | MS m/z 397.20 (M + 1)+. | 0.175 | 0.392 | >10 |
| X-204 | 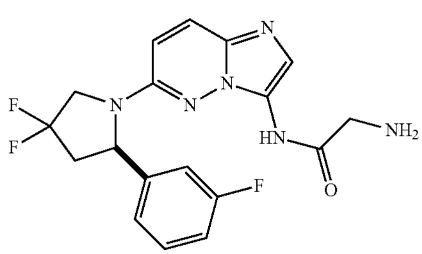 [SMILES: NCC(=O)Nc1cnc2ccc(N3CC(F)(F)C[C@@H]3c3cccc(F)c3)nn12] | MS m/z 391.1 (M + 1)+. | 0.036 | 0.028 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-209 | 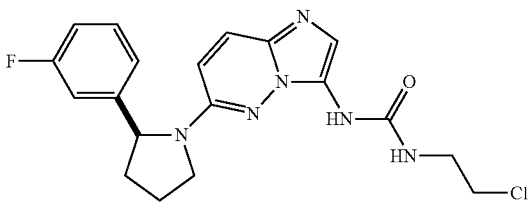 [SMILES: O=C(NCCCl)Nc1cnc2ccc(N3CCC[C@H]3c3cccc(F)c3)nn12] | MS m/z 403.10 (M + 1)+. | 0.149 | 0.252 | >10 |
| X-226 | 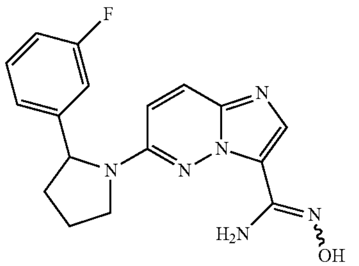 [SMILES: NC(=NO)c1cnc2ccc(N3CCCC3c3cccc(F)c3)nn12] | 1H NMR (400 MHz, DMSO-d6) δ 9.66 (s, 1H), 7.89 (d, J = 10.0 Hz, 1H), 7.67 (s, 1H), 7.46-7.41 (m, 1H), 7.19-7.10 (m, 3H), 6.78 (s, 1H), 6.02 (s, 2H), 5.17 (bd, J = 8.0 Hz, 1H), 4.00-3.98 (m, 1H), 3.67 (q, J = 8.4 Hz, 1H), 2.52-2.48 (m, 1H), 2.10-2.08 (m, 2H), 1.93-1.90 (m, 1H). MS m/z 341.1 (M + 1)+. | 0.192 | 0.165 | >10 |
| X-227 | 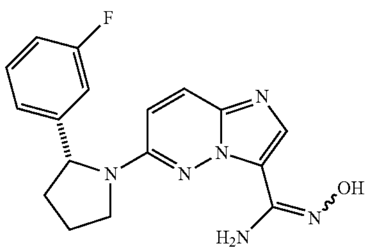 [SMILES: NC(=NO)c1cnc2ccc(N3CCC[C@@H]3c3cccc(F)c3)nn12] | 1H NMR (400 MHz, DMSO-d6) δ 9.66 (s, 1H), 7.89 (d, J = 10.0 Hz, 1H), 7.67 (s, 1H), 7.46-7.41 (m, 1H), 7.19-7.10 (m, 3H), 6.78 (s, 1H), 6.02 (s, 2H), 5.17 (bd, J = 8.0 Hz, 1H), 4.00-3.98 (m, 1H), 3.67 (q, J = 8.4 Hz, 1H), 2.52-2.48 (m, 1H), 2.10-2.08 (m, 2H), 1.93-1.90 (m, 1H). MS m/z 341.1 (M + 1)+. | 0.049 | 0.044 | >10 |
| X-228 | 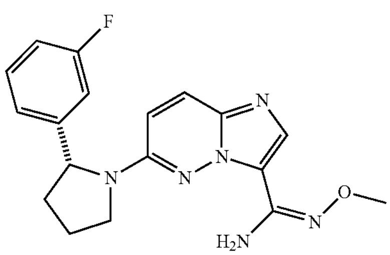 [SMILES: CO/N=C(/N)c1cnc2ccc(N3CCC[C@@H]3c3cccc(F)c3)nn12] | MS m/z 355.1 (M + 1)+. | 0.099 | 0.132 | >10 |
| X-229 | 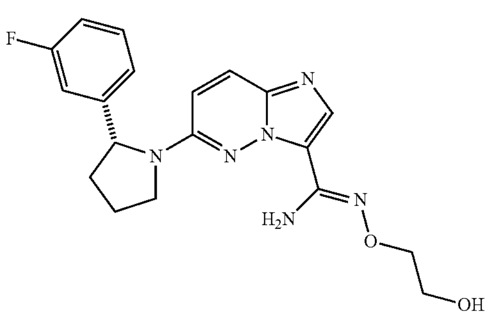 [SMILES: N/C(=N\OCCO)c1cnc2ccc(N3CCC[C@@H]3c3cccc(F)c3)nn12] | 1H NMR (400 MHz,CDCl3) δ 7.79 (s, 1H), 7.62 (d, J = 10.0 Hz, 1H), 7.24 (q, J = 8.0 Hz, 1H), 6.94-6.81 (m, 3H), 6.48 (bd, J = 9.6 Hz, 1H), 5.75 (s, 2H), 4.93 (bd, J = 8.0 Hz, 1H), 4.10 (bs, 2H), 3.85 (bs, 2H), 3.83-3.79 (m, 1H), 3.68-3.59 (m, 1H), 2.45-2.40 (m, 1H), 2.05-1.93 (m, 3H). MS m/z 385.1 (M + 1)+. | 0.106 | 0.331 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-233 | 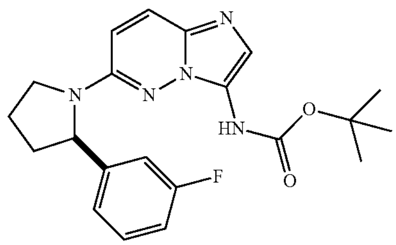 [SMILES: CC(C)(C)OC(=O)Nc1cnc2ccc(N3CCC[C@@H]3c3cccc(F)c3)nn12] | MS m/z 398.20 (M + 1)+. | 0.15 | 0.379 | >10 |
| X-234 | 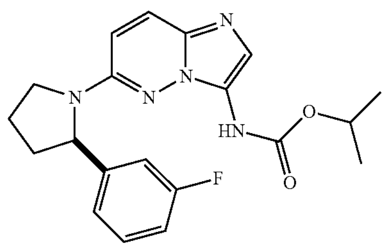 [SMILES: CC(C)OC(=O)Nc1cnc2ccc(N3CCC[C@@H]3c3cccc(F)c3)nn12] | MS m/z 384.10 (M + 1)+. | 0.395 | 0.449 | >10 |
| X-235 | 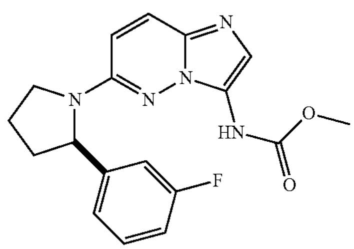 [SMILES: COC(=O)Nc1cnc2ccc(N3CCC[C@@H]3c3cccc(F)c3)nn12] | MS m/z 356.10 (M + 1)+. | 0.143 | 0.586 | >10 |
| X-236 | 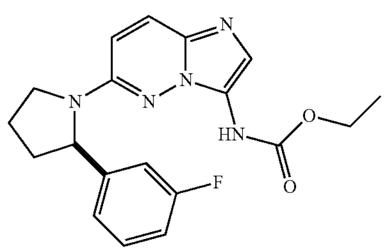 | $^1$H NMR (400 MHz, CDCl$_3$) δ 7.64 ( br s, 1H), 7.52 (d, J = 9.6 Hz, 1H), 7.33-7.26 (m, 1H), 7.01 (d, J = 7.6 Hz, 1H), 6.51 (d, J = 7.6 Hz, 1H), 6.97-6.88 (m, 2 H), 6.31 (d, J = 10 Hz, 1H), 4.97 (dd, J = 3.2, 8.2 Hz, 1 H), 4.30 (q, J = 7.2 Hz, 2H), 3.93-3.85 (m, 1H), 3.74-3.65 (m, 1H), 2.54-2.42 (m, 1H), 2.15-1.97 (m, 3 H), 1.37 (t, J = 7.2 Hz, 3H). MS m/z 370.10 (M + 1)+. | 0.295 | 0.545 | >10 |
| X-237 | 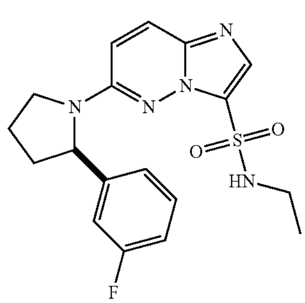 [SMILES: CCNS(=O)(=O)c1cnc2ccc(N3CCC[C@@H]3c3cccc(F)c3)nn12] | MS m/z 390.1 (M + 1)+. | 0.839 | 3.32 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-238 | 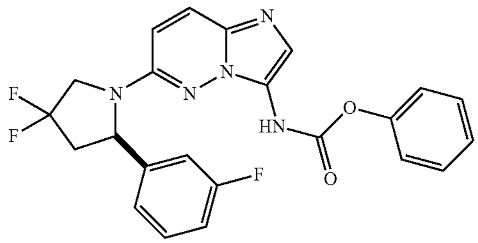 [SMILES: O=C(Nc1cnc2ccc(N3CC(F)(F)C[C@@H]3c3cccc(F)c3)nn12)Oc1ccccc1] | $^1$H NMR (400 MHz, MeOD-d$_4$) δ 7.55 (d, J = 10 Hz, 1 H), 7.41 (s, 1H), 7.37-7.33 (m, 2H), 7.28 (q, J = 8.0 Hz, 1H), 7.20-7.14 (m, 3H), 7.10 (d, J = 7.6 Hz, 1H), 7.04 (d, J = 10 Hz, 1H), 6.93 (dt, J = 8.4, 2.0 Hz, 1H), 6.55 (d, J = 10 Hz, 1H), 5.33 (dd, J = 8.8, 4.8 Hz, 1H), 4.28-4.11 (m, 2H), 3.09-2.96 (m, 1 H), 2.46 (dt, J = 12.8, 4.8, 1 H). MS m/z 454.10 (M + 1)$^+$. | 0.361 | 0.445 | >10 |
| X-239 | 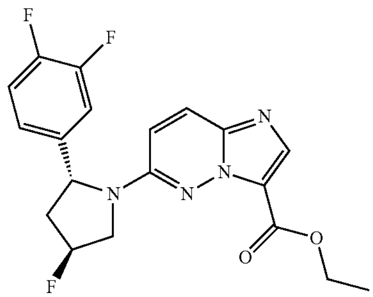 [SMILES: CCOC(=O)c1cnc2ccc(N3C[C@@H](F)C[C@@H]3c3ccc(F)c(F)c3)nn12] | MS m/z 391.10 (M + 1)$^+$. | 0.178 | 0.194 | >10 |
| X-240 | 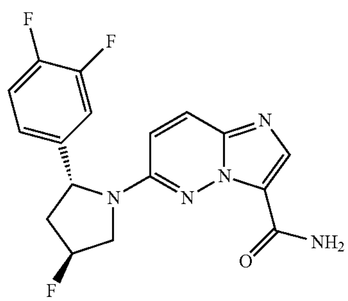 [SMILES: NC(=O)c1cnc2ccc(N3C[C@@H](F)C[C@@H]3c3ccc(F)c(F)c3)nn12] | $^1$H NMR (400 MHz, CDCl$_3$) δ 8.25 (s, 1H), 7.90 (br s, 1 H), 7.80 (d, J = 10 Hz, 1H), 7.21-7.13 (m, 1H), 7.10-6.99 (m, 2H), 6.64 (d, J = 10 Hz, 1H), 5.66 (br s, 1 H), 5.42 (d, J = 51.2 Hz, 1 H), 5.12 (dd, J = 6.8, 10 Hz, 1H), 4.22-4.16 (m, 1H), 4.15-4.06 (m, 1H), 2.89 (td, J = 6.8, 14.8 Hz, 1H), 2.11 (dddd, J = 3.6, 10.0, 14.0, 40.8 Hz, 1H). MS m/z 362.10 (M + 1)$^+$. | 0.130 | 0.198 | >10 |
| X-241 | 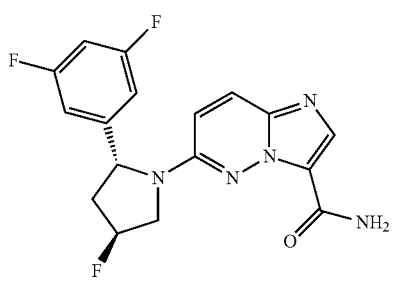 [SMILES: NC(=O)c1cnc2ccc(N3C[C@@H](F)C[C@@H]3c3cc(F)cc(F)c3)nn12] | $^1$H NMR (400 MHz, CDCl$_3$) δ 8.25 (s, 1H), 7.85 (br s, 1 H), 7.84 (d, J = 10 Hz, 1H), 6.84-6.78 (m, 1H), 6.78-6.72 (m, 1H), 6.67 (d, J = 9.6 Hz, 1H), 5.55 (br s, 1 H), 5.42 (d, J = 52.0 Hz, 1 H), 5.13 (dd, J = 6.8, 10.0 Hz, 1H), 4.20-4.16 (m, 1 H), 4.12-4.04 (m, 1H), 2.96-2.84 (m, 1H), 2.13 (dddd, J = 3.6, 10.0, 14.0, 40.8 Hz, 1H). MS m/z 362.10 (M + 1)$^+$. | 0.008 | 0.003 | 6.7 |
| X-242 | 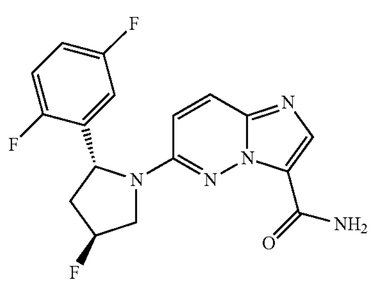 [SMILES: NC(=O)c1cnc2ccc(N3C[C@@H](F)C[C@@H]3c3cc(F)ccc3F)nn12] | $^1$H NMR (400 MHz, CDCl$_3$) δ 8.24 (s, 1H), 7.97 (br s, 1 H), 7.84 (d, J = 10 Hz, 1H), 7.08 (td, J = 4.4, 9.2 Hz, 1 H), 7.00-6.93 (m, 1H), 6.91-6.85 (m, 1H), 6.69 (d, J = 10 Hz, 1H), 5.55 (br s, 1H), 5.45 (d, J = 50.8 Hz, 1H), 5.43 (dd, J = 7.2, 9.2 Hz, 1H), 4.20-4.15 (m, 1 H), 4.10-4.05 (m, 1H), 2.99 (td, J = 7.2, 15.2 Hz, 1 H), 2.16 (dddd, J = 3.6, 9.6, 13.6, 40.4 Hz, 1H). MS m/z 362.10 (M + 1)$^+$. | 0.001 | 0.0005 | 2.45 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-243 | 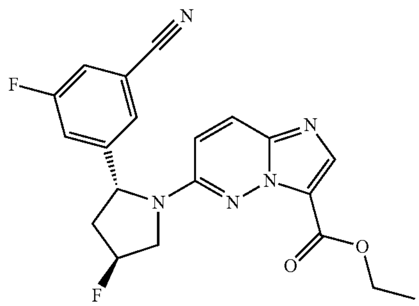 [SMILES: CCOC(=O)c1cnc2ccc(N3C[C@@H](F)C[C@@H]3c3cc(F)cc(C#N)c3)nn12] | $^1$H NMR (400 MHz, CDCl$_3$) δ 8.12 (s, 1H), 7.75 (d, J = 9.6 Hz, 1H), 7.59 (s, 1H), 7.42-7.37 (m, 1H), 7.25-7.21 (m, 1H), 6.60 (d, J = 9.6 Hz, 1H), 5.44 (d, J = 52 Hz, 1H), 5.28 (dd, J = 6.8, 9.6 Hz, 1H), 4.45-4.36 (m, 2H), 4.28-4.08 (m, 2H), 2.95-2.82 (m, 1H), 2.16 (dddd, J = 3.6, 10, 14, 40 Hz, 1H), 1.40 (t, J = 7.2 Hz, 3H). MS m/z 398.10 (M + 1)$^+$. | 0.002 | 0.002 | >10 |
| X-244 | 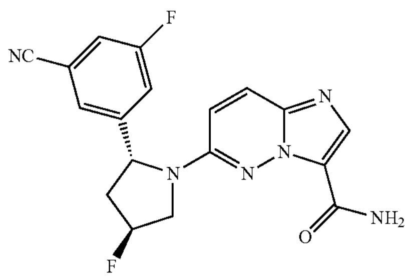 [SMILES: N#Cc1cc(F)cc([C@H]2C[C@H](F)CN2c2ccc3ncc(C(N)=O)n3n2)c1] | $^1$H NMR (400 MHz, CDCl$_3$) δ 8.26 (s, 1H), 7.88 (d, J = 10 Hz, 1H), 7.70 (br s, 1H), 7.40 (s, 1H), 7.33-7.29 (m, 1H), 7.26-7.22 (m, 1H), 6.68 (d, J = 10 Hz, 1H), 5.54 (br s, 1H), 5.44 (d, J = 52.4 Hz, 1H), 5.20 (dd, J = 6.8, 10.4 Hz, 1H), 4.26-4.10 (m, 2H), 2.95 (td, J = 6.8, 14.8 Hz, 1H), 2.11 (dddd, J = 3.6, 10, 14, 40.8 Hz, 1H). MS m/z 369.10 (M + 1)$^+$. | 0.043 | 0.061 | >10 |
| X-245 | 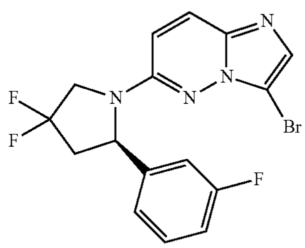 [SMILES: Fc1cccc([C@H]2CC(F)(F)CN2c2ccc3ncc(Br)n3n2)c1] | $^1$H NMR (400 MHz, CD$_3$OD) δ 8.00 (s, 1H), 7.96 (d, J = 10 Hz, 1H), 7.38 (q, J = 6.8 Hz, 1H), 7.24-7.15 (m, 3H), 7.02 (dt, J = 8.4, 2.4 Hz, 1H), 5.46 (dd, J = 8.8, 8.8 Hz, 1H), 4.41 (q, J = 12 Hz, 1H), 4.27 (q, J = 12 Hz, 1H), 3.22-3.10 (m, 1H), 2.58 (dq, J = 13.2, 4.8 Hz, 1H). MS m/z 397.1, 399.1 (M + 1)$^+$. | 0.032 | 0.044 | >10 |
| X-246 | 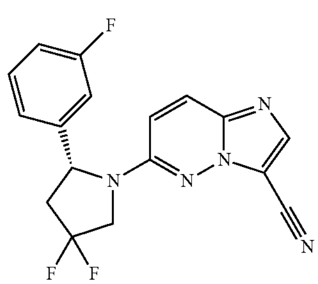 [SMILES: N#Cc1cnc2ccc(N3CC(F)(F)C[C@@H]3c3cccc(F)c3)nn12] | $^1$H NMR (400 MHz, DMSO) δ 8.06 (d, J = 10 Hz, 1H), 7.96 (s, 1H), 7.70 (s, 1H), 7.59 (s, 1H), 7.39 (dt, J = 6.0, 8.0 Hz, 1H), 7.22-7.19 (m, 2H), 7.10 (dt, J = 2.0, 8.0 Hz, 1H), 6.92 (d, J = 10 Hz, 1H), 5.44 (dd, J = 4.5, 9.0 Hz, 1H), 4.48 (q, J = 12.0 Hz, 1H), 4.23 (q, J = 12 Hz, 1H), 3.23-3.09 (m, 1H), 2.50-2.42 (m, 1H). MS m/z 344.1 (M + 1)$^+$. | 0.037 | 0.056 | >10 |
| X-247 | 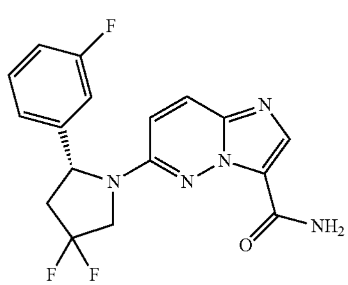 [SMILES: NC(=O)c1cnc2ccc(N3CC(F)(F)C[C@@H]3c3cccc(F)c3)nn12] | $^1$H NMR (400 MHz, CD$_3$OD) δ 7.96 (s, 1H), 7.79 (d, J = 10 Hz, 1H), 7.29 (q, J = 8.0 Hz, 1H), 7.08 (d, J = 8.0 Hz, 1H), 7.02 (d, J = 9.6 Hz, 1H), 6.95-6.89 (m, 2H), 5.31 (dd, J = 8.8, 8.8 Hz, 1H), 4.30 (q, J = 12 Hz, 1H), 4.12 (q, J = 12 Hz, 1H), 3.11-3.98 (m, 1H), 2.39 (dq, J = 13.2, 4.8 Hz, 1H). MS m/z 362.1 (M + 1)$^+$. | 0.018 | 0.034 | >10 |

TABLE 1-continued

| Compound No. | STRUCTURE | NMR and LC/MS | BaF3/TRKA-NGF (uM) | Ba/F3 Tel-TrkA (uM) | BAF3/WT (uM) |
|---|---|---|---|---|---|
| X-248 | 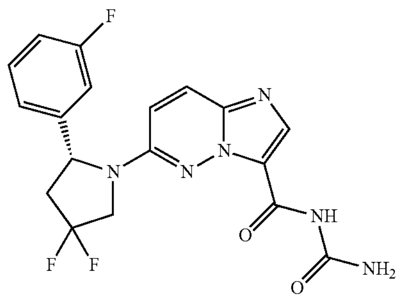 [SMILES: NC(=O)NC(=O)c1cnc2ccc(N3CC(F)(F)C[C@@H]3c3cccc(F)c3)nn12] | $^1$H NMR (400 MHz, CD$_3$OD) δ 8.49 (bs, 1H), 7.92 (bs, 1H), 7.36 (dd, J = 7.8, 6.1 Hz, 1H), 7.22 (d, J = 7.8 Hz, 1H), 7.17 (d, J = 9.8 Hz, 1H), 7.0 (m, 2H), 5.53 (dd, J = 4.7, 4.2 Hz, 1 H), 4.44 (q, J = 11.7 Hz, 1 H), 4.27 (q, J = 13.1 Hz, 1 H), 3.19 (m, 1H), 2.55 (m, 1H). MS m/z 405.1 (M + 1)$^+$. | 0.020 | 0.019 | >10 |
| X-249 | 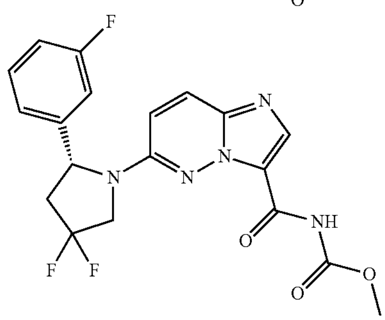 | $^1$H NMR (400 MHz, DMSO-d$_6$) δ 10.84 (bs, 1H), 8.19 (s, 1H), 8.10 (d, J = 10.0 Hz, 1H), 7.38 (m, 1H), 7.22 (d, J = 10.0 Hz, 1H), 7.18 (d, J = 7.9 Hz, 1H), 7.10 (dt, J = 8.4, 2.2 Hz, 1 H), 6.91 (bd, J = 9.9 Hz, 1 H), 5.53 (dd, J = 5.5, 3.5 Hz, 1H), 4.41 (m, 1H), 4.22 (m, 1H), 3.7 (s, 3H), 3.23 (m, 1H), 2.56 (m, 1H). MS m/z 420.1 (M + 1)$^+$. | 0.019 | 0.018 | >10 |
| X-250 | 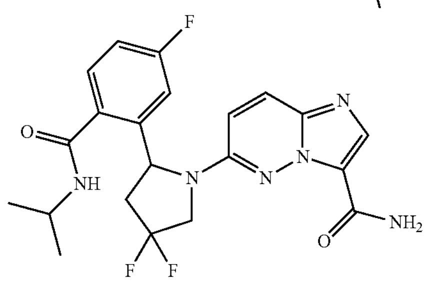 | NMR (400 MHz, MeOD) δ 8.23 (s, 1H), 7.99 (d, J = 9.8 Hz, 1H), 7.52 (dd, J = 5.6, 8.5 Hz, 1H), 7.18 (d, J = 9.8 Hz, 2H), 7.11 (td, J = 2.6, 8.3 Hz, 1H), 5.85 (dd, J = 5.0, 9.1 Hz, 1H), 4.42 (q, J = 11.6 Hz, 1H), 4.24 (q, J = 12.8 Hz, 1H), 4.17 (sept, J = 6.6 Hz, 1H), 3.21-3.07 (m, 1H), 2.69-2.58 (m, 1H), 1.26 (d, J = 6.6 Hz, 3H), 1.23 (d, J = 6.6 Hz, 3H). MS m/z 447.1 (M + H)+. | 0.059 | 0.064 | >10 |

Assays

Preparation of Compound Dilutions

Test compounds were dissolved in DMSO (10 mM) and transferred into 1.4 mL flat bottom or V-shaped Matrix tubes carrying a unique 2D matrix chip by individual compound hubs. The numbers of these chips were distinctively linked to the individual compound identification numbers. The stock solutions were stored at −20° C. if not used immediately. For the test procedure the vials were defrosted and identified by a scanner whereby a working sheet is generated that guides the subsequent working steps.

Compound dilutions were made in 384 well plates. This format enabled the assay of maximally 28 individual test compounds at 11 concentrations (single points) including 2 reference compounds. The dilution protocol included the production of pre-dilution plates, master plates and assay plates: Compound plates: 30 μL of individual compound (10 mM) DMSO solution including reference compound were transferred into columns 1 and 13 of a 384 well plate. 20 μL of DMSO were added to the rest of the wells and the compounds were serially diluted (1:3) by transferring 10 μL from a well in column 1 or 13 to the next well in column 2 or 14 respectively and successively with the help of a Minitrack robot.

Assay plates: Identical assay plates were then prepared by adding 50 nL each of compound dilutions of the compound plates into 384-well "assay plates". In the following the compounds were mixed with 50 μL of assays components (cells or enzyme) and tested for their inhibitory activity.

Compounds of Formula (I) were assayed to measure their capacity to inhibit TrkA, TrkB, and/or TrkC protein kinases. Other compounds of Formula (I) were assayed to measure their capacity to inhibit a Ba/F3 kinase panel, including but not limited to Ros, KDR, FMS, c-FMS, FLT3, c-Kit, JAK2, PDGFR, Lck, TrkA, TrkB, TrkC, IGF-1R and ALK protein kinases.

Ba/F3 Cell Proliferation Assay Panel

Compounds were tested for their ability to inhibit the proliferation of wt Ba/F3 cells and Ba/F3 cells transformed with constitutively expressed luciferase reporter and BCR-ABL or Tel-FMS or other Tel fusion kinases (EGFR, JAK2, ALK, BMX, FGFR3, FGFR4, FGR2, FLT1, FLT3, IGF1R, INSR, KDR, KIT, LCK, LYN, MEK, MET, PDGFRα, PDGFRβ, RET, RON, ROS, SRC, SYK, TIE and TYRO) or BRafV600E. Parental Ba/F3 cells were maintained in media containing recombinant mouse IL3 and the kinase transformed Ba/F3 cells were maintained in media without IL-3. 7.5 nl of compounds were spotted to each well of 1536-well assay plates by Liquid handling System Echo 555 (Labcyte). 700 cells were then plated into each well of the assay plates in 7 uL culture media per well and compounds were tested at 0.17 nM to 10 uM in 3-fold serial dilutions. The cells were then incubated for 48 hours at 37° C. 3 uL of Bright-Glo® (Promega) was added to each well and the plates were read using ViewLux (PerkinElmer).

Inhibition of Cellular TrkA, TrkB and TrkC Dependent Proliferation

Compounds of Formula (I) were assayed to measure their capacity to selectively inhibit cell proliferation of Ba/F3 cells expressing activated TrkA, TrkB or TrkC through fusion to the dimerization domain of Tel (ETV6) transcription factor as well as Ba/F3 cells co-expressing full length rTrkA and mNGF compared with parental BaF3 cells.

The cell line used is the luciferase expressing Ba/F3 murine hematopoietic progenitor cell line transformed with human Tel-TrkA, Tel-TrkB or Tel-TrkC cDNAs (Ba/F3 EN A/B/C). These cells maintained in RPMI/10% fetal bovine serum (RPMI/FCS) supplemented with penicillin 50 mg/mL, streptomycin 50 mg/mL and L-glutamine 200 mM. Untransformed Ba/F3 cells were similarly maintained with the addition 5 ng/ml of murine recombinant IL3. 50 µl of a Ba/F3 or Ba/F3 EN A/B/C cell suspension were plated in Greiner 384 well microplates (white)) at a density of 2000 cells per well. 50 nl of serially diluted test compound (10-0.0001 mM in DMSO solution) is added to each well. The cells were incubated for 48 hours at 37° C., 5% $CO_2$. 25 µl of Bright Glo® (Promega) luciferase substrate is added to each well. The emited luminiscence is quantified using ViewLux (PerkinElmer). $IC_{50}$ values were calculated by linear regression analysis of the percentage inhibition of each compound at 11 concentrations.

Certain Assay Results

Various compounds of Formula (I) in free form or in pharmaceutically acceptable salt form, exhibit pharmacological properties, for example, as indicated by the in vitro and in vivo tests described in this application. The $IC_{50}$ value in those experiments is given as that concentration of the test compound in question that results in a cell count that is 50% lower than that obtained using the control without inhibitor. In certain examples compounds of Formula (I) have $IC_{50}$ values from 0.1 nM to 100 µM. In other examples, compounds of Formula (I) have $IC_{50}$ values from 0.0001 µM to 50 µM. In other examples, compounds of Formula (I) have $IC_{50}$ values from 0.0001 µM to 25 µM. In other examples, compounds of Formula (I) have $IC_{50}$ values from 0.0001 µM to 20 µM. In other examples, compounds of Formula (I) have $IC_{50}$ values from 0.0001 µM to 15 µM. In other examples, compounds of Formula (I) have $IC_{50}$ values from 0.0001 µM to 10 µM. In other examples, compounds of Formula (I) have $IC_{50}$ values from 0.0001 µM to 5 µM. In other examples, compounds of Formula (I) have $IC_{50}$ values from 0.0001 µM to 2 µM. In other examples, compounds of Formula (I) have $IC_{50}$ values from 0.0001 µM to 1 µM. In other examples, compounds of Formula (I) have $IC_{50}$ values from 0.0001 µM to 0.8 µM. In other examples, compounds of Formula (I) have $IC_{50}$ values from 0.0001 µM to 0.6 µM. In other examples, compounds of Formula (I) have $IC_{50}$ values from 0.0001 µM to 0.4 µM. In other examples, compounds of Formula (I) have $IC_{50}$ values from 0.0001 µM to 0.2 µM. In other examples, compounds of Formula (I) have $IC_{50}$ values from 0.0001 µM to 0.1 µM. In other examples, compounds of Formula (I) have $IC_{50}$ values from 0.0001 µM to 0.08 µM. In other examples, compounds of Formula (I) have $IC_{50}$ values from 0.0001 µM to 0.06 µM. In other examples, compounds of Formula (I) have $IC_{50}$ values from 0.0001 µM to 0.04 µM. In other examples, compounds of Formula (I) have $IC_{50}$ values from 0.0001 µM to 0.02 µM. In other examples, compounds of Formula (I) have $IC_{50}$ values from 0.0001 µM to 0.01 µM.

In some examples, compounds of Formula (I) have $IC_{50}$ values from 0.01 µM to 5 µM. In other examples, compounds of Formula (I) have $IC_{50}$ values from 0.01 µM to 1 µM. In yet other examples, compounds of Formula (I) have $IC_{50}$ values of less than 1 nM. In certain embodiments, compounds of Formula (I) exhibit a percentage inhibition of greater than 50%, or in other embodiments compounds of Formula (I) exhibit a percentage inhibition greater than about 70%.

WO2010/033941 describes a class of TRK inhibitors which are imidazo[1,2-b]pyridazine compounds bearing an aryl or heteroaryl-substituted heterocyclic group at the 6-position and a group having the formula $NR_aC(=O)R_b$ at the 3-position. The antagonist activity of these TRK inhibitors was evaluated using a TrkA ELISA assay, wherein $IC_{50}$ values ranging between 1 µM and 2 nM were reported. However, pharmacokinetic properties, such as clearance, half life and bioavailability, of these TRK inhibitors were not presented.

The compounds of Formula (I) provided herein, wherein $R^B$ is $—C(O)NH_2$, inhibit TRK and exhibit unexpected and improved pharmacokinetic properties, such as in-vivo clearance, oral exposure, bioavailability and half life. Significant improvements in the pharmacokinetic profiles of such compounds of the Formula (I) were obtained and were expressed quantitatively in terms of reduced clearance (Cl), increases in the in-vivo half-life (T½), increases of the maximum concentration (Cmax), increases in oral exposure (increases in area under the dose response curve (AUC)) and increases in bioavailability (% F). By way of example, in Table 2 the $IC_{50}$, Clearance, Cmax and AUC values for compound X-242 (a compound of Formula (I) wherein the $R^B$ is $—C(O)NH_2$) are compared to the $IC_{50}$, Cmax and AUC values for compound #3 of WO2010/033941, which has the $—NHC(O)CH_3$ group at the 3-position of the imidazo[1,2-b]pyridazine. Compound X-242 was found to have significantly lower $IC_{50}$ than compound #3 of WO2010/033941. These $IC_{50}$ values were obtained using the assay described herein. In addition, compound X-242 was found to have significant and unexpected increases in AUC and Cmax values.

TABLE 2

| Example | STRUCTURE | BaF3/TRKA-NGF (uM) | Ba/F3_Tel-Trk-A (uM) | Rat PK PO 10 mg/kg, IV 3 mg/Kg |
|---|---|---|---|---|
| # 3 (WO2010/033941 A1) | 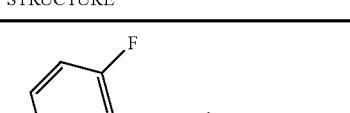 | 0.029 | 0.018 | MC/Tween 80 suspensionPO AUC: 87 Hr.nM Cmax: 61 nM F = 1.5% IVparameters T1/2 = 0.2 h Vss: 1 L/kg Cl: 79.17 mL/min/kg |

TABLE 2-continued

| Example | STRUCTURE | BaF3/TRKA-NGF (uM) | Ba/F3_Te1-Trk-A (uM) | Rat PK PO 10 mg/kg, IV 3 mg/Kg) |
|---|---|---|---|---|
| X-242 | 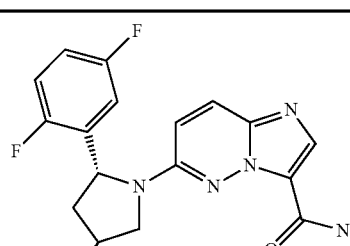 | 0.001 | 0.0005 | MC/Tween 80 suspensionPO AUC: 7090 Hr.nM Cmax: 1734 nM F = 28.2% IVparameters T1/2 = 1.24 h Vss: 1.58 L/kg Cl: 18.4 mL/min/kg |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I):

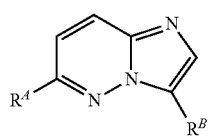
Formula (I)

wherein:

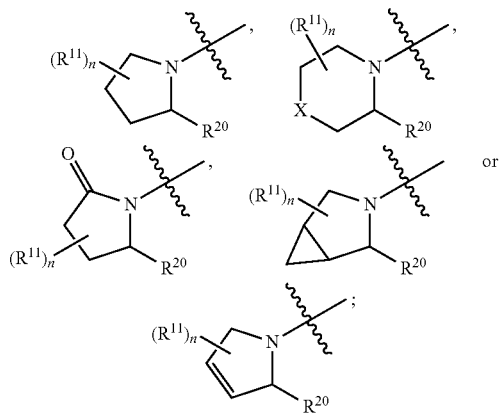

X is $C(R^3)_2$, O or $NR^3$;

$R^B$ is —CN, —C(O)NH$_2$, -L$^1$R$^2$, -L$^2$R$^7$, —C(O)NHOR$^3$, —C(O)NR$^3$OR$^8$, —C(O)NHNH$_2$, —C(O)NR$^3$C(O)OR$^3$, —C(O)NR$^3$C(O)NH$_2$, —NR$^3$C(O)NR$^3$R$^5$,

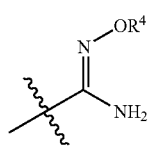

or —SO$_2$NR$^3$R$^3$;

L$^1$ is —C(O)NR$^3$—, —C(O)NR$^3$(CR$^4$R$^4$)$_q$—, —C(O)—, —C(O)NR$^3$O(CR$^4$R$^4$)$_q$—, —C(O)O—, —C(O)—C$_1$-C$_8$alkylene or —C(O)—C$_2$-C$_8$alkenylene;

L$^2$ is —NR$^3$C(O)(CR$^4$R$^4$)$_q$—;

each L$^3$ is independently selected from a C$_1$-C$_8$alkylene and a C$_1$-C$_8$alkylene substituted with 1 to 3 substituents independently selected from C$_1$-C$_6$alkyl;

R$^2$ is selected from R$^9$, —N(R$^3$)$_2$, C$_1$-C$_6$alkyl, phenyl, C$_{10}$aryl, C$_{14}$aryl, C$_3$-C$_8$cycloalkyl, 4-6 membered heterocycloalkyl containing 1 to 2 heteroatoms selected from N, O and S, a 5, 6, 9 or 10 membered heteroaryl containing 1 to 3 N heteroatoms and C$_1$-C$_8$alkyl substituted with 1 to 6 groups independently selected from halo, C$_1$-C$_4$alkyl, and —R$^6$, or R$^2$ is selected from phenyl, C$_{10}$aryl, C$_{14}$aryl, C$_3$-C$_8$cycloalkyl, 4-6 membered heterocycloalkyl containing 1 to 2 heteroatoms selected from N, O and S, and a 5, 6, 9 or 10 membered heteroaryl containing 1 to 3 N heteroatoms, each of which is substituted with 1 to 3 substituents independently selected from halo, C$_1$-C$_6$alkyl, C$_1$-C$_6$alkyl substituted with 1 to 4 hydroxyl groups, 4-6 membered heterocycloalkyl containing 1 to 2 heteroatoms selected from N, O and S, —CN, —R$^8$, —OR$^4$, —C(O)R$^4$, —C(O)OR$^4$, —C(O)L$^3$R$^6$, —S(O)$_2$R$^4$, and —S(O)$_2$NR$^4$R$^4$;

each R$^3$ is independently selected from H, C$_1$-C$_6$alkyl;

each R$^4$ is independently selected from H, C$_1$-C$_6$alkyl, and C$_1$-C$_6$alkyl substituted with 1 to 4 hydroxyl groups;

R$^5$ is C$_1$-C$_4$haloalkyl or —OR$^3$;

R$^6$ is selected from —OC(O)R$^4$, —NHC(O)OR$^4$, —NR$^3$R$^3$, —C(O)N(R$^3$R$^3$), —S(O)$_2$R$^4$, —S(O)$_2$NR$^4$R$^4$, —C(O)OR$^4$ and —OR$^4$;

R$^7$ is —OC(O)R$^{12}$—CN, —NHC(O)OR$^{12}$, —NHC(O)R$^{12}$ or —NR$^3$R$^3$;

R$^8$ is a 4-6 membered heterocycloalkyl containing 1 to 2 heteroatoms selected from N, O and S, or a 4-6 membered heterocycloalkyl containing 1 to 2 heteroatoms selected from N, O and S substituted with 1 to 4 substituents independently selected from halo, —OR$^4$, C$_1$-C$_6$alkyl and C$_1$-C$_6$haloalkyl;

R$^9$ is cyclohexyl having a C$_1$-C$_6$alkyl bridge,

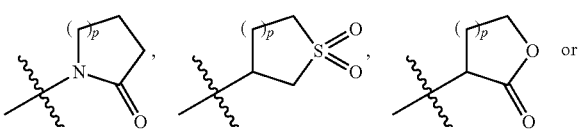

-continued

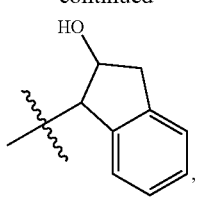, wherein each is optionally substituted with 1-3 substituents independently selected from halo, —CN, $C_1$-$C_6$alkyl, —$R^8$, and —$OR^3$;

each $R^{10}$ is independently selected from halo, $C_1$-$C_6$alkyl, $C_1$-$C_6$haloalkyl, —C=$NOR^3$, —CN, —$(CR^4R^4)_q$CN, —$NR^3R^3$, —C(O)$OR^4$, —C(O)$NR^3R^3$, —$(CR^4R^4)_q R^6$, —$NR^3$C(O)$NR^3R^3$, —$NR^3$S(O)$_2R^4$, —$NR^3$S(O)$_2$$NR^4R^4$, —S(O)$_2$$NR^4R^4$, —S(O)$_2R^4$, —$OR^4$, 4-6 membered heterocycloalkyl containing 1 to 2 heteroatoms selected from N, O and S and a 5 membered heteroaryl containing 1 to 4 N heteroatoms;

each $R^{11}$ is independently selected from halo, —$OR^3$, deuterium, $C_1$-$C_6$alkyl, hydroxyl substituted $C_1$-$C_6$alkyl, $C_1$-$C_6$halolkyl;

$R^{12}$ is H, $C_1$-$C_6$alkyl, phenyl or phenyl substituted with 1 to 3 groups independently selected from halo, $C_1$-$C_4$alkyl, and —$R^6$;

$R^{20}$ is selected from

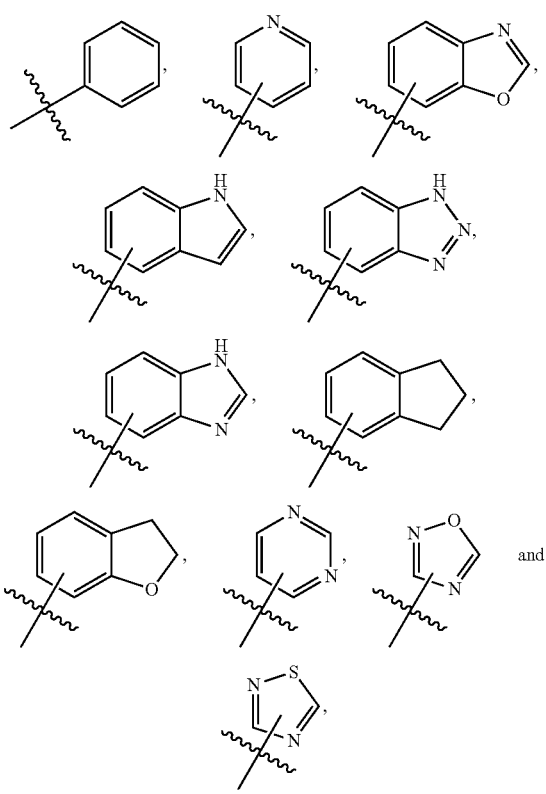

each of which is substituted with 1 to 3 substituents independently selected from $R^{10}$, or $R^{20}$ is selected from

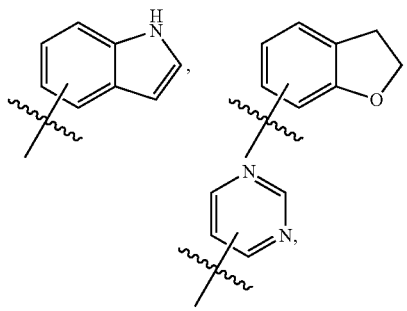

each of which is optionally substituted with 1 to 3 substituents independently selected from $R^{10}$;

n is 0, 1, 2, 3, 4, 5, 6 or 7;

p is 1 or 2 and q is 1, 2, 3, 4, 5 or 6, or a pharmaceutically acceptable salt thereof.

2. The compound of claim 1, wherein the compound of Formula (I) is a compound having the structure of Formula (I-a) or Formula (I-b):

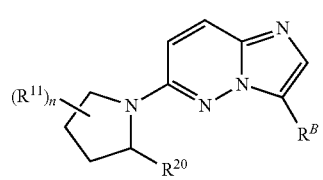

Formula (I-a)

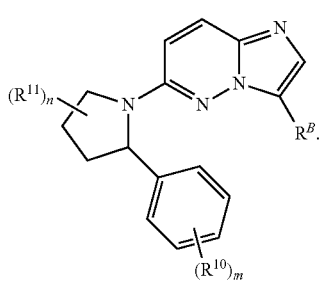

Formula (I-b)

wherein m is 1, 2 or 3.

3. The compound of claim 1, wherein the compound of Formula (I) is a compound having the structure of Formula (II-a) or Formula (II-b):

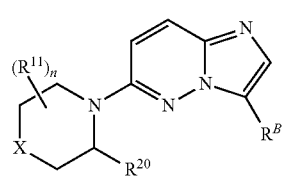

Formula (II-a)

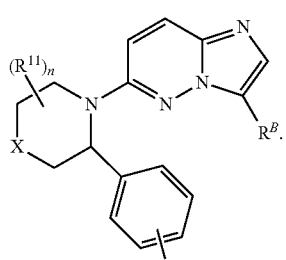

Formula (II-b)

wherein m is 1, 2 or 3.

4. The compound of claim 1, wherein the compound of Formula (I) is a compound having the structure of Formula (III-a) or of Formula (III-b):

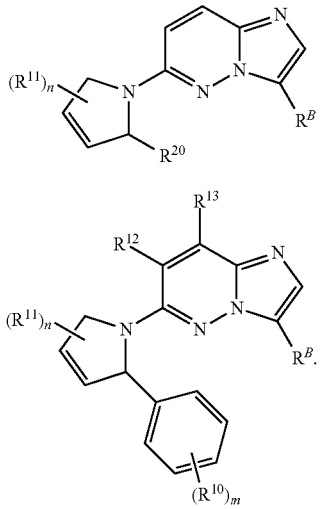

Formula (III-a)

Formula (III-b)

wherein m is 1, 2 or 3.

5. The compound of claim 1, wherein $R^B$ is —C(O)NH$_2$.

6. The compound of claim 1, wherein $R^B$ is -L$^1$R$^2$.

7. The compound of claim 6, wherein L$^1$ is —C(O)NR$^3$—, —C(O)NR$^3$(CR$^4$R$^4$)$_q$— or —C(O)NR$^3$O(CR$^4$R$^4$)$_q$—.

8. The compound of claim 6, wherein L$^1$ is —C(O)— or —C(O)O—.

9. The compound of claim 6, wherein L$^1$ is —C(O)—C$_1$-C$_8$alkylene or —C(O)—C$_2$-C$_8$alkenylene.

10. The compound of claim 6, wherein:
   R$^2$ is phenyl, cyclopropyl, cyclobutyl, cyclopentyl or cyclohexyl, or
   R$^2$ is phenyl, cyclopropyl, cyclobutyl, cyclopentyl or cyclohexyl), each of which is substituted with 1 to 3 substituents independently selected from halo, C$_1$-C$_6$alkyl, C$_1$-C$_6$alkyl substituted with 1 to 4 hydroxyl groups, 4-6 membered heterocycloalkyl containing 1 to 2 heteroatoms selected from N, O and S, —CN, —R$^8$, —OR$^4$, —C(O)R$^4$, —C(O)OR$^4$, —C(O)L$^3$R$^6$, —S(O)$_2$R$^4$, and —S(O)$_2$NR$^4$R$^4$.

11. The compound of claim 6, wherein:
   R$^2$ is tetrahydro-2H-pyranyl, tetrahydrofuranyl, piperidinyl, pyrrolidinyl, oxetanyl, morpholinyl, tetrahydro-2H-thiopyranyl, azetidinyl, piperazinyl, pyridyl, pyrazolyl, benzthiazolyl or pyrrolyl, or
   R$^2$ is tetrahydro-2H-pyranyl, tetrahydrofuranyl, piperidinyl, pyrrolidinyl, oxetanyl, morpholinyl, tetrahydro-2H-thiopyranyl, azetidinyl, piperazinyl, pyridyl, pyrazolyl, benzthiazolyl or pyrrolyl, each of which is substituted with 1 to 3 substituents independently selected from halo, C$_1$-C$_6$alkyl, C$_1$-C$_6$alkyl substituted with 1 to 4 hydroxyl groups, 4-6 membered heterocycloalkyl containing 1 to 2 heteroatoms selected from N, O and S, —CN, —R$^8$, —OR$^4$, —C(O)R$^4$, —C(O)OR$^4$, —C(O)L$^3$R$^6$, —S(O)$_2$R$^4$, and —S(O)$_2$NR$^4$R$^4$.

12. The compound of claim 1, wherein $R^B$ is —C(O)NHOR$^3$, —C(O)NR$^3$OR$^8$, —C(O)NHNH$_2$, —NR$^3$C(O)NR$^3$R$^5$ or

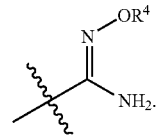

13. The compound of claim 12, wherein R$^8$ is pyrrolidinyl, tetrahydro-2H-pyranyl, morpholinyl or piperidinyl, or wherein R$^8$ is pyrrolidinyl, tetrahydro-2H-pyranyl, morpholinyl or piperidinyl each of which is substituted with 1 to 2 —OR$^4$ groups.

14. The compound of claim 6, wherein R$^2$ is R$^9$, —N(R$^3$)$_2$, methyl, ethyl, propyl, isopropyl, isobutene, t-butyl, or C$_1$-C$_8$alkyl substituted with 1 to 6 groups independently selected from halo, C$_1$-C$_4$alkyl, and —R$^6$.

15. The compound of claim 14, wherein R$^9$ is cyclohexyl having a C$_1$alkyl bridge,

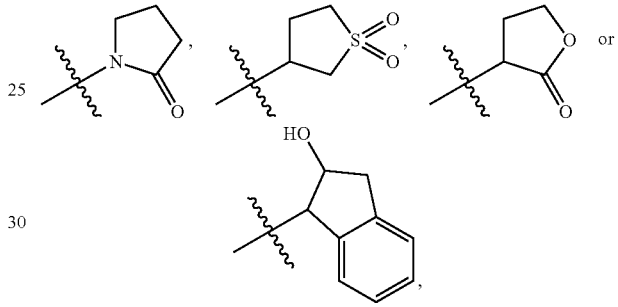

wherein each is optionally substituted with 1-3 substituents independently selected from C$_1$-C$_6$alkyl.

16. The compound of claim 1, wherein $R^B$ is -L$^2$R$^7$.

17. The compound of claim 1, wherein $R^B$ is —CN and —SO$_2$NR$^3$R$^3$.

18. The compound of claim 2, wherein $R^B$ is —C(O)NH$_2$.

19. The compound of claim 18, wherein each R$^{10}$ is independently selected from F, Cl, methyl, —CF$_3$, —C=NOR$^3$, —CN, —(CR$^4$R$^4$)$_q$CN, —NR$^3$R$^3$, —C(O)OR$^4$, —C(O)NR$^3$R$^3$, —(CR$^4$R$^4$)$_q$R$^6$, —NR$^3$C(O)NR$^3$R$^3$, —NR$^3$S(O)$_2$R$^4$, —NR$^3$S(O)$_2$NR$^4$R$^4$, —S(O)$_2$NR$^4$R$^4$, —S(O)$_2$R$^4$, —OR$^4$, morpholinyl and tetrazolyl.

20. The compound of claim 19, wherein R$^6$ is selected from —OC(O)R$^4$, —NHC(O)OR$^4$, —NR$^3$R$^3$, —C(O)N(R$^3$R$^3$), —S(O)$_2$R$^4$, —S(O)$_2$NR$^4$R$^4$, —C(O)OR$^4$ and —OR$^4$, and wherein each R$^4$ is independently selected from H, methyl, ethyl, propyl, isopropyl, t-butyl or a C$_1$-C$_6$alkyl substituted with 1 to 4 hydroxyl groups.

21. The compound of claim 20, wherein each R$^{11}$ is independently selected from F, —OR$^3$, deuterium, methyl, hydroxyl substituted C$_1$-C$_6$alkyl or C$_1$-C$_6$haloalkyl.

22. The compound of claim 21, wherein R$^3$ is H, methyl or ethyl.

23. The compound of claim 1 selected from:
   6-[(2R)-2-(3-fluorophenyl)pyrrolidin-1-yl]imidazo[1,2-b]pyridazine-3-carbonitrile;
   6-[3-(3-fluorophenyl)morpholin-4-yl]imidazo[1,2-b]pyridazine-3-carbonitrile;
   6-[(2R,4S)-3,3-difluoro-2-(3-fluorophenyl)-4-methylpyrrolidin-1-yl]imidazo[1,2-b]pyridazine-3-carbonitrile;
   6-[2-(3-fluorophenyl)pyrrolidin-1-yl]imidazo[1,2-b]pyridazine-3-carboxamide;

6-[(2R)-2-(3-fluorophenyl)pyrrolidin-1-yl]imidazo[1,2-b]pyridazine-3-carboxamide;
6-[(2R,4S)-4-fluoro-2-(3-fluorophenyl)pyrrolidin-1-yl]imidazo[1,2-b]pyridazine-3-carboxamide;
6-[2-(3-fluorophenyl)-2-hydrogeniopyrrolidin-1-yl]imidazo[1,2-b]pyridazine-3-carboxamide;
6-[(2S)-2-(3-fluorophenyl)-2-hydrogeniopyrrolidin-1-yl]imidazo[1,2-b]pyridazine-3-carboxamide;
6-[(5S)-5-(3-fluorophenyl)-2,2-dihydrogeniopyrrolidin-1-yl]imidazo[1,2-b]pyridazine-3-carboxamide;
6-[(5R)-5-(3-fluorophenyl)-2,2-dihydrogeniopyrrolidin-1-yl]imidazo[1,2-b]pyridazine-3-carboxamide;
6-[5-(3-fluorophenyl)-2,2,3,3,4,4-hexahydrogeniopyrrolidin-1-yl]imidazo[1,2-b]pyridazine-3-carboxamide;
6-[2-(3-fluorophenyl)-2,3,3,4,4,5,5-heptahydrogeniopyrrolidin-1-yl]imidazo[1,2-b]pyridazine-3-carboxamide;
6-[(2R,4S)-4-fluoro-2-(3-fluorophenyl)pyrrolidin-1-yl]-N-(oxan-4-yl)imidazo[1,2-b]pyridazine-3-carboxamide;
6-[(2R)-2-(3-fluorophenyl)-2,5-dihydro-1H-pyrrol-1-yl]imidazo[1,2-b]pyridazine-3-carboxamide;
6-[3-(3-fluorophenyl)morpholin-4-yl]imidazo[1,2-b]pyridazine-3-carboxamide;
6-[(3R)-3-(3-fluorophenyl)morpholin-4-yl]imidazo[1,2-b]pyridazine-3-carboxamide;
6-[2-(3-fluorophenyl)piperidin-1-yl]imidazo[1,2-b]pyridazine-3-carboxamide;
6-[(2R)-2-(3-fluorophenyl)piperidin-1-yl]imidazo[1,2-b]pyridazine-3-carboxamide;
6-[(2R)-2-(3-fluorophenyl)pyrrolidin-1-yl]-N-(4-hydroxybutyl)imidazo[1,2-b]pyridazine-3-carboxamide;
N-ethyl-6-[2-(3-fluorophenyl)pyrrolidin-1-yl]imidazo[1,2-b]pyridazine-3-carboxamide;
N-(cyclobutylmethyl)-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-[2-(oxolan-2-yl)ethyl]imidazo[1,2-b]pyridazine-3-carboxamide;
N-[(4-fluorophenyl)methyl]-6-[2-(3-fluorophenyl)pyrrolidin-1-yl]imidazo[1,2-b]pyridazine-3-carboxamide;
6-[(2R)-2-(3-fluorophenyl)pyrrolidin-1-yl]-N-{[6-(morpholin-4-yl)pyridin-2-yl]methyl}imidazo[1,2-b]pyridazine-3-carboxamide;
2-(4-fluorophenoxy)-N-{6-[(2R)-2-(3-fluoropyrrolidin-1-yl]imidazo[1,2-b]pyridazin-3-yl}acetamide;
N-[1-(ethanesulfonyl)piperidin-4-yl]-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-[(1R,2S)-2-(hydroxymethyl)cyclohexyl]imidazo[1,2-b]pyridazine-3-carboxamide;
6-[(2R)-2-(3-fluorophenyl)pyrrolidin-1-yl]-N-(1-sulfamoylpiperidin-4-yl)imidazo[1,2-b]pyridazine-3-carboxamide;
6-[(2R)-2-(3-fluorophenyl)pyrrolidin-1-yl]-N-[(3S)-1-methanesulfonylpyrrolidin-3-yl]imidazo[1,2-b]pyridazine-3-carboxamide;
6-[(2R)-2-(3-fluorophenyl)pyrrolidin-1-yl]-N-[(3S)-1-(propane-2-sulfonyl)pyrrolidin-3-yl]imidazo[1,2-b]pyridazine-3-carboxamide;
6-[(2R)-2-(3-fluorophenyl)pyrrolidin-1-yl]-N-[1-(propane-2-sulfonyl)piperidin-4-yl]imidazo[1,2-b]pyridazine-3-carboxamide;
(2S)-1-(4-{6-[(2R)-2-(3-fluorophenyl)pyrrolidin-1-yl]imidazo[1,2-b]pyridazine-3-amido}piperidin-1-yl)-1-oxopropan-2-yl acetate;
6-[(2R)-2-(3-fluorophenyl)pyrrolidin-1-yl]-N-{1-[(2S)-2-hydroxypropanoyl]piperidin-4-yl}imidazo[1,2-b]pyridazine-3-carboxamide;
6-[(2R)-2-(3-fluorophenyl)pyrrolidin-1-yl]-N-[1-(propane-1-sulfonyl)piperidin-4-yl]imidazo[1,2-b]pyridazine-3-carboxamide;
N-[(5,5-dimethyloxolan-2-yl)methyl]-6-[(2R)-2-(3-fluorophenyl)pyrrolidin-1-yl]imidazo[1,2-b]pyridazine-3-carboxamide;
N-[2-(4-fluorophenyl)ethyl]-6-[(2R)-2-(3-fluorophenyl)pyrrolidin-1-yl]imidazo[1,2-b]pyridazine-3-carboxamide;
N-(1,3-benzothiazol-2-ylmethyl)-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-(propan-2-yl)imidazo[1,2-b]pyridazine-3-carboxamide;
N-[3-(diethylamino)propyl]-6-[(2R)-2-(3-fluorophenyl)pyrrolidin-1-yl]imidazo[1,2-b]pyridazine-3-carboxamide;
N-[1-(4-fluorophenyl)-2-methylpropan-2-yl]-6-[(2R)-2-(3-fluorophenyl)pyrrolidin-1-yl]imidazo[1,2-b]pyridazine-3-carboxamide;
N-[1-(4-fluorophenyl)ethyl]-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-methylimidazo[1,2-b]pyridazine-3-carboxamide;
N-cyclopropyl-6-[(2R)-2-(3-fluorophenyl)pyrrolidin-1-yl]imidazo[1,2-b]pyridazine-3-carboxamide;
N-tert-butyl-6-[(2R)-2-(3-fluorophenyl)pyrrolidin-1-yl]imidazo[1,2-b]pyridazine-3-carboxamide;
N-cyclobutyl-6-[(2R)-2-(3-fluorophenyl)pyrrolidin-1-yl]imidazo[1,2-b]pyridazine-3-carboxamide;
N-[(4-fluorophenyl)methyl]-6-[(2R)-2-(3-fluorophenyl)pyrrolidin-1-yl]imidazo[1,2-b]pyridazine-3-carboxamide;
N-cyclopentyl-6-[(2R)-2-(3-fluorophenyl)pyrrolidin-1-yl]imidazo[1,2-b]pyridazine-3-carboxamide;
N-cyclohexyl-6-[(2R)-2-(3-fluorophenyl)pyrrolidin-1-yl]imidazo[1,2-b]pyridazine-3-carboxamide;
ethyl 4-{6-[(2R)-2-(3-fluorophenyl)pyrrolidin-1-yl]imidazo[1,2-b]pyridazine-3-amido}piperidine-1-carboxylate;
6-[(2R)-2-(3-fluorophenyl)pyrrolidin-1-yl]-N-(2-methoxyethyl)imidazo[1,2-b]pyridazine-3-carboxamide;
6-[(2R)-2-(3-fluorophenyl)pyrrolidin-1-yl]-N-[2-(morpholin-4-yl)ethyl]imidazo[1,2-b]pyridazine-3-carboxamide;
6-[(2R)-2-(3-fluorophenyl)pyrrolidin-1-yl]-N-(2,2,2-trifluoroethyl)imidazo[1,2-b]pyridazine-3-carboxamide;
6-[(2R)-2-(3-fluorophenyl)pyrrolidin-1-yl]-N-[(2S)-1-methoxypropan-2-yl]imidazo[1,2-b]pyridazine-3-carboxamide;
N-ethyl-6-[(2R)-2-(3-fluorophenyl)pyrrolidin-1-yl]imidazo[1,2-b]pyridazine-3-carboxamide;
N-[2-(dimethylamino)ethyl]-6-[(2R)-2-(3-fluorophenyl)pyrrolidin-1-yl]imidazo[1,2-b]pyridazine-3-carboxamide;
N-[(6-chloropyridin-3-yl)methyl]-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-[3-(morpholin-4-yl)propyl]imidazo[1,2-b]pyridazine-3-carboxamide;
6-[(2R)-2-(3-fluorophenyl)pyrrolidin-1-yl]-N-(thian-4-yl)imidazo[1,2-b]pyridazine-3-carboxamide;

6-[(2R)-2-(3-fluorophenyl)pyrrolidin-1-yl]-N-(2,2,3,3,3-pentafluoropropyl)imidazo[1,2-b]pyridazine-3-carboxamide;
tert-butyl 3-{6-[(2R)-2-(3-fluorophenyl)pyrrolidin-1-yl]imidazo[1,2-b]pyridazine-3-amido}azetidine-1-carboxylate;
tert-butyl (3R)-3-{6-[(2R)-2-(3-fluorophenyl)pyrrolidin-1-yl]imidazo[1,2-b]pyridazine-3-amido}pyrrolidine-1-carboxylate;
tert-butyl 4-{6-[(2R)-2-(3-fluorophenyl)pyrrolidin-1-yl]imidazo[1,2-b]pyridazine-3-amido}piperidine-1-carboxylate;
N-(1-acetylazetidin-3-yl)-6-[(2R)-2-(3-fluorophenyl)pyrrolidin-1-yl]imidazo[1,2-b]pyridazine-3-carboxamide;
N-(3-cyanophenyl)-6-[(2R)-2-(3-fluorophenyl)pyrrolidin-1-yl]imidazo[1,2-b]pyridazine-3-carboxamide;
N-[(3R)-1-acetylpyrrolidin-3-yl]-6-[(2R)-2-(3-fluorophenyl)pyrrolidin-1-yl]imidazo[1,2-b]pyridazine-3-carboxamide;
N-(1-acetylpiperidin-4-yl)-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-(1-methanesulfonylazetidin-3-yl)imidazo[1,2-b]pyridazine-3-carboxamide;
N-[(2-fluorophenyl)methyl]-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-[(3R)-1-methanesulfonylpyrrolidin-3-yl]imidazo[1,2-b]pyridazine-3-carboxamide;
6-[(2R)-2-(3-fluorophenyl)pyrrolidin-1-yl]-N-(1-methanesulfonylpiperidin-4-yl)imidazo[1,2-b]pyridazine-3-carboxamide;
2-(4-{6-[(2R)-2-(3-fluorophenyl)pyrrolidin-1-yl]imidazo[1,2-b]pyridazine-3-amido}piperidin-1-yl)-2-oxoethyl acetate;
N-[(3-fluorophenyl)methyl]-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-[1-(2-hydroxyacetyl)piperidin-4-yl]imidazo[1,2-b]pyridazine-3-carboxamide;
6-[(2R)-2-(3-fluorophenyl)pyrrolidin-1-yl]-N-(3,3,3-trifluoropropyl)imidazo[1,2-b]pyridazine-3-carboxamide;
N-(1-ethyl-1H-pyrazol-5-yl)-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-(2-hydroxyethyl)imidazo[1,2-b]pyridazine-3-carboxamide;
6-[(2R)-2-(3-fluorophenyl)pyrrolidin-1-yl]-N-(4-hydroxycyclohexyl)imidazo[1,2-b]pyridazine-3-carboxamide;
6-[(2R)-2-(3-fluorophenyl)pyrrolidin-1-yl]-N-[(1R,2R)-2-hydroxycyclopentyl]imidazo[1,2-b]pyridazine-3-carboxamide;
6-[(2R)-2-(3-fluorophenyl)pyrrolidin-1-yl]-N-[(1S,2S)-2-hydroxycyclohexyl]imidazo[1,2-b]pyridazine-3-carboxamide;
6-[(2R)-2-(3-fluorophenyl)pyrrolidin-1-yl]-N-(1-hydroxy-2-methylpropan-2-yl)imidazo[1,2-b]pyridazine-3-carboxamide;
6-[(2R)-2-(3-fluorophenyl)pyrrolidin-1-yl]-N-[(2R)-oxolan-2-ylmethyl]imidazo[1,2-b]pyridazine-3-carboxamide;
6-[(2R)-2-(3-fluorophenyl)pyrrolidin-1-yl]-N-[(2S)-oxolan-2-ylmethyl]imidazo[1,2-b]pyridazine-3-carboxamide;
6-[(2R)-2-(3-fluorophenyl)pyrrolidin-1-yl]-N-[2-(2-oxopyrrolidin-1-yl)ethyl]imidazo[1,2-b]pyridazine-3-carboxamide;
methyl N-[(2S)-1-({6-[(2R)-2-(3-fluorophenyl)pyrrolidin-1-yl]imidazo[1,2-b]pyridazin-3-yl}formamido)propan-2-yl]carbamate;
6-((2R,4S)-4-fluoro-2-(3-fluorophenyl)pyrrolidin-1-yl)-N-(1,1-dioxo-tetrahydrothiophen-3-yl)imidazo[1,2-b]pyridazine-3-carboxamide
N-[(4-cyanophenyl)methyl]-6-[(2R)-2-(3-fluorophenyl)pyrrolidin-1-yl]imidazo[1,2-b]pyridazine-3-carboxamide;
N-(cyclopropylmethyl)-6-[(2R)-2-(3-fluorophenyl)pyrrolidin-1-yl]imidazo[1,2-b]pyridazine-3-carboxamide;
N-(2-cyclohexylethyl)-6-[(2R)-2-(3-fluorophenyl)pyrrolidin-1-yl]imidazo[1,2-b]pyridazine-3-carboxamide;
N-(2,2-difluoroethyl)-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-(oxan-4-yl)imidazo[1,2-b]pyridazine-3-carboxamide;
6-[(2R)-2-(3-fluorophenyl)pyrrolidin-1-yl]-N-(2-methylpropyl)imidazo[1,2-b]pyridazine-3-carboxamide;
N-(cyclohexylmethyl)-6-[(2R)-2-(3-fluorophenyl)pyrrolidin-1-yl]imidazo[1,2-b]pyridazine-3-carboxamide;
N-(2-fluoroethyl)-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-(oxan-3-yl)imidazo[1,2-b]pyridazine-3-carboxamide;
methyl (2R)-2-({6-[(2R)-2-(3-fluorophenyl)pyrrolidin-1-yl]imidazo[1,2-b]pyridazin-3-yl}formamido)-3-hydroxypropanoate;
6-[(2R)-2-(3-fluorophenyl)pyrrolidin-1-yl]-N-({6-[(3R)-3-hydroxypyrrolidin-1-yl]pyridin-3-yl}methyl)imidazo[1,2-b]pyridazine-3-carboxamide;
6-[(2R)-2-(3-fluorophenyl)pyrrolidin-1-yl]-N-[(3R)-2-oxooxolan-3-yl]imidazo[1,2-b]pyridazine-3-carboxamide;
N-[1,3-dihydroxy-2-(hydroxymethyl)propan-2-yl]-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-[(2R)-1-hydroxy-3-methylbutan-2-yl]imidazo[1,2-b]pyridazine-3-carboxamide;
6-[(2R)-2-(3-fluorophenyl)pyrrolidin-1-yl]-N-[(2S)-1-hydroxy-3,3-dimethylbutan-2-yl]imidazo[1,2-b]pyridazine-3-carboxamide;
6-[(2R)-2-(3-fluorophenyl)pyrrolidin-1-yl]-N-[(2S)-1-hydroxy-4-methylpentan-2-yl]imidazo[1,2-b]pyridazine-3-carboxamide;
N-[(2S)-2,3-dihydroxypropyl]-6-[(2R)-2-(3-fluorophenyl)pyrrolidin-1-yl]imidazo[1,2-b]pyridazine-3-carboxamide;
6-[(2R)-2-(3-fluorophenyl)pyrrolidin-1-yl]-N-[(1R,2R)-2-hydroxy-2,3-dihydro-1H-inden-1-yl]imidazo[1,2-b]pyridazine-3-carboxamide;
6-[(2R)-2-(3-fluorophenyl)pyrrolidin-1-yl]-N-[(2R)-1-hydroxy-4-methylpentan-2-yl]imidazo[1,2-b]pyridazine-3-carboxamide;
N-(2-cyclopentylethyl)-6-[(2R)-2-(3-fluorophenyl)pyrrolidin-1-yl]imidazo[1,2-b]pyridazine-3-carboxamide;
N-(cyclopentylmethyl)-6-[(2R)-2-(3-fluorophenyl)pyrrolidin-1-yl]imidazo[1,2-b]pyridazine-3-carboxamide;

N-{[(1S,2R,5S)-6,6-dimethylbicyclo[3.1.1]heptan-2-yl]methyl}-6-[(2R)-2-(3-fluorophenyl)pyrrolidin-1-yl]imidazo[1,2-b]pyridazine-3-carboxamide;

6-[2-(3-fluorophenyl)pyrrolidin-1-yl]-N-(2,2,2-trifluoroethyl)imidazo[1,2-b]pyridazine-3-carboxamide;

6-[(2R,4S)-4-fluoro-2-(3-fluorophenyl)pyrrolidin-1-yl]-N-(2-fluoroethyl)imidazo[1,2-b]pyridazine-3-carboxamide;

6-[(2R,4S)-4-fluoro-2-(3-fluorophenyl)pyrrolidin-1-yl]-N-[2-(morpholin-4-yl)ethyl]imidazo[1,2-b]pyridazine-3-carboxamide;

N-(2,2-difluoroethyl)-6-[(2R,4S)-4-fluoro-2-(3-fluorophenyl)pyrrolidin-1-yl]imidazo[1,2-b]pyridazine-3-carboxamide;

tert-butyl 4-{6-[(2R,4S)-4-fluoro-2-(3-fluorophenyl)pyrrolidin-1-yl]imidazo[1,2-b]pyridazine-3-amido}piperidine-1-carboxylate;

6-((R)-2-(3-fluorophenyl)pyrrolidin-1-yl)-N-(1,1-dioxotetrahydrothiophen-3-yl)imidazo[1,2-b]pyridazine-3-carboxamide;

2-({6-[(2R,4S)-4-fluoro-2-(3-fluorophenyl)pyrrolidin-1-yl]imidazo[1,2-b]pyridazin-3-yl}formamido)acetamide;

6-[(2R,4S)-4-fluoro-2-(3-fluorophenyl)pyrrolidin-1-yl]-N-(2-sulfamoylethyl)imidazo[1,2-b]pyridazine-3-carboxamide;

6-[(2R,4S)-4-fluoro-2-(3-fluorophenyl)pyrrolidin-1-yl]-N-(2-hydroxyethyl)imidazo[1,2-b]pyridazine-3-carboxamide;

6-[(2R,4S)-4-fluoro-2-(3-fluorophenyl)pyrrolidin-1-yl]-N-(piperidin-4-yl)imidazo[1,2-b]pyridazine-3-carboxamide;

6-[(2R,4S)-4-fluoro-2-(3-fluorophenyl)pyrrolidin-1-yl]-N-(1-methanesulfonylpiperidin-4-yl)imidazo[1,2-b]pyridazine-3-carboxamide;

(2E)-3-(6-bromopyridin-2-yl)-1-{6-[(2R)-2-(3-fluorophenyl)pyrrolidin-1-yl]imidazo[1,2-b]pyridazin-3-yl}prop-2-en-1-one;

1-{6-[(2R)-2-(3-fluorophenyl)pyrrolidin-1-yl]imidazo[1,2-b]pyridazin-3-yl}propan-1-one;

2,2-difluoro-1-{6-[(2R)-2-(3-fluorophenyl)pyrrolidin-1-yl]imidazo[1,2-b]pyridazin-3-yl}ethan-1-one;

1-{6-[(2R)-2-(3-fluorophenyl)pyrrolidin-1-yl]imidazo[1,2-b]pyridazin-3-yl}ethan-1-one;

(2Z)-3-(3-fluorophenyl)-1-{6-[(2R)-2-(3-fluorophenyl)pyrrolidin-1-yl]imidazo[1,2-b]pyridazin-3-yl}prop-2-en-1-one;

3-(3-fluorophenyl)-1-{6-[(2R)-2-(3-fluorophenyl)pyrrolidin-1-yl]imidazo[1,2-b]pyridazin-3-yl}propan-1-one;

(2E)-1-{6-[(2R)-2-(3-fluorophenyl)pyrrolidin-1-yl]imidazo[1,2-b]pyridazin-3-yl}-3-[6-(morpholin-4-yl)pyridin-2-yl]prop-2-en-1-one;

1-{6-[(2R)-2-(3-fluorophenyl)pyrrolidin-1-yl]imidazo[1,2-b]pyridazin-3-yl}-3-[6-(morpholin-4-yl)pyridin-2-yl]propan-1-one;

(2E)-1-{6-[(2R)-2-(3-fluorophenyl)pyrrolidin-1-yl]imidazo[1,2-b]pyridazin-3-yl}-3-(1-methyl-1H-pyrrol-2-yl)prop-2-en-1-one;

(2E)-1-{6-[(2R)-2-(3-fluorophenyl)pyrrolidin-1-yl]imidazo[1,2-b]pyridazin-3-yl}-3-(6-methoxypyridin-2-yl)prop-2-en-1-one;

N-ethoxy-6-[(2R,4S)-4-fluoro-2-(3-fluorophenyl)pyrrolidin-1-yl]imidazo[1,2-b]pyridazine-3-carboxamide;

N-(cyclopropylmethoxy)-6-[(2R)-2-(3-fluorophenyl)pyrrolidin-1-yl]imidazo[1,2-b]pyridazine-3-carboxamide;

6-[(2R)-2-(3-fluorophenyl)pyrrolidin-1-yl]-N-(oxan-2-yloxy)imidazo[1,2-b]pyridazine-3-carboxamide;

N-(tert-butoxy)-6-[(2R)-2-(3-fluorophenyl)pyrrolidin-1-yl]imidazo[1,2-b]pyridazine-3-carboxamide;

N-[2-(dimethylamino)ethoxy]-6-[(2R)-2-(3-fluorophenyl)pyrrolidin-1-yl]imidazo[1,2-b]pyridazine-3-carboxamide;

6-[(2R)-2-(3-fluorophenyl)pyrrolidin-1-yl]-N-(2-hydroxyethoxy)imidazo[1,2-b]pyridazine-3-carboxamide;

6-[(2R)-2-(3-fluorophenyl)pyrrolidin-1-yl]-N-(2-methoxyethoxy)imidazo[1,2-b]pyridazine-3-carboxamide;

N-ethoxy-6-[(2R)-2-(3-fluorophenyl)pyrrolidin-1-yl]imidazo[1,2-b]pyridazine-3-carboxamide;

6-[(2R)-2-(3-fluorophenyl)pyrrolidin-1-yl]-N-hydroxyimidazo[1,2-b]pyridazine-3-carboxamide;

6-[(2R)-2-(3-fluorophenyl)pyrrolidin-1-yl]-N-methoxyimidazo[1,2-b]pyridazine-3-carboxamide;

N-ethoxy-6-[2-(3-fluorophenyl)pyrrolidin-1-yl]imidazo[1,2-b]pyridazine-3-carboxamide;

6-[(2R,4S)-4-fluoro-2-(3-fluorophenyl)pyrrolidin-1-yl]-N-hydroxyimidazo[1,2-b]pyridazine-3-carboxamide;

6-[(2R)-2-(3-fluorophenyl)pyrrolidin-1-yl]-N-(4-methylpiperazin-1-yl)imidazo[1,2-b]pyridazine-3-carboxamide;

6-[(2R)-2-(3-fluorophenyl)pyrrolidin-1-yl]imidazo[1,2-b]pyridazine-3-carbohydrazide;

ethyl 6-[2-(3-fluorophenyl)piperidin-1-yl]imidazo[1,2-b]pyridazine-3-carboxylate;

methyl 6-[(2R)-2-(3-fluorophenyl)pyrrolidin-1-yl]imidazo[1,2-b]pyridazine-3-carboxylate;

ethyl 6-[(2R)-2-(3-fluorophenyl)pyrrolidin-1-yl]imidazo[1,2-b]pyridazine-3-carboxylate;

ethyl 6-[2-(3-fluorophenyl)-3-oxopyrrolidin-1-yl]imidazo[1,2-b]pyridazine-3-carboxylate;

ethyl 6-[(2R,4R)-2-(3-fluorophenyl)-4-hydroxypyrrolidin-1-yl]imidazo[1,2-b]pyridazine-3-carboxylate;

ethyl 6-[5-(3-fluorophenyl)-2,2,3,3,4,4-hexahydrogeniopyrrolidin-1-yl]imidazo[1,2-b]pyridazine-3-carboxylate;

ethyl 6-[2-(3-fluorophenyl)-2-hydrogeniopyrrolidin-1-yl]imidazo[1,2-b]pyridazine-3-carboxylate;

ethyl 6-[2-(3-fluorophenyl)-2,3,3,4,4,5,5-heptahydrogeniopyrrolidin-1-yl]imidazo[1,2-b]pyridazine-3-carboxylate;

ethyl 6-[(2S)-3,3,4,4-tetrafluoro-2-(3-fluorophenyl)pyrrolidin-1-yl]imidazo[1,2-b]pyridazine-3-carboxylate;

ethyl 6-[(2R,4S)-4-fluoro-2-(3-fluorophenyl)pyrrolidin-1-yl]imidazo[1,2-b]pyridazine-3-carboxylate;

ethyl 6-[(2S,4R)-4-fluoro-2-(3-fluorophenyl)pyrrolidin-1-yl]imidazo[1,2-b]pyridazine-3-carboxylate;

2-ethoxy-N-{6-[(2R)-2-(3-fluorophenyl)pyrrolidin-1-yl]imidazo[1,2-b]pyridazin-3-yl}acetamide;

({6-[(2R)-2-(3-fluorophenyl)pyrrolidin-1-yl]imidazo[1,2-b]pyridazin-3-yl}carbamoyl)methyl acetate;

2-cyano-N-{6-[(2R)-2-(3-fluorophenyl)pyrrolidin-1-yl]imidazo[1,2-b]pyridazin-3-yl}acetamide;

N-{6-[(2R)-2-(3-fluorophenyl)pyrrolidin-1-yl]imidazo[1,2-b]pyridazin-3-yl}-2-(4-methoxyphenoxy)acetamide;

1-({6-[(2R)-2-(3-fluorophenyl)pyrrolidin-1-yl]imidazo[1,2-b]pyridazin-3-yl}carbamoyl)-1-methylethyl acetate;

tert-butyl N-[({6-[(2R)-2-(3-fluorophenyl)pyrrolidin-1-yl]imidazo[1,2-b]pyridazin-3-yl}carbamoyl)methyl]carbamate;

2-amino-N-{6-[(2R)-2-(3-fluorophenyl)pyrrolidin-1-yl]imidazo[1,2-b]pyridazin-3-yl}acetamide;

2-acetamido-N-{6-[(2R)-2-(3-fluorophenyl)pyrrolidin-1-yl]imidazo[1,2-b]pyridazin-3-yl}acetamide;

2-amino-N-{6-[(2R)-4,4-difluoro-2-(3-fluorophenyl)pyrrolidin-1-yl]imidazo[1,2-b]pyridazin-3-yl}acetamide;
3-(2-chloroethyl)-1-{6-[(2R)-2-(3-fluorophenyl)pyrrolidin-1-yl]imidazo[1,2-b]pyridazin-3-yl}urea;
6-[2-(3-fluorophenyl)pyrrolidin-1-yl]-N'-hydroxyimidazo[1,2-b]pyridazine-3-carboximidamide;
6-[(2R)-2-(3-fluorophenyl)pyrrolidin-1-yl]-N'-hydroxyimidazo[1,2-b]pyridazine-3-carboximidamide;
6-[(2R)-2-(3-fluorophenyl)pyrrolidin-1-yl]-N'-methoxyimidazo[1,2-b]pyridazine-3-carboximidamide;
6-[(2R)-2-(3-fluorophenyl)pyrrolidin-1-yl]-N'-(2-hydroxyethoxy)imidazo[1,2-b]pyridazine-3-carboximidamide;
tert-butyl N-{6-[(2R)-2-(3-fluorophenyl)pyrrolidin-1-yl]imidazo[1,2-b]pyridazin-3-yl}carbamate;
propan-2-yl N-{6-[(2R)-2-(3-fluorophenyl)pyrrolidin-1-yl]imidazo[1,2-b]pyridazin-3-yl}carbamate;
methyl N-{6-[(2R)-2-(3-fluorophenyl)pyrrolidin-1-yl]imidazo[1,2-b]pyridazin-3-yl}carbamate;
ethyl N-{6-[(2R)-2-(3-fluorophenyl)pyrrolidin-1-yl]imidazo[1,2-b]pyridazin-3-yl}carbamate;
N-ethyl-6-[(2R)-2-(3-fluorophenyl)pyrrolidin-1-yl]imidazo[1,2-b]pyridazine-3-sulfonamide;
phenyl N-{6-[(2R)-4,4-difluoro-2-(3-fluorophenyl)pyrrolidin-1-yl]imidazo[1,2-b]pyridazin-3-yl}carbamate;
ethyl 6-[(2R,4S)-2-(3,4-difluorophenyl)-4-fluoropyrrolidin-1-yl]imidazo[1,2-b]pyridazine-3-carboxylate;
6-[(2R,4S)-2-(3,4-difluorophenyl)-4-fluoropyrrolidin-1-yl]imidazo[1,2-b]pyridazine-3-carboxamide;
6-[(2R,4S)-2-(3,5-difluorophenyl)-4-fluoropyrrolidin-1-yl]imidazo[1,2-b]pyridazine-3-carboxamide;
6-[(2R,4S)-2-(2,5-difluorophenyl)-4-fluoropyrrolidin-1-yl]imidazo[1,2-b]pyridazine-3-carboxamide;
ethyl 6-[(2R,4S)-2-(3-cyano-5-fluorophenyl)-4-fluoropyrrolidin-1-yl]imidazo[1,2-b]pyridazine-3-carboxylate;
6-[(2R,4S)-2-(3-cyano-5-fluorophenyl)-4-fluoropyrrolidin-1-yl]imidazo[1,2-b]pyridazine-3-carboxamidine;
6-[(2R)-4,4-difluoro-2-(3-fluorophenyl)pyrrolidin-1-yl]imidazo[1,2-b]pyridazine-3-carboxamide;
6-[(2R)-4,4-difluoro-2-(3-fluorophenyl)pyrrolidin-1-yl]imidazo[1,2-b]pyridazine-3-carbonitrile;
6-(4,4-difluoro-2-{5-fluoro-2-[(propan-2-yl)carbamoyl]phenyl}pyrrolidin-1-yl)imidazo[1,2-b]pyridazine-3-carboxamide;
{6-[(2R)-4,4-difluoro-2-(3-fluorophenyl)pyrrolidin-1-yl]imidazo[1,2-b]pyridazin-3-yl}carbonylurea, and
methyl N-({6-[(2R)-4,4-difluoro-2-(3-fluorophenyl)pyrrolidin-1-yl]imidazo[1,2-b]pyridazin-3-yl}carbonyl)carbamate.

24. The compound of claim 1, wherein the compound of Formula (I) is 6-[(2R)-4,4-difluoro-2-(3-fluorophenyl)pyrrolidin-1-yl]imidazo[1,2-b]pyridazine-3-carboxamide.

25. The compound of claim 1, wherein the compound of Formula (I) is 6-[(2R,4S)-4-fluoro-2-(3-fluorophenyl)pyrrolidin-1-yl]imidazo[1,2-b]pyridazine-3-carboxamide.

26. The compound of claim 1, wherein the compound of Formula (I) is 6-[(2R,4S)-2-(3-cyano-5-fluorophenyl)-4-fluoropyrrolidin-1-yl]imidazo[1,2-b]pyridazine-3-carboxamide.

27. A compound selected from:
N-{6-[(2R)-2-(3-fluorophenyl)pyrrolidin-1-yl]imidazo[1,2-b]pyridazin-3-yl}-3-methoxypropanamide, and
N-{6-[(2R)-2-(3-fluorophenyl)pyrrolidin-1-yl]imidazo[1,2-b]pyridazin-3-yl}-2-methoxyacetamide.

28. A pharmaceutical composition comprising a therapeutically effective amount of a compound of claim 1 and a pharmaceutically acceptable carrier.

29. A method for inhibiting a TRK kinase comprising administering to a system or a subject in need thereof, a therapeutically effective amount of a compound of claim 1, or pharmaceutically acceptable salts or pharmaceutical compositions thereof.

* * * * *